(12) United States Patent
Chen et al.

(10) Patent No.: US 12,286,442 B2
(45) Date of Patent: Apr. 29, 2025

(54) METHODS AND MATERIALS FOR INCREASING TRANSCRIPTION FACTOR EB POLYPEPTIDE LEVELS

(71) Applicant: University of Pittsburgh—Of the Commonwealth System of Higher Education, Pittsburgh, PA (US)

(72) Inventors: Beibei Chen, Sewickley, PA (US); Toren Finkel, Pittsburgh, PA (US); Yuan Liu, Sewickley, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 632 days.

(21) Appl. No.: 17/420,597

(22) PCT Filed: Jan. 3, 2020

(86) PCT No.: PCT/US2020/012268
§ 371 (c)(1),
(2) Date: Jul. 2, 2021

(87) PCT Pub. No.: WO2020/142748
PCT Pub. Date: Jul. 9, 2020

(65) Prior Publication Data
US 2022/0112218 A1    Apr. 14, 2022

Related U.S. Application Data

(60) Provisional application No. 62/879,374, filed on Jul. 26, 2019, provisional application No. 62/788,049, filed on Jan. 3, 2019.

(51) Int. Cl.
*C07D 519/00*  (2006.01)
*A61P 25/28*  (2006.01)

(52) U.S. Cl.
CPC ............ *C07D 519/00* (2013.01); *A61P 25/28* (2018.01)

(58) Field of Classification Search
CPC .............................. C07D 519/00; A61P 25/28
See application file for complete search history.

(56) References Cited

U.S. PATENT DOCUMENTS

| | | | |
|---|---|---|---|
| 5,304,121 | A | 4/1994 | Sahatjian |
| 5,886,026 | A | 3/1999 | Hunter et al. |
| 6,099,562 | A | 8/2000 | Ding et al. |
| 6,803,031 | B2 | 10/2004 | Rabinowitz et al. |
| 8,343,980 | B2 | 1/2013 | Gonzalez, III et al. |
| 8,957,088 | B2 * | 2/2015 | Fiegen ............ A61P 9/00 514/300 |
| 2003/0078166 | A1 | 4/2003 | Davies et al. |
| 2009/0209536 | A1 | 8/2009 | Gahman et al. |

FOREIGN PATENT DOCUMENTS

| | | |
|---|---|---|
| CN | 1469874 | 1/2004 |
| CN | 102947306 | 2/2013 |
| JP | 2004-509113 | 3/2004 |
| JP | 2006-522119 | 9/2006 |
| JP | 2011-529931 | 12/2011 |
| JP | 2011-529932 | 12/2011 |
| JP | 2013-525405 | 6/2013 |
| JP | 2017-536363 | 12/2017 |
| RU | 2015120217 | 1/2017 |
| WO | WO 2002/022601 | 3/2002 |
| WO | WO 2003/057695 | 7/2003 |
| WO | WO 2004/037814 | 5/2004 |
| WO | WO 2004/078733 | 9/2004 |
| WO | WO 2004/101512 | 11/2004 |
| WO | WO 2004/101513 | 11/2004 |
| WO | WO 2010/015518 | 2/2010 |
| WO | WO 2010/015520 | 2/2010 |
| WO | WO 2011/134971 | 11/2011 |
| WO | WO 2011/135351 | 11/2011 |
| WO | WO 2014/079787 | 5/2014 |

(Continued)

OTHER PUBLICATIONS

Chauhan, S., et al. Pharmaceutical screen identifies novel target processes for activation of autophagy with a broad translational potential. Nat Commun 6, 8620 (2015). (Year: 2015).*

(Continued)

*Primary Examiner* — Matthew P Coughlin
*Assistant Examiner* — Quincy McKoy
(74) *Attorney, Agent, or Firm* — Fish & Richardson P.C.

(57) ABSTRACT

This document provides methods and materials for increasing TFEB polypeptide levels. For example, compounds (e.g., organic compounds) having the ability to increase TFEB polypeptide levels within cells and/or within a nucleus of cells, formulations containing compounds having the ability to increase TFEB polypeptide levels within cells and/or within a nucleus of cells, methods for making compounds having the ability to increase TFEB polypeptide levels within cells and/or within a nucleus of cells, methods for making formulations containing compounds having the ability to increase TFEB polypeptide levels within cells and/or within a nucleus of cells, methods for increasing TFEB polypeptide levels within cells and/or within a nucleus of cells, and methods for treating mammals (e.g., humans) having a condition responsive to an increase in TFEB polypeptide levels are provided.

20 Claims, 12 Drawing Sheets

Specification includes a Sequence Listing.

(56) References Cited

FOREIGN PATENT DOCUMENTS

| WO | WO 2016/081365 | 5/2016 |
|---|---|---|
| WO | WO 2018/089433 | 5/2018 |
| WO | WO 2018/089493 | 5/2018 |
| WO | WO 2018/089499 | 5/2018 |
| WO | WO 2018/191146 | 10/2018 |

OTHER PUBLICATIONS

EP Extended Search Report in European Appln. No. 20736104.9, dated Oct. 12, 2022, 16 pages.

Johns et al., "1,3,4-Oxadiazole substituted naphthyridines as HIV-1 integrase inhibitors. Part 2: SAR of the C5 position," Bioor. Med. Chem. Letters, Mar. 15, 2009, 19(6):1807-1810.

Johns et al., "The use of oxadiazole and triazole substituted naphthyridines as HIV-1 integrase inhibitors. Part 1: Establishing the pharmacophore," Bioorg. Med. Chem. Letters, Mar. 15, 2009, 19(6):1802-1806.

Van Eis et al., "2,6-Naphthyridines as potent and selective inhibitors of the novel protein kinase C isozymes," Bioorg. Med. Chem. Letters, Dec. 15, 2011, 21(24):7367-7372.

Cywin et al., "Discovery and SAR of Novel [1,6]Naphthyridines as Potent Inhibitors of Spleen Tyrosine Kinase (SYK)," Bioorg. Med. Chem. Lett., 2003, 13:1415-1418.

Martini-Stoica et al., "The Autophagy-Lysosomal Pathway in Neurodegeneration :A TFEB Perspective," Trends Neurosci., Apr. 2016, 39(4):221-234.

Singh et al., "Discovery and Development of Spleen Tyrosine Kinase (SYK) Inhibitors," J. Med. Chem., Jan. 2012, 55: 3614-364.

Thoma et al., "Orally bioavailable Syk inhibitors with activity in a rat PK/PD model," Bioorg. Med. Chem. Lett., Oct. 2015, 25(20):4642-4647.

CAS Registry No. 1381678-54-1, "1,6-Naphthyridin-5-amine, N-cyclohexyl-7-(4-pyridinyl)-," Jul. 5, 2012, p. 5 (Answer 8 of 79), search dated on Nov. 16, 2023, 51 pages.

Alvarado et al., "Wdr68 Mediates Dorsal and Ventral Patterning Events for Craniofacial Development," PLoS One, Nov. 23, 2016, 11(11):e0166984, 30 pages.

Chauhan et al., "Pharmaceutical screen identifies novel target processes for activation of autophagy with a broad translational potential," Nat. Communications, Oct. 27, 2015, 6:8620, 15 pages.

Glenewinkel et al., "The adaptor protein DCAF7 mediates the interaction of the adenovirus E1A oncoprotein with the protein kinases DYRK1A and HIPK2," Sci. Reports, Jun. 16, 2016, 6:28241, 15 pages.

Haile et al., "Discovery of a First-in-Class Receptor Interacting Protein 2 (RIP2) Kinase Specific Clinical Candidate, 2-((4-(Benzo[d]thiazol-5-ylamino)-6-(tert-butylsulfonyl)quinazolin-7-yl)oxy)ethyl Dihydrogen Phosphate, for the Treatment of Inflammatory Diseases," J. Med. Chemistry, Jul. 2, 2019, 62(14):6482-6496.

Ilium, "Transport of drugs from the nasal cavity to the central nervous system," Eur. J. Pharm. Sciences, Jul. 2000, 11(1):1-18.

Illum, "Is nose-to-brain transport of drugs in man a reality?," J. Pharm. Pharmacology, Jan. 2004, 56(1):3-17.

Kuroiwa et al., "Synthesis and Structure-Activity Relationship Study of 1-Phenyl-1-(quinazolin-4-yl)ethanols as Anticancer Agents," ACS Med. Chem, Letters, Jan. 10, 2015, 6(3):287-291.

Ma et al., "Transcription Factor EB Activation Rescues Advanced aB-Crystallin Mutation-Induced Cardiomyopathy by Normalizing Desmin Localization," J. Am. Heart Association, Feb. 16, 2019, 8(4):e010866, 78 pages.

Napolitano et al., "TFEB at a glance," J. Cell Science, Jul. 1, 2016, 129(13):2475-2481.

PCT International Preliminary Report on Patentability in International Appln. No. PCT/US2020/012268, dated Jun. 16, 2021, 7 pages.

PCT International Search Report and Written Opinion in International Appln. No. PCT/US2020/012268, dated May 22, 2020, 12 pages.

Pubchem CID 10425575, "(2-Phenylquinazolin-4-yl)-pyridin-3-ylmethanone;" dated Oct. 25, 2006, 7 pages.

Sardiello et al., "A gene network regulating lysosomal biogenesis and function," Science, Jul. 24, 2009, 325(5939):473-477.

Settembre et al., "A lysosome-to-nucleus signalling mechanism senses and regulates the lysosome via mTOR and TFEB," EMBO Journal, Mar. 7, 2012, 31(5):1095-1108.

Wang et al., "Small-molecule TFEB pathway agonists that ameliorate metabolic syndrome in mice and extend C. elegans lifespan," Nat. Communications, Dec. 22, 2017, 8:2270, 14 pages.

Seminsky, "Diseases of cellular organelles (Lecture 13)," Baikal Medical Journal: Clinical Medicine, 2004, 42(1):93-98 (with English abstract).

Szeto et al., "Current Treatment Options for Alzheimer's Disease and Parkinson's Disease Dementia, " Curr. Neuropharmacol., May 2016, 14(4):326-338.

CAS Registry No. 1381240-41-0, "1,6-Naphthyridin-5-amine, N-cyclopentyl-7-(4-pyridinyl)-," dated Jul. 4, 2012, p. 25 (Answer 39 of 79), search conducted on Nov. 16, 2023, 51 pages.

* cited by examiner

MASRIGLRMQLMREQAQQEEQRERMQQQAVMHYMQQQQQQQQQQLGGPPTPAINTPVH
QSPPPVPGEVLKVQSYLENPTSYHLQQSQHQKVREYLSETYGNKFAAHISPAQGSPKPPPA
ASPGVRAGHVLSSSAGNSAPNSPMAMLHIGSNPERELDDVIDNIMRLDDVLGYINPEMQM
PNTLPLSSSHLNVYSSDPQVTASILVGVTSSSCPADLTQKRELTDAESRALAKERQKKDNH
NLIERRRFNINDRIKELGMLIPKANDLDVRWNKGTILKASVDYIRRMQKDLQKSRELEN
HSRRLEMTNKQLWLRIQELEMQARVHGLPTTSPSGMNMAELAQQVVKQELPSEEGPGEAL
MLGAFVPDPFPIPALPPQAPLPLPTQPPSPFHHLDFSHSLSFGGREDEGPPGYPEPLAPG (SEQ ID NO:1)

FIG. 1

SEQUENCE LISTING

<160> NUMBER OF SEQ ID NOS: 1

<210> SEQ ID NO 1
<211> LENGTH: 419
<212> TYPE: PRT
<213> ORGANISM: Homo sapiens

<400> SEQUENCE: 1

```
Met Ala Ser Arg Ile Gly Leu Arg Met Gln Leu Met Arg Glu Gln Ala
 1               5                  10                  15

Gln Gln Glu Glu Gln Arg Glu Arg Met Gln Gln Gln Ala Val Met His
            20                  25                  30

Tyr Met Gln Gln Gln Gln Gln Gln Gln Gln Gln Leu Gly Gly Pro
        35                  40                  45

Pro Thr Pro Ala Ile Asn Thr Pro Val His Gln Ser Pro Pro Val
    50                  55                  60

Pro Gly Glu Val Leu Lys Val Gln Ser Tyr Leu Glu Asn Pro Thr Ser
65                  70                  75                  80

Tyr His Leu Gln Gln Ser Gln His Gln Lys Val Arg Glu Tyr Leu Ser
                85                  90                  95

Glu Thr Tyr Gly Asn Lys Phe Ala Ala His Ile Ser Pro Ala Gln Gly
            100                 105                 110

Ser Pro Lys Pro Pro Ala Ala Ser Pro Gly Val Arg Ala Gly His
        115                 120                 125

Val Leu Ser Ser Ser Ala Gly Asn Ser Ala Pro Asn Ser Pro Met Ala
130                 135                 140

Met Leu His Ile Gly Ser Asn Pro Glu Arg Glu Leu Asp Asp Val Ile
145                 150                 155                 160

Asp Asn Ile Met Arg Leu Asp Asp Val Leu Gly Tyr Ile Asn Pro Glu
                165                 170                 175

Met Gln Met Pro Asn Thr Leu Pro Leu Ser Ser Ser His Leu Asn Val
            180                 185                 190

Tyr Ser Ser Asp Pro Gln Val Thr Ala Ser Leu Val Gly Val Thr Ser
        195                 200                 205

Ser Ser Cys Pro Ala Asp Leu Thr Gln Lys Arg Glu Leu Thr Asp Ala
    210                 215                 220

Glu Ser Arg Ala Leu Ala Lys Glu Arg Gln Lys Lys Asp Asn His Asn
225                 230                 235                 240

Leu Ile Glu Arg Arg Arg Arg Phe Asn Ile Asn Asp Arg Ile Lys Glu
                245                 250                 255

Leu Gly Met Leu Ile Pro Lys Ala Asn Asp Leu Asp Val Arg Trp Asn
            260                 265                 270

Lys Gly Thr Ile Leu Lys Ala Ser Val Asp Tyr Ile Arg Arg Met Gln
        275                 280                 285

Lys Asp Leu Gln Lys Ser Arg Glu Leu Glu Asn His Ser Arg Arg Leu
    290                 295                 300

Glu Met Thr Asn Lys Gln Leu Trp Leu Arg Ile Gln Glu Leu Glu Met
305                 310                 315                 320

Gln Ala Arg Val His Gly Leu Pro Thr Thr Ser Pro Ser Gly Met Asn
                325                 330                 335

Met Ala Glu Leu Ala Gln Gln Val Val Lys Gln Glu Leu Pro Ser Glu
            340                 345                 350

Glu Gly Pro Gly Glu Ala Leu Met Leu Gly Ala Glu Val Pro Asp Pro
        355                 360                 365
```

```
Glu Pro Leu Pro Ala Leu Pro Pro Gln Ala Pro Leu Pro Leu Pro Thr
    370             375             380

Gln Pro Pro Ser Pro Phe His His Leu Asp Phe Ser His Ser Leu Ser
385             390             395             400

Phe Gly Gly Arg Glu Asp Glu Gly Pro Pro Gly Tyr Pro Glu Pro Leu
            405             410             415

Ala Pro Gly
```

METHODS AND MATERIALS FOR INCREASING TRANSCRIPTION FACTOR EB POLYPEPTIDE LEVELS

CLAIM OF PRIORITY

This application is a National Stage application under 35 U.S.C. § 371 of International Application No. PCT/US2020/012268, having an International Filing Date of Jan. 3, 2020, which claims priority to U.S. Patent Application Ser. No. 62/788,049, filed on Jan. 3, 2019, and U.S. Patent Application Ser. No. 62/879,374, filed on Jul. 26, 2019, the entire contents of which are hereby incorporated by reference.

FEDERALLY SPONSORED RESEARCH AND DEVELOPMENT

This invention was made with government support under grant number 1R35HL139860 and 1R01HL142777 awarded by National Institutes of Health (NIH). The government has certain rights in the invention.

TECHNICAL FIELD

This document relates to methods and materials for increasing transcription factor EB (TFEB) polypeptide levels. For example, the document provides compounds (e.g., organic compounds) having the ability to increase TFEB polypeptide levels within cells, formulations containing compounds having the ability to increase TFEB polypeptide levels within cells, methods for making compounds having the ability to increase TFEB polypeptide levels within cells, methods for increasing TFEB polypeptide levels within cells, and methods for treating mammals (e.g., humans) having a condition responsive to an increase in TFEB polypeptide levels.

BACKGROUND

Lysosomes are membrane-bound cellular organelles that contain a variety of digestive enzymes responsible for metabolism and degradation of various biomolecules, such as proteins, lipids and nucleic acids, which are either damaged or no longer needed by the cell. In the absence of functional lysosomes, undegraded molecules rapidly accumulate within the lysosome and subsequently in the cytoplasm, leading to cellular damage and contributing to a number of pathological conditions.

TFEB is an important transcription factor that regulates the expression of hundreds of genes that control autophagy, lysosome biogenesis, and lipolysis (Sardiello et al., *Science*, 325(5939):473-7 (2009); and Wang et al., *Nat. Commun.*, 8:2270 (2017)). When TFEB translocates from the cytoplasm of a cell to the nucleus, it activates expression of its target genes, which was shown to induce lysosomal biogenesis and increase the degradation of complex molecules including glycosaminoglycans and pathogenic protein aggregates such as those involved in Huntington's disease, Parkinson's disease, and Alzheimer's disease (Sardiello et al., *Science*, 325(5939):473-7 (2009); and Napolitano et al., *J. Cell Sci.*, 129:2475-2481 (2016)). Several small-molecule activators of TFEB were shown to be useful for treating metabolic and age-related disorders (Wang et al., *Nat. Commun.*, 8:2270 (2017)).

SUMMARY

This document provides methods and materials for increasing TFEB polypeptide levels. For example, the document provides compounds (e.g., organic compounds) having the ability to increase TFEB polypeptide levels within cells, formulations containing compounds having the ability to increase TFEB polypeptide levels within cells, methods for making compounds having the ability to increase TFEB polypeptide levels within cells, methods for making formulations containing compounds having the ability to increase TFEB polypeptide levels within cells, methods for increasing TFEB polypeptide levels within cells, and methods for treating mammals (e.g., humans) having a condition responsive to an increase in TFEB polypeptide levels. This document also provides compounds (e.g., organic compounds) having the ability to increase TFEB polypeptide levels within the nucleus of cells, formulations containing compounds having the ability to increase TFEB polypeptide levels within the nucleus of cells, methods for making compounds having the ability to increase TFEB polypeptide levels within the nucleus of cells, methods for making formulations containing compounds having the ability to increase TFEB polypeptide levels within the nucleus of cells, methods for increasing TFEB polypeptide levels within the nucleus of cells, and methods for treating mammals (e.g., humans) having a condition responsive to an increase in TFEB polypeptide levels within the nucleus of cells.

As described herein, the compounds provided herein can be used to increase TFEB polypeptide levels within cells in vitro or in vivo and/or within the nucleus of cells in vitro or in vivo. For example, the compounds provided herein can be used to increase the nuclear polypeptide levels of endogenously produced TFEB polypeptide within cells of a mammal (e.g., a human). In addition, the compounds provided herein can be used to treat mammals (e.g., humans) having a disease, disorder, or condition associated with a low cellular and/or nuclear level of TFEB polypeptides. In some cases, the compounds provided herein can be used to treat mammals (e.g., humans) having a disease, disorder, or condition that is responsive to an increase in TFEB polypeptide levels within cells and/or within the nucleus of cells.

In some embodiments, this document provides a method for increasing TFEB polypeptide levels within a cell and/or within the nucleus of a cell. The method comprises (or consists essentially of or consists of) administering, to a mammal (e.g., a human) containing the cell, a compound of Formula (I):

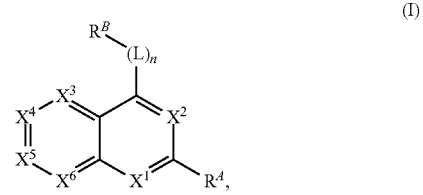

or a pharmaceutically acceptable salt thereof, wherein $X^1$, $X^2$, $X^3$, $X^4$, $X^5$, $X^6$, $R^A$, $R^B$, L, and n are as described herein. In some cases, the administering step can result in an increase in the TFEB polypeptide level within the nucleus of the cell as compared to the TFEB polypeptide level within the nucleus of the cell before the administering step.

In some embodiments, this document provides a method for treating a disease, disorder, or condition selected from the group consisting of lysosomal storage diseases (LSDs), acute or chronic inflammatory disorders, neurological diseases, and conditions of age-related functional decline in a mammal (e.g., a human). The method comprises (or consists essentially of or consists of) administering, to a mammal (e.g., a human) having the disease, disorder, or condition, a compound of Formula (I):

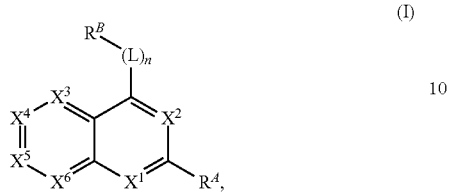
(I)

or a pharmaceutically acceptable salt thereof, wherein $X^1$, $X^2$, $X^3$, $X^4$, $X^5$, $X^6$, $R^A$, $R^B$, L, and n are as described herein. In some cases, the administering step can reduce the severity of a symptom of the disease, disorder, or condition. In some cases, the administering step can result in an increase in the TFEB polypeptide level within the nucleus of a cell of the mammal as compared to the TFEB polypeptide level within the nucleus of the cell before the administering step.

In some embodiments, this document provides a compound of Formula (IIa):

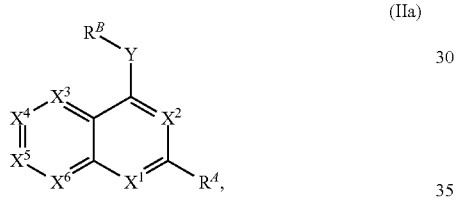
(IIa)

or a pharmaceutically acceptable salt thereof, wherein $X^1$, $X^2$, $X^3$, $X^4$, $X^5$, $X^6$, $R^A$, $R^B$, and Y are as described herein.

In some embodiments, this document provides a compound of Formula (IIb):

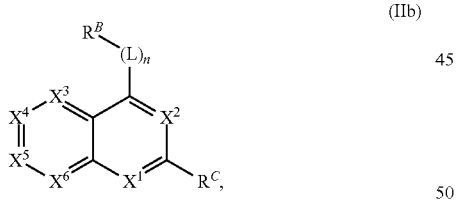
(IIb)

or a pharmaceutically acceptable salt thereof, wherein $X^1$, $X^2$, $X^3$, $X^4$, $X^5$, $X^6$, $R^B$, L, and n are as described herein.

In some embodiments, this document provides a compound selected from any one of the following Formulae:

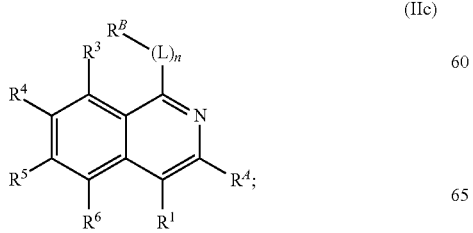
(IIc)

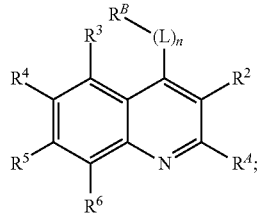
(IId)

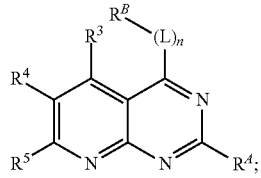
(IIe)

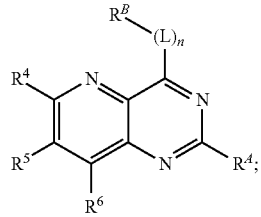
(IIf)

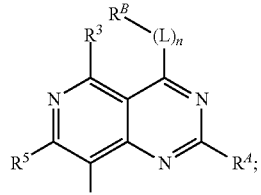
(IIg)

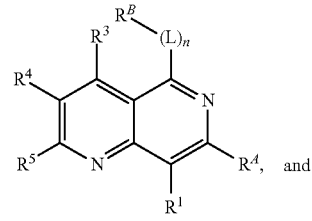
(IIh)

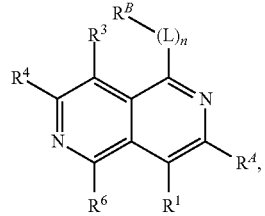
(IIi)

or a pharmaceutically acceptable salt thereof, wherein $R^1$, $R^2$, $R^3$, $R^4$, $R^5$, $R^6$, $R^A$, $R^B$, L, and n are as described herein.

In some embodiments, this document provides a compound of Formula (III):

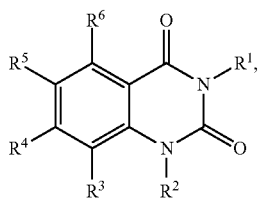

(III)

or a pharmaceutically acceptable salt thereof, wherein $R^1$, $R^2$, $R^3$, $R^4$, $R^5$, and $R^6$ are as described herein.

In some embodiments, this document provides a pharmaceutical composition comprising any of the compounds described herein (or a pharmaceutically acceptable salt thereof) and a pharmaceutically acceptable carrier.

In some embodiments, this document provides a method for increasing TFEB polypeptide levels within a cell and/or within the nucleus of a cell. The method comprises (or consists essentially of or consists of) administering, to a mammal (e.g., a human) containing the cell, a therapeutically effective amount of any one or more of the compounds described herein (or one or more pharmaceutically acceptable salts thereof).

In some embodiments, this document provides a method for treating a disease, disorder, or condition selected from the group consisting of lysosomal storage diseases (LSDs), acute or chronic inflammatory disorders, neurological diseases, conditions of age-related functional decline in a mammal (e.g., a human), and inherited or acquired diseases of muscle. The method comprises (or consists essentially of or consists of) administering, to a mammal (e.g., a human) having the disease, disorder, or condition, a therapeutically effective amount of any one or more of the compounds described herein (or one or more pharmaceutically acceptable salts thereof).

In some embodiments, this document provides a method for treating a disease, disorder, or condition selected from the group consisting of lysosomal storage diseases (LSDs), acute or chronic inflammatory disorders, neurological diseases, and conditions of age-related functional decline in a mammal (e.g., a human). The method comprises (or consists essentially of or consists of) administering, to a mammal (e.g., a human) having the disease, disorder, or condition, a therapeutically effective amount of any one or more of the compounds described herein (or one or more pharmaceutically acceptable salts thereof).

Unless otherwise defined, all technical and scientific terms used herein have the same meaning as commonly understood by one of ordinary skill in the art to which the present application pertains. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 1. Amino acid sequence of human TFEB polypeptide (SEQ ID NO:1).

DETAILED DESCRIPTION

Figure 2A:
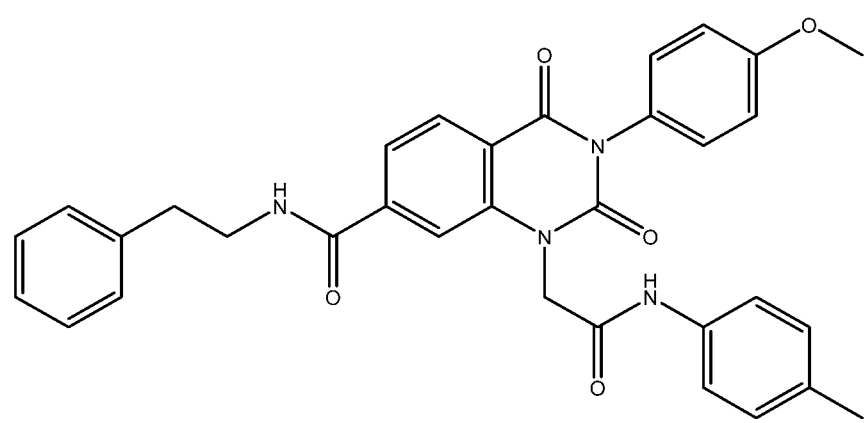
FIGS. 2A-C. BC1753 increases TFEB polypeptide levels. A. The structure of BC1753 is provided. B. MLE12 cells stably expressing TFEB-EGFP were treated with the indicated amounts of BC1753 for 24 hours before immunoblotting for TFEB-GFP and β-actin. C. MLE12 cells stably expressing TFEB-EGFP were treated with the indicated amounts of BC1753 for 24 hours before imaging by confocal microscopy (scale bar=10 μm).

This document provides methods and materials for increasing TFEB polypeptide levels. For example, the document provides therapeutic compounds (e.g., therapeutic organic compounds) having the ability to increase TFEB polypeptide levels within cells, formulations containing therapeutic compounds having the ability to increase TFEB polypeptide levels within cells, methods for making therapeutic compounds having the ability to increase TFEB polypeptide levels within cells, methods for making formulations containing therapeutic compounds having the ability to increase TFEB polypeptide levels within cells, methods for increasing TFEB polypeptide levels within cells, and methods for treating mammals (e.g., humans) having a condition responsive to an increase in TFEB polypeptide levels. This document also provides therapeutic compounds (e.g., organic compounds) having the ability to increase TFEB polypeptide levels within the nucleus of cells, formulations containing therapeutic compounds having the ability to increase TFEB polypeptide levels within the nucleus of cells, methods for making therapeutic compounds having the ability to increase TFEB polypeptide levels within the nucleus of cells, methods for making formulations containing therapeutic compounds having the ability to increase TFEB polypeptide levels within the nucleus of cells, methods for increasing TFEB polypeptide levels within the nucleus of cells, and methods for treating mammals (e.g., humans) having a condition responsive to an increase in TFEB polypeptide levels within the nucleus of cells.

Methods of Treatment

The lysosome is the compartment within the cell which is responsible for the degradation of damaged proteins and organelles (e.g., mitochondria). Inside the lysosome, a very acidic pH is maintained, and there are a variety of digestive enzymes that can efficiently degrade organelles and various biomolecules such as proteins, lipids and nucleic acids, that are either damaged or no longer needed by the cell. Delivery of damaged contents to the lysosome can occur through multiple means, but one way the damaged cargo gets to the lysosome is through the process of macroautophagy ("autophagy" herein). In this case, the damaged biomolecules and organelles are wrapped within a double membrane structure known as the autophagosome that then fuses with the lysosome. This process is responsible for homeostatic maintenance of cells and tissues. In the absence of autophagic flux and functional lysosomes, damage biomolecules and organelles accumulate in the cell. These damaged and dysfunctional components can fuel a cycle of further damage. Breakdown of this system generally leads to a number of pathological conditions. In rare inherited conditions called lysosomal storage diseases (LSD), a child often has inherited two copies of a defective lysosomal enzyme. LSDs are a collection of roughly 50 different inherited conditions that render the patient's lysosomes incapable of metabolizing a specific molecule, which the missing enzyme normally degrades. This deficiency causes the undegraded molecules to build up within the lysosome and the lysosome to massively swell. As the lysosome enlarges and fills with undegraded material, it ultimately becomes dysfunctional not only for the degradation of the specific molecule typically digested by the missing enzyme, but for all of its recycling capacity. Although recently a number of disease-specific replacement therapies have become available in which the child is given back the 'missing' enzyme to partially compensate for their inherited defect, in many lysosomal storage diseases no replacement therapy is currently available. Moreover, even when replacement therapies exist, these protein-based therapies are often only modestly successful as they often cannot treat conditions in the central nervous system (due to the blood-brain barrier) or gain entry to certain cell types. Besides LSDs, it is known that this process of autophagy and lysosomal degradation naturally slows with aging. The natural consequence is the age-dependent accumulation of damaged contents within cells and tissues. This can be harmful and can contribute to a range of age-dependent diseases. Augmenting autophagy and lysosomal function as described herein can be used to reverse this damage. In other conditions, stimulation of autophagy and lysosomal function can be beneficial. This includes metabolic conditions (e.g., non-alcoholic steatohepatitis (NASH) or fatty liver), neurodegenerative conditions (e.g. Parkinson's disease, ALS, Alzheimer's disease, and Huntington's disease), a range of other general age-related conditions (e.g., macular degeneration, sarcopenia, and frailty), non-neurological disorders of protein aggregation (e.g., α-1 antitrypsin, amyloidosis, and retinitis pigmentosa), or in conditions of impaired immunity (e.g., aiding the removal of microbiological pathogens including intracellular pathogens such as *Mycobacterium tuberculosis* or in conditions characterized by chronic bacterial colonization such as cystic fibrosis).

TFEB is a master regulator of lysosomal biogenesis. Increasing TFEB polypeptide levels within cells and/or within the nucleus of cells using a compound provided herein (e.g., a compound set forth in Formula (I), (IIa-IIi), or (III), or a pharmaceutically acceptable salt thereof) as described herein can result in one or more benefits for the cell and/or mammal. For example, increasing TFEB polypeptide levels within cells and/or within the nucleus of cells using a compound provided herein (e.g., a compound set forth in Formula (I), (IIa-IIi), or (III), or a pharmaceutically acceptable salt thereof) as described herein can result in increased lysosomal numbers within cells and/or increased lysosomal function within cells. In some cases, increasing TFEB polypeptide levels within cells and/or within the nucleus of cells using a compound provided herein (e.g., a compound set forth in Formula (I), (IIa-Ill), or (III), or a pharmaceutically acceptable salt thereof) as described herein can result in (a) an increased level of lysosomal exocytosis (the process of excreting the contents of the lysosome out of the cell and into the serum), (b) transcriptionally augmenting multiple factors that regulate autophagy, and/or (c) a coordinated increase in intracellular recycling capacity and the removal of intracellular debris (e.g., increasing autophagy, lysosomal numbers, and lysosomal exocytosis). In some cases, increasing TFEB polypeptide levels within cells and/or within the nucleus of cells using a compound provided herein (e.g., a compound set forth in Formula (I), (IIa-IIi), or (III), or a pharmaceutically acceptable salt thereof) as described herein can result in reducing one or more symptoms associated with a LSD, an α-1 antitrypsin deficiency, a neurodegenerative disease (e.g., Alzheimer's disease, Parkinson's disease, ALS, or Huntington's disease), a metabolic disease (e.g., NASH), or an age-related condition (e.g., sarcopenia).

In some cases, this document provides methods for increasing TFEB polypeptide levels within cells and/or within the nucleus of cells by contacting the cell with one or more compounds provided herein (e.g., a compound set forth in Formula (I), (IIa-IIi), or (III), or a pharmaceutically acceptable salt thereof). The increase in TFEB polypeptide levels can be as compared to the TFEB polypeptide levels prior to the contacting step. In some cases, methods for increasing TFEB polypeptide levels within cells and/or within the nucleus of cells can be performed in vivo. For example, one or more compounds provided herein (e.g., a compound set forth in Formula (I), (IIa-IIi), or (III), or a pharmaceutically acceptable salt thereof) can be administered to a mammal (e.g., a human) to increase TFEB polypeptide levels within cells and/or within the nucleus of cells within that mammal. In some cases, methods for increasing TFEB polypeptide levels within cells and/or within the nucleus of cells can be performed in vitro. For example, one or more compounds provided herein (e.g., a compound set forth in Formula (I), (IIa-IIi), or (III), or a pharmaceutically acceptable salt thereof) can be added to a cell culture containing cells (e.g., human cells) to increase TFEB polypeptide levels within those cells and/or within the nucleus of those cells. In some cases, such intervention can improve the quality of the cell while in culture or subsequently. In some cases, one or more of the compounds provided herein can be used during an ex vivo expansion of a genetically engineered T cell (e.g., CAR T cell) or tumor-infiltrating T cell (e.g., TIL) so that the treated T cells exhibit improved in vivo persistence and/or efficacy. A range of other cellular products that are to be ultimately infused into a mammal (e.g., a human) can be treated as described herein during their in vitro expansion.

In some cases, this document provides methods for increasing lysosomal exocytosis in a cell by contacting the cell with one or more compounds provided herein (e.g., a compound set forth in Formula (I), (IIa-IIi), or (III), or a pharmaceutically acceptable salt thereof). The increase in lysosomal exocytosis can be as compared to the lysosomal exocytosis levels prior to the contacting step. In some cases, methods for increasing lysosomal exocytosis in a cell can be performed in vivo. For example, one or more compounds provided herein (e.g., a compound set forth in Formula (I), (IIa-IIi), or (III), or a pharmaceutically acceptable salt thereof) can be administered to a mammal (e.g., a human) to increase lysosomal exocytosis in a cell within that mammal. In some cases involving a LSD, one or more compounds provided herein can be administered to a mammal having a LSD so that undegraded lysosomal material that accumulated is released via exocytosis from the diseased cell, tissue, and/or organ. In some cases, methods for increasing lysosomal exocytosis in a cell can be performed in vitro. For example, one or more compounds provided herein (e.g., a compound set forth in Formula (I), (IIa-IIi), or (III), or a pharmaceutically acceptable salt thereof) can be added to a cell culture containing cells (e.g., human cells) to increase lysosomal exocytosis in those cells.

In some cases, this document provides methods for increasing cellular autophagy in a cell by contacting the cell with one or more compounds provided herein (e.g., a compound set forth in Formula (I), (IIa-IIi), or (III), or a pharmaceutically acceptable salt thereof). The increase in cellular autophagy can be as compared to the cellular autophagy levels prior to the contacting step. In some cases, methods for increasing cellular autophagy in a cell can be performed in vivo. For example, one or more compounds provided herein (e.g., a compound set forth in Formula (I), (IIa-IIi), or (III), or a pharmaceutically acceptable salt thereof) can be administered to a mammal (e.g., a human) to increase cellular autophagy in a cell within that mammal. In some cases, methods for increasing cellular autophagy in a cell can be performed in vitro. For example, one or more compounds provided herein (e.g., a compound set forth in Formula (I), (IIa-IIi), or (III), or a pharmaceutically acceptable salt thereof) can be added to a cell culture containing cells (e.g., human cells) to increase cellular autophagy in those cells.

In some cases, this document provides methods for increasing nuclear localization of TFEB polypeptides in a cell by contacting the cell with one or more compounds provided herein (e.g., a compound set forth in Formula (I), (IIa-IIi), or (III), or a pharmaceutically acceptable salt thereof). The increase in nuclear localization of TFEB polypeptides can be as compared to the level of nuclear localization of TFEB polypeptides prior to the contacting step. In some cases, methods for increasing nuclear localization of TFEB polypeptides in a cell can be performed in vivo. For example, one or more compounds provided herein (e.g., a compound set forth in Formula (I), (IIa-IIi), or (III), or a pharmaceutically acceptable salt thereof) can be administered to a mammal (e.g., a human) to increase nuclear localization of TFEB polypeptides in a cell within that mammal. In some cases, methods for increasing nuclear localization of TFEB polypeptides in a cell can be performed in vitro. For example, one or more compounds provided herein (e.g., a compound set forth in Formula (I), (IIa-IIi), or (III), or a pharmaceutically acceptable salt thereof) can be added to a cell culture containing cells (e.g., human cells) to increase nuclear localization of TFEB polypeptides in those cells.

This document also provides methods for treating diseases, disorders, and conditions in a mammal by administering one or more compounds provided herein (e.g., a compound set forth in Formula (I), (IIa-IIi), or (III), or a pharmaceutically acceptable salt thereof) to a mammal in need thereof. In some cases, the disease, disorder, or condition being treated can be a disease, disorder, or condition that is responsive to an increase in TFEB polypeptide levels within cells and/or within the nucleus of cells within the mammal. In some cases, the disease, disorder, or condition being treated can be a disease, disorder, or condition that is associated with low TFEB polypeptide levels within cells and/or within the nucleus of cells within the mammal. Examples of diseases, disorders, and conditions that can be treated with one or more compounds provided herein (e.g., a compound set forth in Formula (I), (IIa-IIi), or or a pharmaceutically acceptable salt thereof) as described herein include, without limitation, lysosomal storage diseases, acute or chronic inflammation disorders, conditions associated with age-related functional decline, acute or chronic organ failure (e.g., kidney, lung, cardiac, or hepatic organ dysfunction), disorders of protein aggregation, neurodegenerative conditions, and inherited or acquired diseases of muscle. Examples of diseases, disorders, and conditions that can be treated with one or more compounds provided herein (e.g., a compound set forth in Formula (I), (IIa-IIi), or (III), or a pharmaceutically acceptable salt thereof) as described herein include, without limitation, lysosomal storage diseases, acute or chronic inflammation disorders, conditions associated with age-related functional decline, acute or chronic organ failure (e.g., kidney, lung, cardiac, or hepatic organ dysfunction), disorders of protein aggregation, and neurodegenerative conditions.

Examples of lysosomal storage diseases that can be treated with one or more compounds provided herein (e.g., a compound set forth in Formula (I), (IIa-IIi), or or a pharmaceutically acceptable salt thereof) as described herein include, without limitation, Krabbe disease, Sanfilippo syndrome, multiple sulfatase deficiency, alpha-mannosidosis, Fabry disease, Hunter syndrome, Scheie syndrome, Sanfilippo syndrome, Maroteaux-Lamy syndrome, hyaluronidase deficiency, Sialidosis, mucolipidin 1 deficiency, Neuronal ceroid lipofuscinoses (Batten Disease), Mucopolysaccharidoses Type I, II, III, IV, VI, VII, and IX, Hurler-Scheie syndrome, Morquio syndrome, Glycoproteinosis, Glycogen storage disease, Metachromatic Leukodystrophy, Sly syndrome, I-cell disease, Danon disease, Niemann-Pick disease Type A, B, C1, and C2, Sandhoff disease, Lysosomal acid lipase deficiency, GM2 gangliosidoses, Tay-Sachs disease, Gaucher disease, Salla disease, Pompe disease, Danon disease, cholesteryl ester storage disease, Aspartylglucosaminuria, Cystinosis, Mucolipidosis Type I-IV, Schindler Disease Type I and II, Wolman disease, Fucosidosis, Pycnodysostosis, and Free Sialic Acid Storage Disease.

Examples of acute or chronic inflammation disorders that can be treated with one or more compounds provided herein (e.g., a compound set forth in Formula (I), (IIa-IIi), or (III), or a pharmaceutically acceptable salt thereof) as described herein include, without limitation, asthma, chronic obstructive lung disease, pulmonary fibrosis, pneumonitis (e.g., hypersensitivity pneumonitis or radiation pneumonitis), pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (e.g., Crohn's disease or ulcerative colitis), colitis, sepsis, vasculitis, bursitis, connective tissue disease, autoimmune diseases (e.g., systemic lupus erythematosis (SLE)), polymyalgia rheumatica, scleroderma, Wegener's granulomatosis, temporal arteritis, vasculitis, cryoglobulinemia, multiple sclerosis, viral or influenza-induced inflammation, chronic bacterial colonization or persistent intracellular pathogen, and impaired responsiveness to antigenic challenge or vaccines administration.

Examples of conditions associated with age-related functional decline that can be treated with one or more compounds provided herein (e.g., a compound set forth in Formula (I), (IIa-Ill), or (III), or a pharmaceutically acceptable salt thereof) as described herein include, without limitation, neurodegenerative diseases (e.g., Alzheimer's, ALS, Huntington's disease, Parkinson's disease, primary age-related tauopathy, progressive supranuclear palsy, chronic traumatic encephalopathy, acute or chronic traumatic brain injury, and frontotemporal dementia), metabolic diseases (e.g., NASH), metabolic syndrome, diabetes, sarcopenia, frailty, macular degeneration, other inherited or acquired retinal degenerative diseases, age-related hearing loss, early cognitive decline, osteoporosis, acute or age-related organ dysfunction (e.g., heart and/or kidney dysfunction), age-related immune dysfunction (e.g., impaired response to vaccination or immunosenescence), and other non-neurological disorders of protein aggregations (e.g., amyloidosis or α-1 antitrypsin deficiency).

Examples of inherited or acquired diseases of muscle that can be treated with one or more compounds provided herein (e.g., a compound set forth in Formula (I), (IIa-Ill), or (III), or a pharmaceutically acceptable salt thereof) include, without limitation, myofibrillar myopathy, sporadic inclusion body myositis, inclusion body myopathy with frontotemporal dementia (IBMFTD), and cardiomyopathy (e.g., dilated cardiomyopathy, or proteotoxic cardiomyopathy such as advanced proteotoxic cardiomyopathy).

In some cases, one or more compounds provided herein (e.g., a compound set forth in Formula (I), (IIa-IIi), or (III), or a pharmaceutically acceptable salt thereof) can be used as described herein (e.g., to increase TFEB polypeptide levels within the nucleus of cells and/or to treat a disease, disorder, or condition as described herein) as the sole active ingredient(s). For example, a composition containing a compound set forth in Formula (I), (IIa-Ili), or (III), or a pharmaceutically acceptable salt thereof can lack any other active ingredients that increase TFEB polypeptide levels within the nucleus of cells. In some cases, a composition containing a compound set forth in Formula (I), (IIa-Ill), or (III), or a pharmaceutically acceptable salt thereof can lack any other active ingredients that are effective to treat a disease, disorder, or condition as described herein.

Therapeutic Compounds

As described herein, any one or more of the compounds provided herein can be used to increase TFEB polypeptide levels within cells and/or within the nucleus of cells, to increase lysosomal exocytosis in a cell, to increase cellular autophagy in a cell, to increase nuclear localization of TFEB polypeptides in a cell, and/or to treat a disease, disorder, and condition described herein in a mammal.

In some embodiments, this document provides a compound of Formula (I):

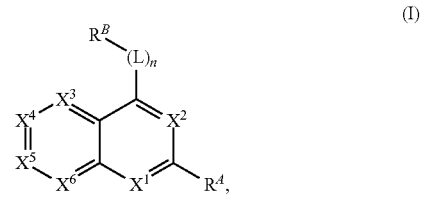

or a pharmaceutically acceptable salt thereof, wherein:

each L is independently selected from O, S, S(=O)$_2$, C$_{1-3}$ alkylene, C(=O), and N(R$^N$), wherein said C$_{1-3}$ alkylene is optionally substituted with 1, 2, or 3 substituents independently selected from halo, CN, NO$_2$, OH, C$_{1-3}$ alkoxy, amino, C$_{1-3}$ alkylamino, and di(C$_{1-3}$ alkyl)amino;

each R$^N$ is independently selected from H and C$_{1-6}$ alkyl, wherein said C$_{1-6}$ alkyl is optionally substituted with 1, 2, or 3 substituents independently selected from halo, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

n is an integer selected from 1, 2, and 3;

X$^1$ is selected from N, N$^+$—O$^-$, and CR$^1$;

X$^2$ is selected from N, N$^+$—O$^-$, and CR$^2$;

X$^3$ is selected from N, N$^+$—O$^-$, and CR$^3$;

X$^4$ is selected from N, N$^+$—O$^-$, and CR$^4$;

X$^5$ is selected from N, N$^+$—O$^-$, and CR$^5$;

X$^6$ is selected from N, N$^+$—O$^-$, and CR$^6$;

provided that no more than four of X$^1$, X$^2$, X$^3$, X$^4$, X$^5$, and X$^6$ are N;

each of R$^1$, R$^2$, R$^3$, R$^4$, R$^5$, and R$^6$ is independently selected from H, halo, CN, NO$_2$, C$_{1-6}$ alkyl, C$_{1-6}$ haloalkyl, C$_{2-6}$ alkenyl, C$_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$ NR$^{c1}$S (O)$_2$R$^{b1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1, 2, or 3 substituents independently selected from CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

R$^A$ is selected from Cy$^{41}$, O-Cy$^{41}$, and N(R$^N$)—Cy$^{41}$;

Cy$^{41}$ is selected from C$_{6-10}$ aryl, C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$;

R$^B$ is selected from C$_{1-6}$ alkyl, C$_{1-6}$ haloalkyl, C$_{2-6}$ alkenyl, C$_{2-6}$ alkynyl, and Cy$^1$, wherein said C$_{1-6}$ alkyl, C$_{2-6}$ alkenyl, and C$_{2-6}$ alkynyl are each optionally substituted with 1, 2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

or, when R$^B$ is attached to L which is N(R$^N$), R$^B$ and R$^N$ together with the N atom to which they are attached form 4-14 membered heterocycloalkyl, which is optionally substituted with 1, 2, or 3 substituents independently selected from Cy$^1$, halo, CN, NO$_2$, C$_{1-6}$ alkyl, C$_{1-6}$ haloalkyl, C$_{2-6}$ alkenyl, C$_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1,2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

each Cy$^1$ is independently selected from C$_{6-10}$ aryl, C$_{3-4}$ cycloalkyl, 5-10 membered heteroaryl, and 4-14 membered heterocycloalkyl, each of which is optionally substituted with 1, 2, 3, 4, or 5 substituents independently selected from R$^{Cy2}$;

R$^{Cy1}$ and R$^{Cy2}$ are each independently selected from oxo, halo, CN, NO$_2$, Cy$^2$, C$_{1-6}$ alkyl, C$_{1-6}$ haloalkyl, C$_{2-6}$ alkenyl, C$_{2-6}$ alkynyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$S(O)$_2$R$^{b2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from Cy$^2$, halo, CN, NO$_2$, OR$^{a2}$, C(O)R$^{b2}$, C(O)NR$^{c2}$R$^{d2}$, C(O)OR$^{32}$, NR$^{c2}$R$^{d2}$, NR$^{c2}$C(O)R$^{b2}$, NR$^{c2}$C(O)OR$^{a2}$, NR$^{c2}$S(O)$_2$R$^{b2}$, S(O)$_2$R$^{b2}$, and S(O)$_2$NR$^{c2}$R$^{d2}$;

each Cy$^2$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, 4, or 5 substituents independently selected from halo, CN, NO$_2$, C$_{1-6}$ alkyl, C$_{1-6}$ haloalkyl, C$_{2-6}$ alkenyl, C$_{2-6}$ alkynyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$S(O)$_2$R$^{b2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from halo, CN, NO$_2$, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$S(O)$_2$R$^{b2}$, S(O)$_2$R$^{b2}$, and S(O)$_2$NR$^{c2}$R$^{d2}$;

each R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-10 membered heterocycloalkyl)-C$_{1-4}$ alkylene are each optionally substituted with 1, 2, 3, 4, or 5 substituents independently selected from R$^g$;

or any R$^{c1}$ and R$^{d1}$ together with the N atom to which they are attached form a 4-7 membered heterocycloalkyl, which is optionally substituted with 1, 2, or 3 substituents independently selected from R$^g$;

or any R$^{c2}$ and R$^{d2}$ together with the N atom to which they are attached form a 4-7 membered heterocycloalkyl, which is optionally substituted with 1, 2, or 3 substituents independently selected from R$^g$; and each R$^g$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkylene, HO—C$_{1-3}$ alkylene, C$_{6-10}$ aryl, C$_{6-10}$ aryloxy, C$_{3-10}$ cycloalkyl, 5-10 membered heteroaryl, 4-10 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-10 membered heterocycloalkyl)-C$_{1-4}$ alkylene, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments:

R$^B$ and R$^N$ together with the N atom to which they are attached form 4-7 membered heterocycloalkyl, which is optionally substituted with 1, 2, or 3 substituents independently selected from Cy$^1$, halo, CN, NO$_2$, C$_{1-6}$ alkyl, C$_{1-6}$ haloalkyl, C$_{2-6}$ alkenyl, C$_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said C$_{1-6}$ alkyl, C$_{2-6}$ alkenyl, and C$_{2-6}$ alkynyl are each optionally substituted with 1, 2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; and each Cy$^1$ is independently selected from C$_{6-10}$ aryl, C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy2}$.

In some embodiments:

R$^A$ is selected from C$_{6-10}$ aryl, C$_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$; and R$^{Cy1}$ and R$^{Cy2}$ are each independently selected from halo, CN, NO$_2$, Cy$^2$, C$_{1-6}$ alkyl, C$_{1-6}$ haloalkyl, C$_{2-6}$ alkenyl, C$_{2-6}$ alkynyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$S(O)$_2$R$^{b2}$, S(O)$_2$R$^{b2}$, and S(O)$_2$NR$^{c2}$R$^{d2}$; wherein said C$_{1-6}$ alkyl, C$_{2-6}$ alkenyl, and C$_{2-6}$ alkynyl are each optionally substituted with 1, 2, or 3 substituents independently selected from Cy$^2$, halo, CN, NO$_2$, OR$^{a2}$, C(O)R$^{b2}$, C(O)NR$^{c2}$R$^{d2}$, C(O)OR$^{32}$, NR$^{c2}$R$^{d2}$, NR$^{c2}$C(O)R$^{b2}$, NR$^{c2}$C(O)OR$^{\#2}$, NR$^{c2}$S(O)$_2$R$^{b2}$, S(O)$_2$R$^{b2}$, and S(O)$_2$NR$^{c2}$R$^{d2}$.

In some embodiments, n is 1. In some embodiments, n is 2. In some embodiments, n is 3.

In some embodiments, L is independently selected from $C_{1-3}$ alkylene, C(=O), and $N(R^N)$, wherein said $C_{1-3}$ alkylene is optionally substituted with OH.

In some embodiments, L is $C_{1-3}$ alkylene, which is optionally substituted with halo, CN, $NO_2$, OH, $C_{1-3}$ alkoxy, or amino.

In some embodiments, L is $C_{1-3}$ alkylene, which is optionally substituted with OH.

In some embodiments, L is C(=O).

In some embodiments, L is $N(R^N)$.

In some embodiments, $R^N$ is selected from H and $C_{1-6}$ alkyl, wherein said $C_{1-6}$ alkyl is optionally substituted with 1, 2, or 3 substituents independently selected from halo, CN, $NO_2$, and $C_{1-3}$ alkoxy.

In some embodiments, $R^N$ is selected from H and $C_{1-6}$ alkyl. In some embodiments, $R^N$ is H. In some embodiments, $R^N$ is $C_{1-6}$ alkyl, optionally substituted with halo, CN, $NO_2$, or $C_{1-3}$ alkoxy.

In some embodiments, L is NH.

In some embodiments, each of $R^1$, $R^2$, $R^3$, $R^4$, $R^5$, and $R^6$ is independently selected from H, halo, CN, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$.

In some embodiments, each of $R^1$, $R^2$, $R^3$, $R^4$, $R^5$, and $R^6$ is independently selected from H, halo, CN, $C_{1-6}$ alkyl, $OR^{a1}$, $NR^{c1}R^{d1}$, and $S(O)_2R^{b1}$.

In some embodiments, each of $R^1$, $R^2$, $R^3$, $R^4$, $R^5$, and $R^6$ is independently selected from H, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$.

In some embodiments, each of $R^1$, $R^2$, $R^3$, $R^4$, $R^5$, and $R^6$ is independently selected from H, halo, $C_{1-6}$ alkyl, and $C_{1-6}$ alkoxy.

In some embodiments, the compound of Formula (I) has formula:

or a pharmaceutically acceptable salt thereof.

In some embodiments, $R^3$, $R^4$, $R^5$, and $R^6$ are each independently selected from H, halo, $C_{1-6}$ alkyl, and $C_{1-6}$ alkoxy. In some embodiments, $R^3$, $R^4$, $R^5$, and $R^6$ are each H.

In some embodiments, the compound of Formula (I) has formula:

or a pharmaceutically acceptable salt thereof.

In some embodiments, each of $R^1$, $R^2$, $R^3$, $R^4$, $R^5$, and $R^6$ is independently selected from H, halo, $C_{1-6}$ alkyl, and $C_{1-6}$ alkoxy. In some embodiments, each of $R^1$, $R^2$, $R^3$, $R^4$, $R^5$, and $R^6$ is H.

In some embodiments, the compound of Formula (I) has formula:

(IIc)

or a pharmaceutically acceptable salt thereof.

In some embodiments, $R^1$, $R^3$, $R^4$, $R^5$, and $R^6$ are each independently selected from H, halo, $C_{1-6}$ alkyl, and $C_{1-6}$ alkoxy. In some embodiments, $R^1$, $R^3$, $R^4$, $R^5$, and $R^6$ are each H.

In some embodiments, the compound of Formula (I) has formula:

(IId)

or a pharmaceutically acceptable salt thereof.

In some embodiments, $R^2$, $R^3$, $R^4$, $R^5$, and $R^6$ are each independently selected from H, halo, $C_{1-6}$ alkyl, and $C_{1-6}$ alkoxy. In some embodiments, $R^2$, $R^3$, $R^4$, $R^5$, and $R^6$ are each H.

In some embodiments, the compound of Formula (I) has formula:

(IIe)

or a pharmaceutically acceptable salt thereof.

In some embodiments, $R^3$, $R^4$, and $R^5$ are each independently selected from H, halo, $C_{1-6}$ alkyl, and $C_{1-6}$ alkoxy. In some embodiments, $R^3$, $R^4$, and $R^5$ are each H.

In some embodiments, the compound of Formula (I) has formula:

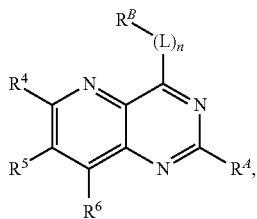

(IIf)

or a pharmaceutically acceptable salt thereof.

In some embodiments, $R^4$, $R^5$, and $R^6$ are each independently selected from H, halo, $C_{1-6}$ alkyl, and $C_{1-6}$ alkoxy. In some embodiments, $R^4$, $R^5$, and $R^6$ are each H.

In some embodiments, the compound of Formula (I) has formula:

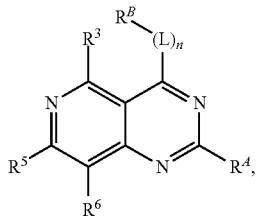

(IIg)

or a pharmaceutically acceptable salt thereof.

In some embodiments, $R^3$, $R^5$, and $R^6$ are each independently selected from H, halo, $C_{1-6}$ alkyl, and $C_{1-6}$ alkoxy. In some embodiments, $R^3$, $R^5$, and $R^6$ are each H.

In some embodiments of the compound of Formula (IIg), the compound of Formula (IIg) is not:

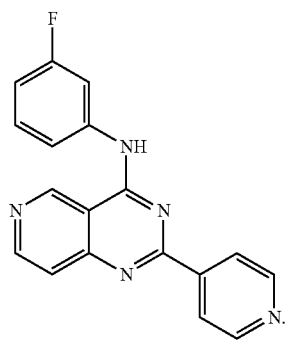 [SMILES: Fc1cccc(Nc2nc(-c3ccncc3)nc3ccncc23)c1]

In some embodiments, of the compound of Formula (IIg), $R^B$ is selected from 4-10 membered heterocycloalkyl and 5-10 membered heteroaryl, each of which is optionally substituted with 1, 2, or 3 substituents independently selected from $R^{Cy2}$.

In some embodiments, of the compound of Formula (IIg), $R^B$ is 5-10 membered heteroaryl, optionally substituted with 1, 2, or 3 substituents independently selected from $R^{Cy2}$. In some embodiments of Formula (IIg), $R^B$ is not $C_{6-10}$ aryl substituted with one halo.

In some embodiments, the compound of Formula (I) has formula (IIh):

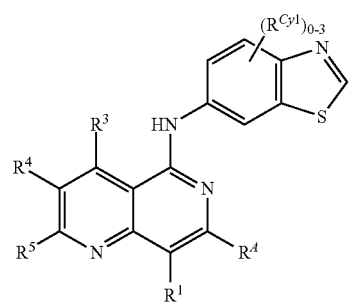

(IIh)

or a pharmaceutically acceptable salt thereof.

In some embodiments, of the compound of Formula (IIh), $R^B$ is 5-10 membered heteroaryl, optionally substituted with 1, 2, or 3 substituents independently selected from $R^{Cy2}$.

In some embodiments, the compound of Formula (IIh) has formula:

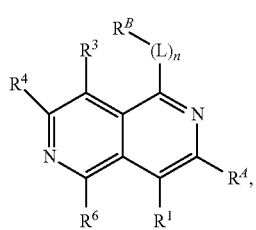

or a pharmaceutically acceptable salt thereof.

In some embodiments of Formula (IIh), each of $R^1$, $R^3$, $R^4$, and $R^5$ is independently selected from H, halo, CN, $C_{1-6}$ alkyl, $OR^{a1}$, $NR^{c1}R^{d1}$, and $S(O)_2R^{b1}$.

In some embodiments of Formula (IIh), $R^3$ is selected from H, halo, CN, $OR^{a1}$, $NR^{c1}R^{d1}$, and $S(O)_2R^{b1}$. In some embodiments of Formula (IIh), $R^1$ is selected from H, halo, and $C_{1-6}$ alkyl.

In some embodiments, the compound of Formula (I) has formula (IIi):

(IIi)

or a pharmaceutically acceptable salt thereof.

In some embodiments, of the compound of Formula (IIi), $R^B$ is 5-10 membered heteroaryl, optionally substituted with 1, 2, or 3 substituents independently selected from $R^{Cy2}$. In some embodiments, of the compound of Formula (IIi), $R^A$ is 5-10 membered heteroaryl, optionally substituted with 1, 2, or 3 substituents independently selected from $R^{Cy1}$. In some embodiments, of the compound of Formula (IIi), $R^1$, $R^3$, $R^4$, and $R^6$ are each H.

In some embodiments, the present disclosure provides a compound selected from any one of the following Formulae (IIc)-(IIi), or a pharmaceutically acceptable salt thereof. In some embodiments, the present disclosure provides a compound selected from any one of the following Formulae (IIc)-(IIg), or a pharmaceutically acceptable salt thereof.

In some embodiments, $R^A$ is selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

In some embodiments, $R^A$ is selected from $C_{6-10}$ aryl, 5-10 membered heteroaryl, and 4-10 membered heterocycloalkyl, each of which is optionally substituted with 1, 2, or 3 substituents independently selected from $R^{Cy1}$.

In some embodiments, $R^A$ is $Cy^{A1}$.

In some embodiments, $R^A$ is $O-Cy^{A1}$.

In some embodiments, $R^A$ is $NH-Cy^{A1}$.

In some embodiments, $Cy^{A1}$ is selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

In some embodiments, $Cy^{A1}$ is selected from $C_{6-10}$ aryl, 5-10 membered heteroaryl, and 4-10 membered heterocycloalkyl, each of which is optionally substituted with 1, 2, 3, 4, or 5 substituents independently selected from $R^{Cy1}$.

In some embodiments, $Cy^{A1}$ is 5-10 membered heteroaryl, optionally substituted with 1, 2, or 3 substituents independently selected from $R^{Cy1}$.

In some embodiments, $Cy^{A1}$ is $C_{6-10}$ aryl, optionally substituted with 1, 2, or 3 substituents independently selected from $R^{Cy1}$. In some embodiments, the $C_{6-10}$ aryl has the formula:

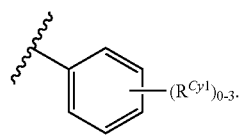

In some embodiments, $Cy^{A1}$ is 5-10 membered heteroaryl, optionally substituted with 1, 2, or 3 substituents independently selected from $R^{Cy1}$.

In some embodiments, the 5-10 membered heteroaryl has the formula selected from:

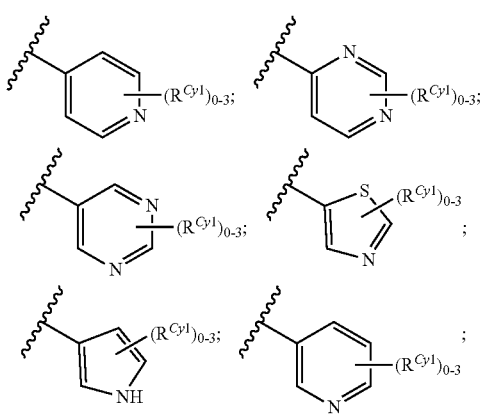

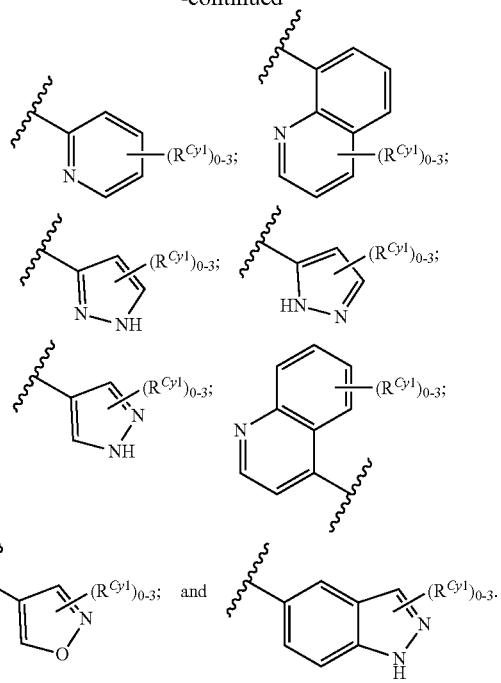

In some embodiments, the 5-10 membered heteroaryl has the formula selected from:

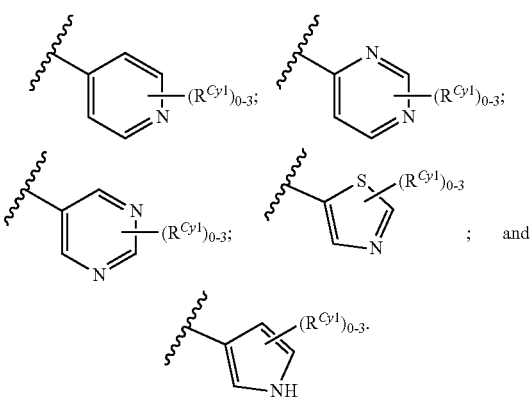

In some embodiments, $Cy^{A1}$ is 4-10 membered heterocycloalkyl, optionally substituted with 1, 2, or 3 substituents independently selected from $R^{Cy1}$.

In some embodiments, the 4-10 membered heterocycloalkyl has the formula selected from:

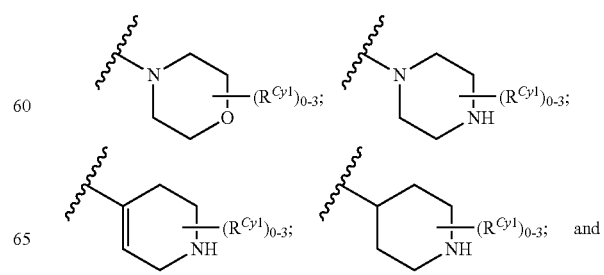

-continued

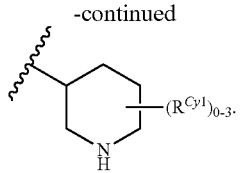

In some embodiments, the 4-10 membered heterocycloalkyl has the formula selected from:

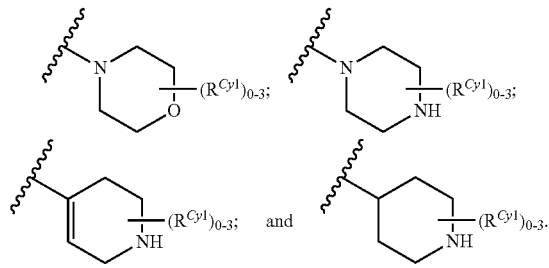

In some embodiments, each $R^{Cy1}$ is independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$.

In some embodiments, each $R^{Cy1}$ is independently selected from halo, $NO_2$, $C_{1-6}$ alkyl, $C_{1-6}$ haloalkyl, $OR^{a2}$, $C(O)OR^{a2}$, $C(O)R^{b2}$, $C(O)NR^{c2}R^{d2}$, $NR^{c2}R^{d2}$, and $S(O)_2R^{b2}$, wherein said $C_{1-6}$ alkyl is optionally substituted with $OR^{a2}$.

In some embodiments, each $R^{Cy1}$ is independently selected from halo, $NO_2$, $C_{1-6}$ alkyl, $OR^{a2}$, and $C(O)OR^{a2}$.

In some embodiments, each $R^{Cy1}$ is independently selected from halo, $NO_2$, $C_{1-6}$ alkyl, OH, $C_{1-6}$ alkoxy, and $C(O)(C_{1-6}$ alkoxy).

In some embodiments, each $R^{Cy1}$ is independently selected from halo, $NO_2$, $C_{1-6}$ alkyl, $C_{1-6}$ alkoxy, and $C(O)(C_{1-6}$ alkoxy).

In some embodiments, $R^{Cy1}$ is selected from $C_1$ and F. In some embodiments, $R^{Cy1}$ is $NO_2$. In some embodiments, $R^{Cy1}$ is $C_{1-6}$ alkyl or $C_{1-6}$ alkoxy.

In some embodiments, $R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{a1}$, $S(O)_2R^{b1}$, and $S(O)_2NR^{c1}R^{d1}$.

In some embodiments, $R^B$ is $C_{1-6}$ alkyl, optionally substituted with 1, 2, or 3 substituents independently selected from $Cy^1$, CN, $OR^{a1}$, $S(O)_2R^{b1}$, and $S(O)_2NR^{c1}R^{d1}$.

In some embodiments, $R^B$ is $C_{1-6}$ alkyl, optionally substituted with 1, 2, or 3 substituents independently selected from $Cy^1$, CN, OH, $S(O)_2CH_3$, and $S(O)_2NH_2$.

In some embodiments, $R^B$ is $Cy^1$.

In some embodiments, $Cy^1$ is $C_{6-10}$ aryl, optionally substituted with 1, 2, or 3 substituents independently selected from $R^{Cy2}$. In some embodiments, the $C_{6-10}$ aryl has formula:

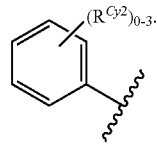

In some embodiments, $Cy^1$ is $C_{3-14}$ cycloalkyl, optionally substituted with 1, 2, or 3 substituents independently selected from $R^{Cy2}$.

In some embodiments, $Cy^1$ is $C_{3-14}$ cycloalkyl having the formula selected from:

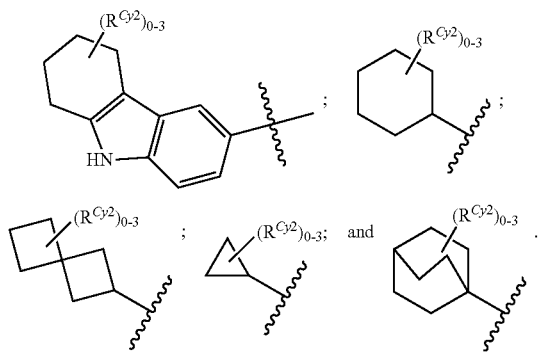

In some embodiments, $Cy^1$ is $C_{3-10}$ cycloalkyl, optionally substituted with 1, 2, or 3 substituents independently selected from $R^{Cy2}$. In some embodiments, the $C_{3-10}$ cycloalkyl has the formula selected from:

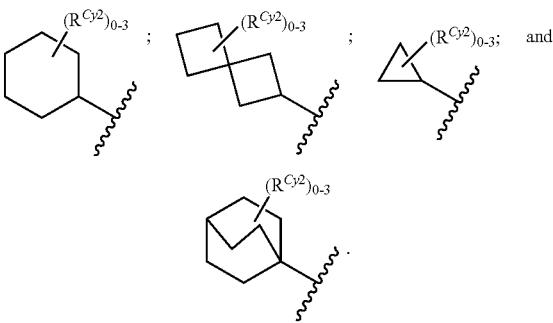

In some embodiments, $Cy^1$ is 4-14 membered heterocycloalkyl, optionally substituted with 1, 2, or 3 substituents independently selected from $R^{Cy2}$.

In some embodiments, $Cy^1$ is 4-14 membered heterocycloalkyl having the formula selected from:

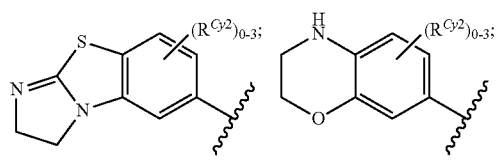

-continued

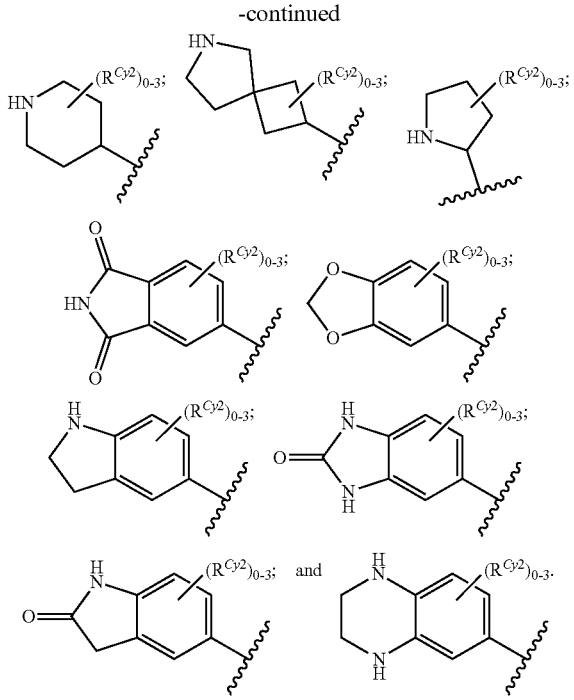

In some embodiments, Cy$^1$ is 4-10 membered heterocycloalkyl, optionally substituted with 1, 2, or 3 substituents independently selected from R$^{Cy2}$. In some embodiments, the 4-10 membered heterocycloalkyl has the formula selected from:

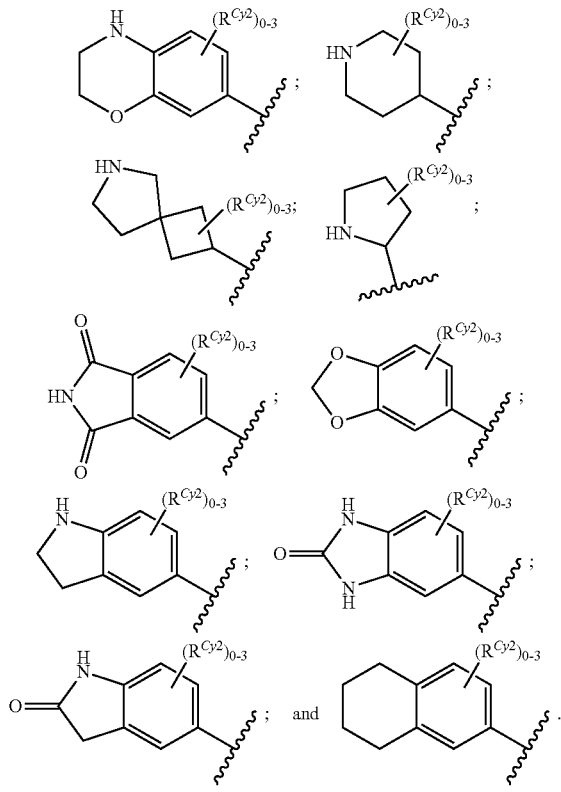

In some embodiments, Cy$^1$ is 3-10 membered heteroaryl, optionally substituted with 1, 2, or 3 substituents independently selected from R$^{Cy2}$.

In some embodiments, the 3-10 membered heteroaryl has the formula selected from:

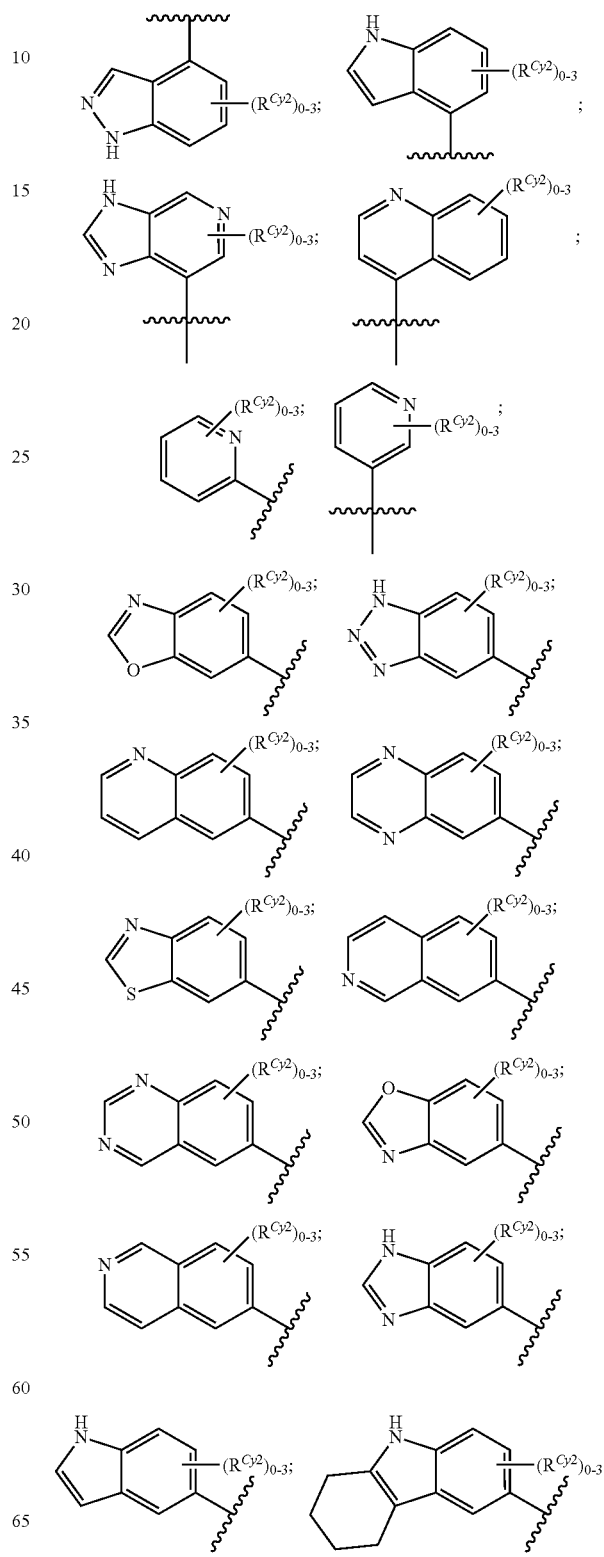

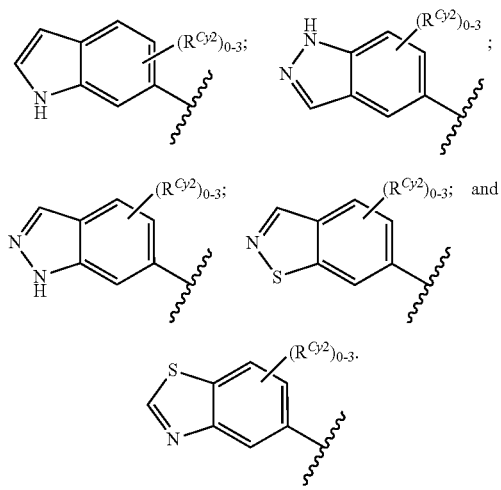

In some embodiments, the 5-10 membered heteroaryl has the formula selected

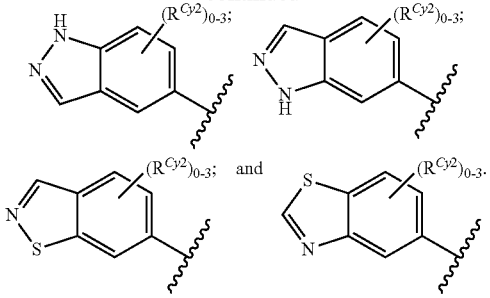

In some embodiments, wherein each $R^{Cy2}$ is independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1,2, or 3 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$.

In some embodiments, each $R^{Cy2}$ is independently selected from halo, $Cy^2$, $C_{1-6}$ alkyl, $C_{1-6}$ haloalkyl, $OR^{a2}$, $C(O)NR^{c2}R^{d2}$, $NR^{c2}R^{d2}$, $NR^{c2}C(O)R^{b2}$, and $S(O)_2R^{b2}$.

In some embodiments, each $R^{Cy2}$ is independently selected from halo, CN, $C_{3-10}$ cycloalkyl, $C_{1-6}$ alkyl, $C_{1-6}$ haloalkyl, $OR^{a2}$, $C(O)R^{b2}$, $C(O)NR^{c2}R^{d2}$, and $NR^{c2}R^{d2}$.

In some embodiments, each $R^{Cy2}$ is independently selected from halo, CN, $C_{3-10}$-cycloalkyl, $C_{1-6}$ alkyl, $C_{1-6}$ haloalkyl, $C_{1-6}$ alkoxy, $C(O)(C_{1-6}$ alkyl), $C(O)NH_2$, and $NH_2$.

In some embodiments, $R^{Cy2}$ is halo.

In some embodiments, $R^{Cy2}$ is $C_{1-6}$ alkyl, $C_{1-6}$ haloalkyl, or $C_{1-6}$ alkoxy.

In some embodiments, $R^{Cy2}$ is $NH_2$.

In some embodiments, each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments, $R^B$ is $C_{6-10}$ aryl, optionally substituted with 1, 2, or 3 substituents independently selected from $R^{Cy2}$; and $R^A$ is $C_{6-10}$ aryl, optionally substituted with 1, 2, or 3 substituents independently selected from $R^{Cy1}$.

In some embodiments, $R^B$ is 3-10 membered heteroaryl, optionally substituted with 1, 2, or 3 substituents independently selected from $R^{Cy2}$; and $R^A$ is $C_{6-10}$ aryl, optionally substituted with 1, 2, or 3 substituents independently selected from $R^{Cy1}$.

In some embodiments, $R^B$ is 3-10 membered heteroaryl, optionally substituted with 1, 2, or 3 substituents independently selected from $R^{Cy2}$; and $R^A$ is 5-10 membered heteroaryl, optionally substituted with 1, 2, or 3 substituents independently selected from $R^{Cy1}$.

In some embodiments, $R^B$ is $C_{6-10}$ aryl, optionally substituted with 1, 2, or 3 substituents independently selected from $R^{Cy2}$; and $R^A$ is 5-10 membered heteroaryl, optionally substituted with 1, 2, or 3 substituents independently selected from $R^{Cy1}$.

In some embodiments:

n is 1;

L is selected from $C_{1-3}$ alkylene, $C(=O)$, and $N(R^N)$, wherein said $C_{1-3}$ alkylene is optionally substituted with OH;

$R^N$ is selected from H and $C_{1-6}$ alkyl;

$R^1$, $R^2$, $R^3$, $R^4$, $R^5$, and $R^6$ are each independently selected from H, halo, CN, $C_{1-6}$ alkyl, $OR^{a1}$, $NR^{c1}R^{d1}$, and $S(O)_2R^{b1}$;

$R^A$ is selected from $Cy^{A1}$, $O$-$Cy^{A1}$, and NH-$Cy^{A1}$;

each $Cy^{A1}$ is selected from $C_{6-10}$ aryl, 5-10 membered heteroaryl, and 4-10 membered heterocycloalkyl, each of which is optionally substituted with 1, 2, or 3 substituents independently selected from $R^{Cy1}$;

$R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{a1}$, $S(O)_2R^{b1}$, and $S(O)_2NR^{c1}R^{d1}$;

or, when $R^B$ is attached to $N(R^N)$, $R^B$ and $R^N$ together with the N atom to which they are attached form 4-14 membered heterocycloalkyl, which is optionally substituted with $Cy^1$, $C_{1-6}$ alkyl, $OR^{a1}$, and halo;

each $R^{Cy1}$ is independently selected from halo, $NO_2$, $C_{1-6}$ alkyl, $C_{1-6}$ haloalkyl, $OR^{a2}$, $C(O)OR^{a2}$, $C(O)R^{b2}$, $C(O)NR^{c2}R^{d2}$, $NR^{c2}R^{d2}$, and $S(O)_2R^{b2}$, wherein said $C_{1-6}$ alkyl is optionally substituted with $OR^{a2}$;

each $Cy^1$ is independently selected from $C_{6-10}$ aryl, $C_{3-4}$ cycloalkyl, 5-10 membered heteroaryl, and 4-14 membered heterocycloalkyl, each of which is optionally substituted with 1, 2, 3, 4, or 5 substituents independently selected from $R^{Cy2}$;

each $R^{Cy2}$ is independently selected from halo, $Cy^2$, $C_{1-6}$ alkyl, $C_{1-6}$ haloalkyl, $OR^{a2}$, $C(O)NR^{c2}R^{d2}$, $NR^{c2}R^{d2}$, $NR^{c2}C(O)R^{b2}$, and $S(O)_2R^{b2}$; and each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments:

n is 1;

L is selected from $C_{1-3}$ alkylene, $C(=O)$, and $N(R^N)$, wherein said $C_{1-3}$ alkylene is optionally substituted with OH;

$R^N$ is selected from H and $C_{1-6}$ alkyl;

$R^1$, $R^2$, $R^3$, $R^4$, $R^5$, and $R^6$ are each independently selected from H, halo, CN, $C_{1-6}$ alkyl, $OR^{a1}$, $NR^{c1}R^{d1}$, and $S(O)_2R^{b1}$;

$R^A$ is selected from $Cy^{A1}$, $O$-$Cy^{A1}$, and NH-$Cy^{A1}$;

each $Cy^{A1}$ is selected from $C_{6-10}$ aryl, 5-10 membered heteroaryl, and 4-10 membered heterocycloalkyl, each of which is optionally substituted with 1, 2, or 3 substituents independently selected from $R^{Cy1}$;

$R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{a1}$, $S(O)_2R^{b1}$, and $S(O)_2NR^{c1}R^{d1}$;

or, when $R^B$ is attached to $N(R^N)$, $R^B$ and $R^N$ together with the N atom to which they are attached form 4-7 membered heterocycloalkyl, which is optionally substituted with $OR^{a1}$;

each $R^{Cy1}$ is independently selected from halo, $NO_2$, $C_{1-6}$ alkyl, $C_{1-6}$ haloalkyl, $OR^{a2}$, $C(O)OR^{a2}$, $C(O)R^{b2}$, $C(O)NR^{c2}R^{d2}$, $NR^{c2}R^{d2}$, and $S(O)_2R^{b2}$, wherein said $C_{1-6}$ alkyl is optionally substituted with $OR^{a2}$;

each $R^{Cy2}$ is independently selected from halo, CN, $C_{3-10}$ cycloalkyl, $C_{1-6}$ alkyl, $C_{1-6}$ haloalkyl, $OR^{a2}$, $C(O)R^{b2}$, $C(O)NR^{c2}R^{d2}$, and $NR^{c2}R^d$; and each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments:

n is 1;

L is selected from $C_{1-3}$ alkylene, $C(=O)$, and $N(R^N)$, wherein said $C_{1-3}$ alkylene is optionally substituted with OH;

$R^N$ is selected from H and $C_{1-6}$ alkyl;

$R^1$, $R^2$, $R^3$, $R^4$, $R^5$, and $R^6$ are each independently selected from H, halo, $C_{1-6}$ alkyl, and $OR^{a1}$;

$R^A$ is selected from $C_{6-10}$ aryl, 5-10 membered heteroaryl, and 4-10 membered heterocycloalkyl, each of which is optionally substituted with 1, 2, or 3 substituents independently selected from $R^{Cy1}$;

$R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{*1}$, $S(O)_2R^{b1}$, and $S(O)_2NR^{c1}R^{d1}$;

or, when $R^B$ is attached to $N(R^N)$, $R^B$ and $R^N$ together with the N atom to which they are attached form 4-7 membered heterocycloalkyl, which is optionally substituted with $OR^{*1}$;

each $R^{Cy1}$ is independently selected from halo, $NO_2$, $C_{1-6}$ alkyl, $OR^{a2}$, and $C(O)OR^{a2}$;

each $R^{Cy2}$ is independently selected from halo, CN, $C_{3-10}$ cycloalkyl, $C_{1-6}$ alkyl, $C_{1-6}$ haloalkyl, $OR^{a2}$, $C(O)R^{b2}$, $C(O)NR^{c2}R^{d2}$, and $NR^{c2}R^d$; and each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments, the compound of Formula (I) is selected from any one of the compounds in Table 1, Table 1a, Table 2, Table 3, Table 3, Table 5a, and Table 6, or a pharmaceutically acceptable salt thereof.

In some embodiments, the compound of Formula (I) is selected from any one of the compounds in Table 1, Table 1a, Table 2, Table 3, Table 3, and Table 6, or a pharmaceutically acceptable salt thereof.

In some embodiments, the compound of Formula (I) is selected from any one of the compounds in Table 1, Table 2, or Table 3, or a pharmaceutically acceptable salt thereof.

In some embodiments, the compound of Formula (I) is selected from any one of the compounds in Table 1, or a pharmaceutically acceptable salt thereof. In some embodiments, the compound of Formula (I) is selected from any one of the compounds in Table 1a, or a pharmaceutically acceptable salt thereof. In some embodiments, the compound of Formula (I) is selected from any one of the compounds in Table 2, or a pharmaceutically acceptable salt thereof. In some embodiments, the compound of Formula (I) is selected from any one of the compounds in Table 3, or a pharmaceutically acceptable salt thereof. In some embodiments, the compound of Formula (I) is selected from any one of the compounds in Table 5, or a pharmaceutically acceptable salt thereof. In some embodiments, the compound of Formula (I) is selected from any one of the compounds in Table 5a, or a pharmaceutically acceptable salt thereof. In some embodiments, the compound of Formula (I) is selected from any one of the compounds in Table 6, or a pharmaceutically acceptable salt thereof.

In some embodiments, the compound of Formula (I) is selected from any one of Formulae (IIc)-(IIi).

In some embodiments, the compound of Formula (I) is selected from any one of the following compounds:

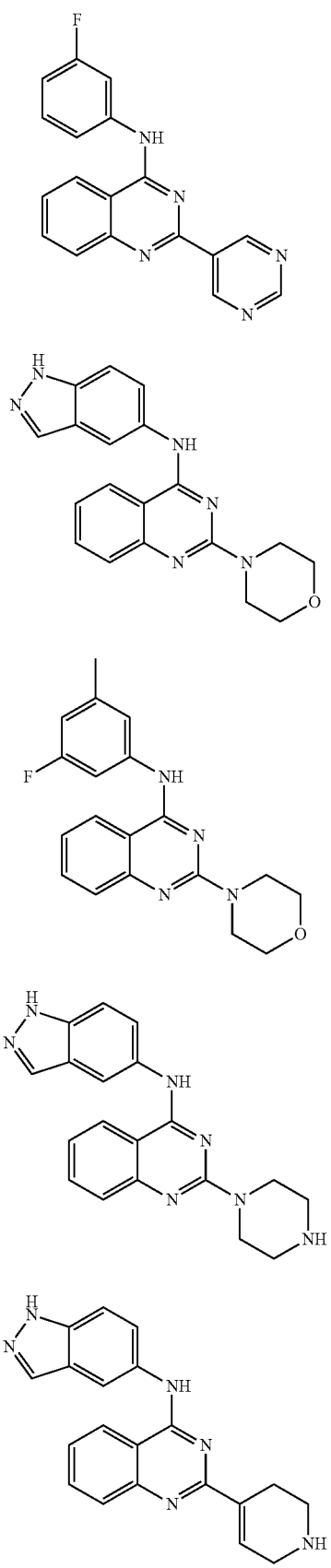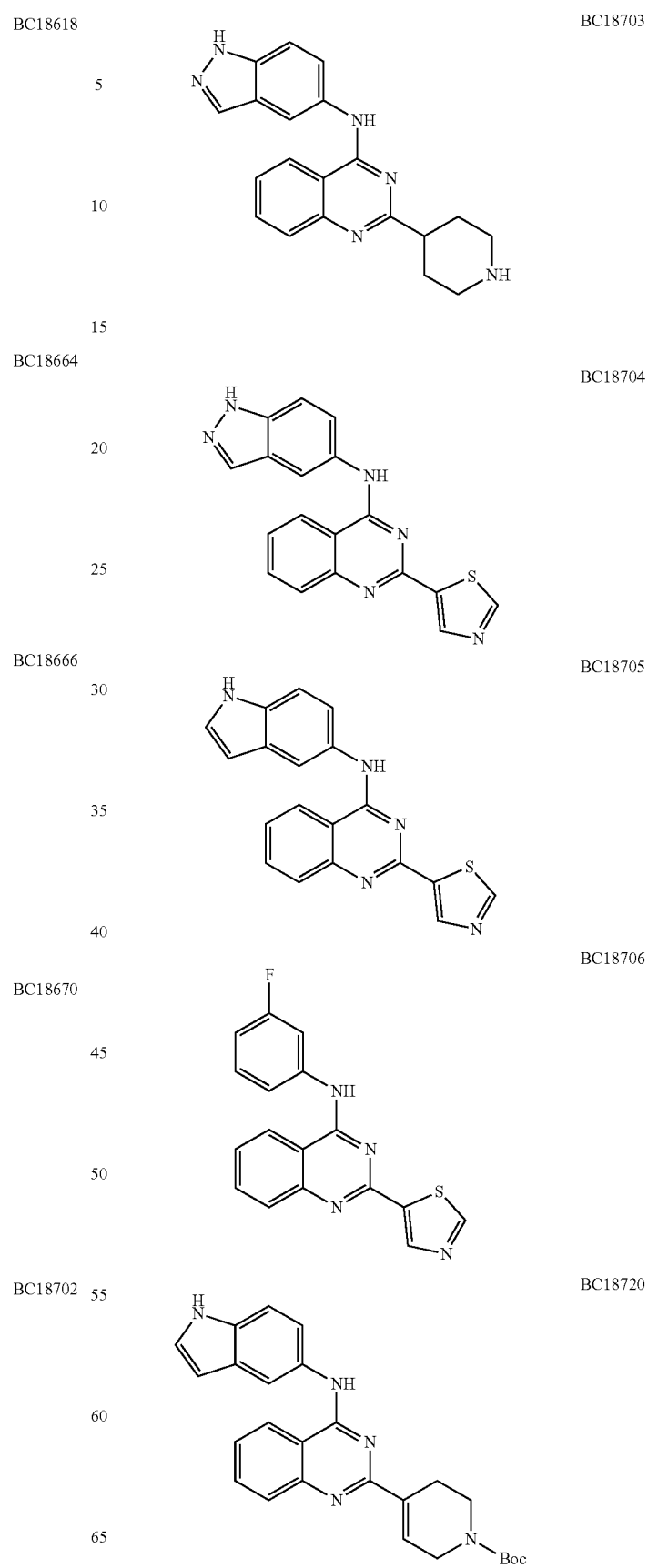

-continued
BC18722
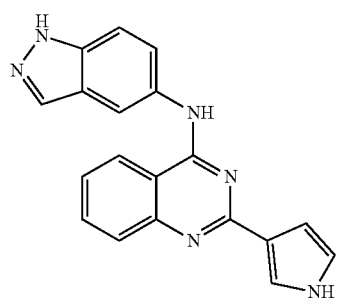
BC18738
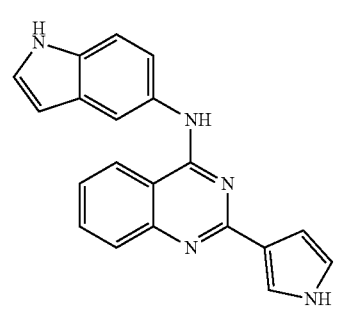
BC18740
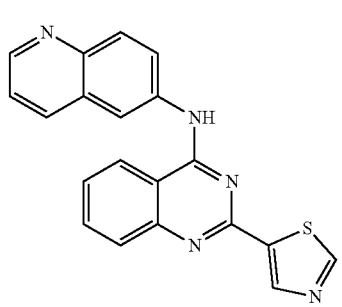
BC18742
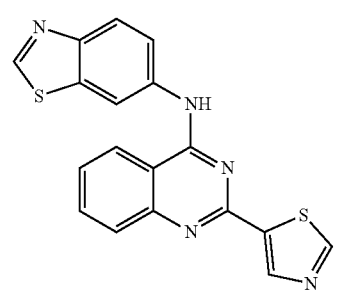
BC18853
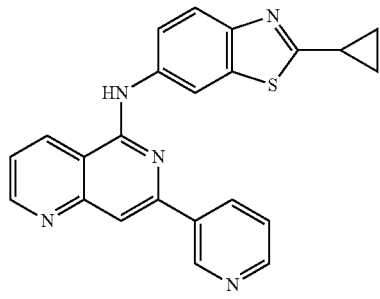
-continued
BC18854
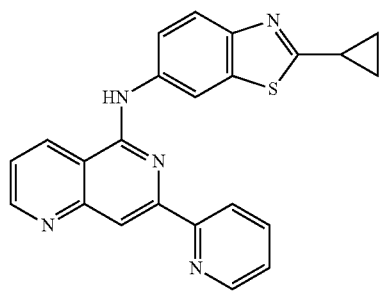
BC191107
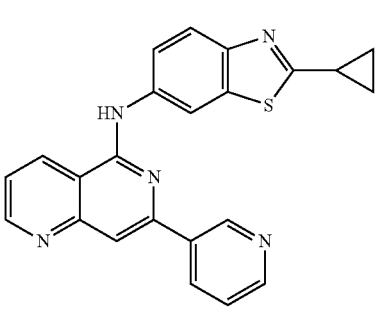
BC191108
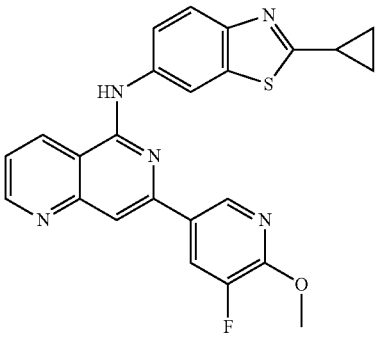
BC191109
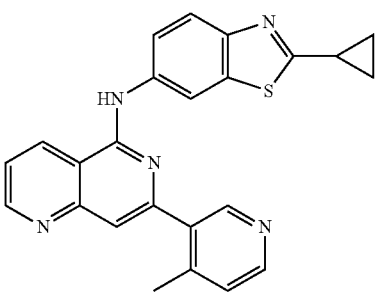
BC191110
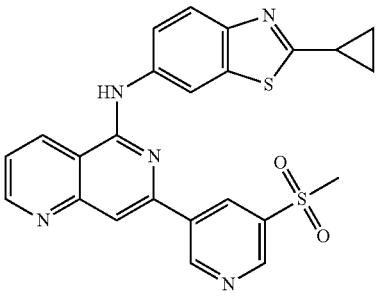

-continued
BC191111
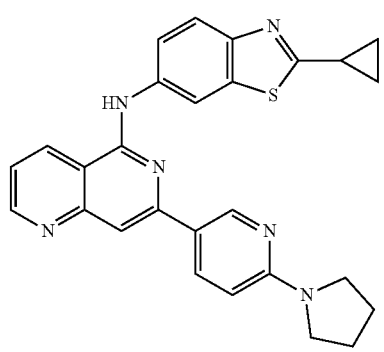
BC191112
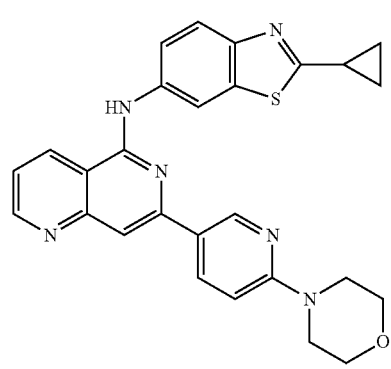
BC191113
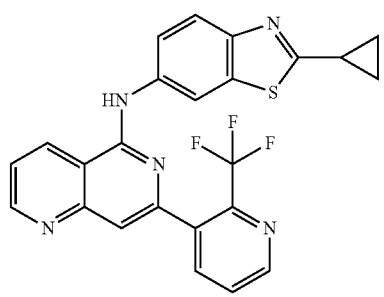
BC191114
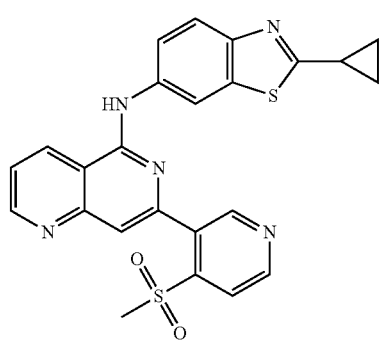
-continued
BC191115
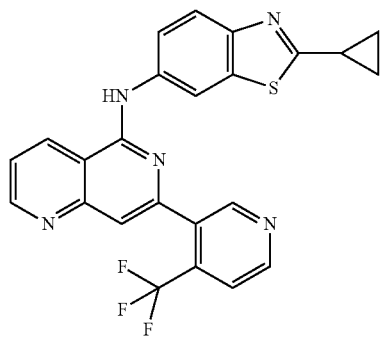
BC191116
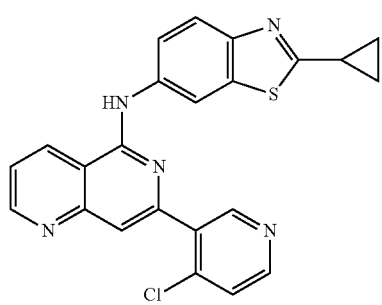
BC191117
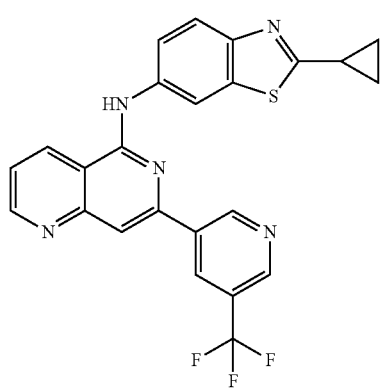
BC191118
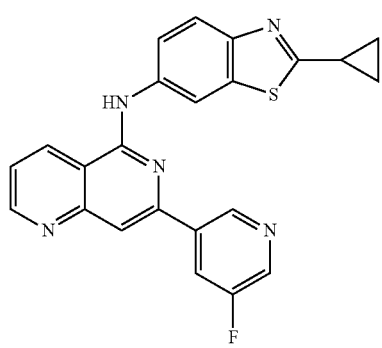

-continued
BC191119
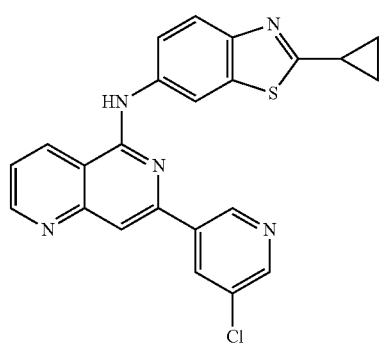
BC191120
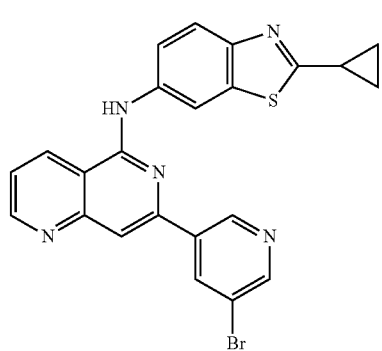
BC191121
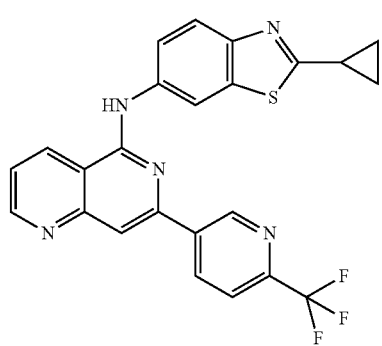
BC191122
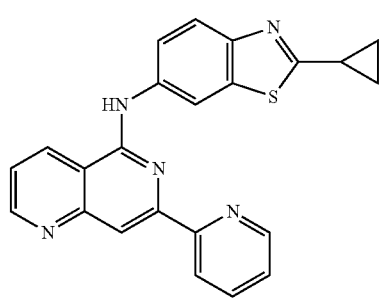
-continued
BC191123
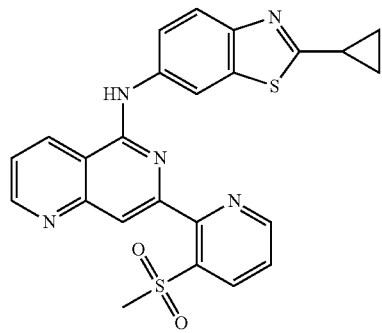
BC191124
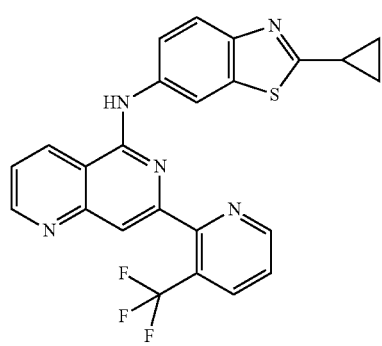
BC191125
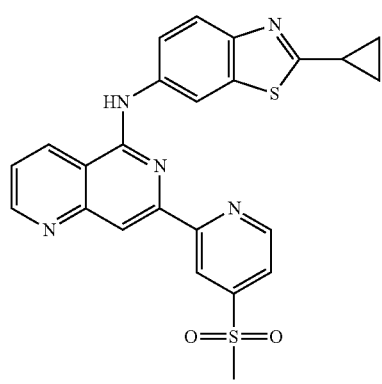
BC191126
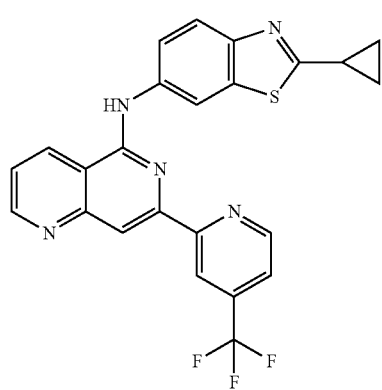

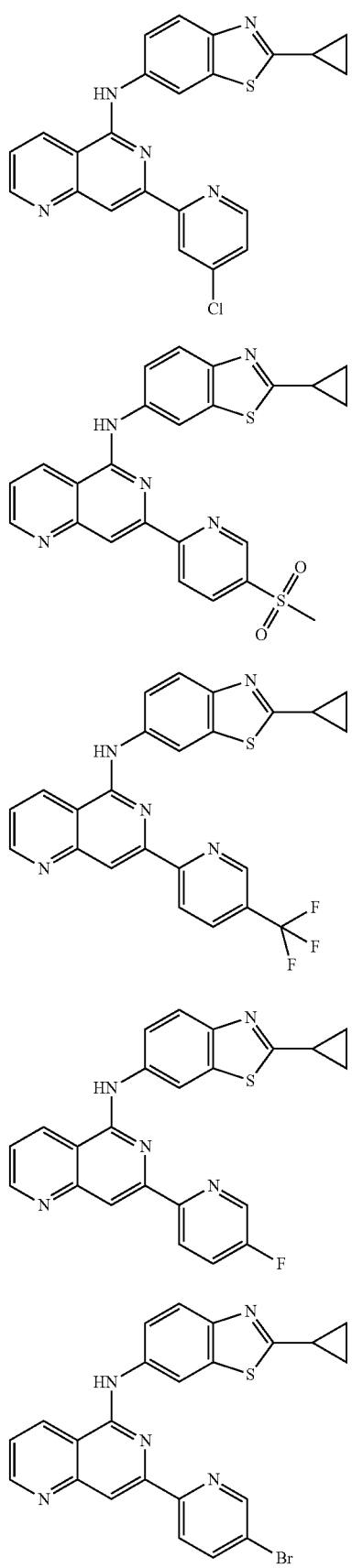
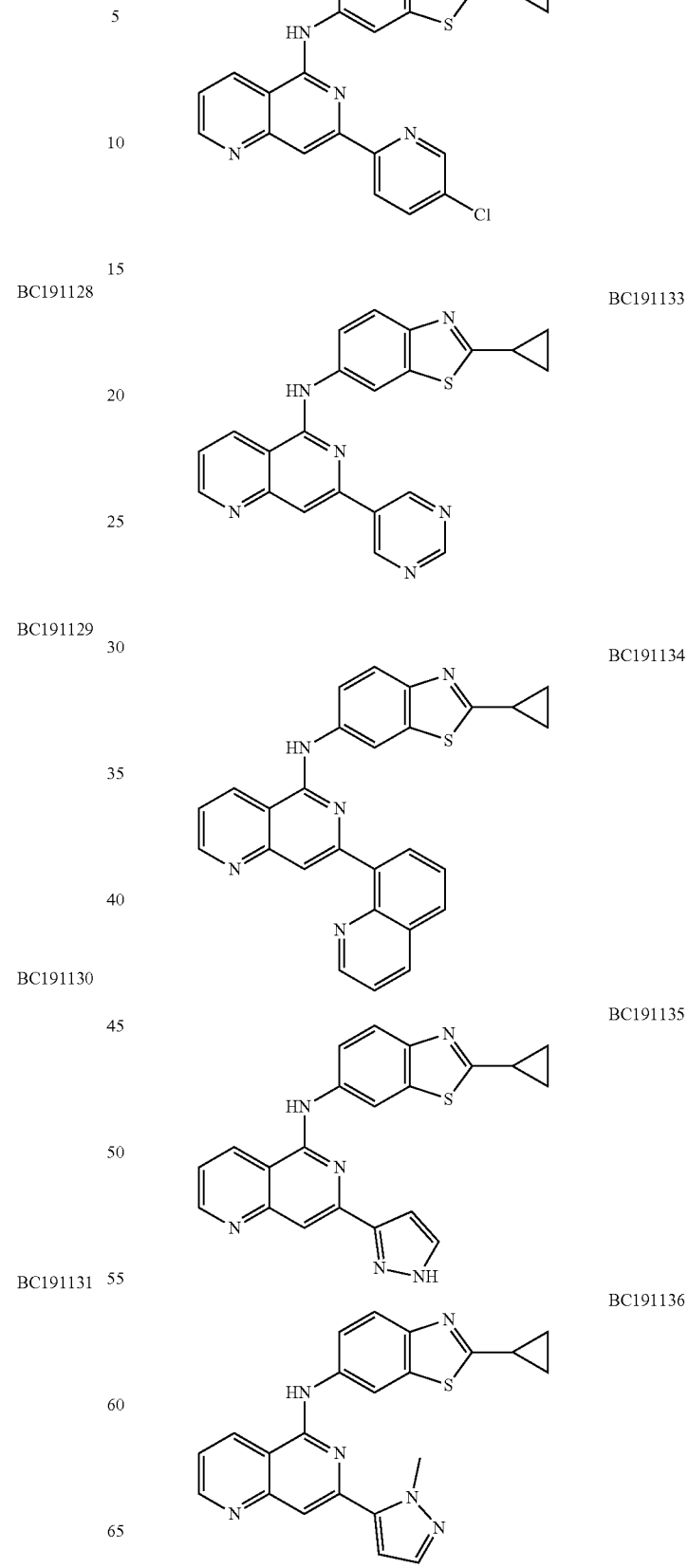

BC191137
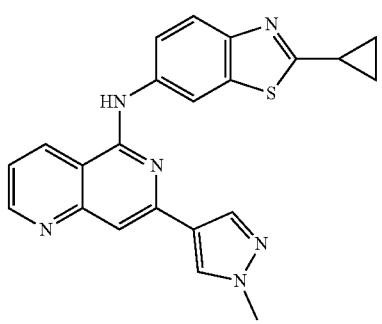
BC191138
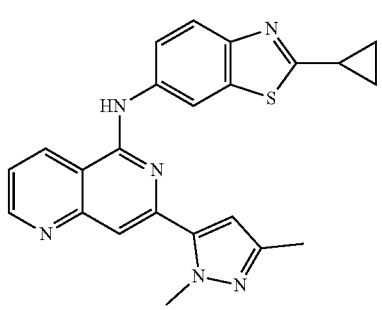
BC191139
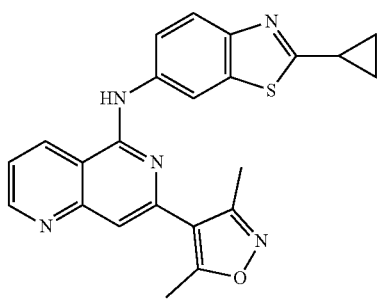
BC191140
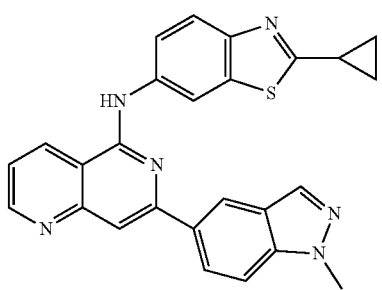
BC191142
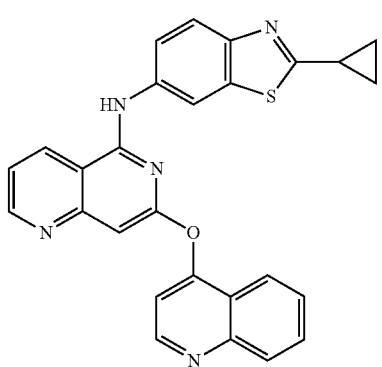
BC191143
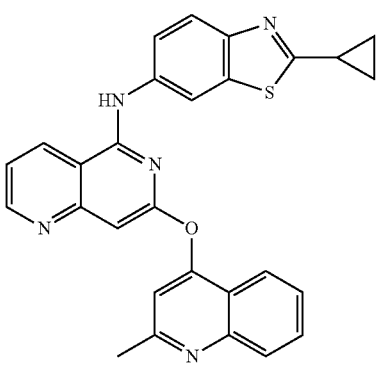
BC191144
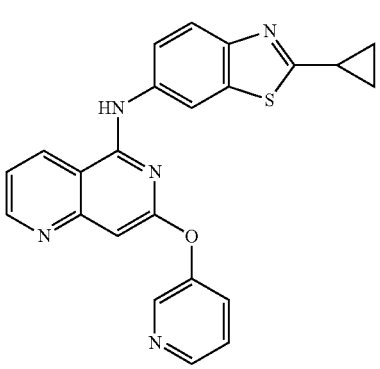
BC191145
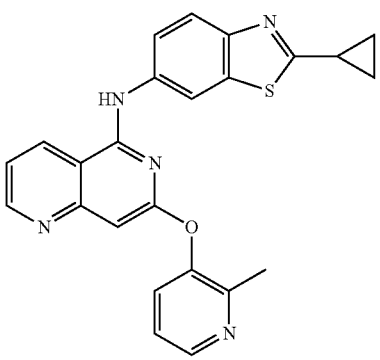
BC191146
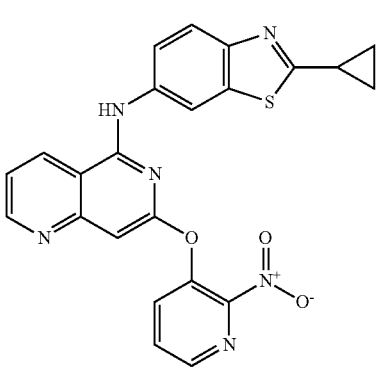

BC191147
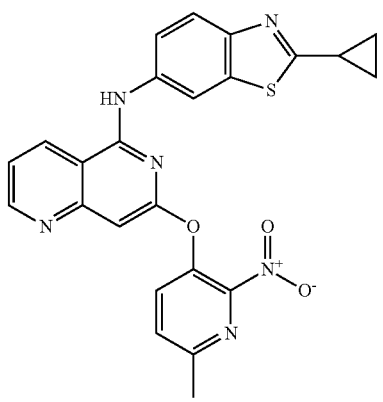
BC191148
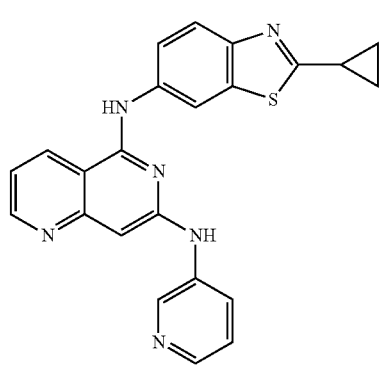
BC191149
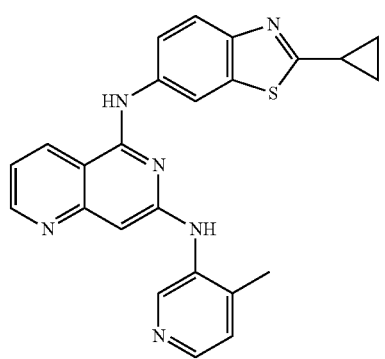
BC191150
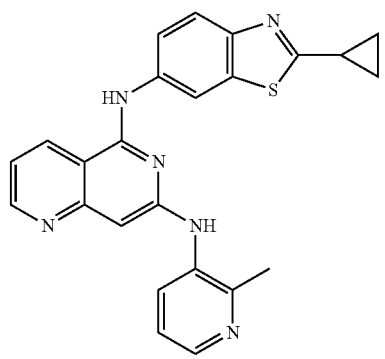
BC191151
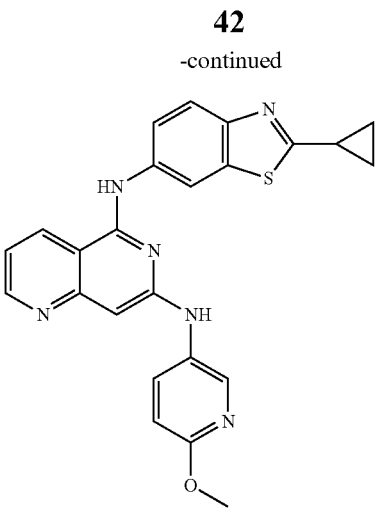
BC191152
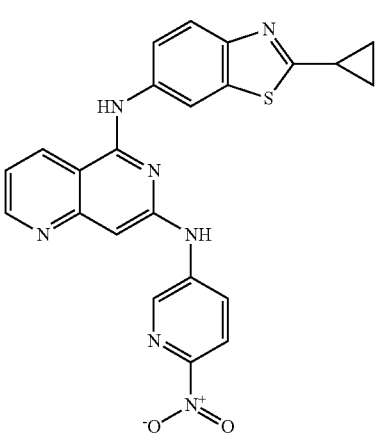
BC191155
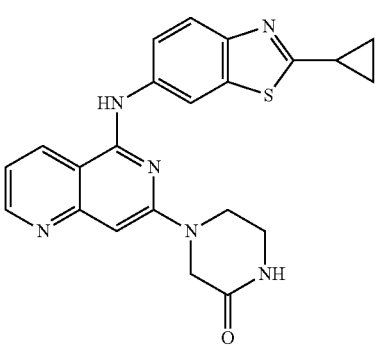
BC191156
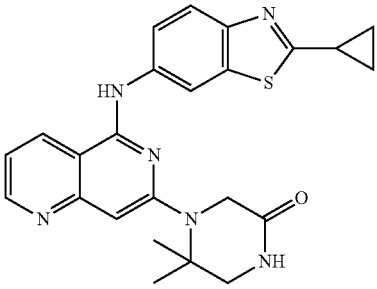

BC191157
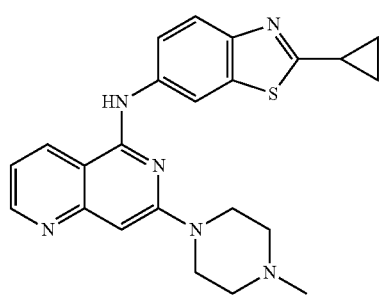
BC191158
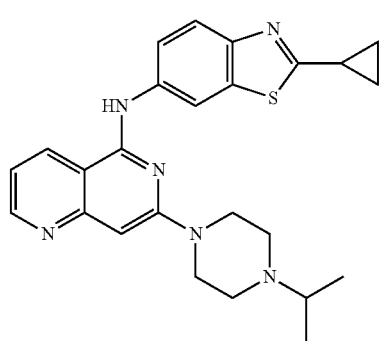
BC191159
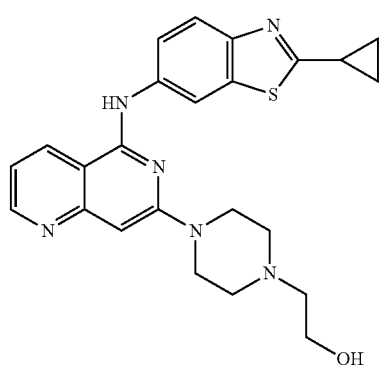
BC191160
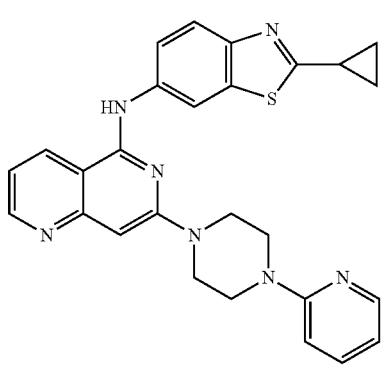
BC191161
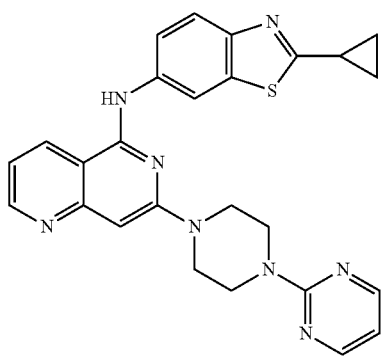
BC191162
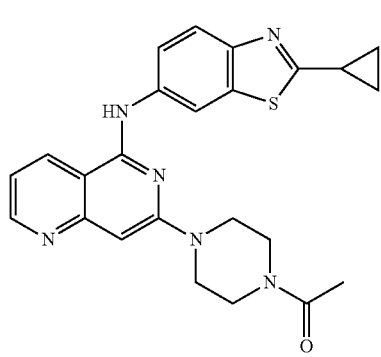
BC191163
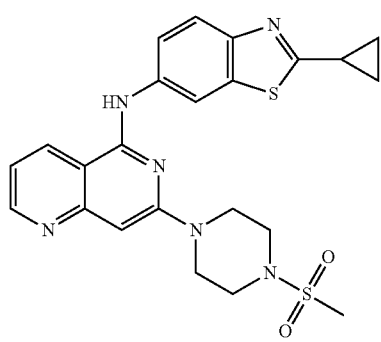
BC191164
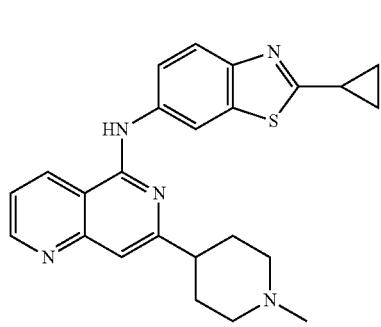

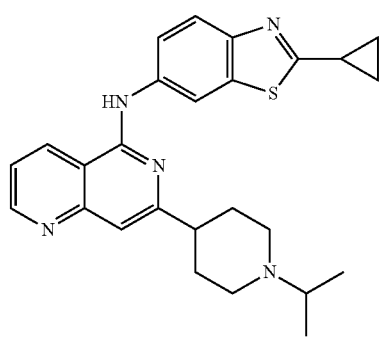
BC191165
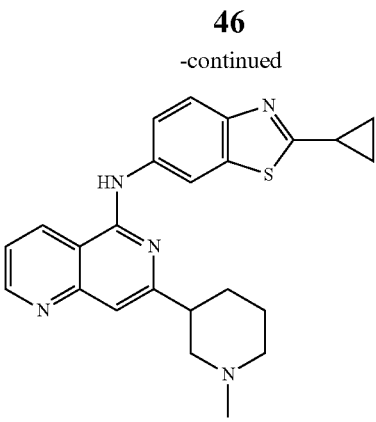
BC191169
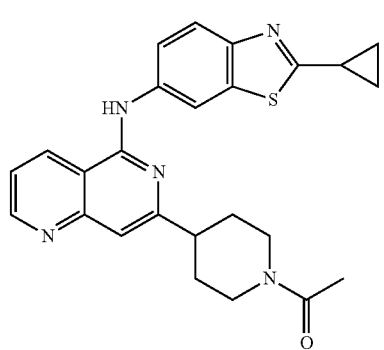
BC191166
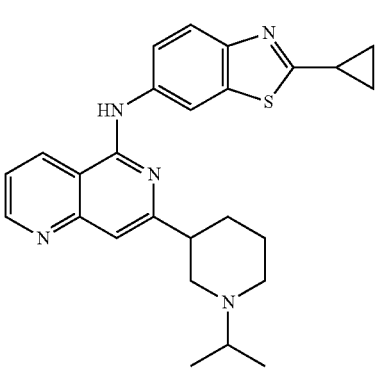
BC191170
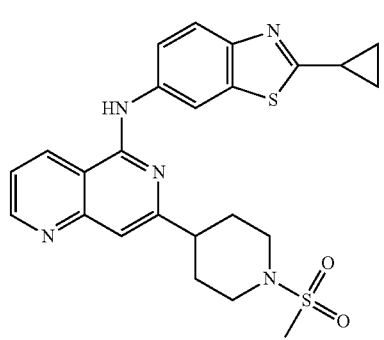
BC191167
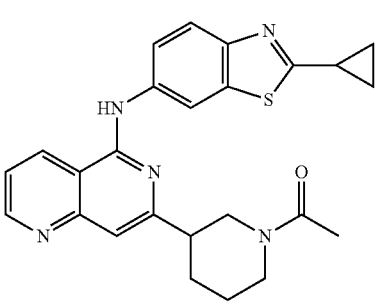
BC191171
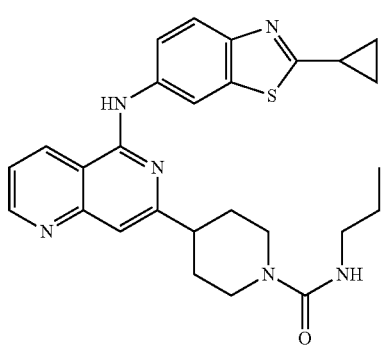
BC191168
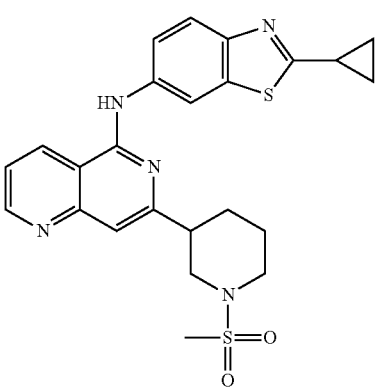
BC191172

BC191173
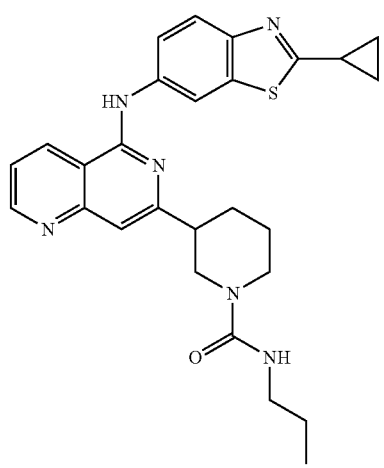
BC191185
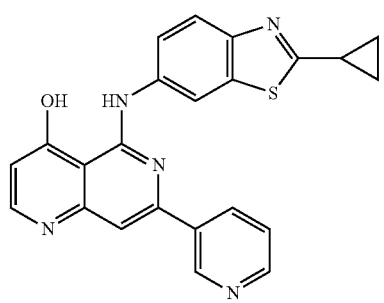
BC191186
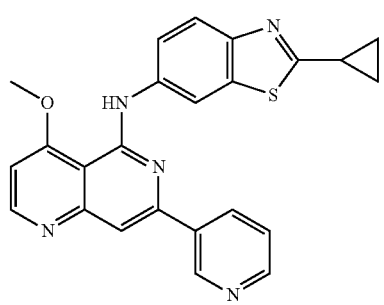
BC191187
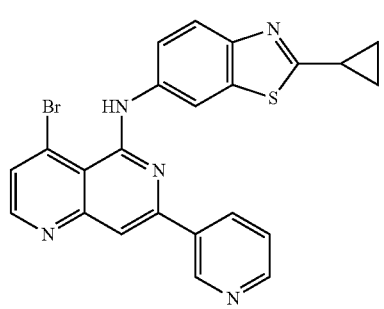
BC191188
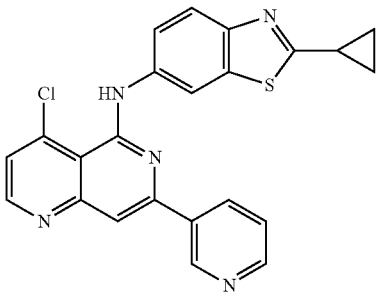
BC191189
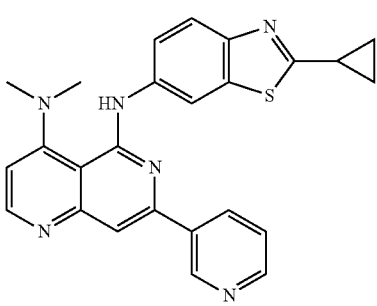
BC191190
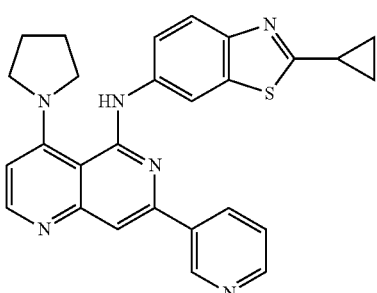
BC191191
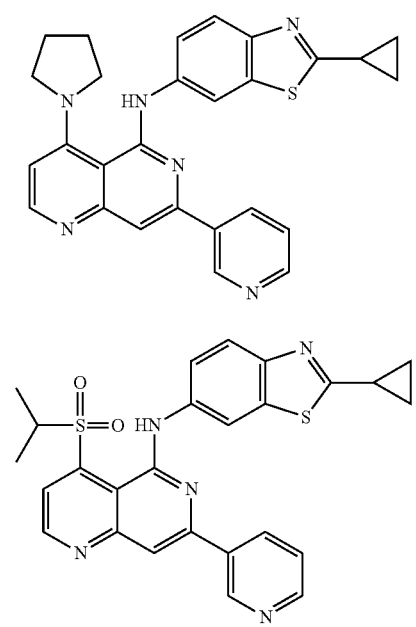
BC191192
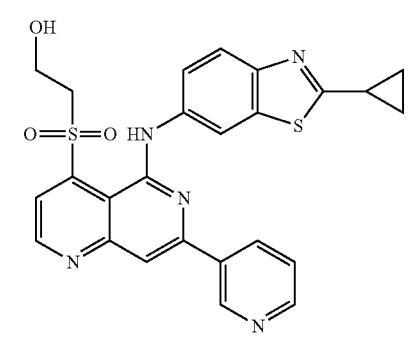

BC191193
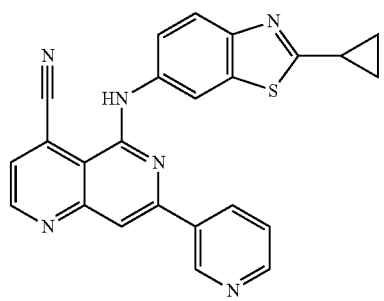
BC191198
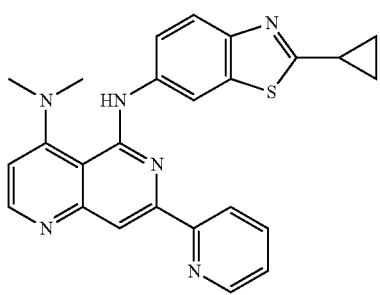
BC191194
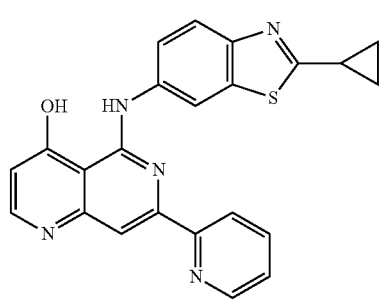
BC191199
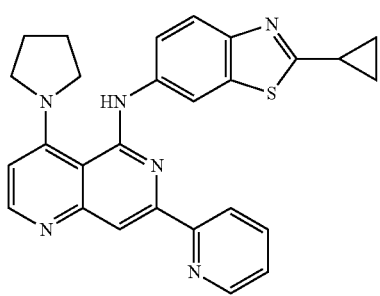
BC191195
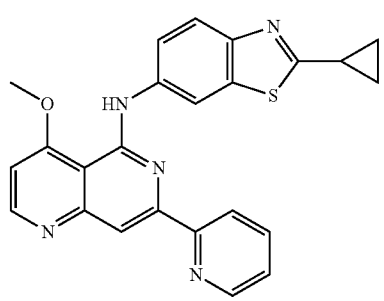
BC191200
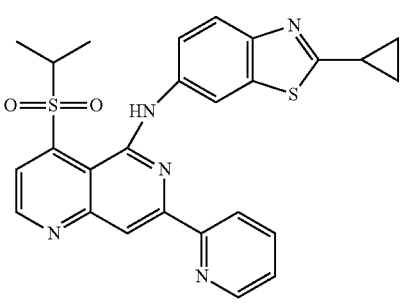
BC191196
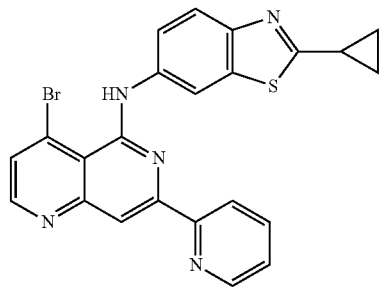
BC191201
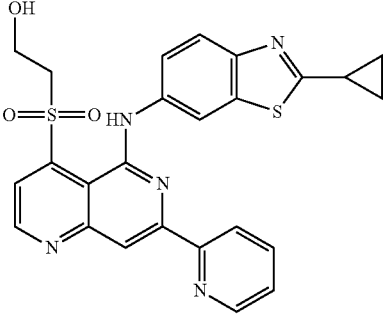
BC191197
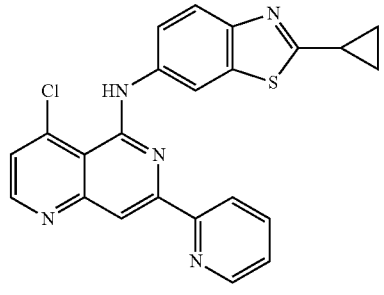
BC191202
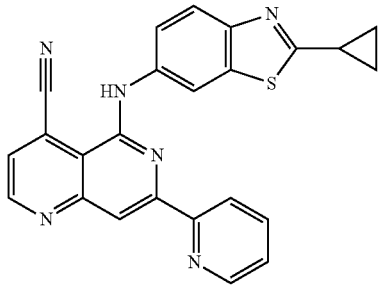

BC18829
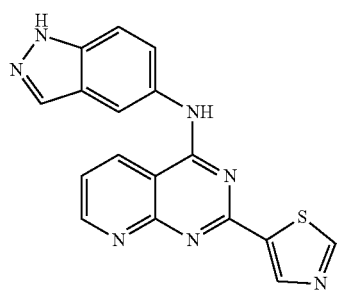
BC18830
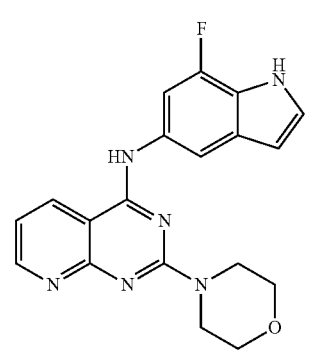
BC18831
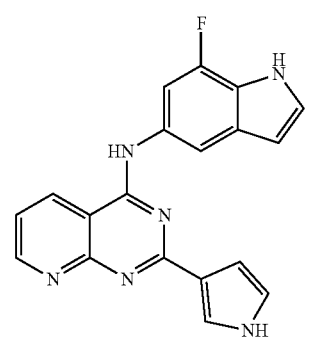
BC18832
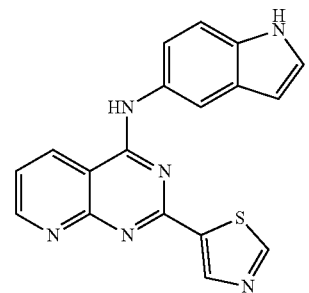
BC18833
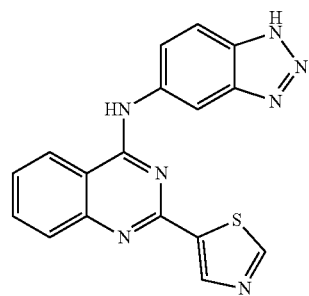
BC18834
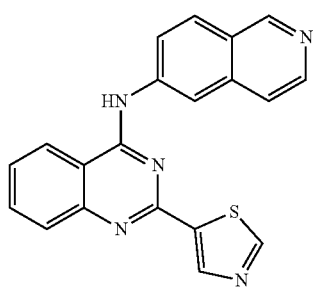
BC18835
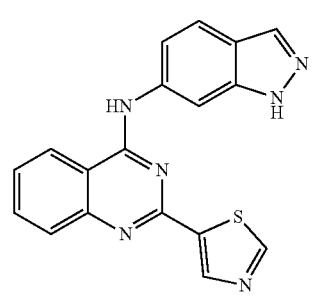
BC18836
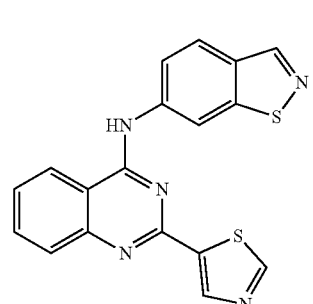
BC18838
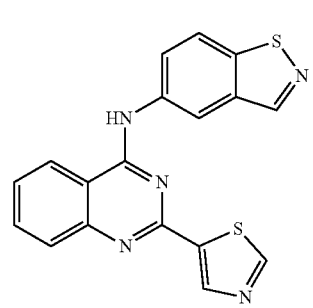
BC18839
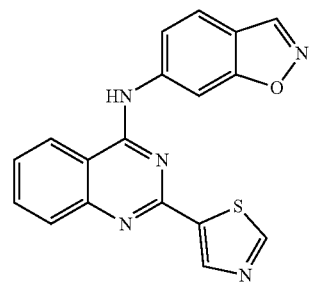

BC18840
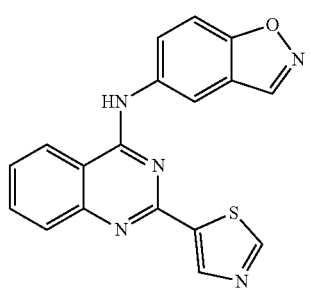
BC18664
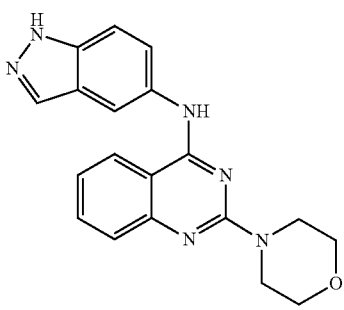
BC18841
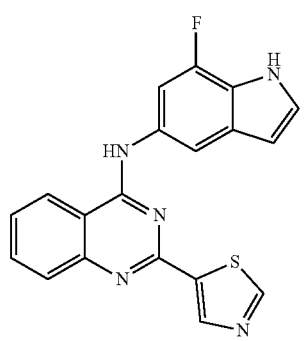
BC18666
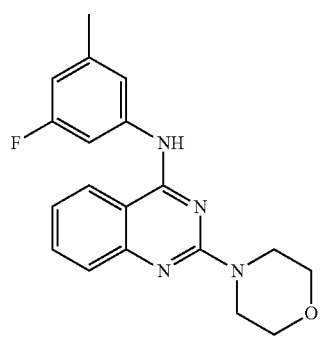
BC18845
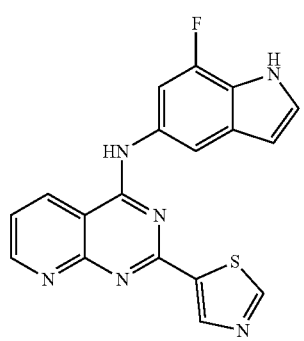
BC18670
or a pharmaceutically acceptable salt thereof.
In some embodiments, the compound of Formula (I) is selected from any one of the following compounds:
BC18702
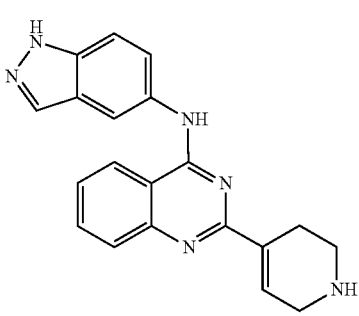
BC18618
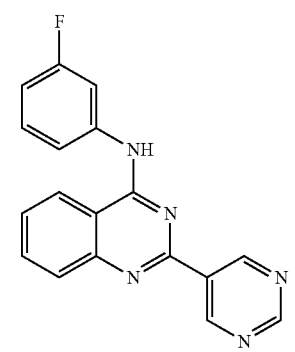
BC18703
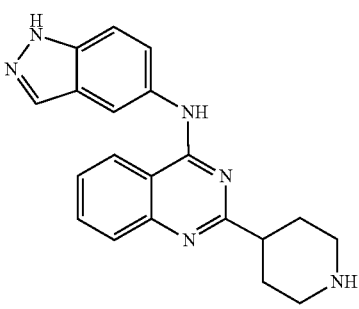

BC18704
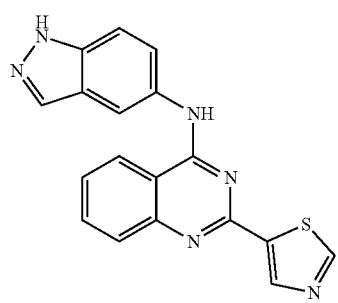
BC18705
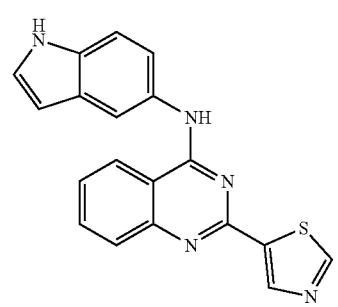
BC18706
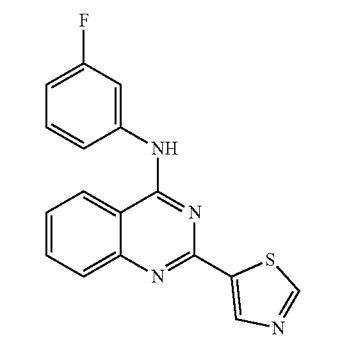
BC18720
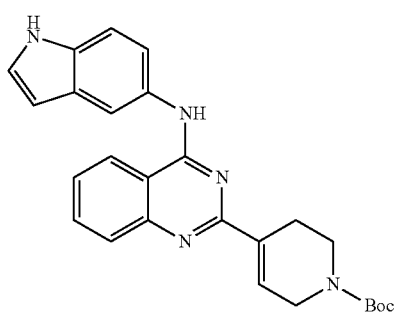
BC18722
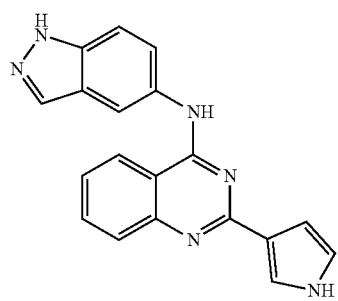
BC18738
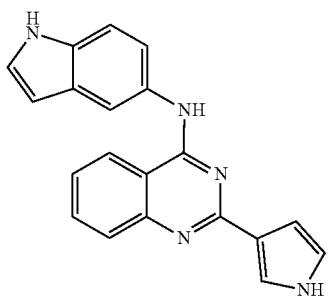
BC18740
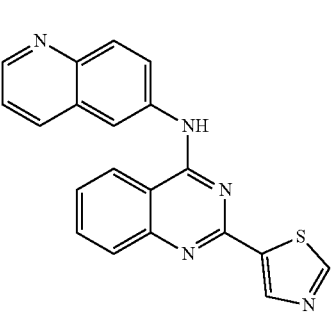
BC18742
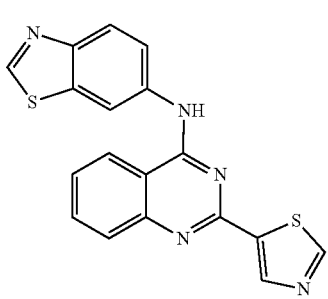
or a pharmaceutically acceptable salt thereof.
In some embodiments, the compound of any one of Formulae (IIc)-(IIi) is selected from any one of the following compounds:
BC18663
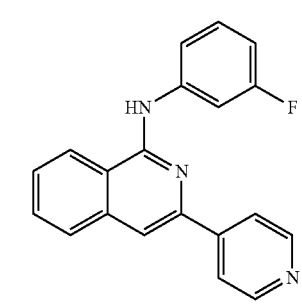

BC18668 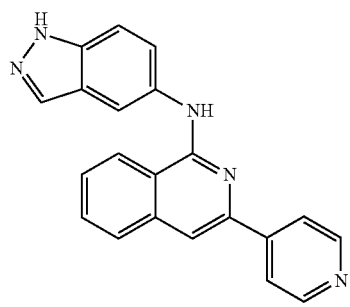
BC18669 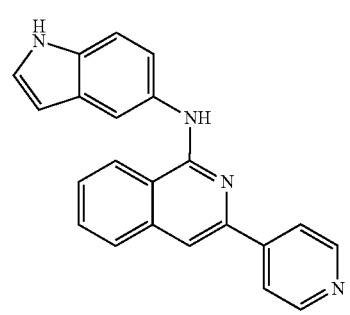
BC18687 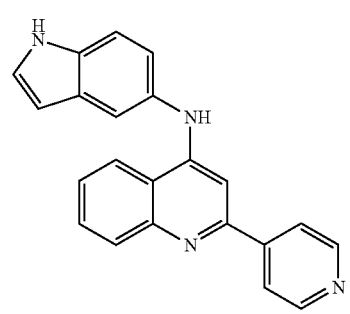
BC18688 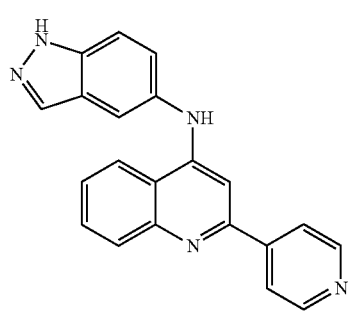
BC18689 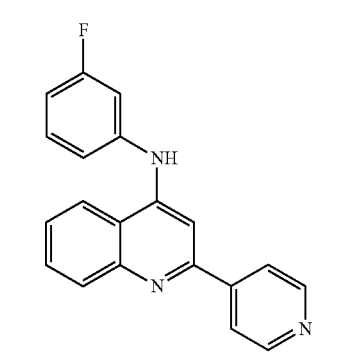
BC18707 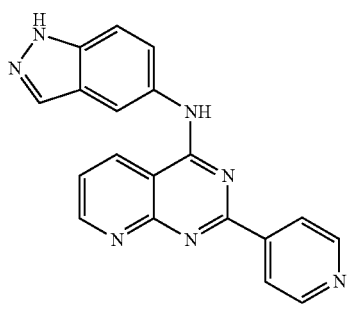
BC18708 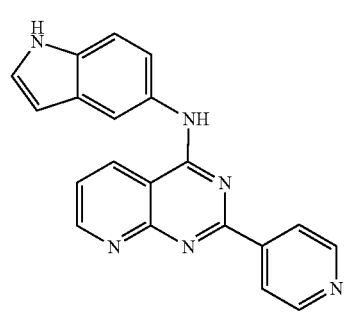
BC18709 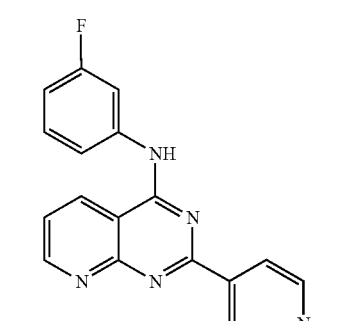
BC18711 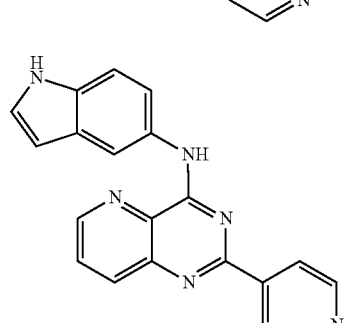
BC18713 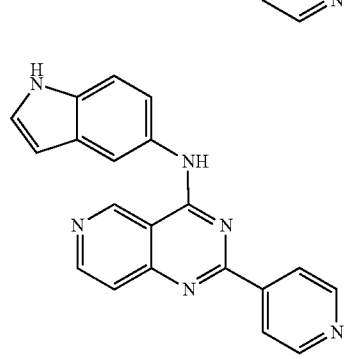

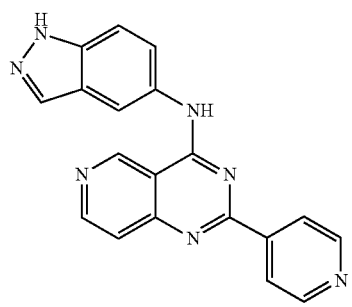
BC18714
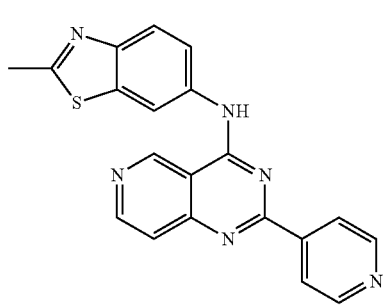
BC18755
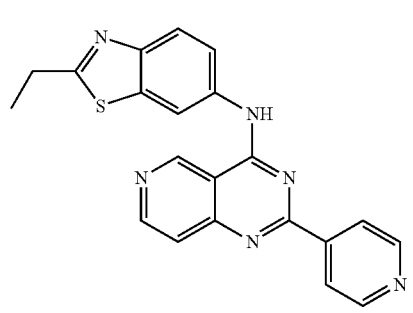
BC18756
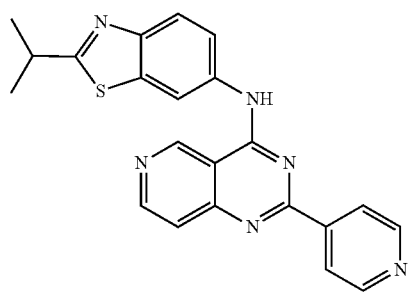
BC18757
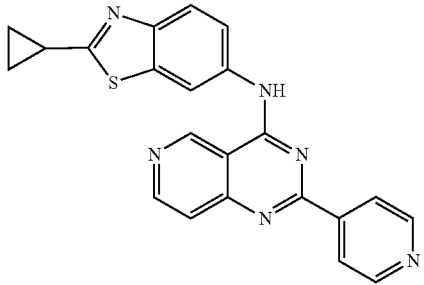
BC18758
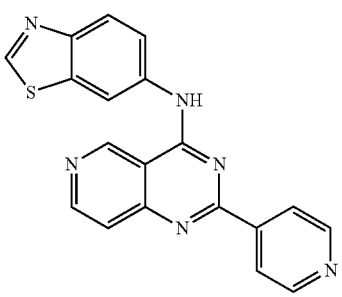
BC18759
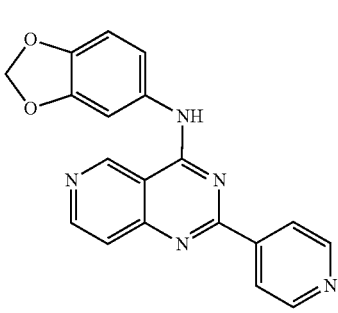
BC18760
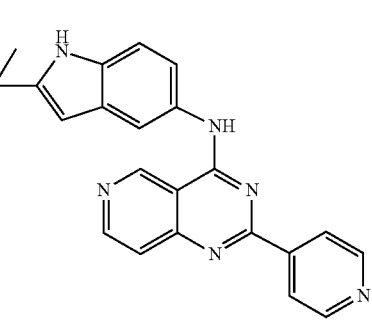
BC18761
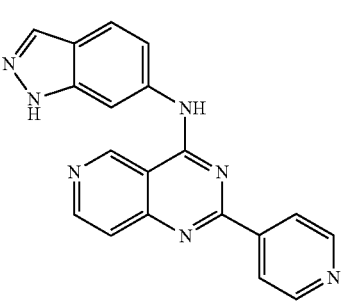
BC18762
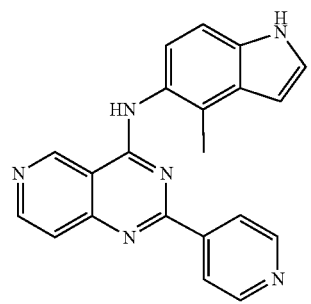
BC18763

-continued
BC18764
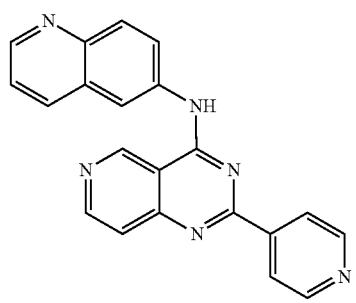
BC18765
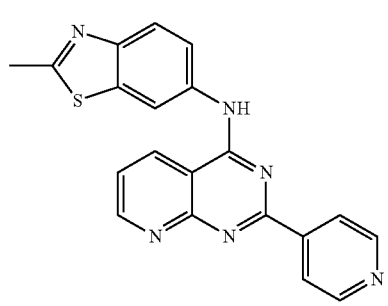
BC18766
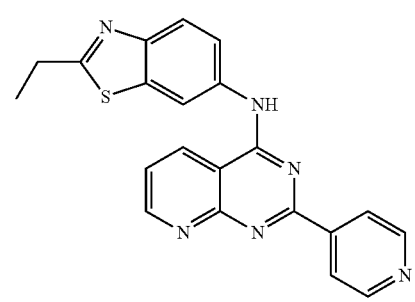
BC18767
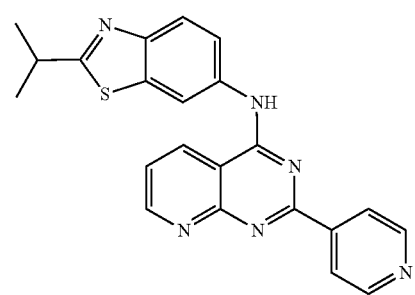
BC18768
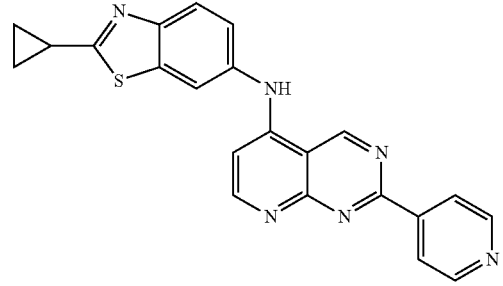
-continued
BC18769
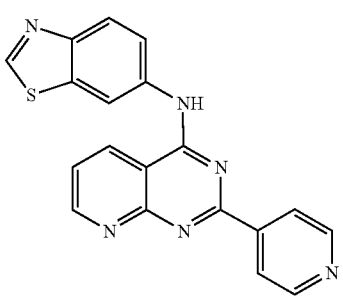
BC18770
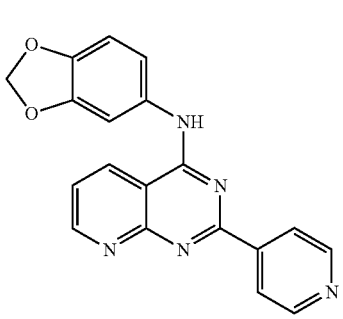
BC18771
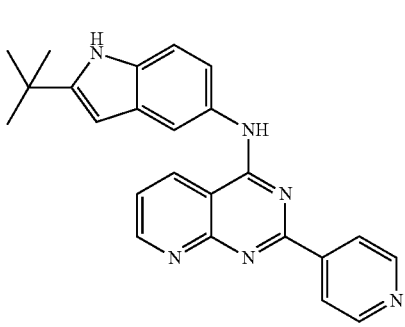
BC18772
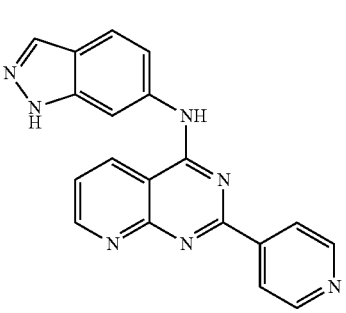
BC18773
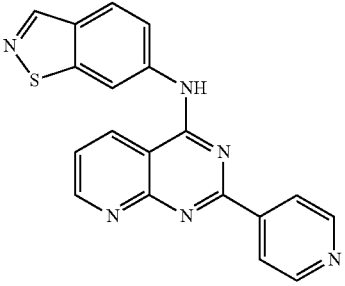

BC18774
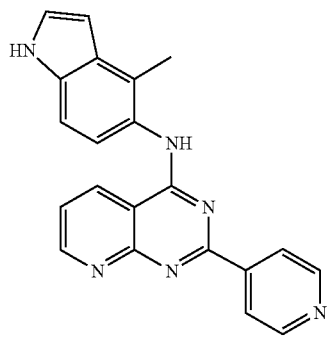
BC18775
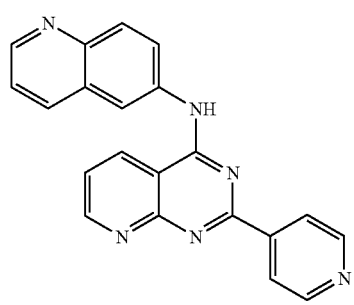
BC18776
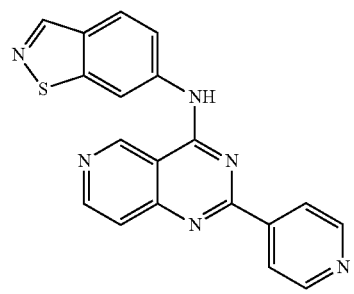
BC18778
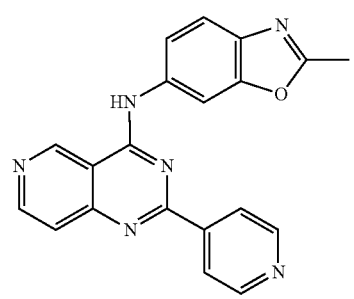
BC18783
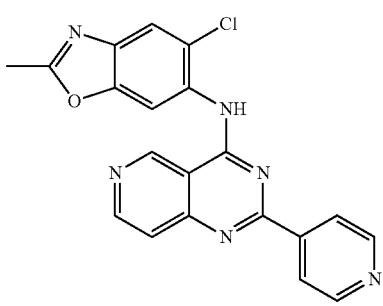
BC18785
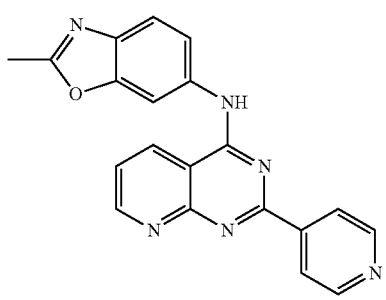
BC18796
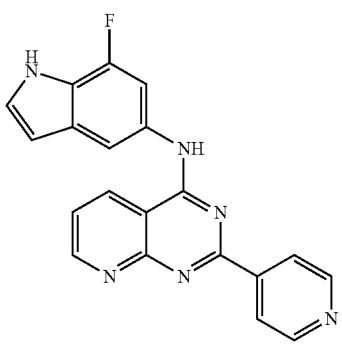
BC18799
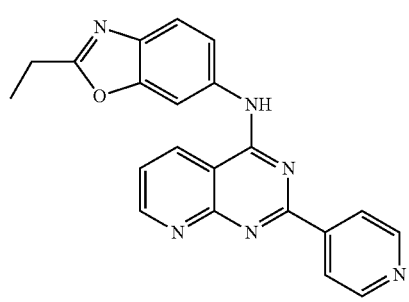
BC18801
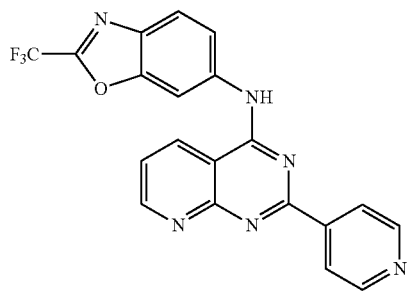
BC18806
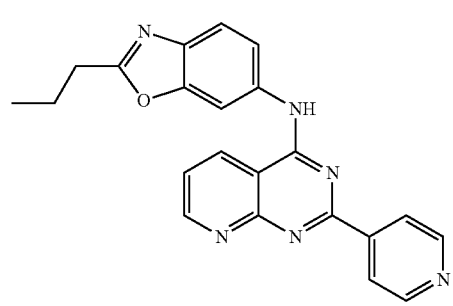

BC18808
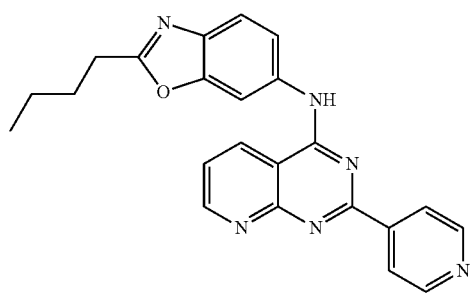
BC18821
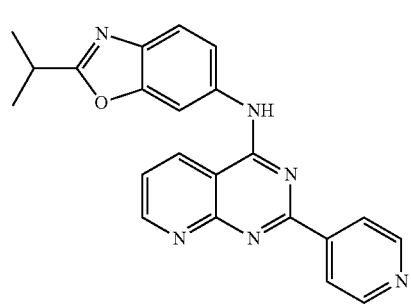
BC18829
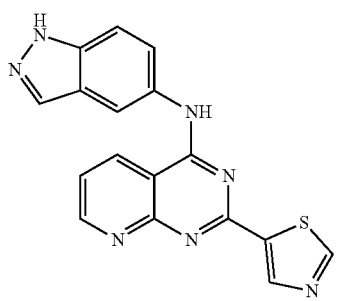
BC18830
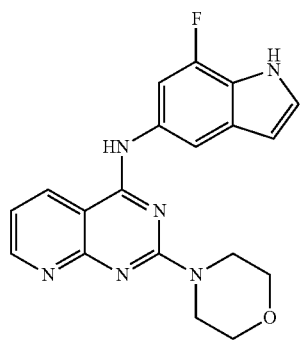
BC18831
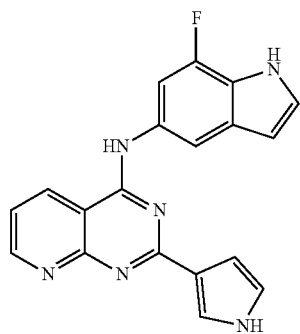
BC18832
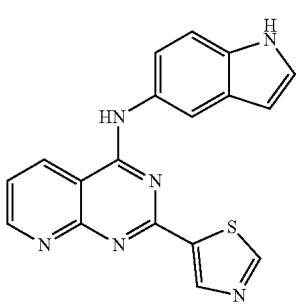
BC18837
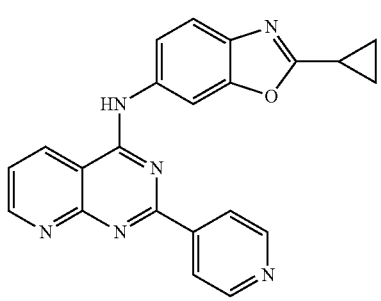
BC18845
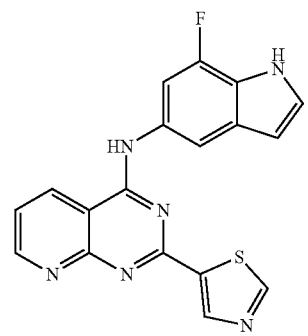
or a pharmaceutically acceptable salt thereof.
In some embodiments, the compound of any one of Formulae (IIc)-(IIi) is selected from any one of the following compounds:
BC18663
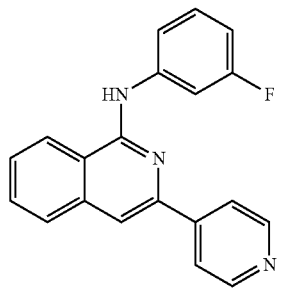

BC18668
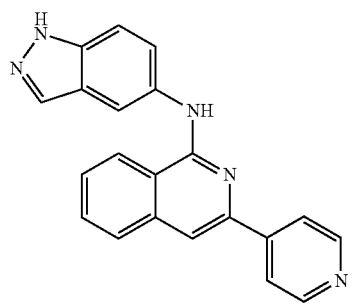
BC18669
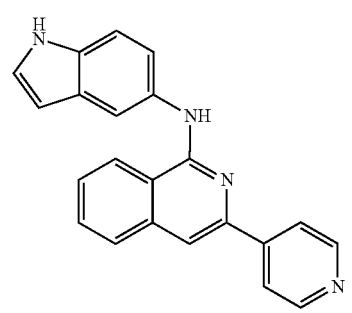
BC18687
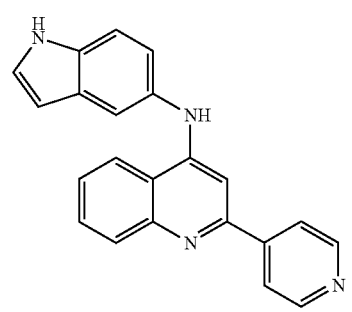
BC18688
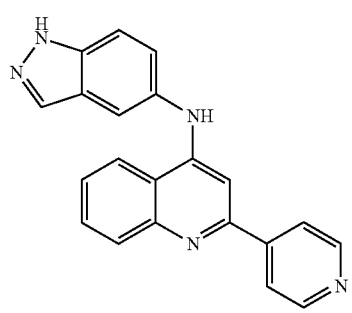
BC18689
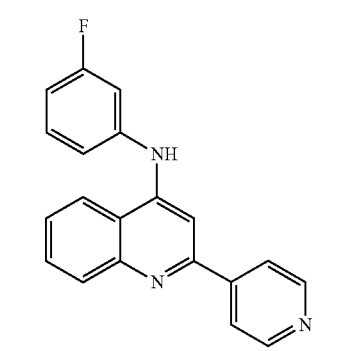
BC18707
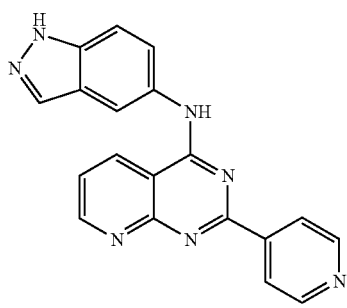
BC18708
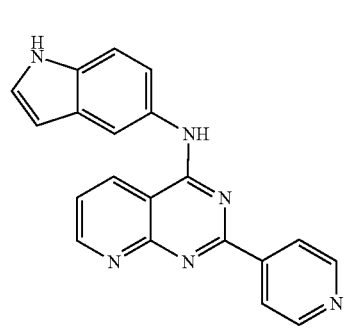
BC18709
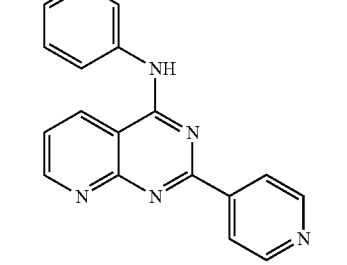
BC18711
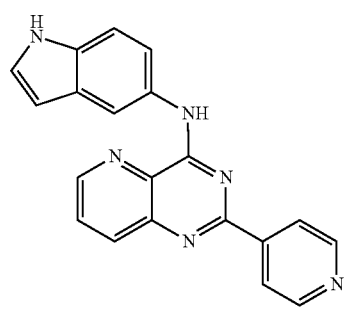
BC18713
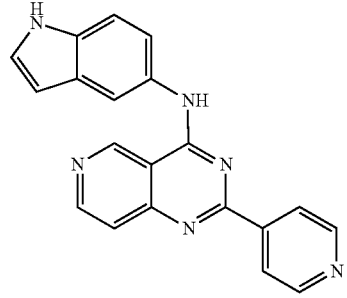

-continued
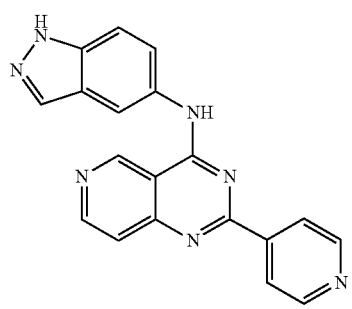
BC18714
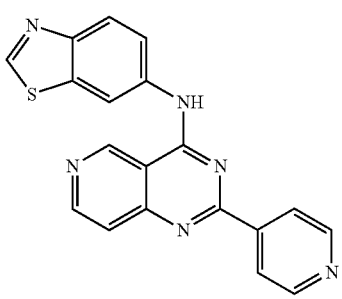
BC18759
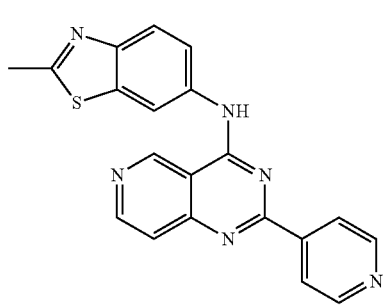
BC18755
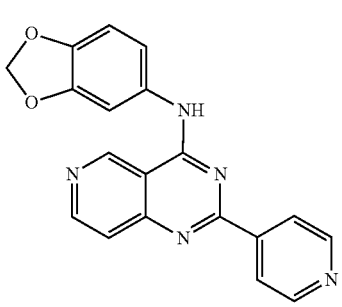
BC18760
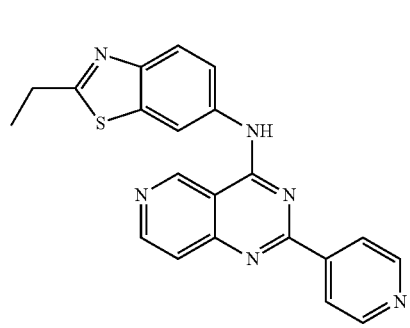
BC18756
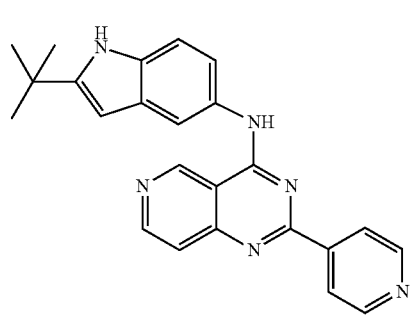
BC18761
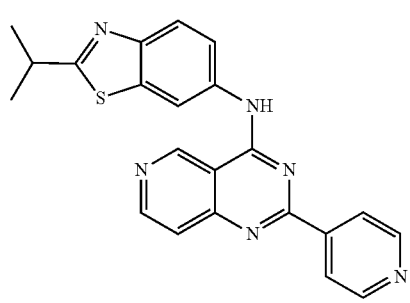
BC18757
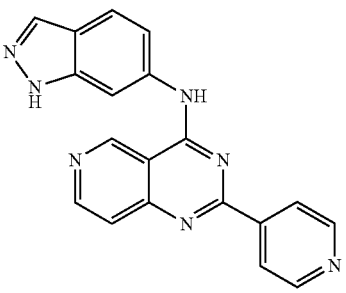
BC18762
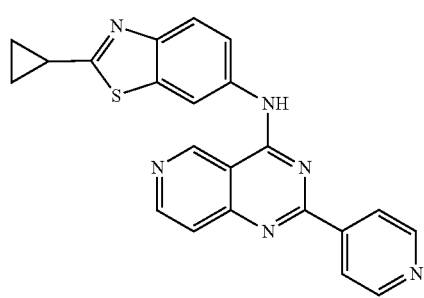
BC18758
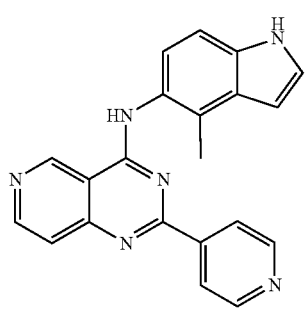
BC18763

BC18764
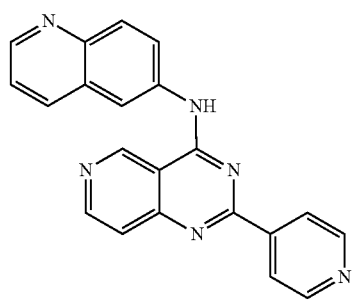
BC18765
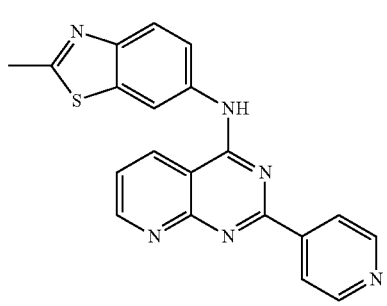
BC18766
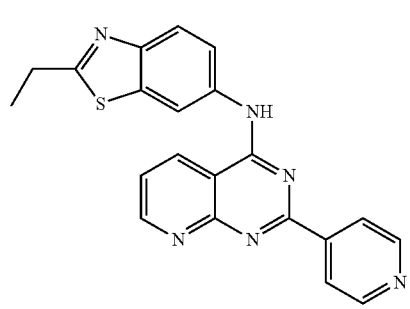
BC18767
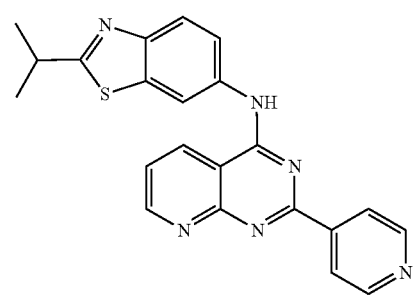
BC18768
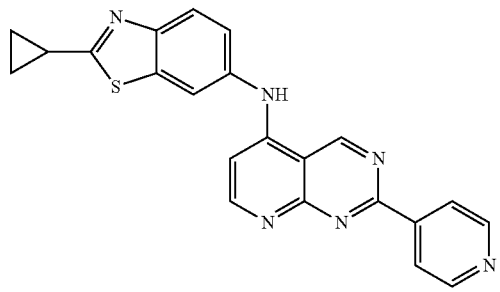
BC18769
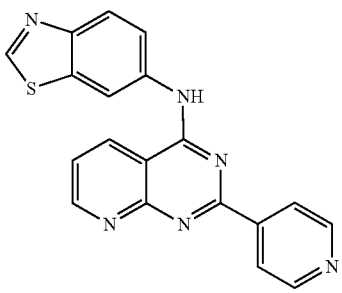
BC18770
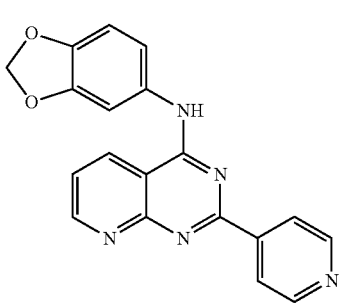
BC18771
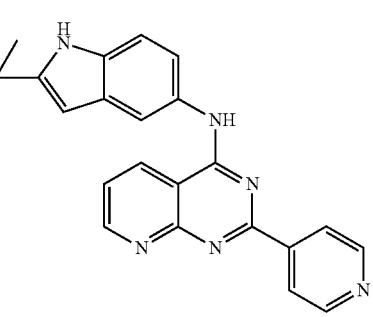
BC18772
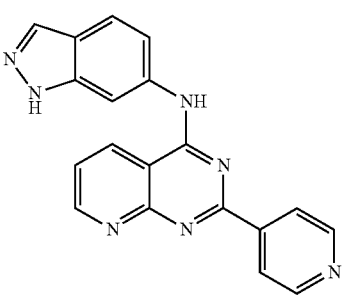
BC18773
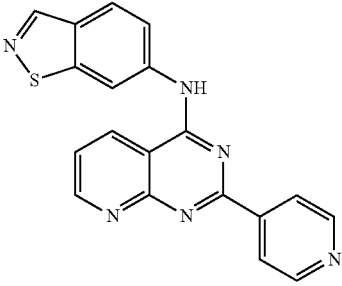

-continued

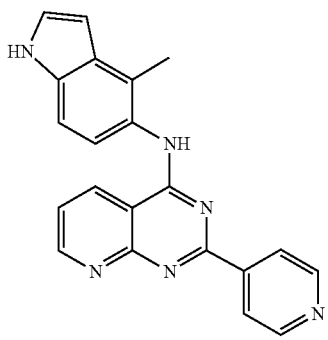

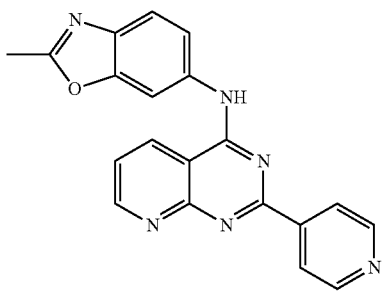

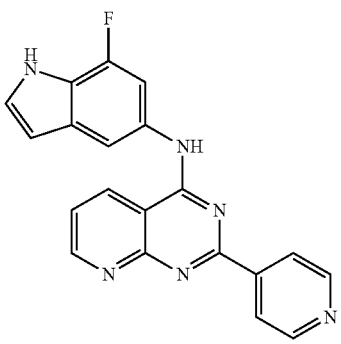

or a pharmaceutically acceptable salt thereof.

In some embodiments, the compound of Formula (IIh) is selected from any one of the compounds listed in Table 5, or a pharmaceutically acceptable salt thereof.

In some embodiments, the compound of Formula (IIh) is selected from any one of the compounds listed in Table 5a, or a pharmaceutically acceptable salt thereof.

In some embodiments, the compound of Formula (IIh) is selected from any one of the compounds listed in Table 5 or Table 5a, or a pharmaceutically acceptable salt thereof.

In some embodiments, the compound of Formula (IIi) is selected from any one of the compounds listed in Table 6, or a pharmaceutically acceptable salt thereof.

In some embodiments, the compound of Formula (I) has Formula (IIa):

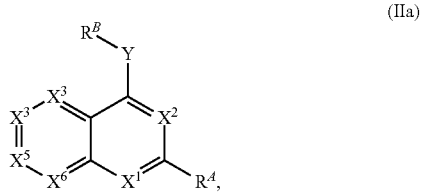

(IIa)

or a pharmaceutically acceptable salt thereof, wherein:
Y is selected from C(=O) and C($R^7$)($R^8$);
$R^7$ and $R^8$ are each independently selected from H, halo, CN, $NO_2$, OH, $C_{1-3}$ alkoxy, amino, $C_{1-3}$ alkylamino, and di($C_{1-3}$alkyl)amino;
$X^1$ is selected from N, $N^+$—$O^-$, and $CR^1$;
$X^2$ is selected from N, $N^+$—$O^-$, and $CR^2$;
$X^3$ is selected from N, $N^+$—$O^-$, and $CR^3$;
$X^4$ is selected from N, $N^+$—$O^-$, and $CR^4$;
$X^5$ is selected from N, $N^+$—$O^-$, and $CR^5$;
$X^6$ is selected from N, $N^+$—$O^-$, and $CR^6$;
provided that no more than four of $X^1$, $X^2$, $X^3$, $X^4$, $X^5$, and $X^6$ are N;

$R^1$, $R^2$, $R^3$, $R^4$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^A$ is selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

$R^B$ is selected from $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

each $R^{Cy1}$ and $R^{Cy2}$ is independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{32}$, $NR^{c2}R^{d2}$, $NR^{c2}C(O)R^{b2}$, $NR^{c2}C(O)OR^{\#2}$, $NR^{c2}S(O)_2R^{b2}$, $S(O)_2R^{b2}$, and $S(O)_2NR^{c2}R^{d2}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{32}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-6}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, CM alkoxy, CM haloalkoxy, cyano-$C_{1-3}$ alkylene, $HO-C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (IIa) has formula:

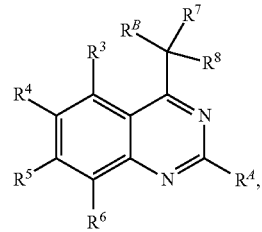

or a pharmaceutically acceptable salt thereof.

In some embodiments, $R^7$ is H, and $R^8$ is selected from H, halo, CN, $NO_2$, OH, and $C_{1-3}$ alkoxy. In some embodiments, $R^7$ is H and $R^8$ is selected from H and OH.

In some embodiments, Y is $CH_2$.

In some embodiments, Y is CH(OH).

In some embodiments, Y is C(=O).

In some embodiments, the compound of Formula (IIa) has formula:

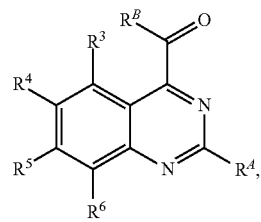

or a pharmaceutically acceptable salt thereof.

In some embodiments of Formula (IIa), $R^1$, $R^2$, $R^3$, $R^4$, $R^5$, and $R^6$ are each independently selected from H, halo, $C_{1-4}$ alkyl, and $C_{1-4}$ alkoxy. In some embodiments, $R^3$, $R^4$, $R^5$, and $R^6$ are each independently selected from H, halo, $C_{1-6}$ alkyl, and $C_{1-6}$ alkoxy. In some embodiments, $R^3$, $R^4$, $R^5$, and $R^6$ are each H.

In some embodiments of Formula (IIa), $R^B$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{Cy2}$.

In some embodiments of Formula (IIa), $R^B$ is $C_{6-10}$ aryl, optionally substituted with halo.

In some embodiments of Formula (IIa), $R^A$ is selected from $C_{6-10}$ aryl, 5-10 membered heteroaryl, and 4-10 membered heterocycloalkyl, each of which is optionally substituted with 1, 2, or 3 substituents independently selected from $R^{Cy1}$.

In some embodiments of Formula (IIa), $R^A$ is 5-10 membered heteroaryl, optionally substituted with halo, $NO_2$, $C_{1-6}$ alkyl, or $C_{1-6}$ alkoxy.

In some embodiments of Formula (IIa):

$R^7$ is H; and $R^8$ is selected from H and OH;

$R^1$, $R^2$, $R^3$, $R^4$, $R^5$, and $R^6$ are each independently selected from H, halo, $C_{1-6}$ alkyl, and $C_{1-6}$ alkoxy;

$R^B$ is $C_{6-10}$ aryl, optionally substituted with halo; and $R^A$ is 5-10 membered heteroaryl, optionally substituted with halo, $NO_2$, $C_{1-6}$ alkyl, or $C_{1-6}$ alkoxy.

In some embodiments, the compound of Formula (IIa) is selected from any one of the following compounds:

BC18615

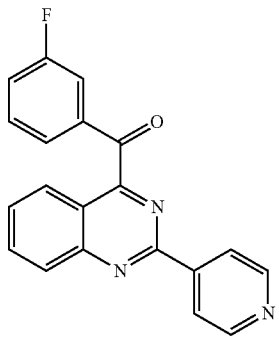

BC18616

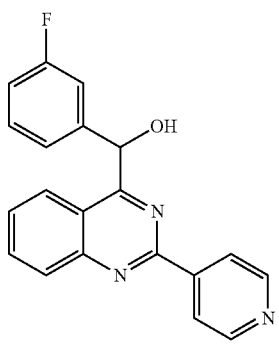

BC18617

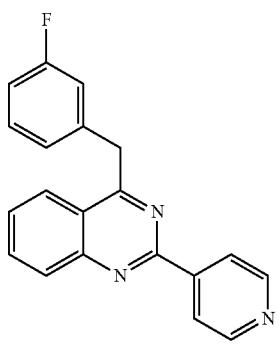

or a pharmaceutically acceptable salt thereof.

In some embodiments, the compound of Formula (I) has Formula (IIb):

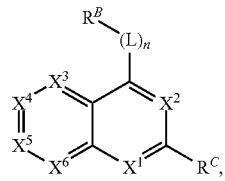

(IIb)

or a pharmaceutically acceptable salt thereof, wherein:

each L is independently selected from O, S, S(=O)$_2$, $C_{1-3}$ alkylene, C(=O), and N($R^N$), wherein said $C_{1-3}$ alkylene is optionally substituted with 1, 2, or 3 substituents independently selected from halo, CN, $NO_2$, OH, $C_{1-3}$ alkoxy, amino, $C_{1-3}$ alkylamino, and di($C_{1-3}$ alkyl)amino;

each $R^N$ is independently selected from H and $C_{1-6}$ alkyl, wherein said $C_{1-6}$ alkyl is optionally substituted with 1, 2, or 3 substituents independently selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

n is an integer selected from 1, 2, and 3;

$X^1$ is selected from N, $N^+$—$O^-$, and $CR^1$;

$X^2$ is selected from N, $N^+$—$O^-$, and $CR^2$;

$X^3$ is selected from N, $N^+$—$O^-$, and $CR^3$;

$X^4$ is selected from N, $N^+$—$O^-$, and $CR^4$;

$X^5$ is selected from N, $N^+$—$O^-$, and $CR^5$;

$X^6$ is selected from N, $N^+$—$O^-$, and $CR^6$;

provided that no more than four of $X^1$, $X^2$, $X^3$, $X^4$, $X^5$, and $X^6$ are N;

each of $R^1$, $R^2$, $R^3$, $R^4$, $R^5$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^C$ is selected from:
(i) 4-10 membered heterocycloalkyl, which is optionally substituted with 1, 2, or 3 substituents independently selected from $R^{Cy1}$; and
(ii) a group selected from O-$Cy^{A1}$, N($R^N$)—$Cy^{A1}$; and $Cy^{A1}$;

each $Cy^{A1}$ is a 5-10 membered heteroaryl group of the formula selected from:

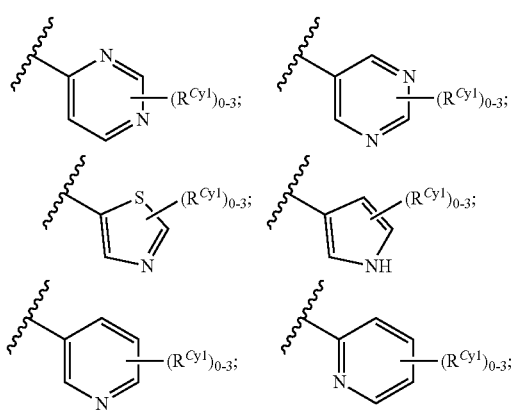

-continued

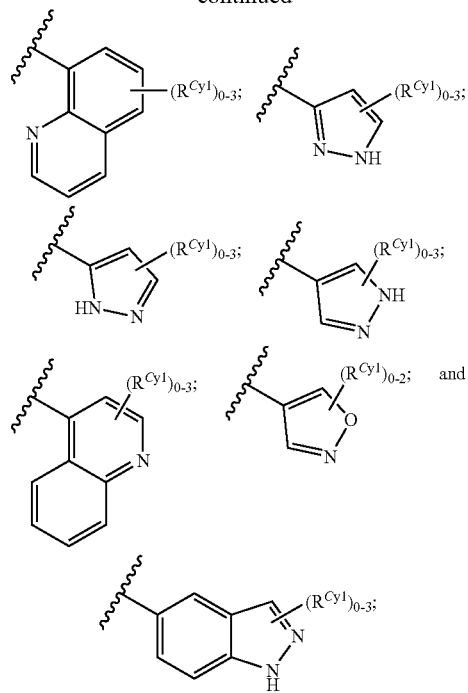

$R^B$ is selected from $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

or, when $R^B$ is attached to $N(R^N)$, $R^B$ and $R^N$ together with the N atom to which they are attached form 4-7 membered heterocycloalkyl, which is optionally substituted with 1, 2, or 3 substituents independently selected from $Cy^1$, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

$R^{Cy1}$ and $R^{Cy2}$ are each independently selected from halo, CN, $NO_2$, $Cy^2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{32}$, $NR^{c2}R^{d2}$, $NR^{c2}C(O)R^{b2}$, $NR^{c2}C(O)OR^{\#2}$, $NR^{c2}S(O)_2R^{b2}$, $S(O)_2R^{b2}$, and $S(O)_2NR^{c2}R^{d2}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1,2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino.

In some embodiments, $R^C$ is selected from 4-10 membered heterocycloalkyl, which is optionally substituted with 1, 2, or 3 substituents independently selected from $R^{Cy1}$; and a 5-10 membered heteroaryl group of the formula selected from:

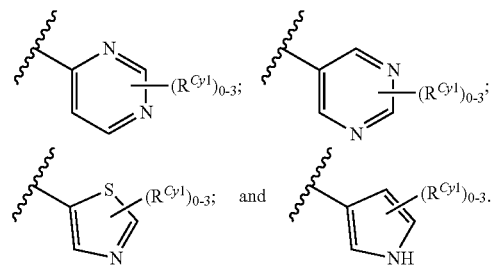

In some embodiments of the compound of Formula (IIb), the 4-10 membered heterocycloalkyl of $R^C$ has the formula selected from:

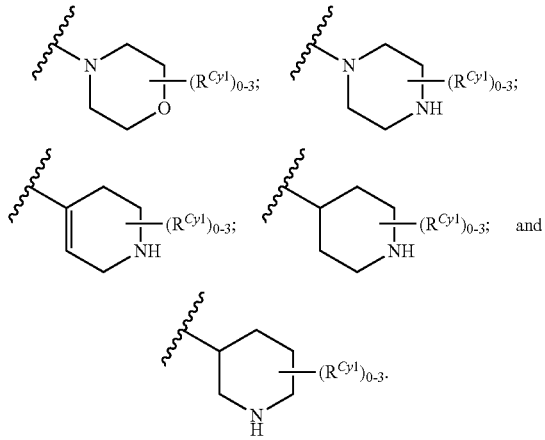

In some embodiments of the compound of Formula (IIb), the 4-10 membered heterocycloalkyl of $R^C$ has the formula selected from:

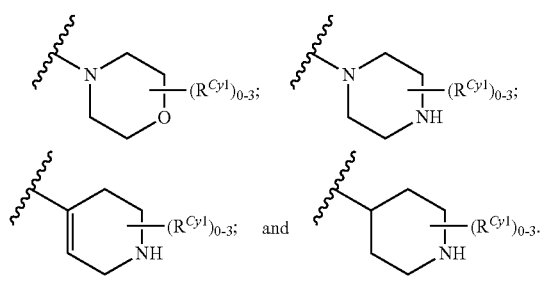

In some embodiments of the compound of Formula (IIb):

n is 1;

L is selected from $C_{1-3}$ alkylene, $C(=O)$, and $N(R^N)$, wherein said $C_{1-3}$ alkylene is optionally substituted with OH;

$R^N$ is selected from H and $C_{1-6}$ alkyl;

$R^1, R^2, R^3, R^4, R^5$, and $R^6$ are each independently selected from H, halo, CN, $C_{1-6}$ alkyl, $OR^{a1}$, $NR^{c1}R^{d1}$, and $S(O)_2R^{b1}$;

$R^C$ is selected from:

(i) 4-10 membered heterocycloalkyl selected from:

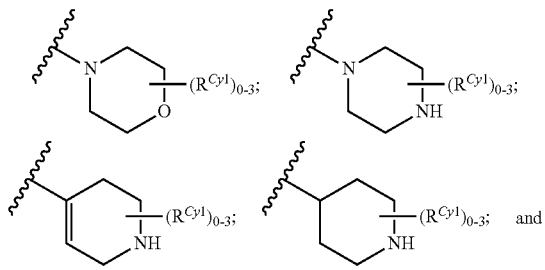

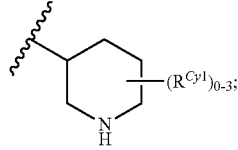

and (ii) a group selected from $O-Cy^{41}$, $N(R^N)—Cy^{41}$; and $Cy^{41}$, wherein each $Cy^{41}$ is a 5-10 membered heteroaryl group of the formula selected from:

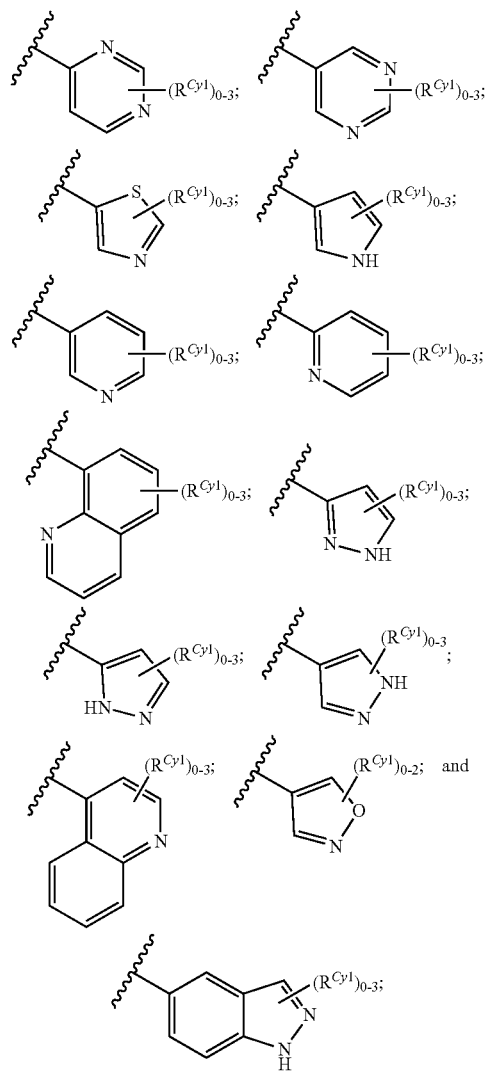

$R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{a1}$, $S(O)_2R^{b1}$, and $S(O)_2NR^{c1}R^{d1}$;

or, when $R^B$ is attached to $N(R^N)$, $R^B$ and $R^N$ together with the N atom to which they are attached form 4-7 membered heterocycloalkyl, which is optionally substituted with $OR^{a1}$;

each $R^{Cy1}$ is independently selected from halo, $NO_2$, $C_{1-6}$ alkyl, $C_{1-6}$ haloalkyl, $OR^{a2}$, $C(O)OR^{a2}$, $C(O)R^{b2}$, C(O)

$NR^{c2}R^{d2}$, $NR^{c2}R^{d2}$, and $S(O)_2R^{b2}$, wherein said $C_{1-6}$ alkyl is optionally substituted with $OR^{a2}$;

each $R^{Cy2}$ is independently selected from halo, CN, $C_{3-10}$ cycloalkyl, $C_{1-6}$ alkyl, $C_{1-6}$ haloalkyl, $OR^{a2}$, $C(O)R^{b2}$, $C(O)NR^{c2}R^{d2}$, and $NR^{c2}R^d$; and each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments of the compound of Formula (IIb):

n is 1;

L is selected from $C_{1-3}$ alkylene, $C(=O)$, and $N(R^N)$, wherein said $C_{1-3}$ alkylene is optionally substituted with OH;

$R^N$ is selected from H and $C_{1-6}$ alkyl;

$R^1$, $R^2$, $R^3$, $R^4$, $R^5$, and $R^6$ are each independently selected from H, halo, $C_{1-6}$ alkyl, and $OR^{a1}$;

$R^C$ is selected from:

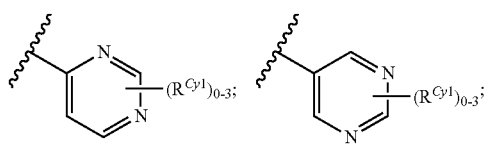

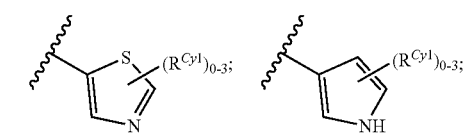

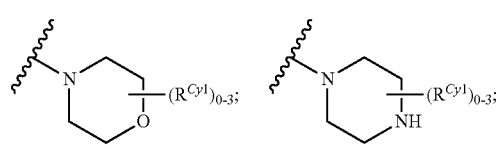

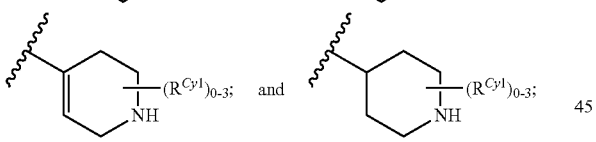

$R^B$ is selected from $C_{1-6}$ alkyl and $Cy^1$, wherein said $C_{1-6}$ alkyl is optionally substituted with 1, 2, or 3 substituents independently selected from $Cy^1$, CN, $OR^{a1}$, $S(O)_2R^{b1}$, and $S(O)_2NR^{c1}R^{d1}$;

or, when $R^B$ is attached to L which is $N(R^N)$, $R^B$ and $R^N$ together with the N atom to which they are attached form 4-7 membered heterocycloalkyl, which is optionally substituted with $OR^{a1}$;

each $R^{Cy1}$ is independently selected from halo, $NO_2$, $C_{1-6}$ alkyl, $OR^{a2}$, and $C(O)OR^{a2}$;

each $R^{Cy2}$ is independently selected from halo, CN, $C_{3-10}$ cycloalkyl, $C_{1-6}$ alkyl, $C_{1-6}$ haloalkyl, $OR^{a2}$, $C(O)R^{b2}$, $C(O)NR^{c2}R^{d2}$, and $NR^{c2}R^d$; and each $R^{a1}$, $R^{b1}$, $R^{c1}$, $R^{d1}$, $R^{a2}$, $R^{b2}$, $R^{c2}$, and $R^{d2}$ is independently selected from H and $C_{1-6}$ alkyl.

In some embodiments, the compound of Formula (IIb) is selected from any one of the following compounds:

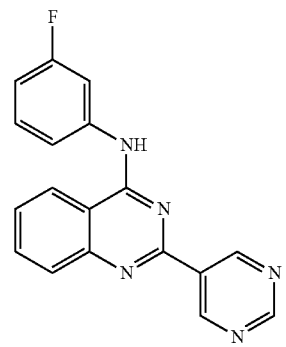

BC18618

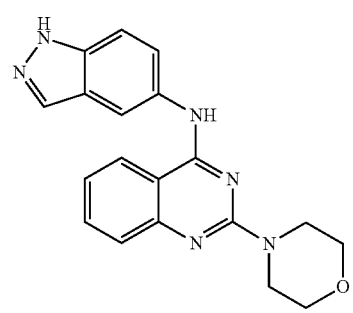

BC18664

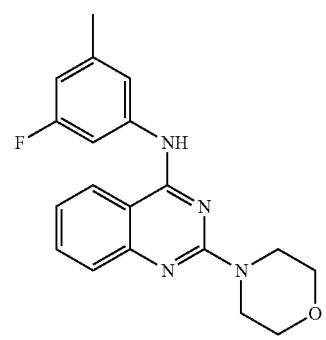

BC18666

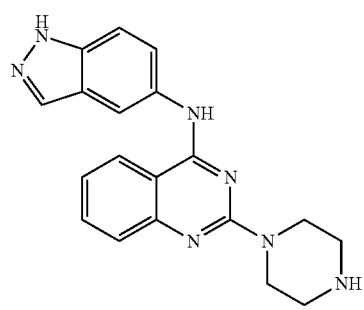

BC18670

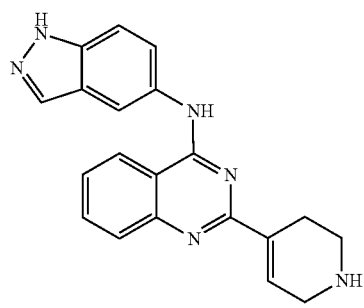

BC18702

BC18703
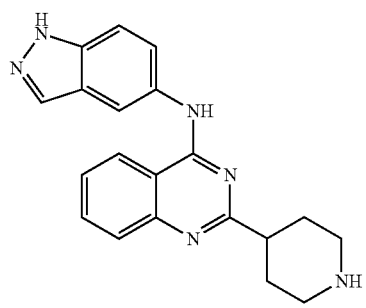
BC18704
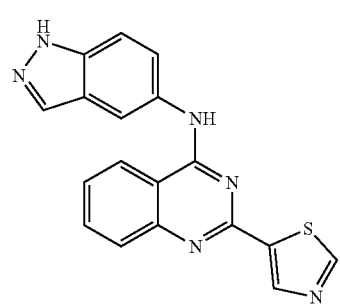
BC18705
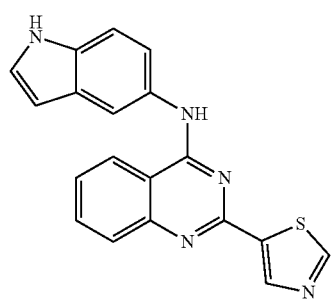
BC18706
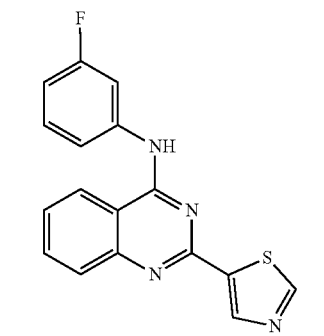
BC18720
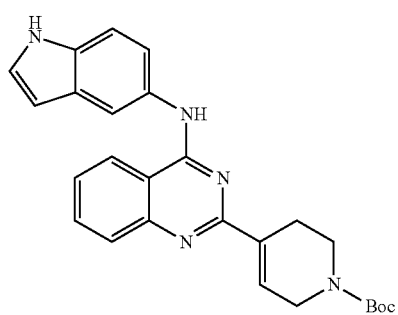
BC18722
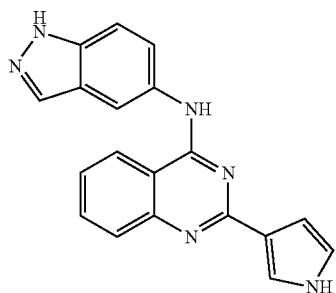
BC18738
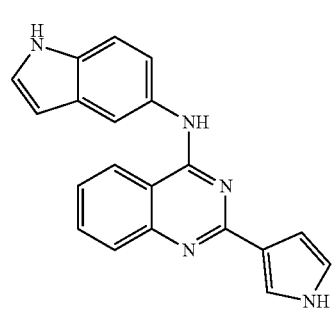
NC18740
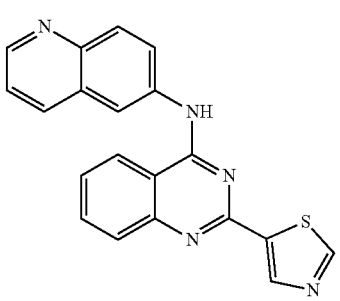
NC18742
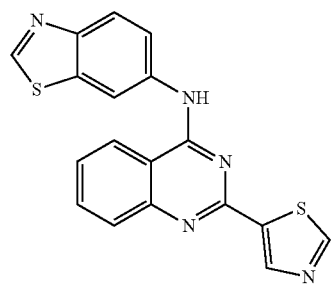
NC18853
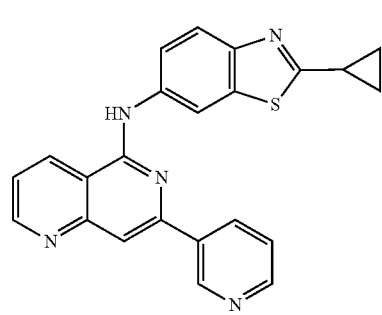

BC18854
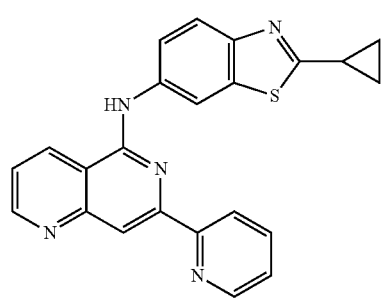
BC191107
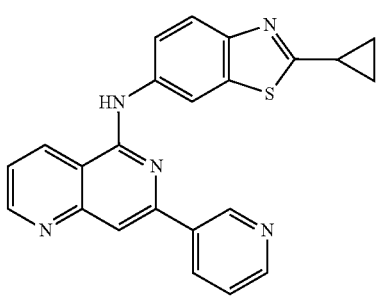
BC191108
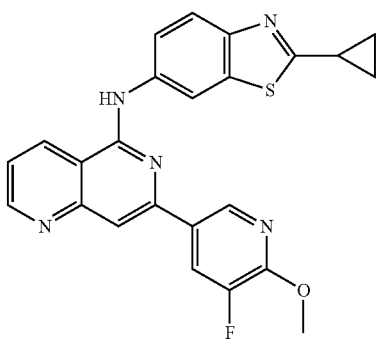
BC19109
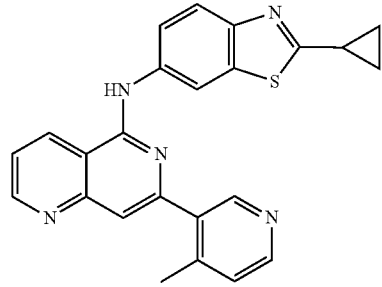
BC191110
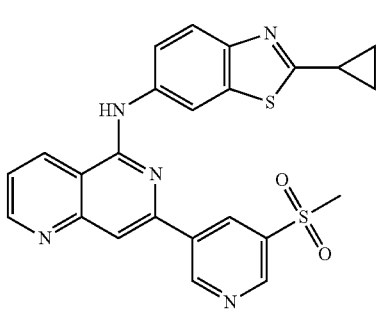
BC191111
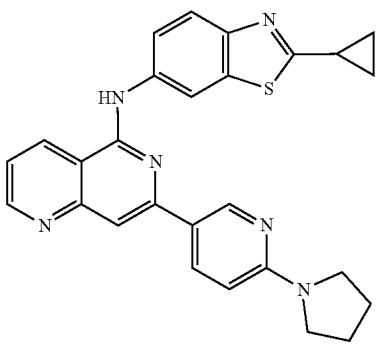
BC191112
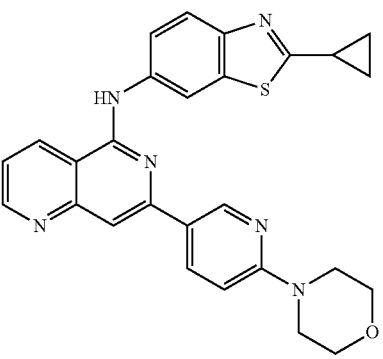
BC191113
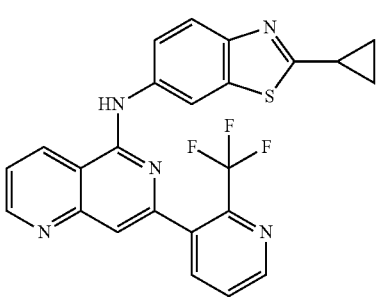
BC191114
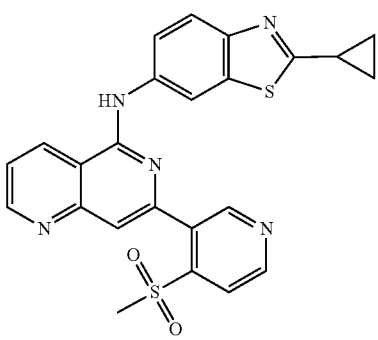

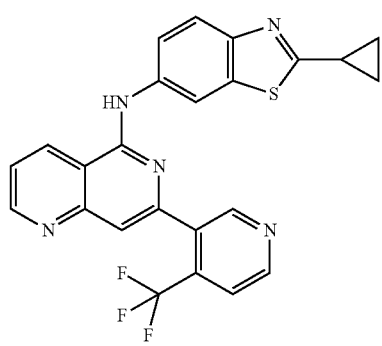
BC1911115
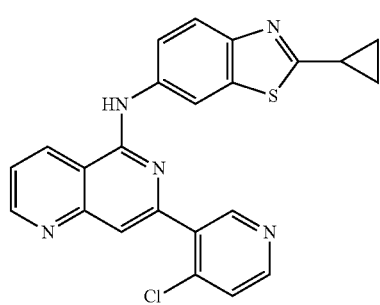
BC191116
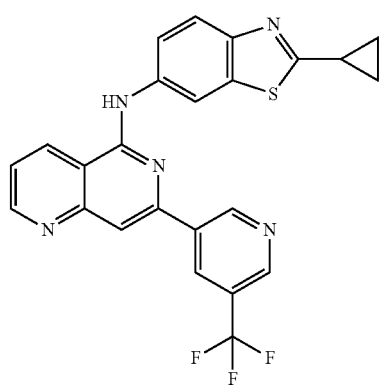
BC191117
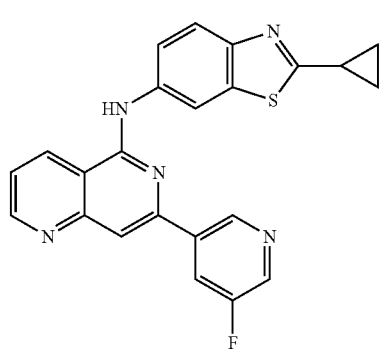
BC191118
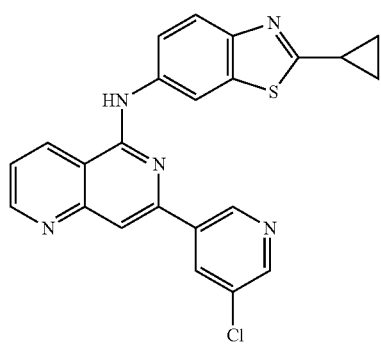
BC191119
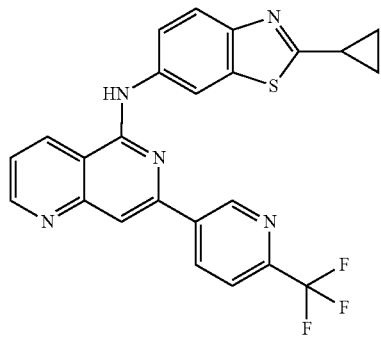
BC191120
BC191121
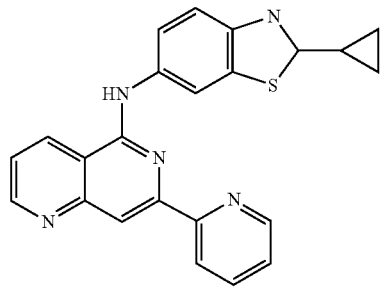
BC191122

BC191123
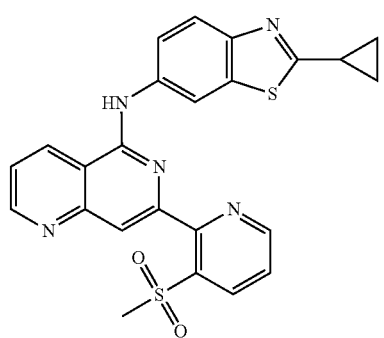
BC191124
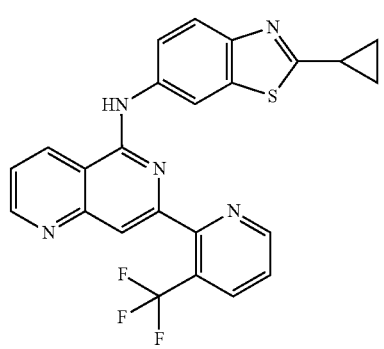
BC191125
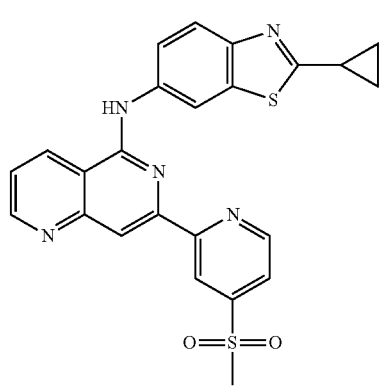
BC191126
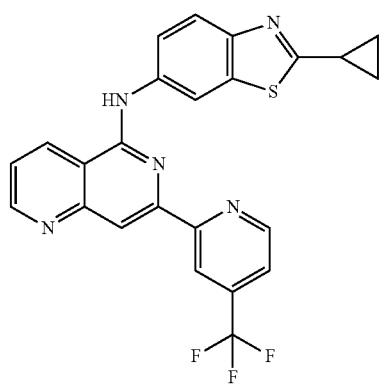
BC191127
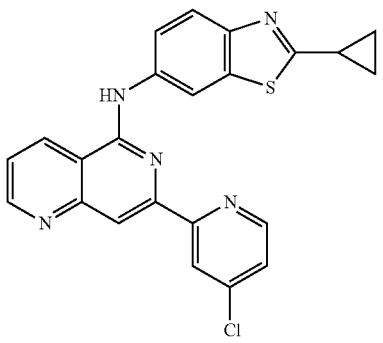
BC191128
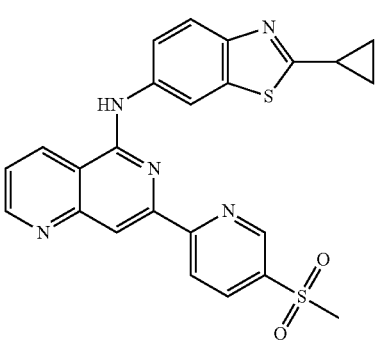
BC191129
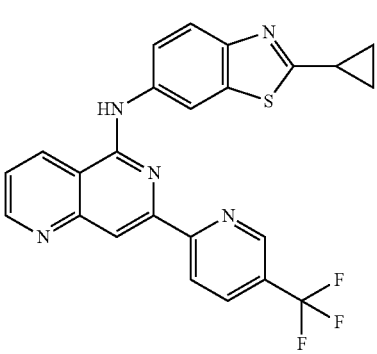
BC191130
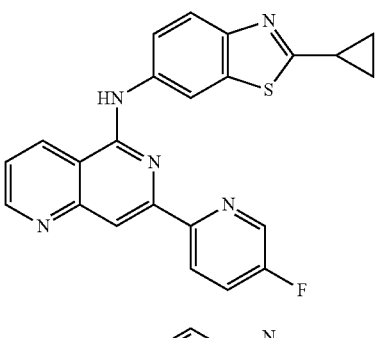
BC191131
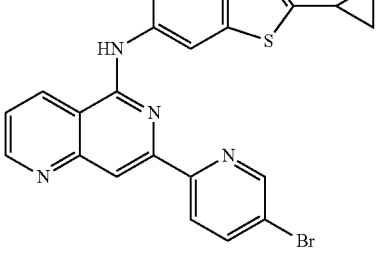

-continued
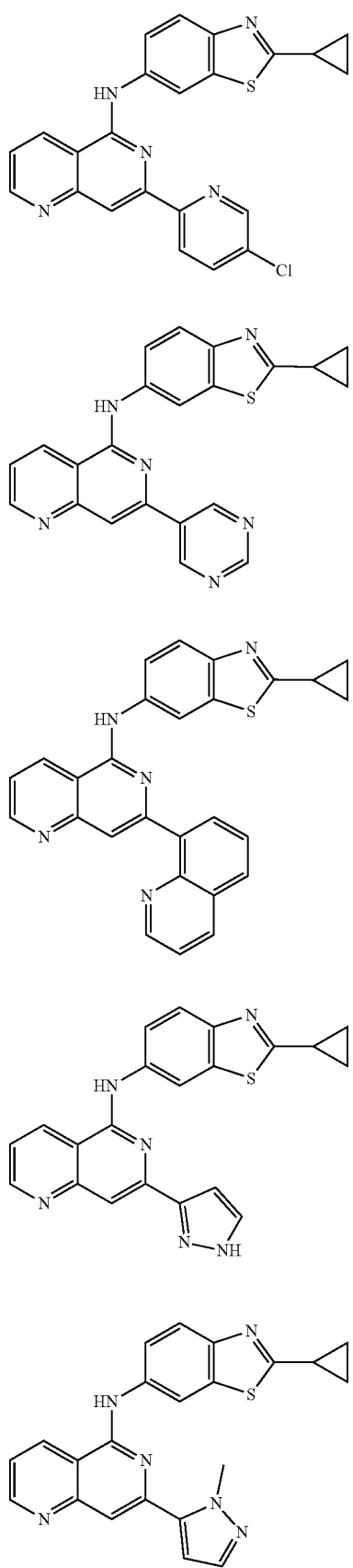
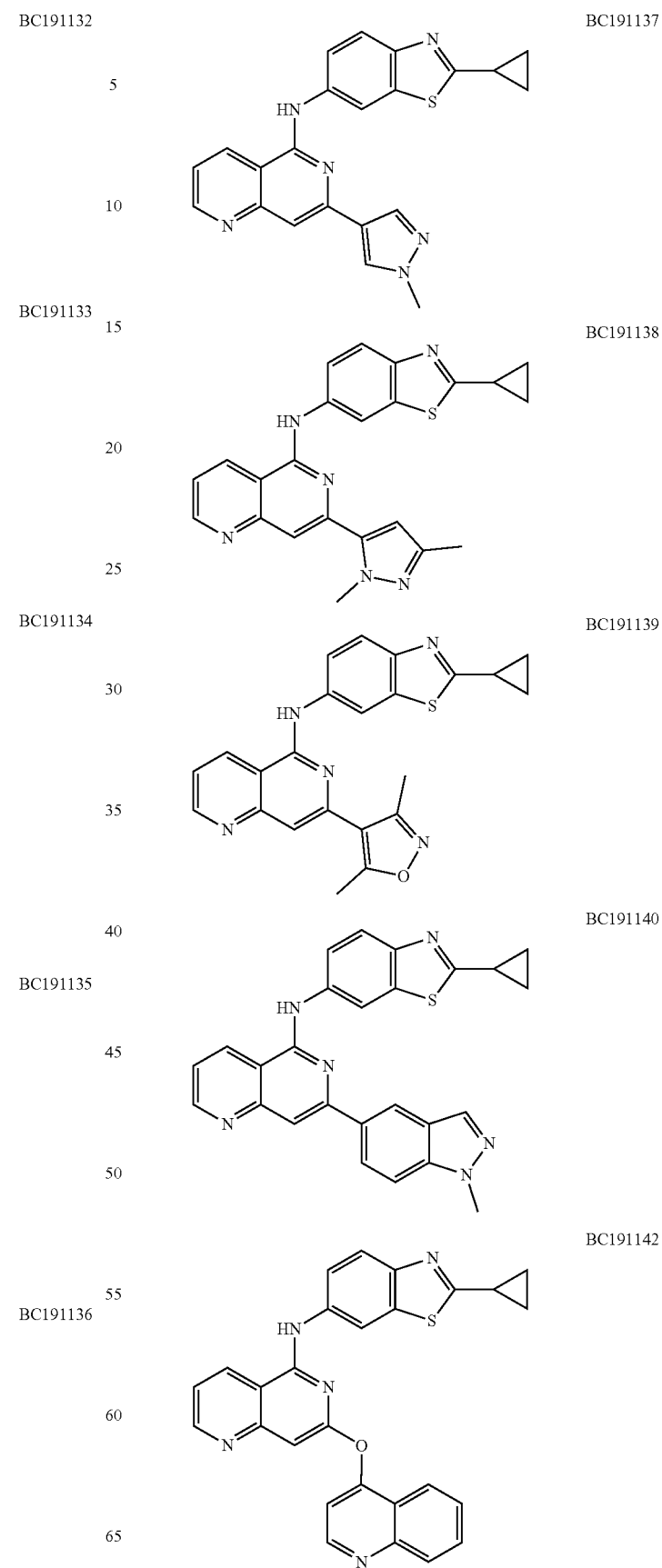

BC191143
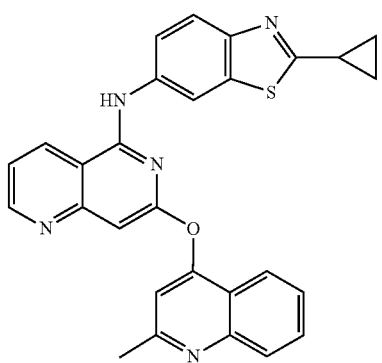
BC191144
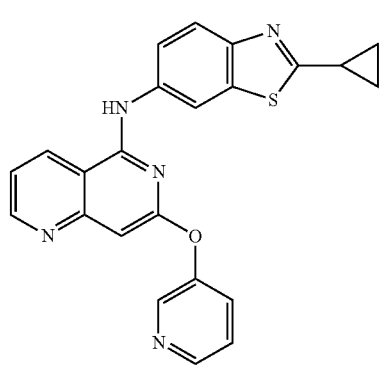
BC191145
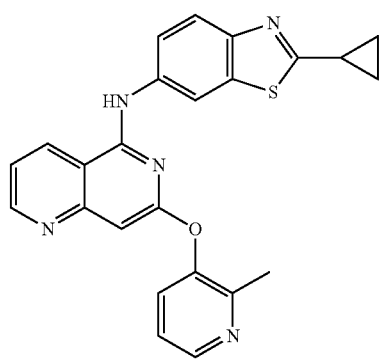
BC191146
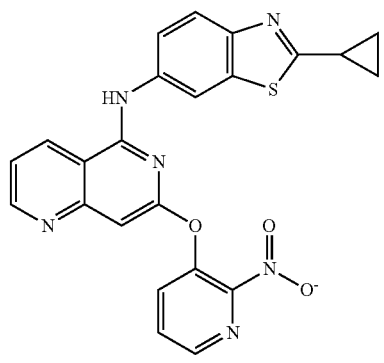
BC191147
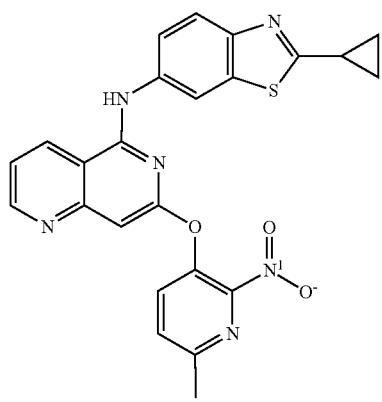
BC191148
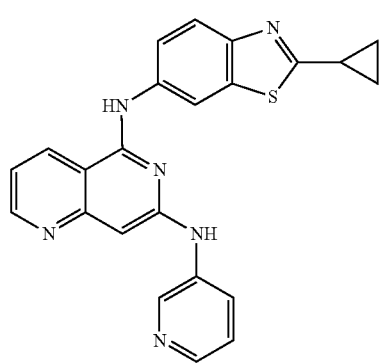
BC191149
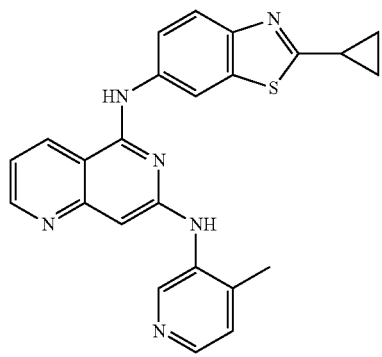
BC191150
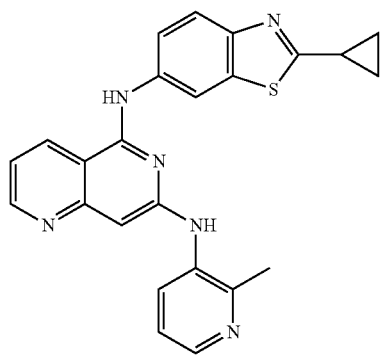

BC191151
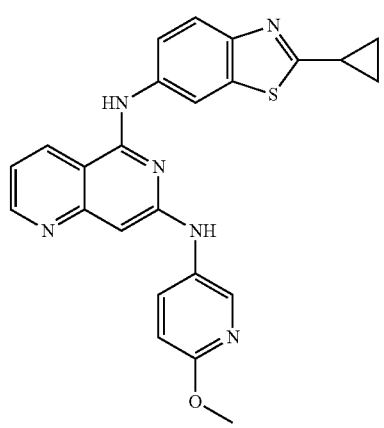
BC191152
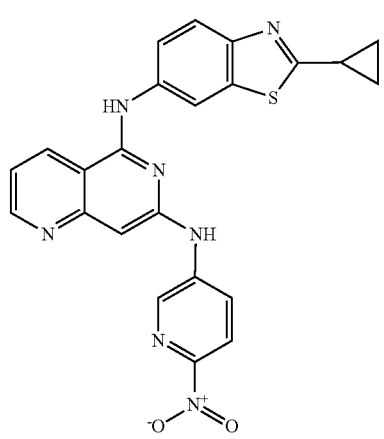
BC191155
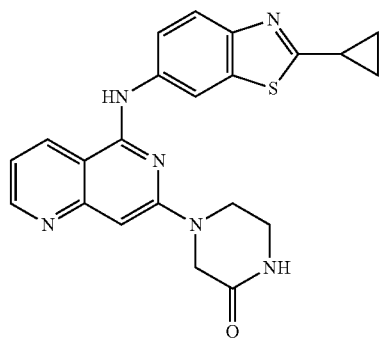
BC191156
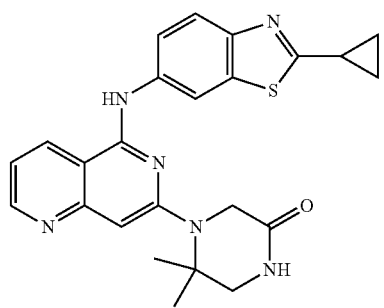
BC191157
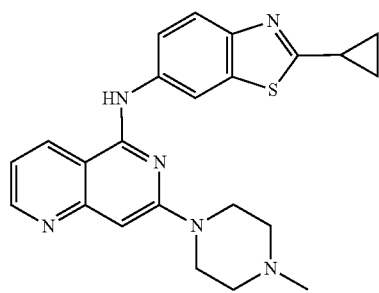
BC191158
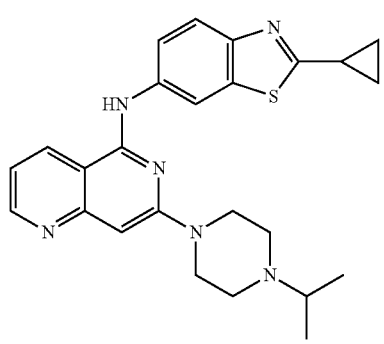
BC191159
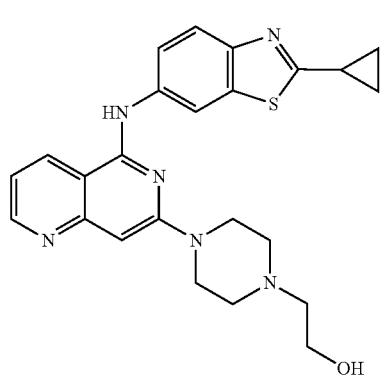
BC191160
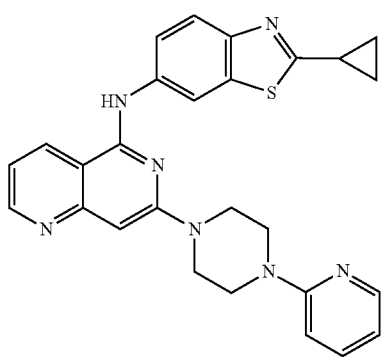

-continued
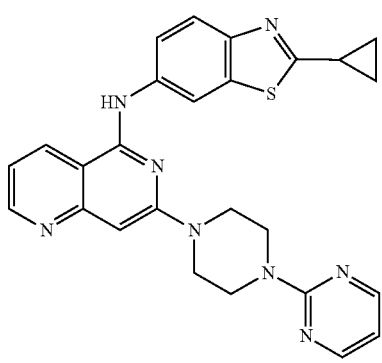
BC191161
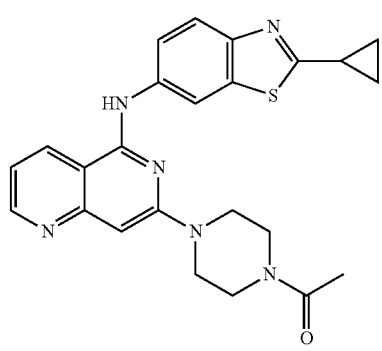
BC191162
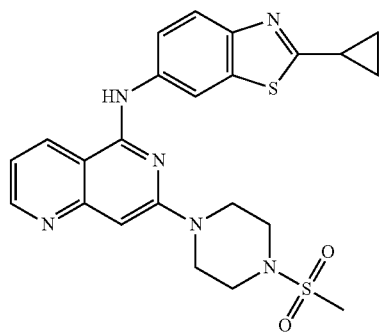
BC191163
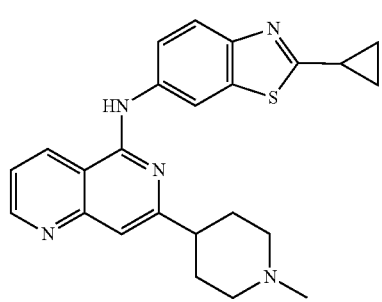
BC191164
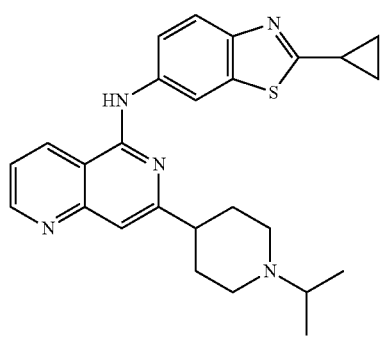
BC191165
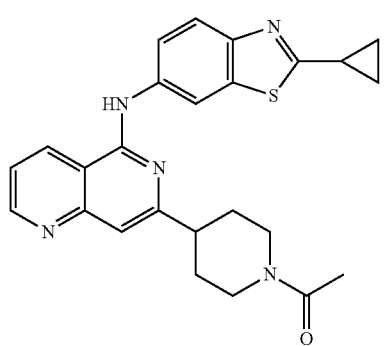
BC191166
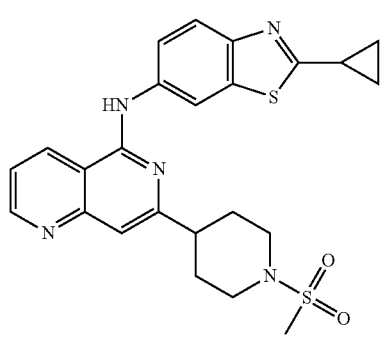
BC191167
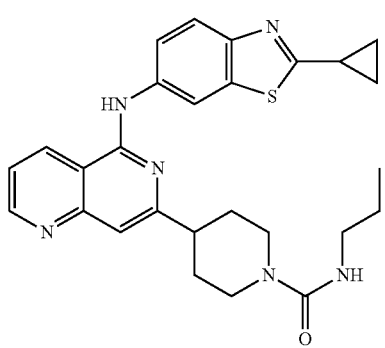
BC191168

-continued
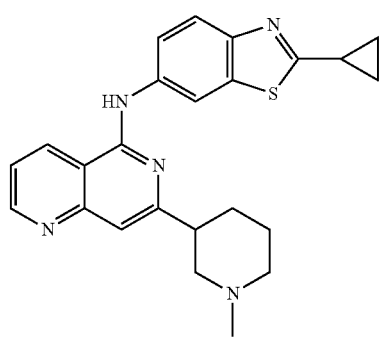
BC191169
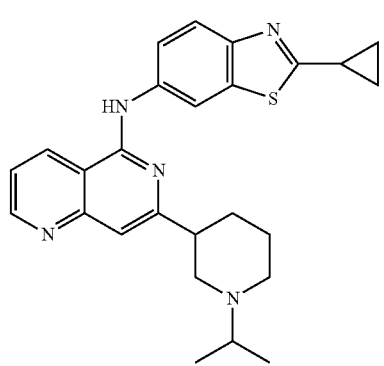
BC191170
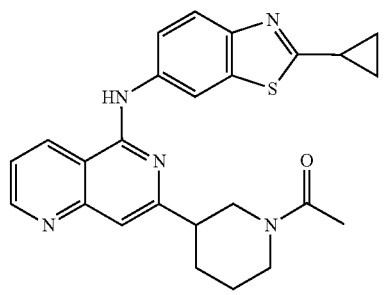
BC191171
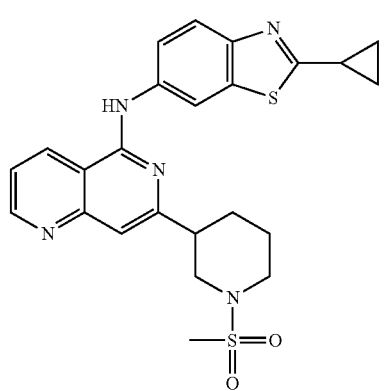
BC191172
-continued
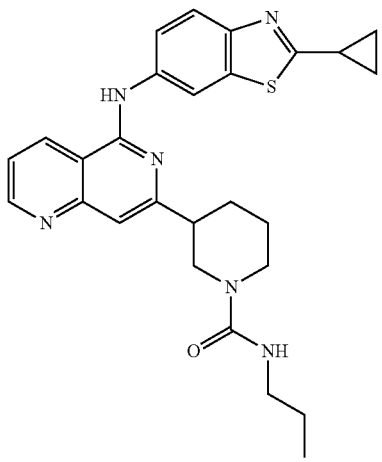
BC191173
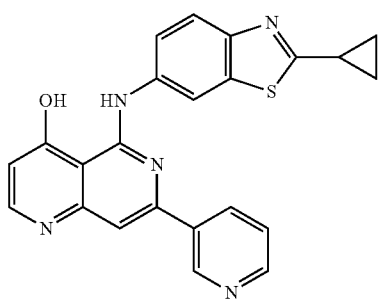
BC191185
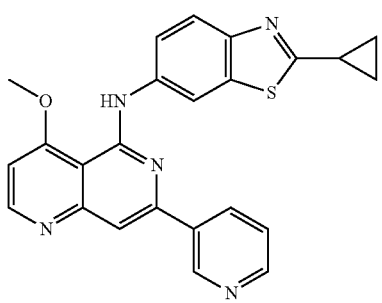
BC191186
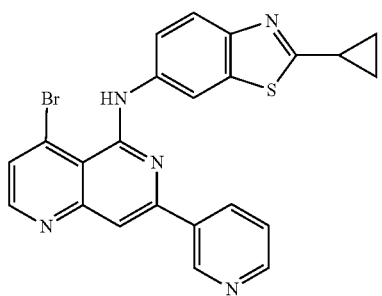
BC191187

-continued
BC191188
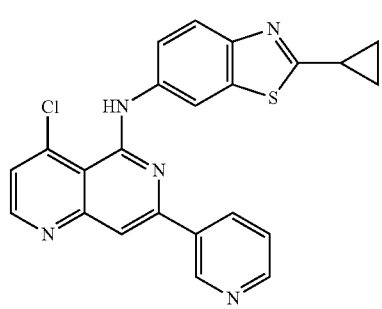
BC191193
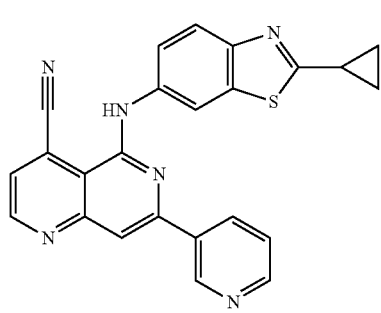
BC191189
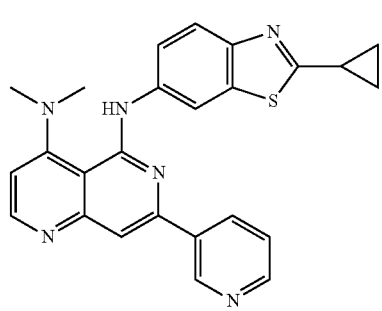
BC191194
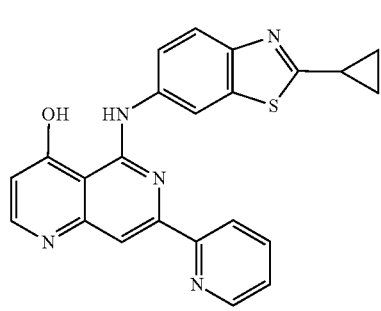
BC191190
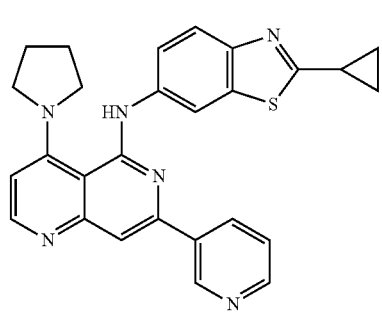
BC191195
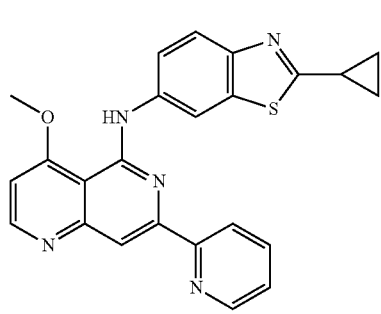
BC181191
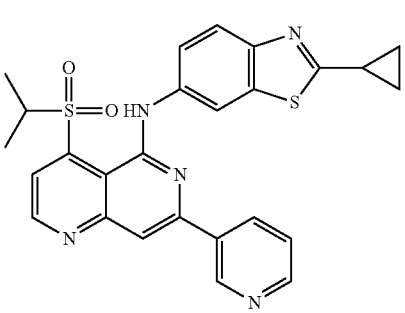
BC191196
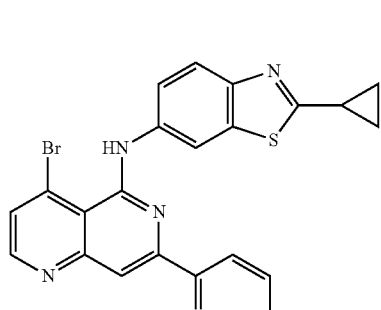
BC191192
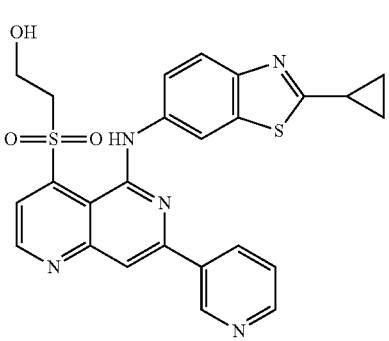
BC191197
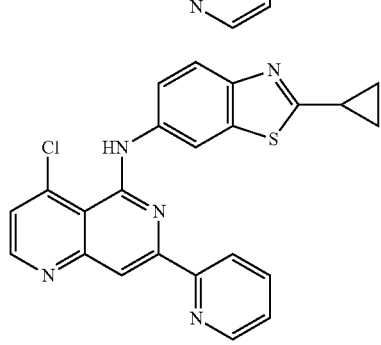

105
-continued
BC191198
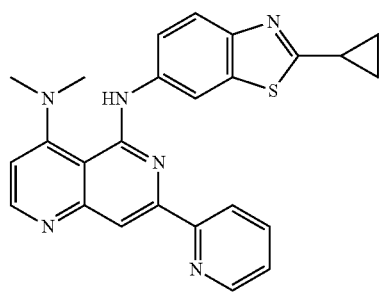
BC1-191199
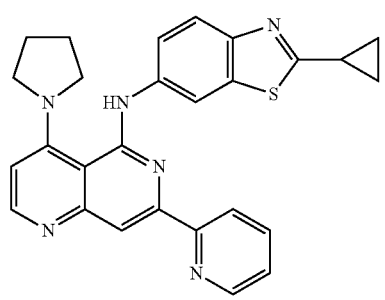
BC191200
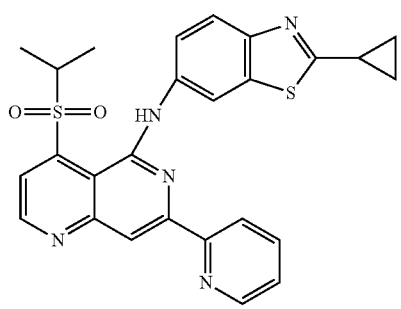
BC191201
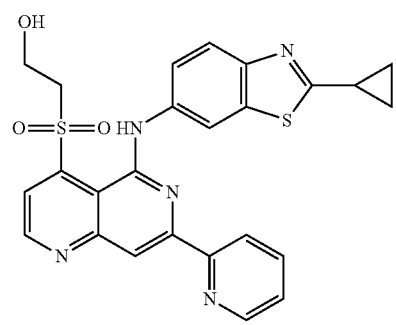
BC191202
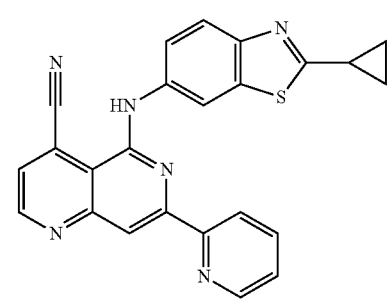
106
-continued
BC18829
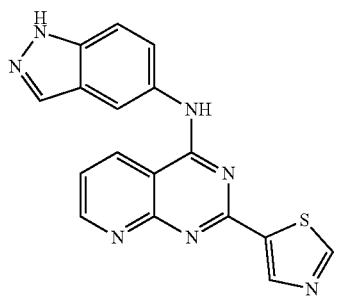
BC18830
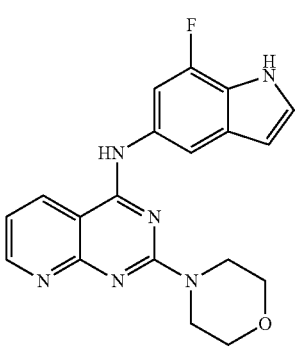
BC18831
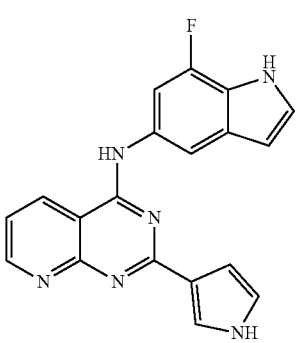
BC18832
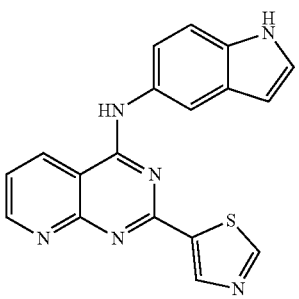
BC18833
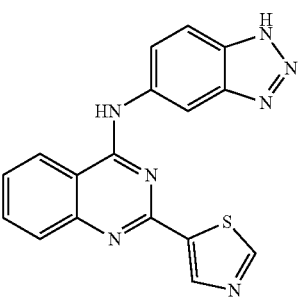

BC18834

BC18835

BC18836

BC18838

BC18839

BC18840

BC18841

BC18845 or a pharmaceutically acceptable salt thereof.

In some embodiments, the compound of Formula (IIb) is selected from any one of the following compounds:

BC18618

-continued
BC18664
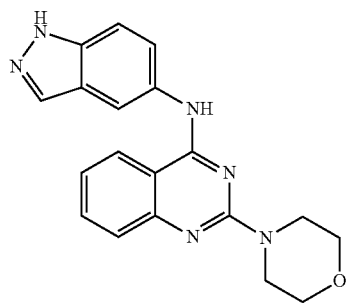
BC18666
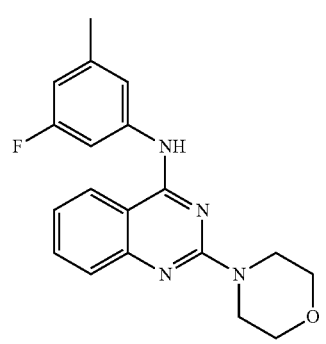
BC18670
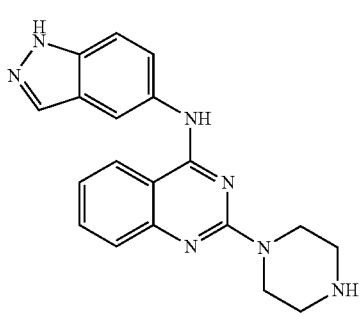
BC18702
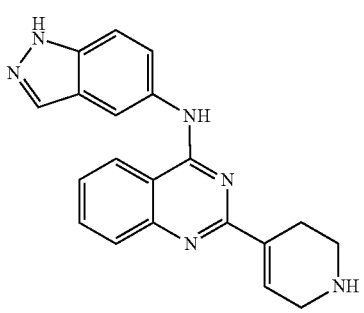
BC18703
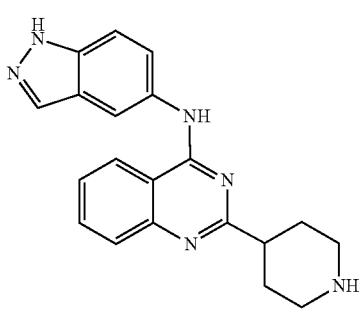
-continued
BC18704
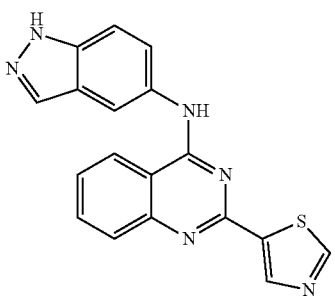
BC18705
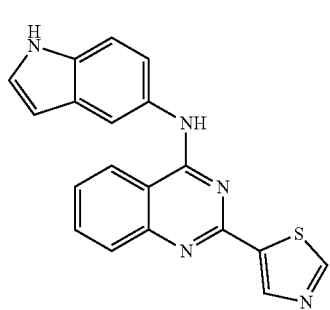
BC18706
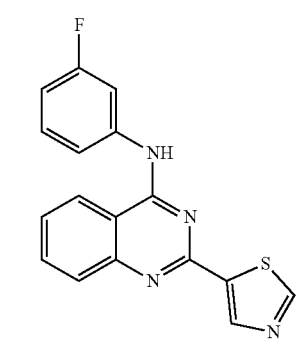
BC18720
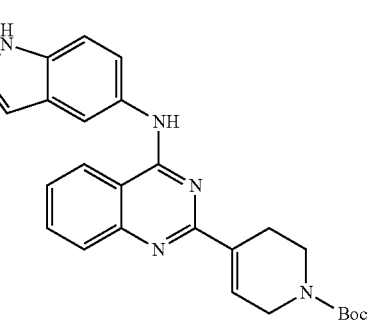
BC18722
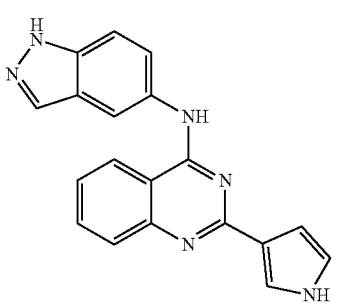

-continued

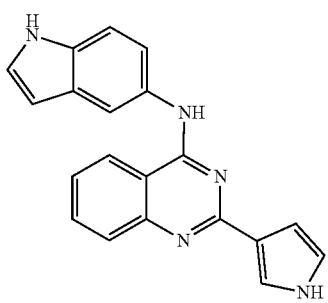
BC18738

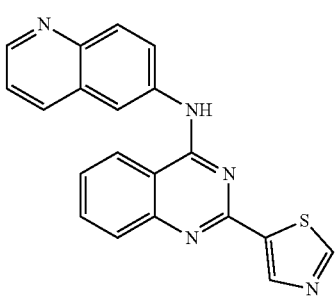
BC18740

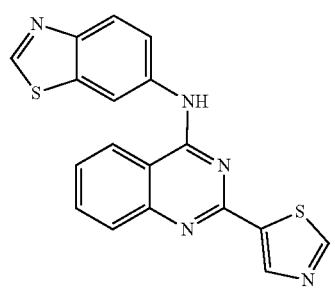
BC18742 or a pharmaceutically acceptable salt thereof.

In some embodiments, the document provides a compound of Formula (III):

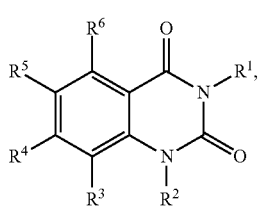

(III)

or a pharmaceutically acceptable salt thereof, wherein:

$R^1$ is selected from $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^2$ is selected from H, $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^3$, $R^4$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy2}$;

each $R^{Cy2}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, and $C(O)R^{b2}$, $C(O)NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-6}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, CM alkenyl, $C_{2-6}$ alkynyl, $C_{1-4}$ haloalkyl, CM alkoxy, CM haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is selected from $C_{1-6}$ alkyl, $C_{2-6}$ alkenyl, and $Cy^1$, wherein said $C_{1-6}$ alkyl is optionally substituted with 1, 2, or 3 substituents independently selected from $Cy^1$.

In some embodiments, $R^1$ is $C_{1-6}$ alkyl, optionally substituted with 1, 2, or 3 substituents independently selected from $Cy^1$.

In some embodiments, $R^1$ is $Cy^1$.

In some embodiments, $R^1$ is $C_{2-6}$ alkenyl.

In some embodiments, $R^2$ is selected from H and $C_{1-6}$ alkyl, wherein said $C_{1-6}$ alkyl is optionally substituted with 1, 2, or 3 substituents independently selected from $Cy^1$, $C(O)NR^{c1}R^{d1}$, and $NR^{c1}R^{d1}$.

In some embodiments, $R^2$ is H.

In some embodiments, $R^2$ is $C_{1-6}$ alkyl, optionally substituted with 1, 2, or 3 substituents independently selected from $Cy^1$, $C(O)NR^{c1}R^{d1}$, and $NR^{c1}R^{d1}$.

In some embodiments, $R^2$ is $C_{1-6}$ alkyl, optionally substituted with $Cy^1$.

In some embodiments, $R^2$ is $C_{1-6}$ alkyl, optionally substituted with $C(O)NR^{c1}R^{d1}$ or $NR^{c1}R^{d1}$.

In some embodiments, $R^2$ is $C_{1-6}$ alkyl, optionally substituted with $C(O)NR^{c1}R^{d1}$.

In some embodiments, $R^2$ is $C_{1-6}$ alkyl, optionally substituted with $NR^{c1}R^{d1}$. In some embodiments, $R^{c1}$ and $R^{d1}$ are each H. In some embodiments, $R^{c1}$ and $R^{d1}$ are each $C_{1-6}$ alkyl. In some embodiments, $R^{c1}$ and $R^{d1}$ together with the N atom to which they are attached form a 4-7 membered heterocycloalkyl, which is optionally substituted with 1, 2, or 3 substituents independently selected from $R^g$.

In some embodiments, $R^3$, $R^4$, $R^5$, and $R^6$ are each independently selected from H and $C(O)NR^{c1}R^{d1}$.

In some embodiments, $R^3$ and $R^6$ are each H.

In some embodiments, $R^4$ is $C(O)NR^{c1}R^{d1}$. In some embodiments, $R^3$, $R^5$, and $R^6$ are each H. In some embodiments, $R^5$ is $C(O)NR^{c1}R^{d1}$. In some embodiments, $R^3$, $R^4$, and $R^6$ are each H. In some embodiments, $R^{c1}$ is H and $R^{d1}$ is selected from $C_{6-10}$ aryl-$C_{1-4}$ alkylene and (5-10 membered heteroaryl)-$C_{1-4}$ alkylene.

In some embodiments, each $Cy^1$ is independently selected from $C_{6-10}$ aryl and 4-10 membered heterocycloalkyl, each of which is optionally substituted with 1, 2, or 3 substituents independently selected from $R^{Cy2}$.

In some embodiments, $Cy^1$ is $C_{6-10}$ aryl (e.g., phenyl), optionally substituted with 1, 2, or 3 substituents independently selected from $R^{Cy2}$.

In some embodiments, $Cy^1$ is 4-10 membered heterocycloalkyl (e.g., pyrrolidinyl, morpholinyl), optionally substituted with 1, 2, or 3 substituents independently selected from $R^{Cy2}$.

In some embodiments, each $R^{Cy2}$ is independently selected from halo, CN, $C_{1-6}$ alkyl, $OR^{a2}$; wherein said $C_{1-6}$ alkyl is optionally substituted with $C(O)NR^{c2}R^{d2}$.

In some embodiments, $R^{Cy2}$ is halo.

In some embodiments, $R^{Cy2}$ is CN, $C_{1-6}$ alkyl, or $C_{1-6}$ alkoxy.

In some embodiments, $R^{Cy2}$ is $C_{1-6}$ alkyl, optionally substituted $C(O)NR^{c2}R^{d2}$. In some embodiments, $R^{c2}$ is H, and $R^{d2}$ is selected from $C_{6-10}$ aryl, 5-10 membered heteroaryl, $C_{6-10}$ aryl-$C_{1-4}$ alkylene, and (5-10 membered heteroaryl)-$C_{1-4}$ alkylene, each of which is optionally substituted with 1, 2, or 3 substituents independently selected from $R^g$.

In some embodiments, each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{6-10}$ aryl, 5-10 membered heteroaryl, $C_{6-10}$ aryl-$C_{1-4}$ alkylene, and (5-10 membered heteroaryl)-$C_{1-4}$ alkylene, wherein said $C_{1-6}$ alkyl, $C_{6-10}$ aryl, 5-10 membered heteroaryl, $C_{6-10}$ aryl-$C_{1-4}$ alkylene, and (5-10 membered heteroaryl)-$C_{1-4}$ alkylene, are each optionally substituted with 1, 2, or 3 substituents independently selected from $R^g$.

In some embodiments, each $R^g$ is independently selected from halo, $C_{1-6}$ alkyl, and $C_{1-6}$ alkoxy.

In some embodiments:
- $R^1$ is selected from $C_{1-6}$ alkyl, $C_{2-6}$ alkenyl, and $Cy^1$, wherein said $C_{1-6}$ alkyl is optionally substituted with 1, 2, or 3 substituents independently selected from $Cy^1$;
- $R^2$ is selected from H and $C_{1-6}$ alkyl, wherein said $C_{1-6}$ alkyl is optionally substituted with 1, 2, or 3 substituents independently selected from $Cy^1$, $C(O)NR^{c1}R^{d1}$, and $NR^{c1}R^{d1}$;
- $R^3$, $R^4$, $R^5$, and $R^6$ are each independently selected from H and $C(O)NR^{c1}R^{d1}$;
- $Cy^1$ is independently selected from $C_{6-10}$ aryl and 4-10 membered heterocycloalkyl, each of which is optionally substituted with 1, 2, or 3 substituents independently selected from $R^{Cy2}$;
- $R^{Cy2}$ is independently selected from halo, CN, $C_{1-6}$ alkyl, and $OR^{a2}$; wherein said $C_{1-6}$ alkyl is optionally substituted with $C(O)NR^{c2}R^{d2}$;
- each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{6-10}$ aryl, 5-10 membered heteroaryl, $C_{6-10}$ aryl-$C_{1-4}$ alkylene, and (5-10 membered heteroaryl)-$C_{1-4}$ alkylene, wherein said $C_{1-6}$ alkyl, $C_{6-10}$ aryl, 5-10 membered heteroaryl, $C_{6-10}$ aryl-$C_{1-4}$ alkylene, and (5-10 membered heteroaryl)-$C_{1-4}$ alkylene are each optionally substituted with 1, 2, or 3 substituents independently selected from $R^g$; and
- each $R^g$ is independently selected from halo, $C_{1-6}$ alkyl, and $C_{1-6}$ alkoxy.

In some embodiments, the compound of Formula (III) is any one of the compounds provided in Table 4, or a pharmaceutically acceptable salt thereof.

In some embodiments, a salt of a compound of any Formulae disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of any Formulae disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compounds of any Formulae include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of any Formulae disclosed herein, or pharmaceutically acceptable salts thereof, are substantially isolated.

In some embodiments, a compound of any Formulae disclosed herein, or a pharmaceutically acceptable salt thereof, can have the ability to increase TFEB polypeptide levels within a cell and/or within a nucleus of a cell. Such cells can be in vitro or in vivo. For example, a compound of any Formulae disclosed herein, or a pharmaceutically acceptable salt thereof, can have the ability to increase TFEB polypeptide levels within the nucleus of cells present within a mammal (e.g., a human) following administration to that mammal.

Methods of Making Therapeutic Compounds

Compounds of any one of the Formulae disclosed herein, including salts thereof, can be prepared using known organic synthesis techniques and can be synthesized according to any of numerous possible synthetic routes. For example, the compounds described herein can be prepared using methods and procedures similar to those described in the Examples 1a-1p herein. A person skilled in the art knows how to select and implement appropriate synthetic protocols, and appreciates that the processes described are not the exclusive means by which compounds provided herein may be synthesized, and that a broad repertoire of synthetic organic reactions is available to be potentially employed in synthesizing compounds provided herein.

Suitable synthetic methods of starting materials, intermediates, and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*J. Heterocyclic Chemistry,* 1964-2012); Carreira et al., (Ed.) *Science of Synthesis*, Vols. 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, $2^{nd}$ Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure, $6^{th}$* Ed. (Wiley, 2007); Trost et al. (Ed.) *Comprehensive Organic Synthesis* (Pergamon Press, 1991).

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* $4^{th}$ Ed., Wiley & Sons, Inc., New York (2006).

Pharmaceutical Compositions and Formulations

This document also provides pharmaceutical compositions comprising an effective amount of a compound of any one of Formulae (I)-(III) disclosed herein, or a pharmaceutically acceptable salt thereof; and a pharmaceutically acceptable carrier. The pharmaceutical composition also can comprise any one of the additional therapeutic agents and/or therapeutic molecules described herein. The carriers) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds set forth in Formula (I), (IIa-IIi), or (III), or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., a compound set forth in Formula (I), (IIa-IIi), or (III), or a pharmaceutically acceptable salt thereof) with a suitable non-irritating excipient that is solid at room temperature but liquid at the rectal temperature and therefore will melt in the rectum to release the active components). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., J. Pharm. Pharmacol., 56:3-17 (2004); and Ilium, L., *Eur. J. Pharm. Sci.,* 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound set forth in Formula (I), (IIa-IIi), or (III), or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., a compound set forth in Formula (I), (IIa-IIi), or (III), or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos. 6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., a compound set forth in Formula (I), (IIa-IIi), or (III), or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein (e.g., a compound set forth in Formula (I), (IIa-IIi), or (III), or a pharmaceutically acceptable salt thereof) can include that compound in an effective amount (e.g., a therapeutically effective amount).

Effective doses can vary, depending on the diseases being treated, the severity of the disease, the route of administration, the sex, age and general health condition of the subject, excipient usage, the possibility of co-usage with other therapeutic treatments such as use of other agents, and the judgment of the treating physician.

In some embodiments, an effective amount of a compound of any one of Formulae (I)-(III), or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated as described herein.

In some cases, an effective amount of a compound of any one of Formulae (I)-(III), or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound of any one of Formulae (I)-(III), or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to increase TFEB polypeptide levels within cells and/or within the nucleus of cells within a mammal (e.g., a human). In some cases, this document provides pharmaceutical kits useful, for example, to treat diseases, disorders, and conditions referred to herein. Such pharmaceutical kits can include one or more containers containing a pharmaceutical composition that includes a therapeutically effective amount of a compound provided herein (e.g., a compound set forth in Formula (I), (IIa-IIi), or (III), or a pharmaceutically acceptable salt thereof). In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein.

Combination Therapy

In some cases, one or more compounds provided herein (e.g., a compound set forth in Formula (I), (IIa-IIi), or (III), or a pharmaceutically acceptable salt thereof) can be combined with one or more therapeutic molecules. Examples of therapeutic molecules that can be used in combination with one or more compounds provided herein (e.g., a compound set forth in Formula (I), (IIa-IIi), or (III), or a pharmaceutically acceptable salt thereof) include, without limitation, enzyme replacement therapy (e.g., approved enzyme therapy) for LSDs (e.g., fabrazyme or cerezyme). In such cases, the addition of one or more such compounds can aid in the treatment of central nervous system disease not approachable by enzyme replacement therapy due to the restriction imposed by the blood-brain barrier to serum proteins. In some cases, the addition of one or more such compounds can increase the cellular uptake of a given lysosomal enzyme replacement therapeutic protein in the periphery by augmenting expression of the mannose-6-phosphate receptor, a TFEB transcriptional target, and the receptor-mediated mechanism through which enzyme replacement therapies gain entry into a disease cell or tissue. Additional examples of therapeutic molecules that can be used in combination with one or more compounds provided herein (e.g., a compound set forth in Formula (I), (IIa-IIi), or (III), or a pharmaceutically acceptable salt thereof) include, without limitation, anti-inflammatory agents (e.g., steroids and antibodies against IL-6 or TNF-alpha), antimicrobial agents (e.g., antibiotics, anti-mycobacterial drugs, and anti-viral agents), anti-cancer agents (e.g., chemotherapeutic agents and cellular products such as engineered T cells), anti-aging agents (e.g., nicotinamide riboside, or rapamycin), neurological agents (e.g., L-DOPA, memantine, and riluzole), therapies for a neurodegenerative disease (e.g., edaravone or tetrabenazine), and agents used to treat chronic organ dysfunction (e.g., ACE inhibitor and lactulose).

One or more compounds provided herein (e.g., a compound set forth in Formula (I), (IIa-IIi), or (III), or a pharmaceutically acceptable salt thereof) and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in this document, substituents of compounds provided herein are disclosed in groups or in ranges. It is specifically intended that these groups and ranges include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in this document various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features described herein, which are, for clarity, described in the context of separate embodiments, can also be provided in combination in a single embodiment. Conversely, various features described herein which are, for brevity, described in the context of a single embodiment, also can be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "Cn-m" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethyl propyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, without limitation, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, without limitation, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl-linking group having n to m carbons. Examples of alkylene groups include, without limitation, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, without limitation, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —NH$_2$.

As used herein, the term "C$_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, without limitation, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "C$_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, without limitation, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxy carbonyl), and the like.

As used herein, the term "C$_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, without limitation, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "C$_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "C$_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkylaminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "C$_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "C$_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)NH$_2$.

As used herein, the term "C$_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "C$_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms. As used herein, the term "carbonyl", employed alone or in combination with other terms, refers to a —C(=O)— group, which may also be written as C(O).

As used herein, the term "carboxy" refers to a —C(O)OH group. In some embodiments, the "carboxy" group also refers to a bioisostere replacement group selected from the group consisting of:

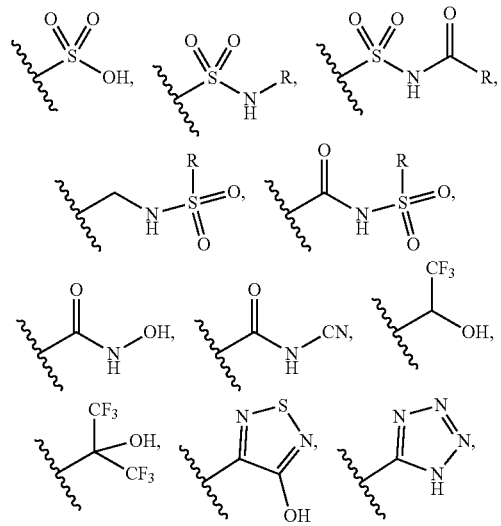

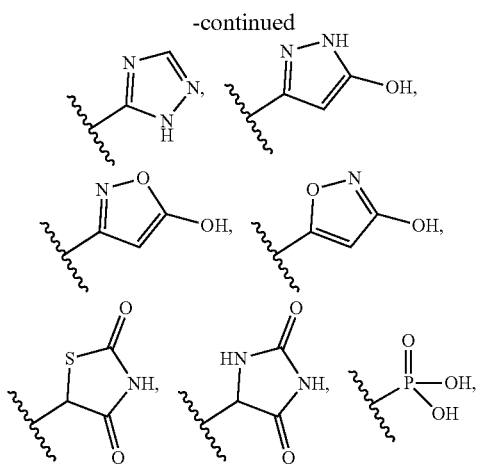

and the like, where R refers to a hydrogen, $(C_1-C_8)$ alkyl, or $C_6$ aryl.

As used herein, the term "cyano-$C_{1-3}$ alkyl" refers to a group of formula —$(C_{1-3}$ alkylene)-CN.

As used herein, the term "HO—$C_{1-3}$ alkyl" refers to a group of formula —$(C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which can be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups can have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3, or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic or non-aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. A cycloalkyl group may contain a fused heterocycloalkyl ring which itself may be fused with another ring such as an aromatic ring. In this situation, the cycloalkyl group can be attached through any ring forming atom, including ring forming atoms of the heterocycloalkyl ring or the aromatic ring. Cycloalkyl groups can have 3, 4, 5, 6, 7, 8, 9, or 10 ring-forming carbons ($C_{3-10}$). Cycloalkyl groups can also have 3, 4, 5, 6, 7, 8, 9, 10, 11, 12, 13, or 14 ring-forming atoms (carbon atoms or heteroatoms if the cycloalkyl group is fused with a heterocycloalkyl ring) ($C_{3-4}$ cycloalkyl). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{3-14}$ bicyclic or tricyclic cycloalkyl. Example cycloalkyl groups include, without limitation, cyclopropyl, cyclobutyl, cyclopentyl, cyclohexyl, cycloheptyl, cyclopentenyl, cyclohexenyl, cyclohexadienyl, cycloheptatrienyl, norbomyl, norpinyl, norcamyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 3-10 membered monocyclic or bicyclic heteroaryl having 1, 2, 3, or 4 heteroatom ring members independently selected from nitrogen, sulfur, and oxygen. In some embodiments, the heteroaryl is a 3-14 membered monocyclic, bicyclic, or tricyclic heteroaryl having 1, 2, 3, or 4 heteroatom ring members independently selected from nitrogen, sulfur, and oxygen. In some embodiments, the heteroaryl is a 3-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazoyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, or 10-membered heterocycloalkyl groups. Included in heterocycloalkyl are mono-, bi-, tri-, and tetracyclic 4-, 5-, 6-, 7-, 8-, 9-, 10-, 11-, 12-, 13-, or 14-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazdidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic or non-aromatic rings fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring can be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Any appropriate method can be used to prepare optically active forms from, for example, optically inactive starting materials. For example, techniques such as resolution of racemic mixtures or stereoselective synthesis can be used to prepare optically active forms of a compound provided herein. Many geometric isomers of olefins, C=N double bonds, N=N double bonds, and the like also can be present in a compound described herein, and all such stable isomers are contemplated herein. Cis and treats geometric isomers of the compounds provided herein are described and can be isolated as a mixture of isomers or as separated isomeric forms. In some embodiments, a compound provided herein has the (R)-configuration. In some embodiments, a compound provided herein has the (S)-configuration.

Compounds provided herein also include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include, without limitation, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution.

For example, in aqueous solution, pyrazoles can exhibit the following isomeric forms, which are referred to as tautomers of each other:

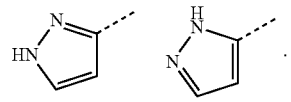

As readily understood by one skilled in the art, a wide variety of functional groups and other structures can exhibit tautomerism, and all tautomers of compounds as described herein are within the scope provided herein.

As used herein, the term "cell" is meant to refer to a cell that is in vitro, ex vivo, or in vivo. In some embodiments, an ex vivo cell can be part of a tissue sample excised from an organism such as a mammal (e.g., a human). In some embodiments, an in vitro cell can be a cell in cell culture. In some embodiments, an in vivo cell is a cell living in an organism such as a mammal (e.g., a human).

As used herein, the term "contacting" refers to the bringing together of indicated moieties or items in an in vitro system, an ex vivo system, or an in vivo system. For example, "contacting" a cell with a compound provided herein includes the act of administering that compound to a mammal (e.g., a human) containing that cell as well as, for example, introducing that compound into a cell culture containing that cell.

As used herein, the term "mammal" includes, without limitation, mice, rats, other rodents, rabbits, dogs, cats, swine, cattle, sheep, horses, elephants, deer, non-human primates (e.g., monkeys and apes), house pets, and humans.

As used herein, the phrase "effective amount" or "therapeutically effective amount" refers to the amount of active compound or pharmaceutical agent that elicits the biological or medicinal response in a tissue, system, mammal, or human that is being sought by a researcher, veterinarian, medical doctor, or other clinician.

As used herein, the term "treating" or "treatment" refers to (a) inhibiting a disease, disorder, or condition, for example, inhibiting a disease, disorder, or condition in a mammal (e.g., human) that is experiencing or displaying the pathology or symptomatology of the disease, disorder, or condition (e.g., arresting further development of the pathology and/or symptomatology), or (b) ameliorating the disease, disorder, or condition, for example, ameliorating a disease, disorder, or condition in a mammal (e.g., a human) that is experiencing or displaying the pathology or symptomatology of the disease, disorder, or condition (e.g., reversing the pathology and/or symptomatology).

As used herein, the term "preventing" or "prevention" of a disease, disorder, or condition refers to decreasing the risk of occurrence of the disease, disorder, or condition in a mammal or group of mammals (e.g., a mammal or group of mammals predisposed to or susceptible to the disease, disorder, or condition). In some embodiments, preventing a disease, disorder, or condition refers to decreasing the possibility of acquiring the disease, disorder, or condition and/or its associated symptoms. In some embodiments, preventing a disease, disorder, or condition refers to completely or almost completely stopping the disease, disorder, or condition from occurring.

EXAMPLES

Material and Methods

All non-aqueous reactions were carried out under a nitrogen atmosphere in oven- or flame-dried glassware unless otherwise noted. Anhydrous tetrahydrofuran and diethyl ether were distilled from sodium benzophenone ketyl solutions; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 F254 plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g Ce $(NH_4)_2(NO_3)_6$, 12 g $(NH_4)_6Mo_7O_{24} \cdot 4H_2O$, and 28 mL conc. $H_2SO_4$ in 235 mL water), or vanillin (6 g vanillin and 1.5 mL conc. $H_2SO_4$ in 100 mL EtOH). Flash chromatography was performed with SiliCycle silica gel 60 (230-400 mesh) or with ISCO MPLC. $^1H$ and $^{13}C$ NMR spectra were recorded on Bruker Avance 300, 400, or 500 MHz spectrometers, using the residual solvent as an internal standard. IR spectra were obtained on a Smiths Identify IR or PerkinElmer Spectrum 100. HRMS data were obtained on a Thermo Scientific Exactive HRMS coupled to a Thermo Scientific Accela HPLC system using a 2.1×50 mm 3.5 μm Waters XTerra C18 column eluting with $MeCN/H_2O$ containing 0.1% formic acid. Purity of compounds was assessed using the same HPLC system with either the PDA or an Agilent 385 ELSD. All final screening samples passed QC based on >95% purity by LC/MS/ELSD analysis.

General synthetic scheme

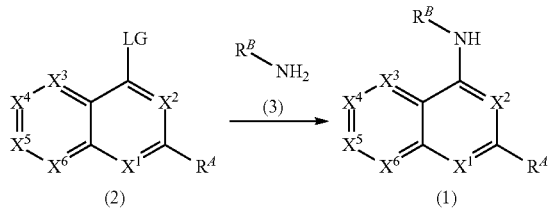

By way of example, to prepare the compounds of Formula (I) where n is 1 and L is NH (1), equimolar amounts of 4-chloroquinazoline analog (2) and an amine (3) are mixed in a suitable solvent (e.g., isopropanol). The resultant reaction mixture is stirred and refluxed for, e.g., 4 hours. Progression of the reaction is monitored by techniques known in the art. Upon consumption of the starting material, the reaction mixture is concentrated, and the target compound is purified through prep-TLC or flash chromatography. Products can be further purified by crystallization as is customary in the art. Referring to the general scheme, $X^1$, $X^2$, $X^3$, $X^4$, $X^5$, $X^6$, $R^A$, and $R^B$ are as described herein, and LG is a leaving group (e.g., Cl, Br, I, or OTf). The compounds of Formula (I) where L is other than NH can be prepared from similar starting materials using reactions and synthetic routes well known in the art. A skill chemist would be able to select and implement appropriate reaction protocols and conditions.

Example 1a—Synthesis of Compound 8 (BC18618)

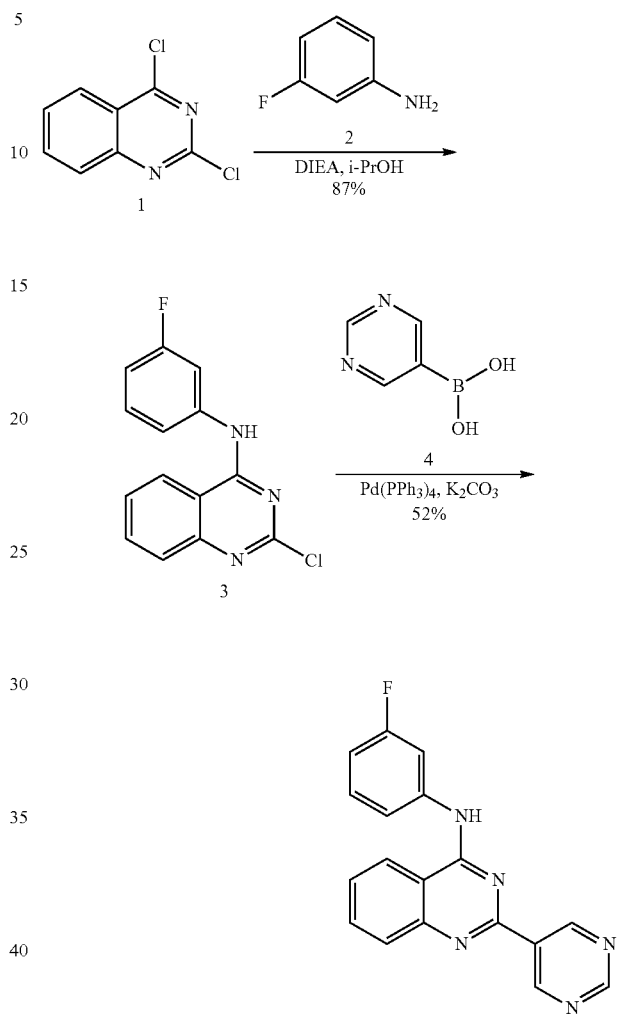

Preparation of Compound 3:

To a solution of 1 (1 g, 5.0 mmol, 1 eq) in i-PrOH (20 mL) was added 2 (615 mg, 5.5 mmol, 1.1 eq) and DIEA (1.29 g, 10 mmol, 2 eq). The reaction was stirred at 85° C. overnight. The mixture was concentrated and the residue was purified by silica column chromatography (PE/EA, 2:1) to give 1.2 g 3 (yellow oil, 87%). MS (ESI) m/z: 274 [M+H]+

Preparation of Compound 8 (BC18618)

To a solution of 3 (273 mg, 1 mmol, 1 eq) in dioxane/$H_2O$ (1:1, 15 mL) was added 4 (248 mg, 2 mmol, 2 eq), $K_2CO_3$ (276 mg, 2 mmol, 2 eq) and $Pd(PPh_3)_4$ (124 mg, 0.1 mmol, 0.1 eq) under $N_2$. The mixture was stirred at 115° C. overnight. Then the mixture was filtered and the filter cake was washed by MeOH to give 205 mg BC18618 (compound 8) (off-white solid, 52%).

MS (ESI) m/z: 318[M+H]+, 316[M−H]−

$^1H$ NMR (400 MHz, DMSO) δ 10.10 (s, 1H), 9.57 (s, 2H), 9.28 (s, 1H), 8.57 (d, J=8.1 Hz, 1H), 7.92-7.88 (m, 3H), 7.73 (d, J=8.2 Hz, 1H), 7.67 (dt, J=7.3, 3.8 Hz, 1H), 7.48 (dd, J=15.4, 8.2 Hz, 1H), 6.99 (td, J=8.5, 2.0 Hz, 1H).

Example 1b—Synthesis of Compound 76 (BC18703)

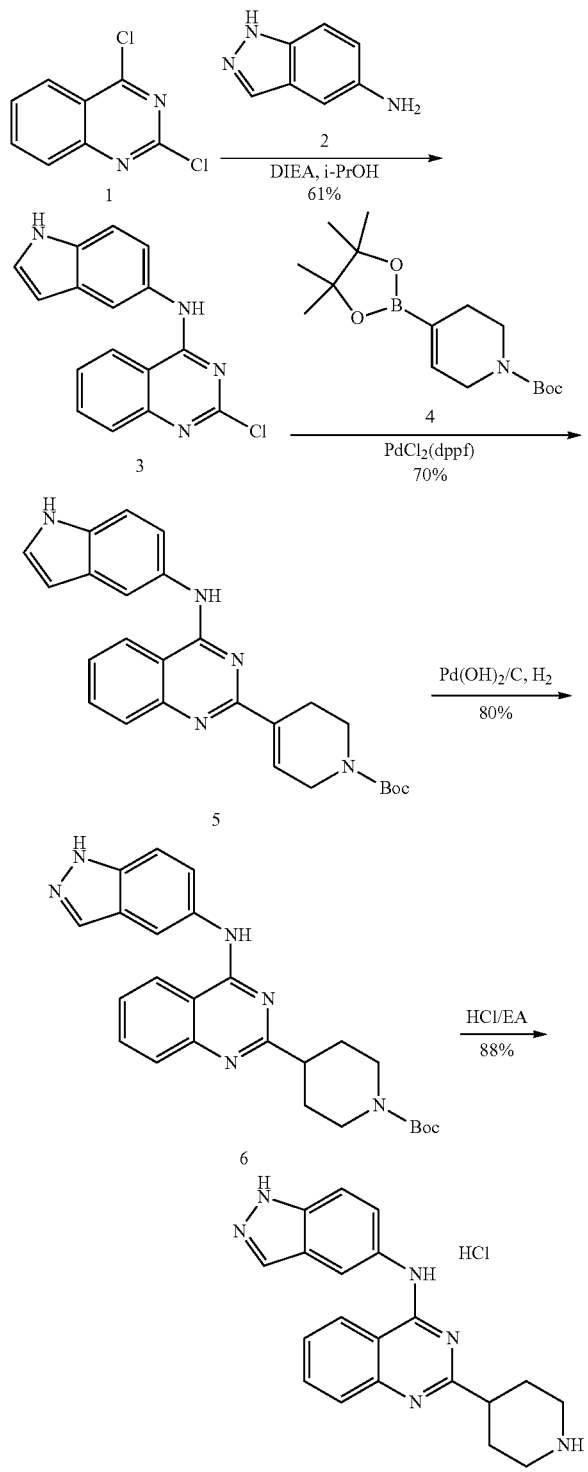

General Procedure for the Preparation of Compound 3:

To a solution of 1 (0.5 g, 2.51 mmol, 1 eq) in i-PrOH (15 mL) was added 2 (367 mg, 2.76 mmol, 1.1 eq) and DIEA (650 mg, 5.02 mmol, 2 eq). The reaction was stirred at 85° C. overnight. The solution was concentrated and the residue was purified by silica column chromatography (PE/EA, 2:1) to give 0.45 g 3 (yellow oil, 61%). MS (ESI) m/z: 296 [M+H]+

General Procedure for the Preparation of Compound 5

To a solution of 3 (0.4 g, 1.36 mmol, 1 eq) in dioxane/$H_2O$ (2:1, 1.5 mL) was added 4 (632 mg, 2.04 mmol, 1.5 eq), $K_2CO_3$ (844 mg, 6.12 mmol, 4.5 eq) and $PdCl_2(dppf)$ (95 mg, 0.13 mmol, 0.1 eq) under $N_2$. The mixture was stirred at 85° C. overnight. The mixture was filtered and the filter cake was washed by EA. The organic phase was washed by brine, then dried and concentrated. The residue was purified by silica column chromatography (PE/EA, 5:1) to give 0.4 g 5 (yellow solid, 70%). MS (ESI) m/z: 443[M+H]+.

General Procedure for the Preparation of Compound 6

To a solution of 5 (0.2 g, 0.45 mmol, 1 eq) in MeOH (5 mL) was added $Pd(OH)_2$ (30 mg, 15% W/W) under $N_2$. The system was evacuated and backfilled with $H_2$ three times. After stirred at rt overnight, the mixture was filtered and the filtrate was concentrated to give 0.16 g 6 (colorless oil, 80%). MS (ESI) m/z: 445[M+H]+.

General Procedure for the Preparation of Compound BC18703

To a solution of 6 (160 mg) in MeOH (2 mL) was added 3M HCl/EA (4 mL). After stirred at rt for 2 h, the solution was concentrated to give 120 mg of BC18703 (gray solid, 88%). MS (ESI) m/z: 345[M+H]+, 343[M−H]−

$^1$HNMR (400 MHz, DMSO) δ 11.85 (s, 1H), 9.13 (d, J=11.3 Hz, 1H), 8.96 (d, J=8.4 Hz, 1H), 8.22 (s, 1H), 8.14 (s, 1H), 8.07-8.03 (m, 2H), 7.79 (ddd, J=8.2, 5.3, 2.6 Hz, 1H), 7.75 (dd, J=9.0, 1.6 Hz, 1H), 7.65 (d, J=9.0 Hz, 1H), 3.36-3.33 (m, 1H), 3.29 (d, J=11.7 Hz, 2H), 2.94 (dd, J=21.0, 11.0 Hz, 2H), 2.11 (d, J=13.0 Hz, 2H), 2.05-1.92 (m, 2H).

Example 1c—Synthesis of Compound 78 (BC18705)

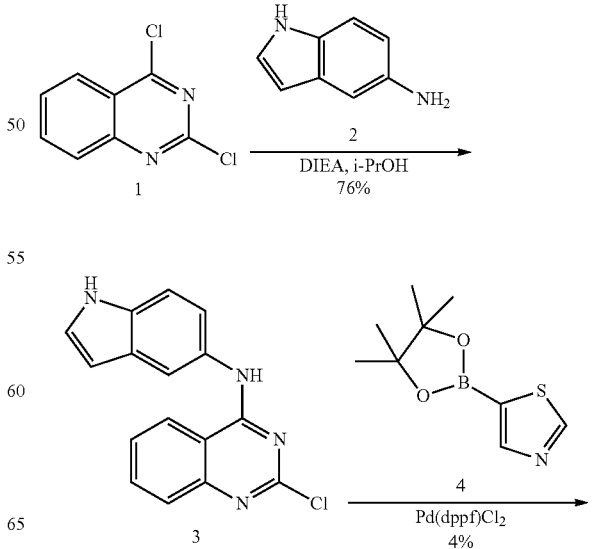

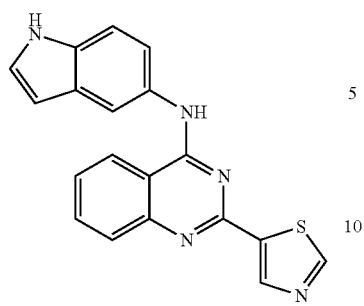

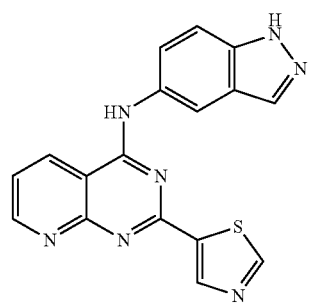

General Procedure for the Preparation of Compound 3

To a solution of 1 (200 mg, 1.0 mmol, 1 eq) in i-PrOH (3 mL) was added DIEA (284 mg, 2.0 mmol, 2 eq) and 2 (146 mg, 1.1 mmol, 1.1 eq). The reaction was stirred at 85° C. overnight. The solution was concentrated and the residue was purified by silica column chromatography (PE/EA, 2:1) to give 150 mg 3 (yellow solid, 76%). MS (ESI) m/z: 295 [M+H]+

General Procedure for the Preparation of Compound BC18705

To a solution of 3 (100 mg, 0.339 mmol, 1 eq) in dioxane/H$_2$O (1:1, 3 mL) was added 4 (215 mg, 1.02 mmol, 3 eq), K$_2$CO$_3$ (210 mg, 1.5 mmol, 4.5 eq) and Pd(dppf)Cl$_2$ (25 mg, 0.034 mmol, 0.1 eq) under N$_2$. The mixture was stirred at 95° C. overnight. The mixture was concentrated and the residue was purified by Prep-HPLC to give 5 mg BC18705 (off-white solid, 4%). MS (ESI) m/z: 344[M+H]+, 342[M−H]−

$^1$H NMR (400 MHz, DMSO) δ 11.09 (s, 1H), 9.88 (s, 1H), 9.11 (s, 1H), 8.54 (d, J=8.2 Hz, 1H), 8.45 (s, 1H), 8.03 (s, 1H), 7.88-7.69 (m, 2H), 7.62-7.47 (m, 20H), 7.43 (d, J=8.6 Hz, 1H), 7.34 (t, J=2.7 Hz, 1H), 6.46 (s, 1H).

Example 1d—Synthesis of Compound 383 (BC18829)

General Procedure for the Preparation of Compound 3-1

To a solution of 1 (0.2 g, 1.01 mmol, 1 eq) in i-PrOH (3 mL) was added 2 (148 mg, 1.11 mmol, 1.1 eq) and DIEA (260 mg, 2.02 mmol, 2 eq). The reaction was stirred at 85° C. overnight. The reaction was filtered. The cake was dried to give 0.29 g 3-1 (yellow solid, 97%). MS (ESI) m/z: 297 [M+H]+.

General Procedure for the Preparation of BC18829

To a solution of 3-1 (50 mg, 0.17 mmol, 1 eq) in dioxane/H$_2$O (4:1, 5 mL) was added 4-1 (40 mg, 0.19 mmol, 1.1 eq), K$_2$CO$_3$ (47 mg, 0.34 mmol, 2 eq) and PdCl$_2$(dppf) (25 mg, 0.03 mmol, 0.2 eq) under N$_2$. The mixture was stirred at 95° C. for 4 h. The mixture was filtered. The filter cake was washed by EA and the organic phase was dried and concentrated. The residue was purified by Prep-TLC (DCM/MeOH, 10:1) to give 5 mg BC18829 (brown solid, 9%). MS (ESI) m/z: 346[M+H]+, 344[M−H]−

$^1$H NMR (400 MHz, DMSO) δ 10.77 (s, 1H), 9.37-9.15 (m, 2H), 9.06 (s, 1H), 8.63 (dd, J=7.1, 5.9 Hz, 1H), 8.37-8.05 (m, 2H), 7.89-7.48 (m, 3H).

Example 1e—Synthesis of Compound 384 (BC18830)

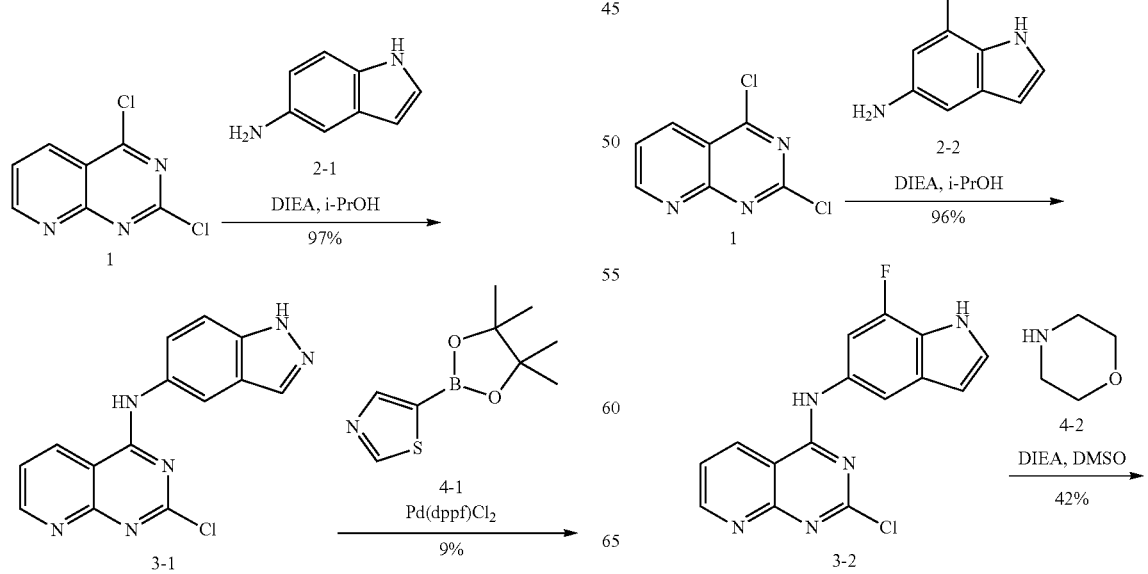

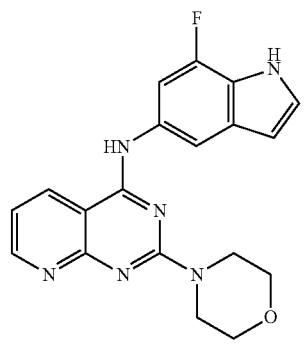

General Procedure for the Preparation of Compound 3-2

To a solution of 1 (0.2 g, 1.01 mmol, 1 eq) in i-PrOH (3 mL) was added 2 (167 mg, 1.11 mmol, 1.1 eq) and DIEA (260 mg, 2.02 mmol, 2 eq). The reaction was stirred at 85° C. overnight. The reaction was filtered. The cake was dried to give 0.3 g 3-2 (yellow solid, 96%). MS (ESI) m/z: 314 [M+H]+

General Procedure for the Preparation of BC18830

To a solution of 3-2 (0.1 g, 0.32 mmol, 1 eq) in DMSO (5 mL) was added 4-2 (34 mg, 0.38 mmol, 1.2 eq) and DIEA (83 mg, 0.64 mmol, 2 eq). The reaction was stirred at 95° C. for 2 h and quenched with H$_2$O (5 mL). The mixture was extracted with EA (10 mL×2). The organic phase was dried and concentrated. The residue was purified by Prep-TLC to give 49 mg BC18830 (yellow solid, 42%). MS (ESI) m/z: 365[M+H]+, 363[M−H]−.

$^1$H NMR (400 MHz, DMSO) δ 11.59 (s, 1H), 9.86 (s, 1H), 8.77-8.60 (m, 2H), 7.66 (s, 1H), 7.47-7.28 (m, 2H), 7.23-7.11 (m, 1H), 6.50 (s, 1H), 3.73 (brs, 4H), 3.62 (d, J=3.7 Hz, 7H).

Example 1f—Synthesis of Compound 385 (BC18831)

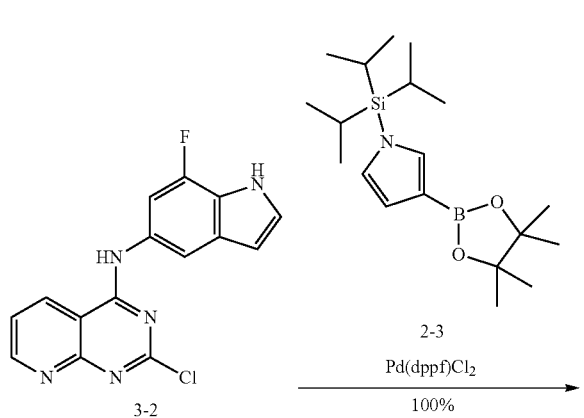

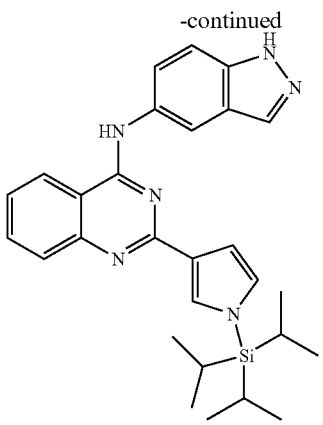

3-3

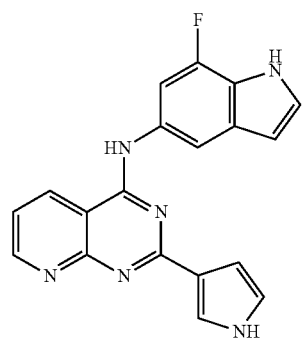

General Procedure for the Preparation of 3-3

To a solution of 3-2 (as prepared in Example 1e) (150 mg, 0.48 mmol, 1 eq) in dioxane/H$_2$O (4:1, 5 mL) was added 2-3 (185 mg, 0.53 mmol, 1.1 eq), K$_2$CO$_3$ (133 mg, 0.96 mmol, 2 eq) and Pd(dppf)Cl$_2$ (37 mg, 0.05 mmol, 0.1 eq) under N$_2$. The mixture was stirred at 95° C. for 4 h. The mixture was filtered. The filter cake was washed by EA and the organic phase was dried and concentrated to give 245 mg 3-3 (yellow solid, 100%). MS (ESI) m/z: 483[M+H]+

General Procedure for the Preparation of Compound BC18831

To a solution of 3-3 (245 mg crude, 0.51 mmol, 1 eq) in THF (2 mL) was added 1 M TBAF in THF (1.02 mL, 1.02 mmol 2 eq). The reaction was stirred at rt for 4 h. The mixture was concentrated and the residue was purified by Prep-HPLC to give 44 mg BC18831 (yellow solid, 25%). MS (ESI) m/z: 345[M+H]+, 343[M−H]−

$^1$HNMR (400 MHz, DMSO) δ 11.58 (s, 1H), 11.18 (s, 1H), 9.83 (s, 1H), 8.88 (dd, J=15.9, 5.5 Hz, 2H), 8.13 (s, 1H), 7.92 (s, 1H), 7.66 (d, J=13.9 Hz, 1H), 7.50 (d, J=1.2 Hz, 1H), 7.47-7.37 (m, 2H), 6.82 (d, J=2.1 Hz, 1H), 6.71 (d, J=1.3 Hz, 1H), 6.57-6.50 (m, 1H).

Example 1g—Synthesis of Compound 43 (BC18663)

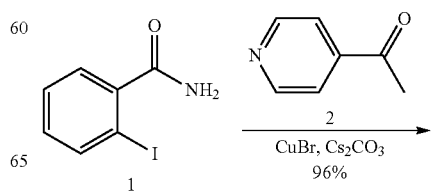

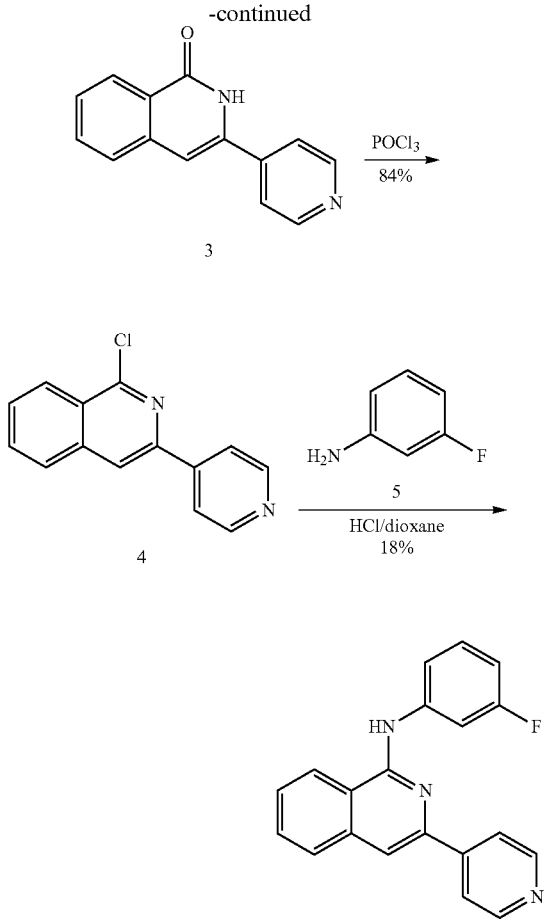

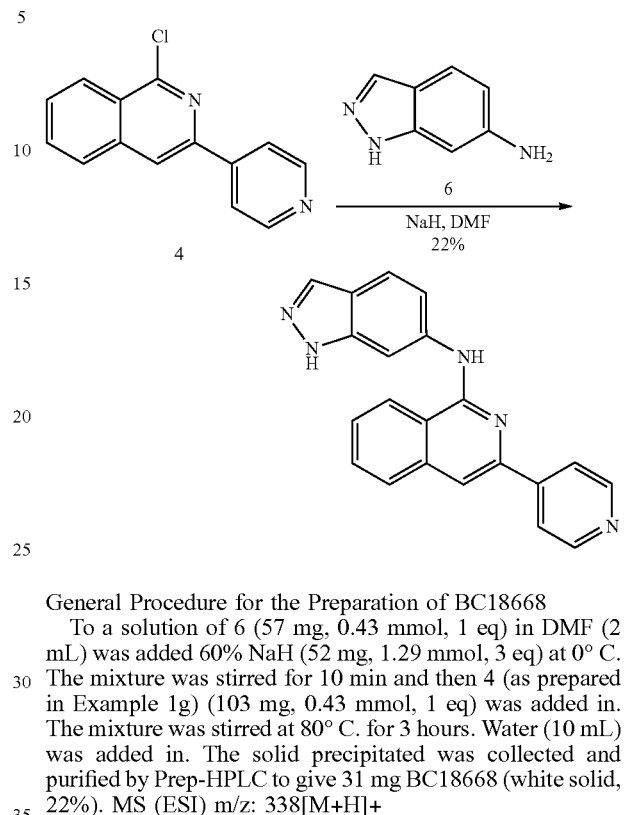

General Procedure for the Preparation of Compound 3

To a solution of 1 (1.5 g, 6.1 mmol, 1 eq) in DMSO (6 mL) was added 2 (1.1 g, 9.1 mmol, 1.5 eq), cesium carbonate (4.0 g, 12.2 mol, 2.0 eq) and copper (I) bromide (86 mg, 0.6 mmol, 0.1 eq). The mixture was stirred at 80° C. for 4 h. The mixture was diluted with water (30 mL). The solid precipitated was collected and dried to give 1.3 g 3 (grey solid, 96%). MS (ESI) m/z: 223 [M+H]+

General Procedure for the Preparation of Compound 4

To a solution of compound 3 (220 mg, 1.0 mmol, 1 eq) in DMSO (0.6 mL) was added phosphorus oxychloride (465 mL, 5.0 mmol, 5 eq). The mixture was stirred at 80° C. for 3.5 h. After completion, the mixture was poured into ice (~1 g). The solid was collected and dried to give 200 mg 4 (yellow solid, 84%). MS (ESI) m/z: 241[M+H]+

General Procedure for the Preparation of Compound BC18663

To a solution of 4 (83 mg, 0.33 mmol, 1.0 eq) in 4 M HCl/dioxane (2 mL) was added 5 (58 mg, 0.53 mmol, 1.5 eq). The reaction was stirred at 92° C. for 96 h. The solution was concentrated and the residue was purified by Prep-HPLC to give 19 mg BC18663 (yellow solid, 18%). MS (ESI) m/z: 316[M+H]+, 314[M−H]−

$^1$H NMR (400 MHz, DMSO) δ 9.50 (s, 1H), 8.67 (dd, J=4.6, 1.6 Hz, 2H), 8.56 (d, J=8.7 Hz, 1H), 8.05 (dd, J=4.5, 1.7 Hz, 3H), 8.00-7.91 (m, 2H), 7.83-7.72 (m, 2H), 7.68 (ddd, J=8.2, 6.9, 1.3 Hz, 1H), 7.39 (dd, J=15.3, 8.2 Hz, 1H), 6.82 (td, J=8.1, 1.9 Hz, 1H).

Example 1h—Synthesis of Compound 48 (BC18668)

General Procedure for the Preparation of BC18668

To a solution of 6 (57 mg, 0.43 mmol, 1 eq) in DMF (2 mL) was added 60% NaH (52 mg, 1.29 mmol, 3 eq) at 0° C. The mixture was stirred for 10 min and then 4 (as prepared in Example 1g) (103 mg, 0.43 mmol, 1 eq) was added in. The mixture was stirred at 80° C. for 3 hours. Water (10 mL) was added in. The solid precipitated was collected and purified by Prep-HPLC to give 31 mg BC18668 (white solid, 22%). MS (ESI) m/z: 338[M+H]+

$^1$H NMR (400 MHz, DMSO) δ 8.73 (d, J=6.1 Hz, 2H), 8.70-8.63 (m, 2H), 8.23-8.17 (m, 4H), 8.15 (d, J=8.0 Hz, 1H), 7.86 (t, J=7.5 Hz, 1H), 7.77-7.69 (m, 1H), 7.54 (d, J=8.6 Hz, 1H), 7.22 (s, 1H), 6.67 (dd, J=8.6, 1.7 Hz, 1H), 5.60 (s, 2H).

Example 1i—Synthesis of Compound 69 (BC18689)

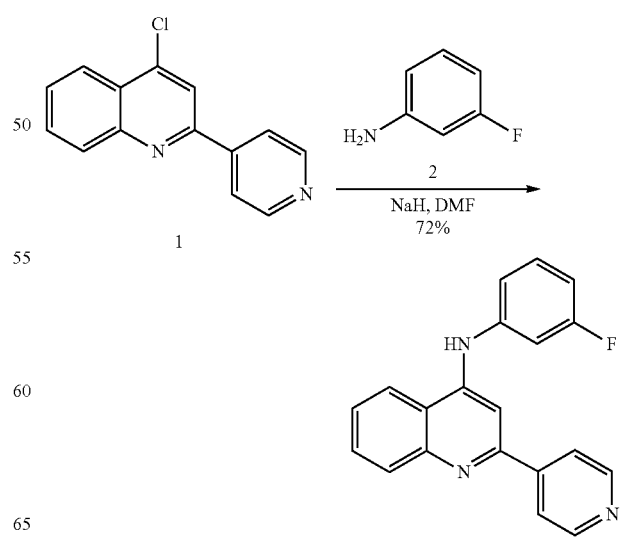

General Procedure for the Preparation of Compound BC18689

To a solution of 2 (111 mg, 1.0 mmol, 1.2 eq) in DMF (4 mL) was added 60% NaH (100 mg, 2.49 mmol, 3 eq) at 0° C. and the mixture was stirred for 15 min, then 1 (prepared by the same literature, 0.2 g, 0.83 mmol, 1 eq) was added into the above solution. The mixture was heated to 80° C. for 3 h. After cooled to rt, H$_2$O (5 mL) was added slowly. The mixture was extracted by EA (10 mL×2) and the organic phase was concentrated. The residue was purified by Prep-TLC to give 187 mg BC18689 (white solid, 72%). MS (ESI) m/z: 316 [M+H]+

$^1$H NMR (400 MHz, DMSO) δ 9.25 (s, 1H), 8.67 (dd, J=4.5, 1.6 Hz, 2H), 8.37 (dd, J=8.2, 0.8 Hz, 1H), 8.01-7.96 (m, 3H), 7.76 (ddd, J=8.3, 6.8, 1.2 Hz, 1H), 7.61 (s, 1H), 7.58 (ddd, J=8.2, 7.0, 1.2 Hz, 1H), 7.47-7.40 (m, 1H), 7.29 (dd, J=7.7, 2.3 Hz, 1H), 7.24 (dt, J=11.1, 2.3 Hz, 1H), 6.93 (td, J=8.5, 2.4 Hz, 1H).

Example 1j—Synthesis of Compound 126 (BC18763)

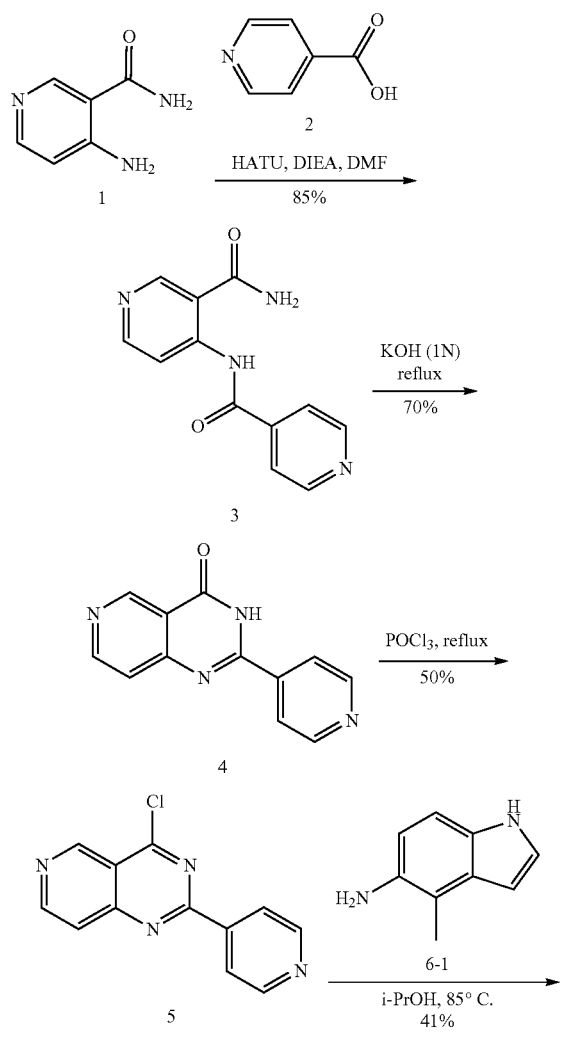

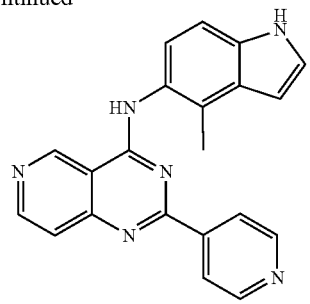

General Procedure for the Preparation of Compound 3

To a solution of 1 (7.7 g, 56 mmol, 1.0 eq) in DMF (80 mL) was added 2 (8.2 g, 67.2 mmol, 1.2 eq), HATU (27.6 g, 73 mmol, 1.3 eq) and DIEA (14.4 g, 112 mmol, 2.0 eq) under N$_2$. The reaction was stirred at rt overnight. The reaction mixture was concentrated and the residue was purified by silica column chromatography (DCM/MeOH, 50:1) to give 11.5 g 3 (yellow solid, 85%). MS (ESI) m/z:243 [M+H]+

General Procedure for the Preparation of Compound 4

A solution of 3 (2 g, 8.26 mmol, 1.0 eq) in KOH (1N, 20 mL) was heated to 100° C. and stirred for 3 h. TLC showed no 3 left. The mixture was adjusted to pH 7 with aq HCl (4 M). The mixture was filtered. The solid precipitated was collected and dried to give 1.4 g 4 (white solid, 70%). MS (ESI) m/z: 225 [M+H]+

General Procedure for the Preparation of Compound 5

A solution of 4 (1.4 g, 6.3 mmol, 1.0 eq) in POCl$_3$ (10 mL) was stirred at 100° C. overnight. The reaction was concentrated and the residue was adjusted pH to 9~10 with saturated Na$_2$CO$_3$. The mixture was extracted with CHCl$_3$ (15 mL×3) and the organic phase was dried and concentrated to give 750 mg 5 (yellow solid, 50%). MS (ESI) m/z: 243 [M+H]+

General Procedure for the Preparation of BC18763

To a solution of 5 (50 mg, 0.21 mmol, 1 eq) in i-PrOH (3 mL) was added 6-1 (33 mg, 0.23 mmol, 1.1 eq). The reaction was stirred at 85° C. overnight. The reaction mixture was filtered. The cake was washed by i-PrOH and dried to give 30.1 mg BC18763 (brown solid, 41%). MS (ESI) m/z: 353 [M+H]+, 351 [M−H]−

$^1$H NMR (400 MHz, DMSO) δ 11.26 (s, 1H), 10.81 (s, 1H), 10.05 (s, 1H), 8.80 (d, J=37.3 Hz, 3H), 8.18 (s, 2H), 7.84 (d, J=5.4 Hz, 1H), 7.51-7.25 (m, 2H), 7.16 (d, J=8.3 Hz, 1H), 6.55 (s, 1H), 2.47 (s, 3H)

Example 1k—Synthesis of Compound 127 (BC18764)

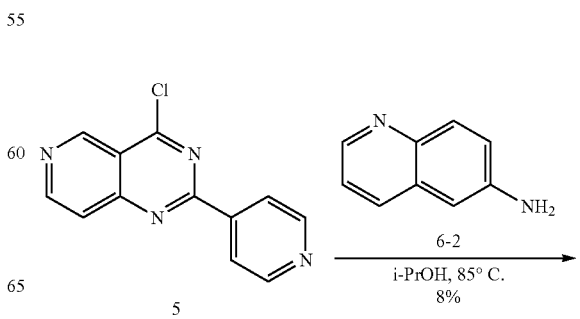

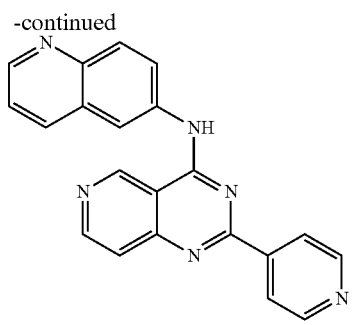

General Procedure for the Preparation of BC18764

To a solution of 5 (as prepared in Example 1j) (100 mg, 0.21 mmol, 1 eq) in i-PrOH (3 mL) was added 6-2 (33 mg, 0.23 mmol, 1.1 eq). The reaction was stirred at 85° C. overnight. The reaction mixture was concentrated and the residue was purified with Prep-HPLC to give 10.6 mg BC18764 (brown solid, 8%). MS (ESI) m/z: 351 [M+H]+, 349 [M−H]−

$^1$H NMR (400 MHz, DMSO) δ 10.85 (s, 1H), 9.95 (s, 1H), 8.85 (d, J=5.7 Hz, 2H), 8.76 (d, J=5.9 Hz, 2H), 8.55 (d, J=2.0 Hz, 1H), 8.42 (d, J=7.6 Hz, 1H), 8.27 (dd, J=5.4, 3.7 Hz, 3H), 8.11 (d, J=9.2 Hz, 1H), 7.77 (d, J=5.9 Hz, 1H), 7.55 (dd, J=8.1, 4.2 Hz, 1H).

Example 1l—Synthesis of Compound 120 (BC18757)

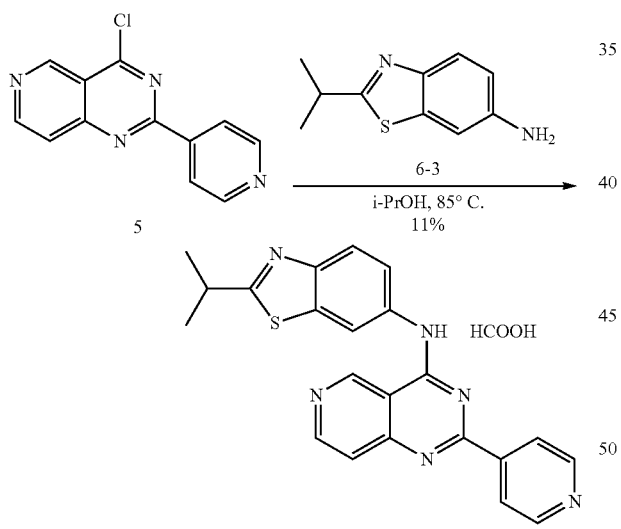

General Procedure for the Preparation of BC18757

To a solution of 5 (as prepared in Example 1j) (100 mg, 0.41 mmol, 1 eq) in i-PrOH (3 mL) was added 6-3 (86 mg, 0.45 mmol, 1.1 eq). The reaction was stirred at 85° C. overnight. The reaction mixture was concentrated and the residue was purified with Prep-HPLC to give 20 mg BC18757 (yellow solid, 11%). MS (ESI) m/z:399 [M+H]+, 397 [M−H]−

$^1$H NMR (400 MHz, DMSO) δ 10.67 (s, 1H), 9.84 (s, 1H), 8.80 (d, J=5.8 Hz, 1H), 8.69 (d, J=5.5 Hz, 2H), 8.52 (d, J=1.8 Hz, 1H), 8.15 (d, J=5.8 Hz, 2H), 7.99 (d, J=8.7 Hz, 1H), 7.89 (dd, J=8.8, 1.9 Hz, 1H), 7.70 (d, J=5.7 Hz, 1H), 4.26 (s, 1H), 1.40 (d, J=6.9 Hz, 6H).

Example 1m—Synthesis of Compound 83 (BC18711)

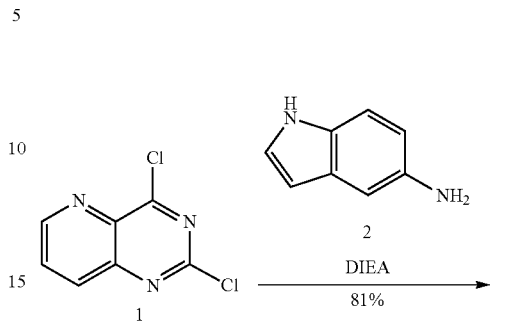

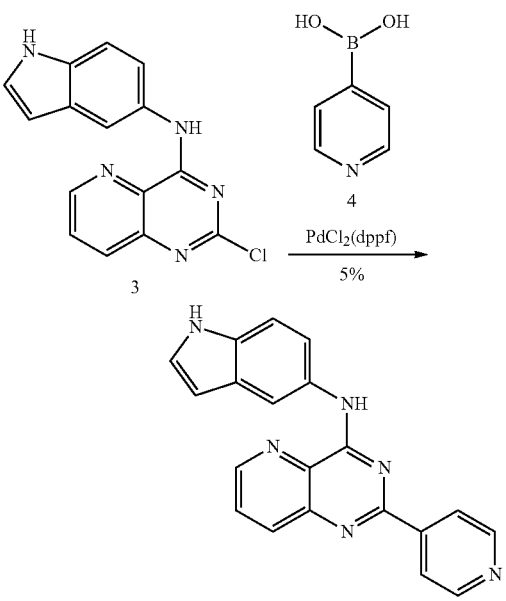

General Procedure for the Preparation of Compound 3

To a solution of 1 (1.0 g, 5.0 mmol, 1 eq) in i-PrOH (15 mL) was added 2 (726 mg, 5.5 mmol, 1.1 eq) and DIEA (1.29 g, 10.0 mmol, 2 eq). The reaction was stirred at 85° C. for 4 h. The mixture was filtered. The cake was washed by i-PrOH and dried to give 1.2 g 3 (yellow solid, 81%). MS (ESI) m/z: 296 [M+H]+

General Procedure for the Preparation of BC18711

To a solution of 3 (700 mg, 2.36 mmol, 1 eq) in dioxane/H$_2$O (4:1, 10 mL) was added 4 (348 mg, 2.83 mmol, 1.2 eq), K$_2$CO$_3$ (651 mg, 4.72 mmol, 2 eq) and PdCl$_2$(dppf) (176 mg, 0.24 mmol, 0.1 eq) under N$_2$. The mixture was stirred at 119° C. overnight. The mixture was filtered. The filter cake was washed by EA and the organic phase was dried and concentrated. The residue was purified by Prep-HPLC to give 34 mg BC18711 (gray solid, 5%). MS (ESI) m/z: 339[M+H]+, 337[M−H]−

$^1$H NMR (400 MHz, DMSO) δ 12.33 (s, 1H), 11.43 (s, 1H), 10.09 (dd, J=4.2, 1.4 Hz, 1H), 9.92 (d, J=5.4 Hz, 2H), 9.44 (ddd, J=11.0, 6.8, 1.8 Hz, 4H), 9.09 (dd, J=8.5, 4.2 Hz, 1H), 8.89 (dd, J=8.7, 1.9 Hz, 1H), 8.65 (d, J=8.7 Hz, 1H), 8.56 (t, J=2.7 Hz, 1H), 7.68 (s, 1H).

Example 1n—Synthesis of Intermediate 8 (Useful in Making Compound BC18847)

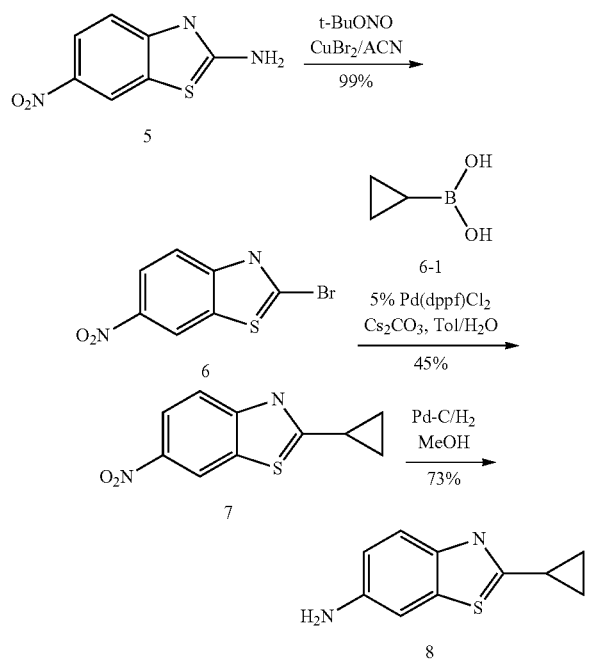

General Procedure for the Preparation of Compound 6

Compound 5 (44 g, 225 mmol, 1 eq), tert-butyl nitrite (45 mL, 375 mmol, 1.67 eq) and CuBr₂ (60 g, 270 mmol, 1.2 eq) was suspended in acetonitrile (500 mL, 10 V) and stirred at room temperature for 1-2 hour. The progress of the reaction was monitored by TLC (PE: EA 5:1). The resulting reaction mixture was quenched with 1 N HCl aqueous solution (3 L) and extracted with CH₂Cl₂ (3×2 L). The combined organic layers were dried over Na₂SO4, and concentrated to give compound 6 (66.4 g, 99%) as yellow powder, which was used for next step without further purification. MS (ESI) m/z: 259[M+H]+.

General Procedure for the Preparation of Compound 7

To a solution of 6 (50.0 g, 194 mmol, 1.0 eq) in toluene/H₂O (V/V=2:1, 2 L) was added 6-1 (50 g, 581 mmol, 3.0 eq), Cs₂CO₃ (126 g, 389 mmol, 2.0 eq) and Pd(dppf)Cl₂ (14.2 g, 19.4 mmol, 0.1 eq). The mixture was evacuated and backfilled with Ar three times and then stirred at 100° C. overnight. The mixture was filtered through a pad of Celite, and washed with ethyl acetate (mL). The organic layers were washed with water and brine and dried over sodium sulfate. Concentrated and the residue was purified by silica column chromatography (PE/EA, 10:1) to give 19.1 g 7 (off-white solid, 45%).

General Procedure for the Preparation of Compound 8

To a solution of compound 7 (20.0 g, 90.9 mmol, 1.0 eq) in MeOH (200 mL) was added 10% Pd—C (6 g, 20% W/W) and stirred under H₂ at r.t for 3~4 h. TLC showed 7 left, another batch of Pd—C (6 g, 20% W/W) was added and the reaction was continued to stir at r.t for 4~6 h. TLC showed no 7 left but there was two spots on TLC. Another batch of Pd—C (6 g, 20% W/W) was added and the reaction was continued to stir at r.t for 3~5 h. The progress of the reaction was monitored by HPLC. After TLC showed only one spot, the mixture was filtered through Celite, washed with methanol (50 mL), and the filtrate was concentrated to give the crude which was recrystallized by EA to give 12.1 g 8 (gray solid, 73%). MS (ESI) m/z: 191[M+H]+

Example 1o—Synthesis of Compound 241 (BC18847)

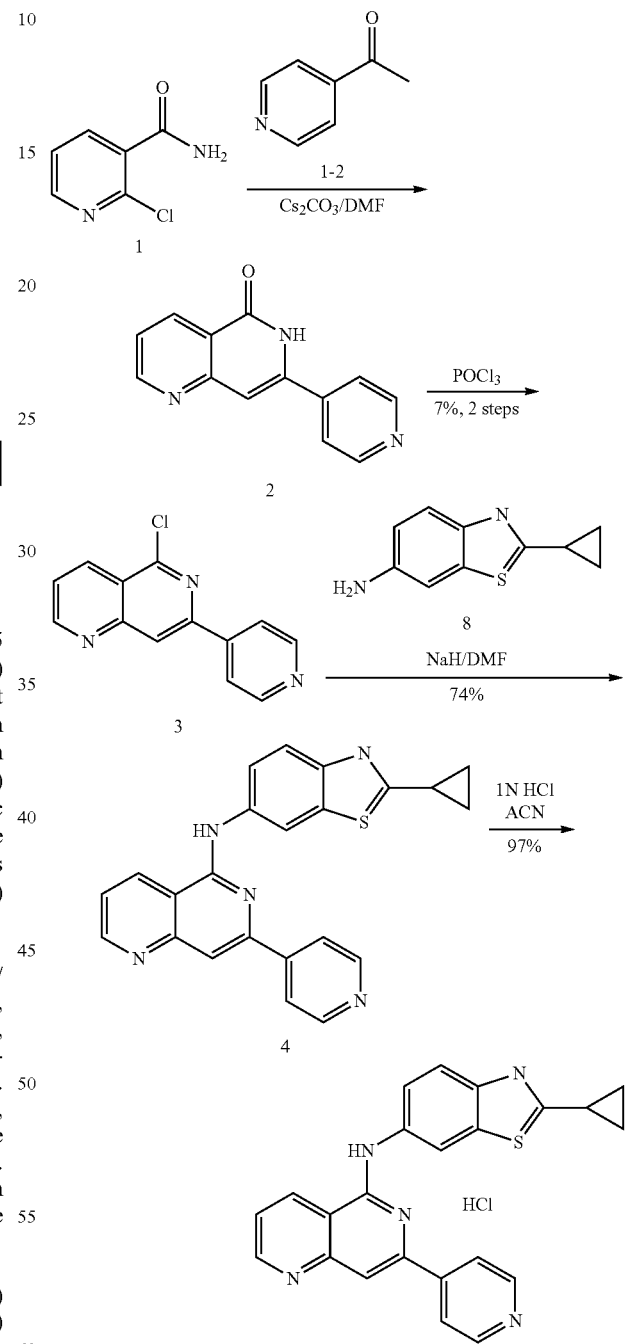

General Procedure for the Preparation of Compound 2

Compound 1 (150.0 g, 960 mmol, 1.0 eq), 1-(pyridin-4-yl)ethanone (174.0 g, 1.44 mol, 1.5 eq), cesium carbonate (630 g, 1.93 mol, 2.0 eq) and copper(I) bromide (13.8 g, 9.6 mmol, 0.1 eq) was dissolved in N,N-dimethylformamide (750 mL) and stirred at 80° C. overnight, the mixture was diluted with water (2 L). The solid was filtered, washed with water, and dried to give a black residue (175.2 g) which was used for next step without further purification.

General Procedure for the Preparation of Compound 3

A solution of compound 2 (175.2 g) in phosphorus oxychloride (500 mL) was stirred at 110° C. overnight and the progress of the reaction checked by LCMS. Excess phosphorus oxychloride was distilled under reduced pressure. EA (400 mL) and water (200 mL) was added to the system. The mixture was adjusted to pH 7 with saturated aqueous NaHCO$_3$. The water phase was extracted with EA (500 mL×3). The organic phase was washed with brine and dried over anhydrous sodium sulfate, and concentrated to give a crude, which was purified by column chromatography on a silica gel (EA: PE=10:1 to 1:1) to afford 14.5 g 3 (yellow solid, 7%, 2 steps). MS (ESI) m/z: 242[M+H]+

General Procedure for the Preparation of Compound 4

To a suspension of NaH (2.4 g, 100 mmol, 3 eq) in DMF (65 mL) at 0° C. was added amine 8 (5.3 g, 33.7 mmol, 1.01 eq). The mixture was stirred at rt for 30 min. To above mixture was added compound 3 (8.0 g, 33.2 mmol, 1 eq). The mixture was stirred at 80° C. for 16 hours. After completion, the mixture was cooled to room temperature and water (350 mL) was added slowly. The solid collected was triturated with EA and dried to give 9.7 g 4 (yellow solid, 74%). MS (ESI) m/z: 396[M+H]+, 394[M−H]−

General Procedure for the Preparation of BC18847

To a solution of compound 4 (30 g, 75.9 mmol, 1 eq) in ACN (60 mL) was added 1N HCl (114 mL, 113.9 mmol, 1.5 eq.). The mixture was stirred for 0.5 h. Then the mixture was lyophilized to give 32 g BC18847 (red solid, 97%). MS (ESI) m/z: 396[M+H]+, 394[M−H]−

$^1$H NMR (400 MHz, DMSO) δ 9.02-8.91 (m, 2H), 8.71 (d, J=6.4 Hz, 2H), 8.37 (d, J=6.5 Hz, 2H), 8.18 (d, J=1.5 Hz, 1H), 7.90 (s, 1H), 7.73-7.62 (m, 3H), 2.47 (s, 1H), 1.30-1.15 (m, 2H), 1.09-0.94 (m, 2H).

Example 1p—Synthesis of Compound 244 (BC18850)

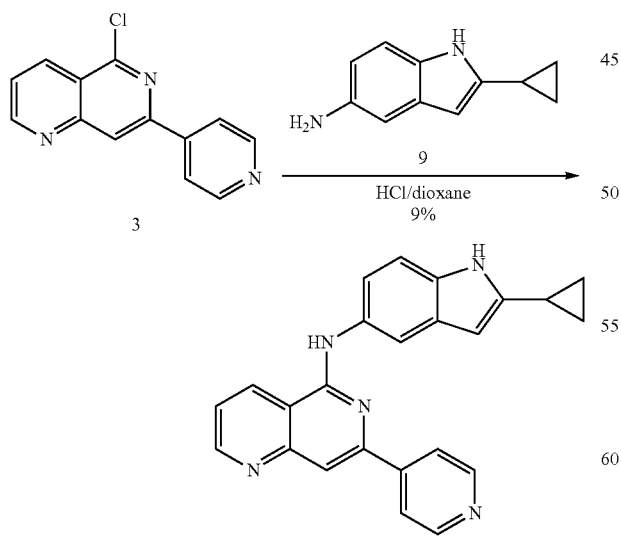

General Procedure for the Preparation of BC18850

To a solution of 3 (as prepared in Example 1o) (0.12 g, 0.50 mmol, 1 eq) and 9 (0.17 g, 1.0 mmol, 2 eq) in NMP (1.5 mL) was added 4 M HCl/dioxane (0.13 mL, 0.50 mmol, 1 eq) and the mixture was stirred at 100° C. overnight. After cooled to rt, the mixture was purified by Prep-HPLC directly to give 17 mg BC18850 (yellow solid, 9%). MS (ESI) m/z: 378[M+H]+.

$^1$H NMR (400 MHz, DMSO) δ 10.80 (s, 1H), 9.39 (s, 1H), 9.04-8.90 (m, 2H), 8.62 (dd, J=4.6, 1.5 Hz, 2H), 8.05 (dd, J=4.6, 1.6 Hz, 2H), 7.87-7.78 (m, 2H), 7.59 (dd, J=8.4, 4.3 Hz, 1H), 7.40 (dd, J=8.6, 2.0 Hz, 1H), 7.25 (d, J=8.6 Hz, 1H), 6.09 (d, J=1.8 Hz, 1H), 1.99 (td, J=8.4, 4.1 Hz, 1H), 0.98-0.89 (m, 2H), 0.82-0.74 (m, 2H).

Example 1—Compound Structures

The compounds in Table 1 were prepared as shown in the general scheme from readily available starting materials.

TABLE 1

| No. | BC code | Structure |
|---|---|---|
| 1 | BC18607 | 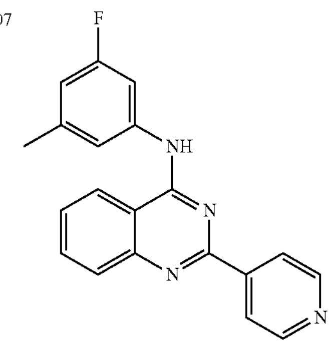 |
| 2 | BC18608 | 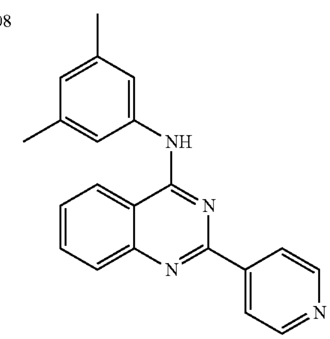 |
| 3 | BC18612 | 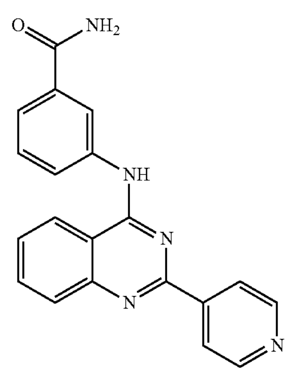 [SMILES: NC(=O)c1cccc(Nc2nc(-c3ccncc3)nc3ccccc23)c1] |

TABLE 1-continued
| No. | BC code | Structure |
|---|---|---|
| 4 | BC18614 | 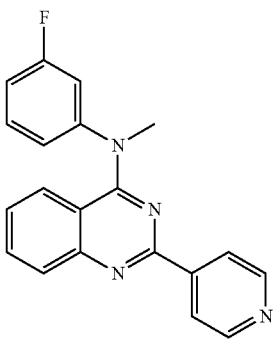 [SMILES: CN(c1cccc(F)c1)c1nc(-c2ccncc2)nc2ccccc12] |
| 5 | BC18615 | 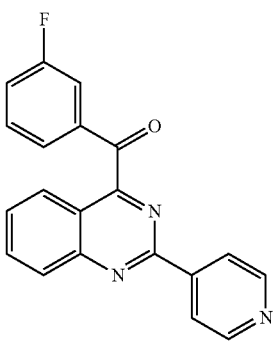 [SMILES: O=C(c1cccc(F)c1)c1nc(-c2ccncc2)nc2ccccc12] |
| 6 | BC18616 | 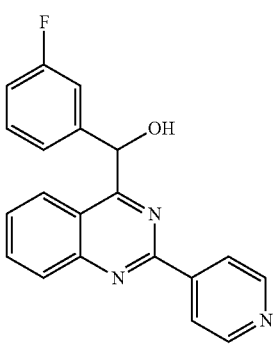 [SMILES: OC(c1cccc(F)c1)c1nc(-c2ccncc2)nc2ccccc12] |
| 7 | BC18617 | 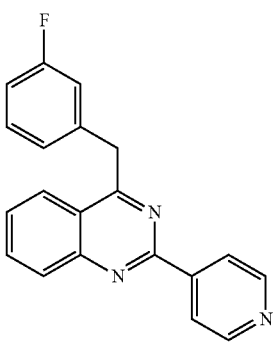 [SMILES: Fc1cccc(Cc2nc(-c3ccncc3)nc3ccccc23)c1] |
| 8 | BC18618 | 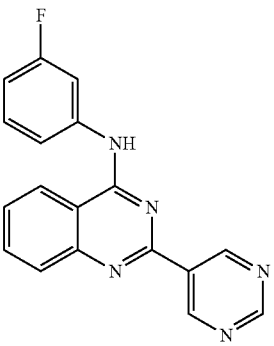 [SMILES: Fc1cccc(Nc2nc(-c3cncnc3)nc3ccccc23)c1] |
| 9 | BC18619 | 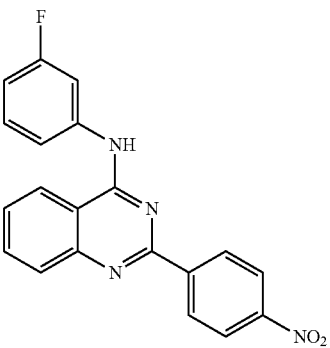 [SMILES: O=[N+]([O-])c1ccc(-c2nc(Nc3cccc(F)c3)c3ccccc3n2)cc1] |
| 10 | BC18625 | 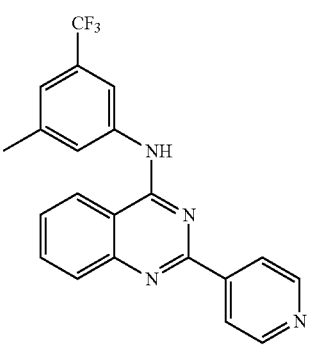 [SMILES: Cc1cc(Nc2nc(-c3ccncc3)nc3ccccc23)cc(C(F)(F)F)c1] |
| 11 | BC18626 | 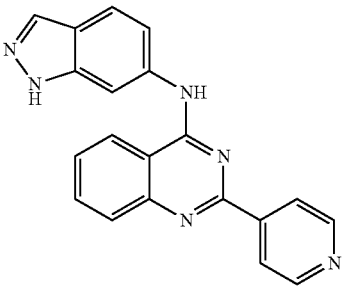 |

TABLE 1-continued

| No. | BC code | Structure |
|---|---|---|
| 12 | BC18627 | 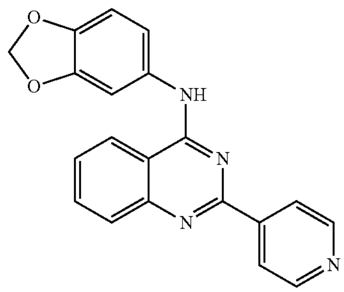 [SMILES: c1ccc2c(Nc3ccc4c(c3)OCO4)nc(-c3ccncc3)nc2c1] |
| 13 | BC18628 | 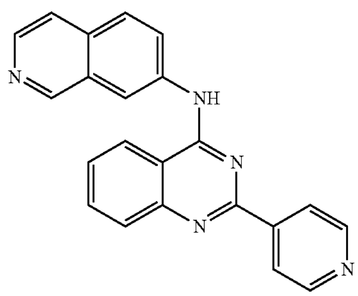 [SMILES: c1ccc2c(Nc3ccc4ccncc4c3)nc(-c3ccncc3)nc2c1] |
| 14 | BC18629 | 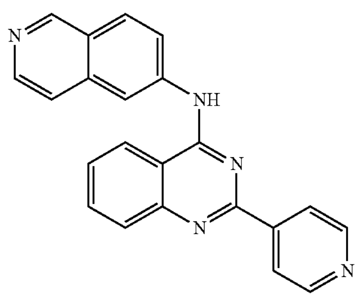 [SMILES: c1ccc2c(Nc3ccc4cnccc4c3)nc(-c3ccncc3)nc2c1] |
| 15 | BC18630 | 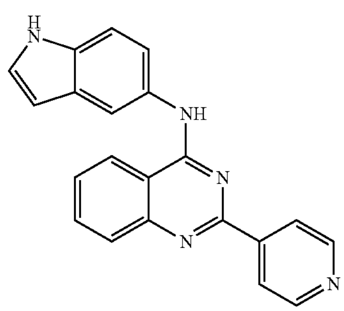 |
| 16 | BC18630 HCl salt | |
| 17 | BC18631 | 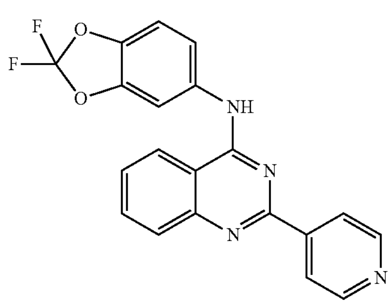 [SMILES: FC1(F)Oc2ccc(Nc3nc(-c4ccncc4)nc4ccccc34)cc2O1] |
| 18 | BC18633 | |
| 19 | BC18634 | |
| 20 | BC18635 | |
| 21 | BC18636 | |

TABLE 1-continued

| No. | BC code | Structure |
|---|---|---|
| 22 | BC18637 | 3-Et, 5-Me-phenyl-NH-[2-(pyridin-4-yl)quinazolin-4-yl] |
| 23 | BC18639 | (1-methyl-1H-indazol-6-yl)-NH-[2-(pyridin-4-yl)quinazolin-4-yl] |
| 24 | BC18640 | (benzo[d]isothiazol-6-yl)-NH-[2-(pyridin-4-yl)quinazolin-4-yl] |
| 25 | BC18641 | (1H-indol-6-yl)-NH-[2-(pyridin-4-yl)quinazolin-4-yl] |
| 26 | BC18642 | (1-methyl-1H-indol-5-yl)-NH-[2-(pyridin-4-yl)quinazolin-4-yl] |
| 27 | BC18643 | (benzo[d]thiazol-5-yl)-NH-[2-(pyridin-4-yl)quinazolin-4-yl] |
| 28 | BC18644 | (1-methyl-1H-benzo[d]imidazol-5-yl)-NH-[2-(pyridin-4-yl)quinazolin-4-yl] |
| 29 | BC18645 | (2-methyl-1H-benzo[d]imidazol-5-yl)-NH-[2-(pyridin-4-yl)quinazolin-4-yl] |
| 30 | BC18646 | (2-methyl-1H-indol-5-yl)-NH-[4-fluoro-2-(pyridin-4-yl)quinazolin-4-yl] |
| 31 | BC18647 | (1-methyl-1H-indazol-5-yl)-NH-[2-(pyridin-4-yl)quinazolin-4-yl] |

TABLE 1-continued

| No. | BC code | Structure |
|-----|---------|-----------|
| 32 | BC18648 | 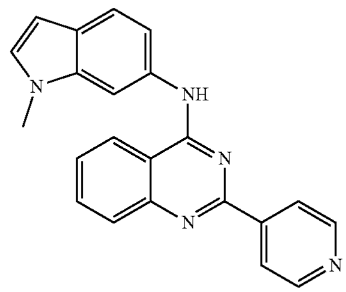 [SMILES: Cn1ccc2ccc(Nc3nc(-c4ccncc4)nc4ccccc34)cc21] |
| 33 | BC18649 | 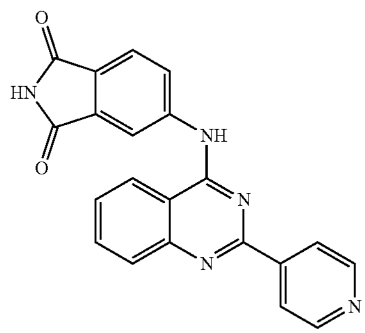 [SMILES: O=C1NC(=O)c2cc(Nc3nc(-c4ccncc4)nc4ccccc34)ccc21] |
| 34 | BC18652 | 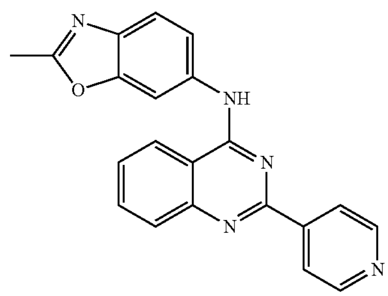 [SMILES: Cc1nc2ccc(Nc3nc(-c4ccncc4)nc4ccccc34)cc2o1] |
| 35 | BC18653 | 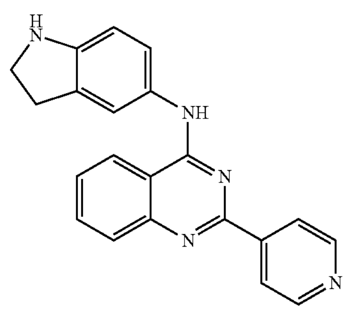 [SMILES: c1ccc2c(Nc3ccc4c(c3)CCN4)nc(-c3ccncc3)nc2c1] |
| 36 | BC18654 | 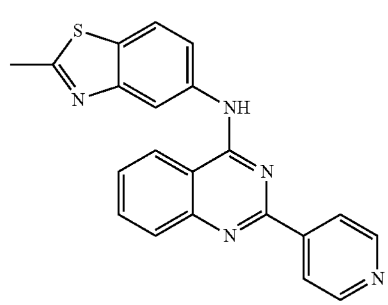 |
| 37 | BC18655 | |
| 38 | BC18656 | |
| 39 | BC18657 | |
| 40 | BC18658 | |
| 41 | BC18659 | |

TABLE 1-continued

| No. | BC code | Structure |
|---|---|---|
| 42 | BC18660 | 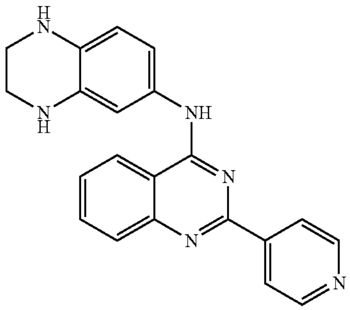 [SMILES: c1ccc2c(Nc3ccc4c(c3)NCCN4)nc(-c3ccncc3)nc2c1] |
| 43 | BC18663 | 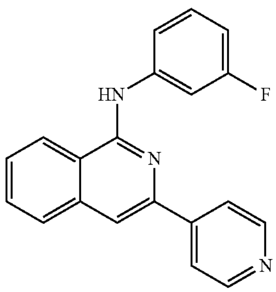 [SMILES: Fc1cccc(Nc2nc(-c3ccncc3)cc3ccccc23)c1] |
| 44 | BC18664 | 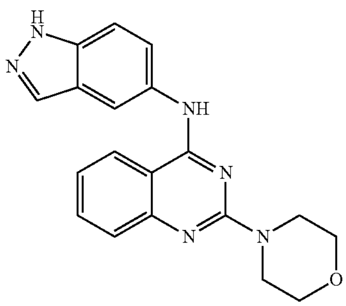 [SMILES: c1ccc2c(Nc3ccc4[nH]ncc4c3)nc(N3CCOCC3)nc2c1] |
| 45 | BC18665 | 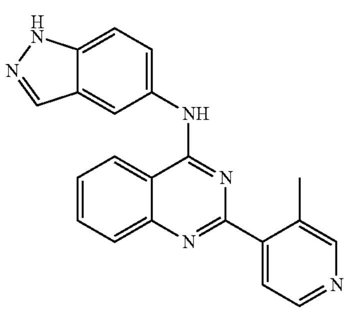 [SMILES: Cc1cnccc1-c1nc(Nc2ccc3[nH]ncc3c2)c2ccccc2n1] |
| 46 | BC18666 | 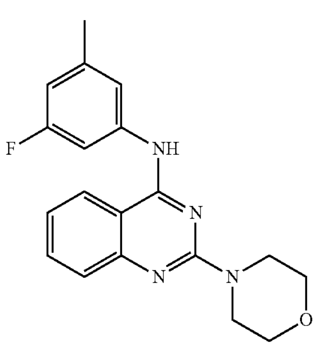 [SMILES: Cc1cc(F)cc(Nc2nc(N3CCOCC3)nc3ccccc23)c1] |
| 47 | BC18667 | |
| 48 | BC18668 | |
| 49 | BC18669 | |
| 50 | BC18670 | |
| 51 | BC18671 | |

TABLE 1-continued

| No. | BC code | Structure |
|---|---|---|
| 52 | BC18672 | 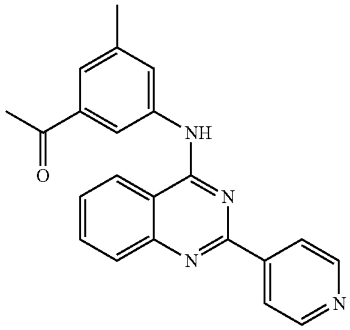 [SMILES: CC(=O)c1cc(C)cc(Nc2nc(-c3ccncc3)nc3ccccc23)c1] |
| 53 | BC18673 | 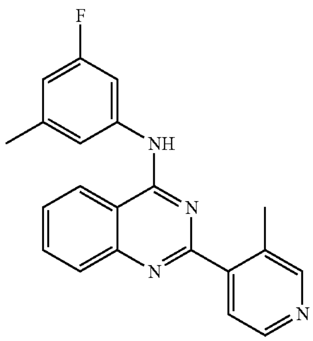 [SMILES: Cc1cc(F)cc(Nc2nc(-c3ccncc3C)nc3ccccc23)c1] |
| 54 | BC18674 | 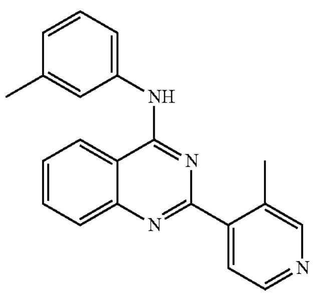 [SMILES: Cc1cccc(Nc2nc(-c3ccncc3C)nc3ccccc23)c1] |
| 55 | BC18675 | 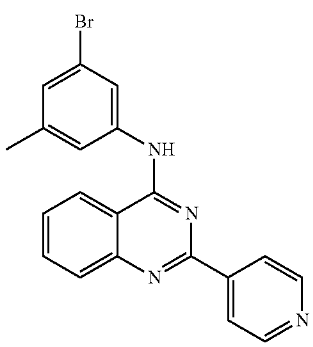 [SMILES: Cc1cc(Br)cc(Nc2nc(-c3ccncc3)nc3ccccc23)c1] |
| 56 | BC18676 | 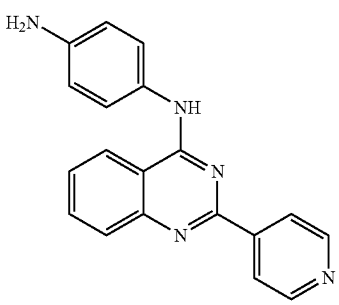 [SMILES: Nc1ccc(Nc2nc(-c3ccncc3)nc3ccccc23)cc1] |
| 57 | BC18677 | 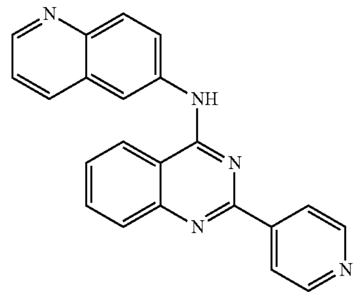 [SMILES: c1cnc2ccc(Nc3nc(-c4ccncc4)nc4ccccc34)cc2c1] |
| 58 | BC18678 | 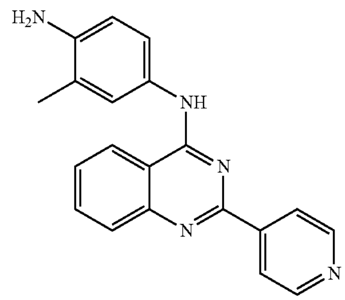 [SMILES: Cc1cc(Nc2nc(-c3ccncc3)nc3ccccc23)ccc1N] |
| 59 | BC18679 | 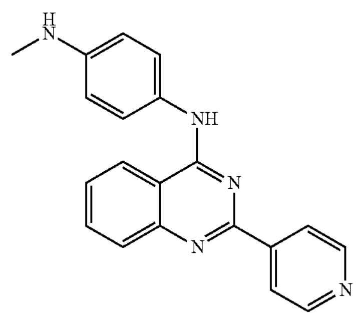 [SMILES: CNc1ccc(Nc2nc(-c3ccncc3)nc3ccccc23)cc1] |
| 60 | BC18680 | 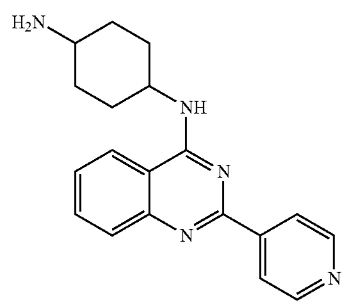 [SMILES: NC1CCC(Nc2nc(-c3ccncc3)nc3ccccc23)CC1] |
| 61 | BC18681 | 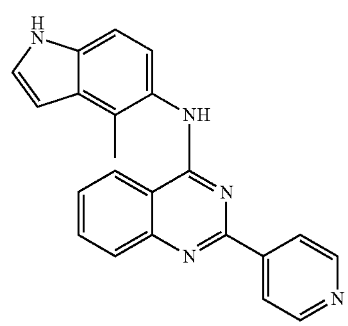 [SMILES: Cc1c(Nc2nc(-c3ccncc3)nc3ccccc23)ccc2[nH]ccc12] |

TABLE 1-continued

| No. | BC code | Structure |
|---|---|---|
| 62 | BC18682 | 2-methyl-1H-indol-5-yl-NH-quinazolin-4-yl, 2-(pyridin-4-yl) |
| 63 | BC18683 | 1H-indol-5-yl-NH-quinazolin-4-yl, 2-(4-hydroxyphenyl) |
| 64 | BC18684 | 1H-indazol-5-yl-NH-quinazolin-4-yl, 2-(4-hydroxyphenyl) |
| 65 | BC18685 | 3-fluorophenyl-NH-quinazolin-4-yl, 2-(4-hydroxyphenyl) |
| 66 | BC18686 | 1H-indol-5-yl-NH-quinazolin-4-yl, 2-(1-hydroxypyridin-4-yl) |
| 67 | BC18687 | 1H-indol-5-yl-NH-quinolin-4-yl, 2-(pyridin-4-yl) |
| 68 | BC18688 | 1H-indazol-5-yl-NH-quinolin-4-yl, 2-(pyridin-4-yl) |
| 69 | BC18689 | 3-fluorophenyl-NH-quinolin-4-yl, 2-(pyridin-4-yl) |
| 70 | BC18690 | 1-acetyl-1H-indol-5-yl-NH-quinazolin-4-yl, 2-(pyridin-4-yl) |

TABLE 1-continued
| No. | BC code | Structure |
|---|---|---|
| 71 | BC18693 | 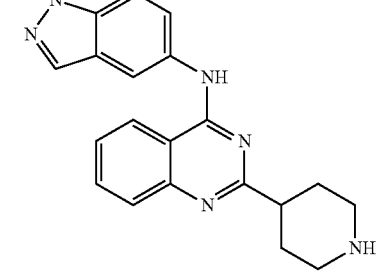 |
| 72 | BC18695 | 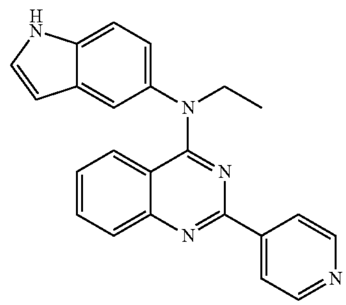 [SMILES: CCN(c1ccc2[nH]ccc2c1)c1nc(-c2ccncc2)nc2ccccc12] |
| 73 | BC18697 | 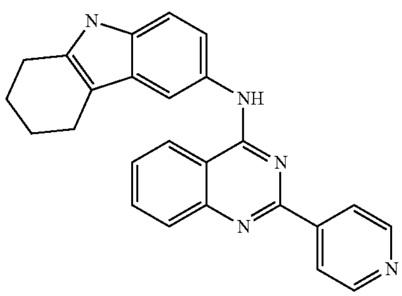 [SMILES: c1ccc2c(Nc3ccc4[nH]c5c(c4c3)CCCC5)nc(-c3ccncc3)nc2c1] |
| 74 | BC18698 | 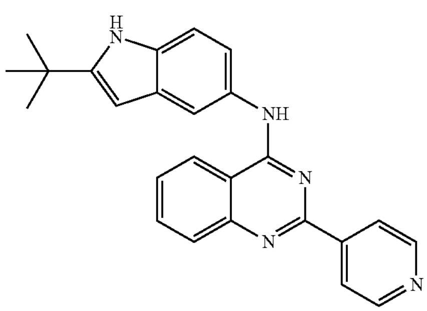 [SMILES: CC(C)(C)c1cc2cc(Nc3nc(-c4ccncc4)nc4ccccc34)ccc2[nH]1] |
| 75 | BC18702 | 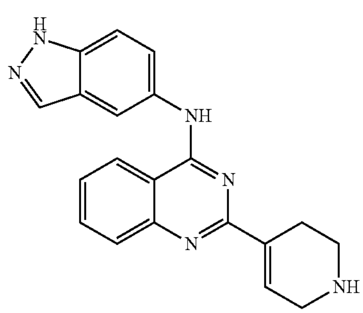 [SMILES: C1=C(c2nc(Nc3ccc4[nH]ncc4c3)c3ccccc3n2)CCNC1] |
TABLE 1-continued
| No. | BC code | Structure |
|---|---|---|
| 76 | BC18703 | 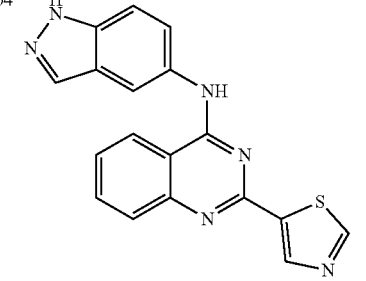 |
| 77 | BC18704 | 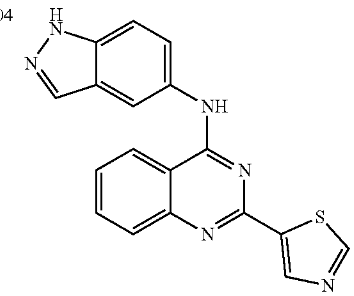 |
| 78 | BC18705 | 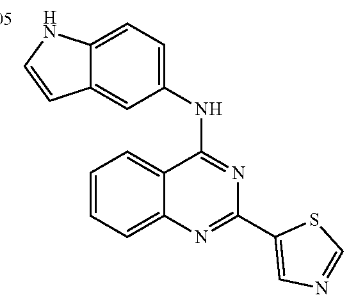 |
| 79 | BC18706 | 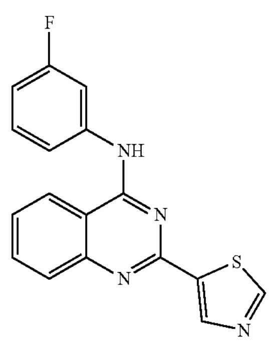 [SMILES: Fc1cccc(Nc2nc(-c3cncs3)nc3ccccc23)c1] |
| 80 | BC18707 | 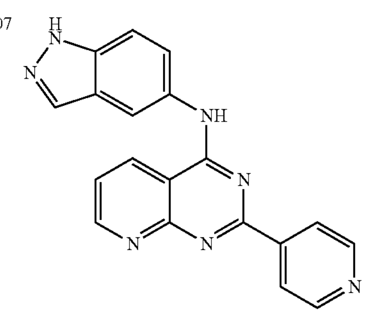 |

TABLE 1-continued

| No. | BC code | Structure |
|---|---|---|
| 81 | BC18708 | 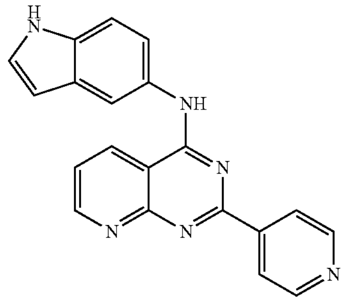 [SMILES: c1cnc2nc(-c3ccncc3)nc(Nc3ccc4[nH]ccc4c3)c2c1] |
| 82 | BC18709 | 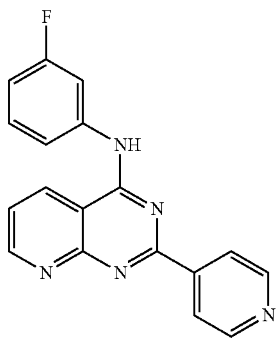 [SMILES: Fc1cccc(Nc2nc(-c3ccncc3)nc3ncccc23)c1] |
| 83 | BC18711 | 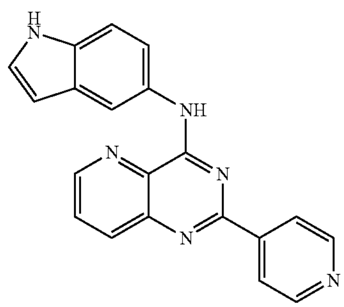 [SMILES: c1cnc2c(Nc3ccc4[nH]ccc4c3)nc(-c3ccncc3)nc2c1] |
| 84 | BC18713 | 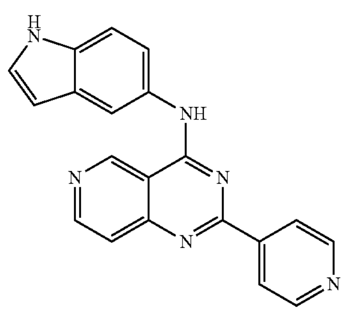 [SMILES: c1cc(-c2nc(Nc3ccc4[nH]ccc4c3)c3cnccc3n2)ccn1] |
| 85 | BC18714 | 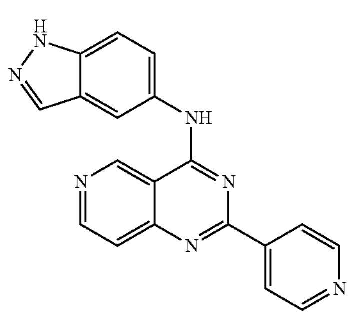 [SMILES: c1cc(-c2nc(Nc3ccc4[nH]ncc4c3)c3cnccc3n2)ccn1] |
| 86 | BC18717 | |
| 87 | BC18718 | |
| 88 | BC18720 | |
| 89 | BC18722 | |
| 90 | BC18724 | |

TABLE 1-continued
| No. | BC code | Structure |
|-----|---------|-----------|
| 91 | BC18725 | 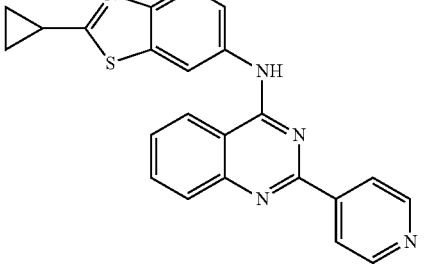 |
| 92 | BC18726 | 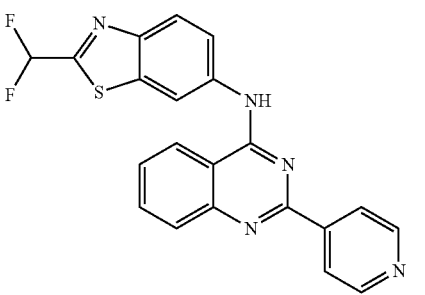 [SMILES: FC(F)c1nc2ccc(Nc3nc(-c4ccncc4)nc4ccccc34)cc2s1] |
| 93 | BC18727 | 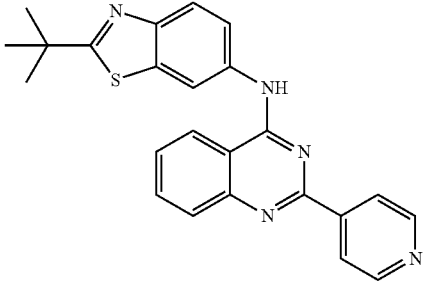 [SMILES: CC(C)(C)c1nc2ccc(Nc3nc(-c4ccncc4)nc4ccccc34)cc2s1] |
| 94 | BC18728 | 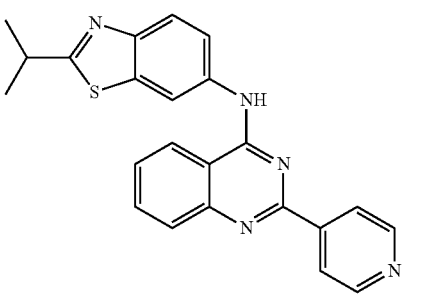 [SMILES: CC(C)c1nc2ccc(Nc3nc(-c4ccncc4)nc4ccccc34)cc2s1] |
| 95 | BC18729 | 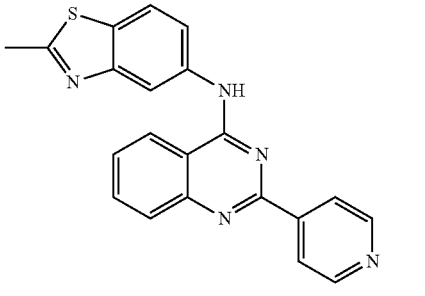 |
| 96 | BC18730 | 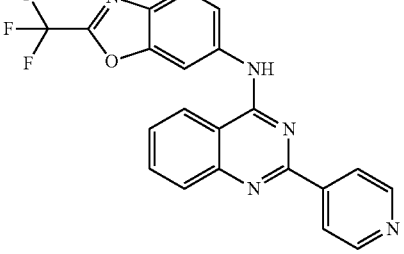 |
| 97 | BC18731 | 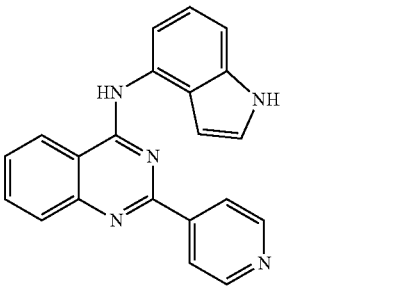 [SMILES: c1ccc2c(Nc3cccc4[nH]ccc34)nc(-c3ccncc3)nc2c1] |
| 98 | BC18732 | 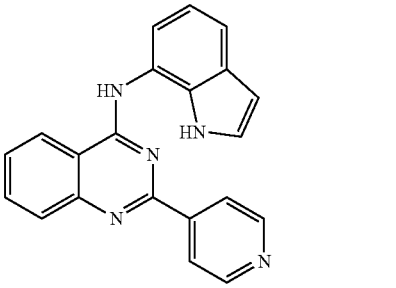 [SMILES: c1cc(Nc2nc(-c3ccncc3)nc3ccccc23)c2[nH]ccc2c1] |
| 99 | BC18733 | 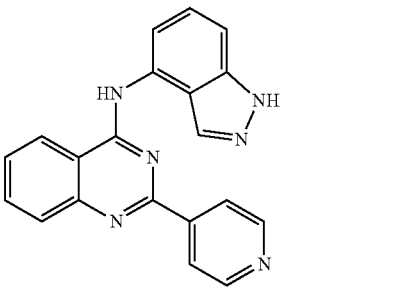 |
| 100 | BC18734 | 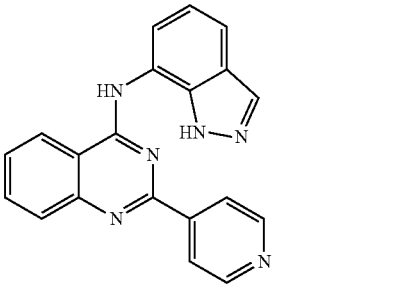 [SMILES: c1cc(Nc2nc(-c3ccncc3)nc3ccccc23)c2[nH]ncc2c1] |

TABLE 1-continued

| No. | BC code | Structure |
|-----|---------|-----------|
| 101 | BC18735 | 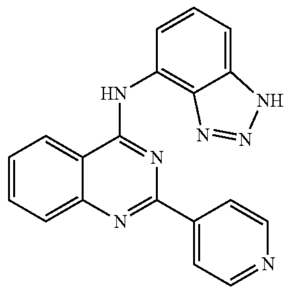 [SMILES: c1ccc2c(Nc3cccc4[nH]nnc34)nc(-c3ccncc3)nc2c1] |
| 102 | BC18736 | 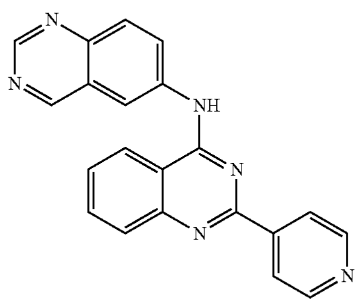 [SMILES: c1ccc2c(Nc3ccc4ncncc4c3)nc(-c3ccncc3)nc2c1] |
| 103 | BC18737 | 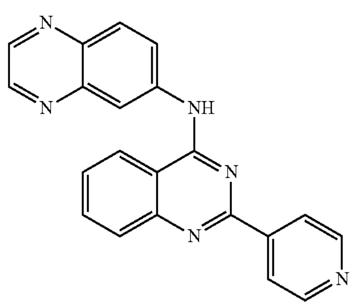 [SMILES: c1ccc2c(Nc3ccc4nccnc4c3)nc(-c3ccncc3)nc2c1] |
| 104 | BC18738 | 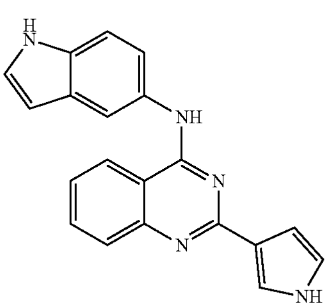 [SMILES: c1ccc2c(Nc3ccc4[nH]ccc4c3)nc(-c3cc[nH]c3)nc2c1] |
| 105 | BC18739 | 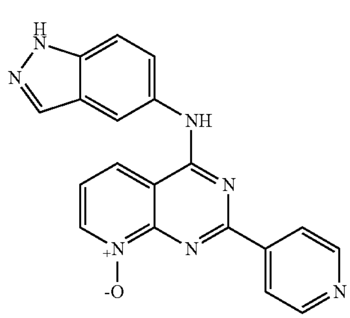 |
| 106 | BC18740 | 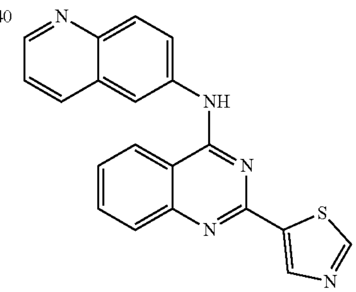 |
| 107 | BC18742 | 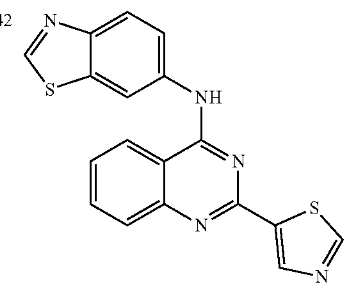 |
| 108 | BC18743 | 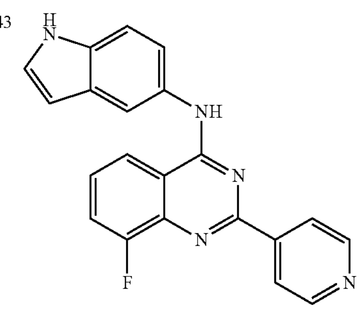 |
| 109 | BC18744 | 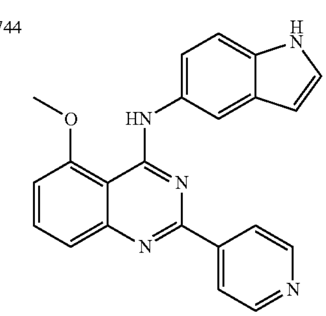 |
| 110 | BC18745 | 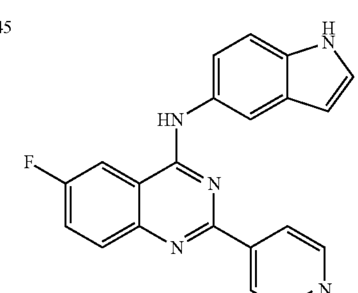 |

TABLE 1-continued

| No. | BC code | Structure |
|---|---|---|
| 111 | BC18746 | 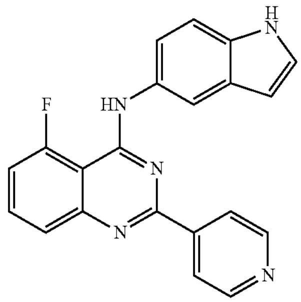 [SMILES: Fc1cccc2nc(-c3ccncc3)nc(Nc3ccc4[nH]ccc4c3)c12] |
| 112 | BC18747 | 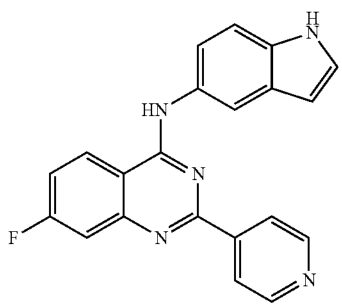 [SMILES: Fc1ccc2c(Nc3ccc4[nH]ccc4c3)nc(-c3ccncc3)nc2c1] |
| 113 | BC18748 | 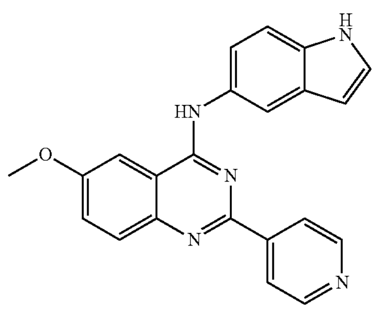 [SMILES: COc1ccc2nc(-c3ccncc3)nc(Nc3ccc4[nH]ccc4c3)c2c1] |
| 114 | BC18749 | 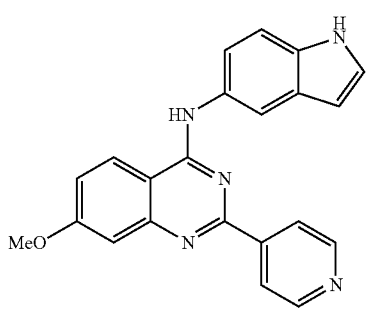 [SMILES: COc1ccc2c(Nc3ccc4[nH]ccc4c3)nc(-c3ccncc3)nc2c1] |
| 115 | BC18750 | 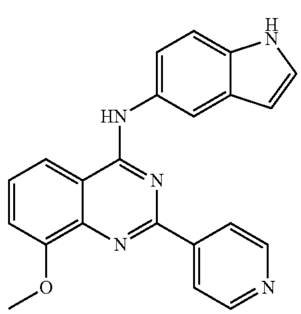 [SMILES: COc1cccc2c(Nc3ccc4[nH]ccc4c3)nc(-c3ccncc3)nc12] |
| 116 | BC18752 | |
| 117 | BC18754 | |
| 118 | BC18755 | |
| 119 | BC18756 | |
| 120 | BC18757 | |

TABLE 1-continued
| No. | BC code | Structure |
|---|---|---|
| 121 | BC18758 | 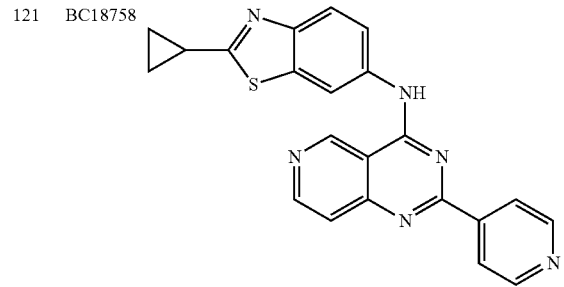 |
| 122 | BC18759 | 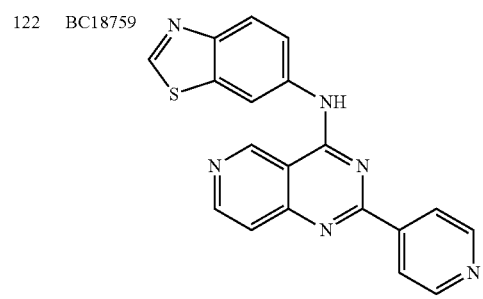 |
| 123 | BC18760 | 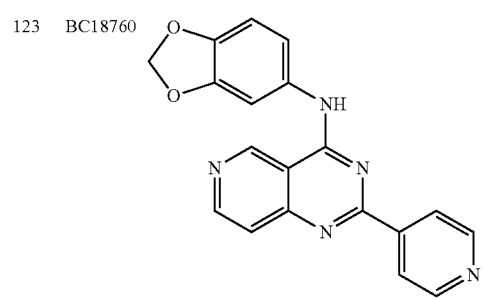 |
| 124 | BC18761 | 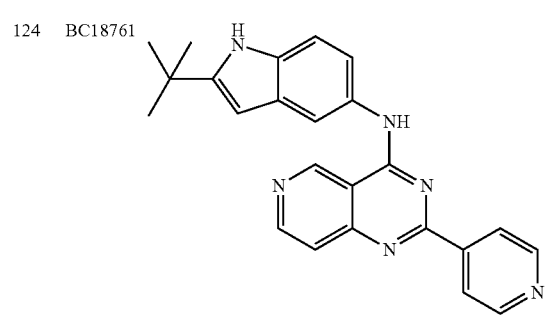 |
| 125 | BC18762 | 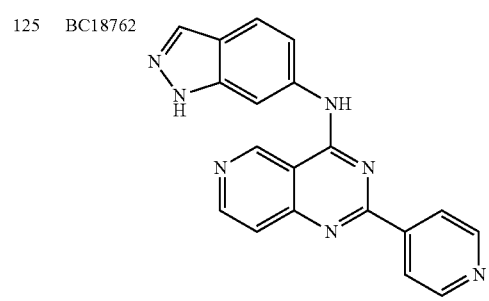 |
| 126 | BC18763 | 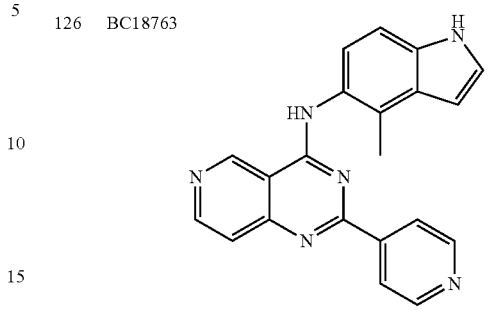 |
| 127 | BC18764 | 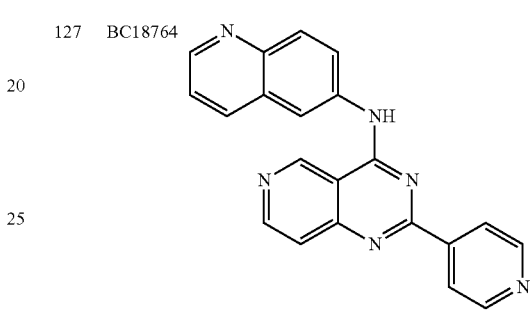 |
| 128 | BC18765 | 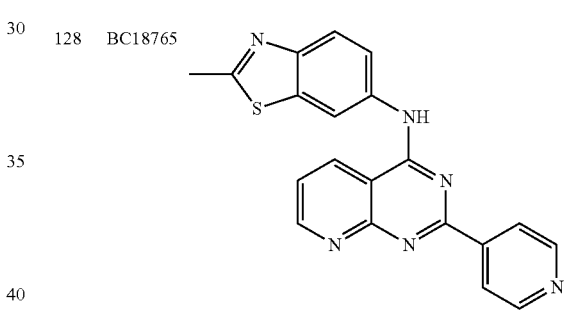 |
| 129 | BC18766 | 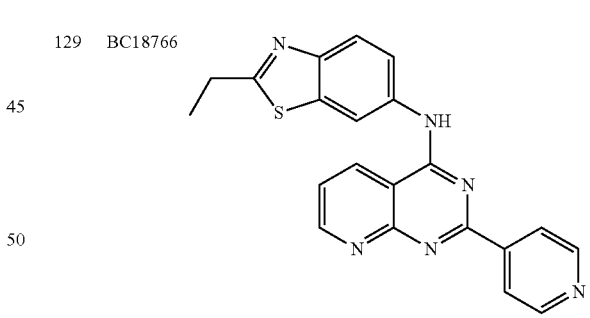 |
| 130 | BC18767 | 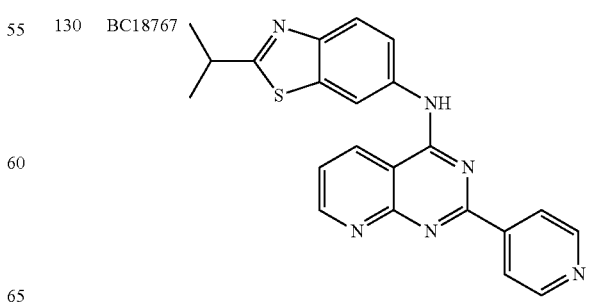 |

TABLE 1-continued
| No. | BC code | Structure |
|---|---|---|
| 131 | BC18768 | 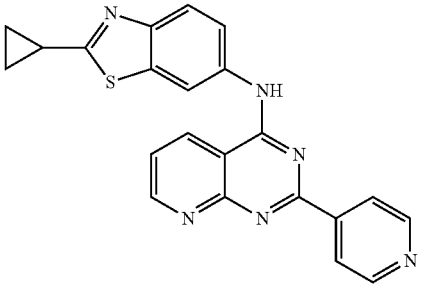 [SMILES: c1cnc2nc(-c3ccncc3)nc(Nc3ccc4nc(C5CC5)sc4c3)c2c1] |
| 132 | BC18769 | 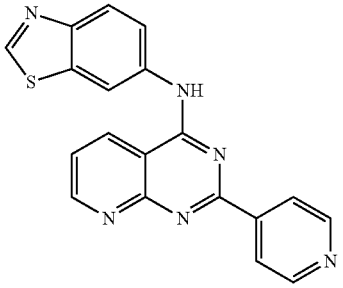 |
| 133 | BC18770 | 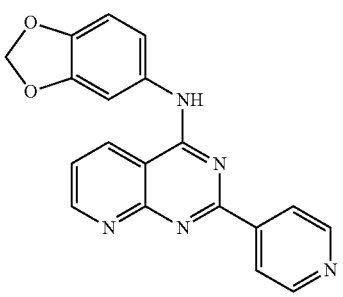 [SMILES: c1cnc2nc(-c3ccncc3)nc(Nc3ccc4c(c3)OCO4)c2c1] |
| 134 | BC18771 | 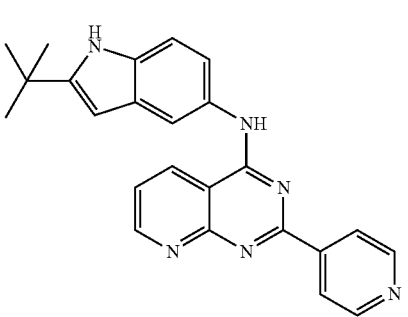 [SMILES: CC(C)(C)c1cc2cc(Nc3nc(-c4ccncc4)nc4ncccc34)ccc2[nH]1] |
| 135 | BC18772 | 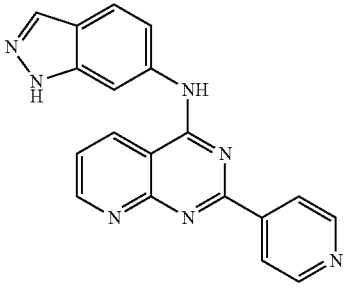 [SMILES: c1cnc2nc(-c3ccncc3)nc(Nc3ccc4cn[nH]c4c3)c2c1] |
| 136 | BC18773 | 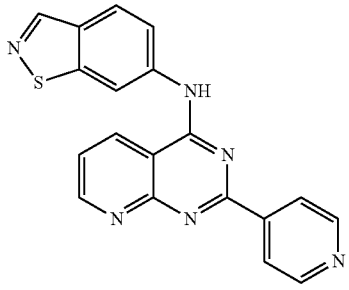 [SMILES: c1cnc2nc(-c3ccncc3)nc(Nc3ccc4cnsc4c3)c2c1] |
| 137 | BC18774 | 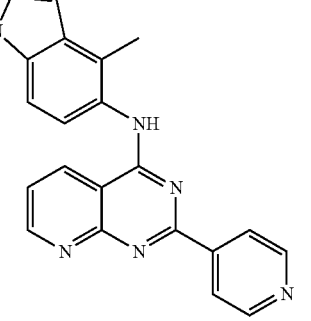 |
| 138 | BC18775 | 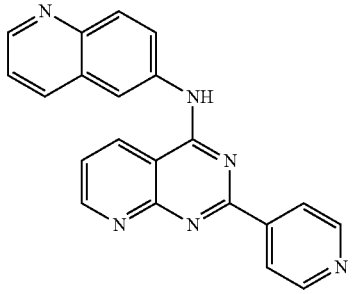 [SMILES: c1cnc2ccc(Nc3nc(-c4ccncc4)nc4ncccc34)cc2c1] |
| 139 | BC18776 | 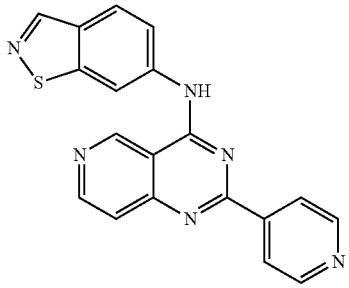 [SMILES: c1cc(-c2nc(Nc3ccc4cnsc4c3)c3cnccc3n2)ccn1] |
| 140 | BC18778 | 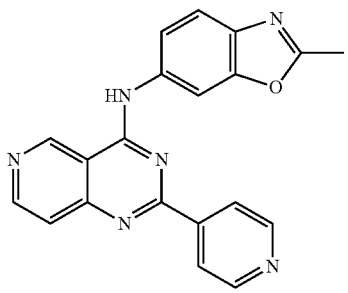 [SMILES: Cc1nc2ccc(Nc3nc(-c4ccncc4)nc4ccncc34)cc2o1] |

TABLE 1-continued

| No. | BC code | Structure |
|---|---|---|
| 141 | BC18779 | 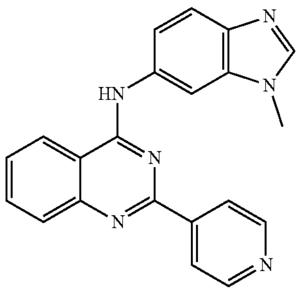 [SMILES: Cn1cnc2ccc(Nc3nc(-c4ccncc4)nc4ccccc34)cc21] |
| 142 | BC18780 | 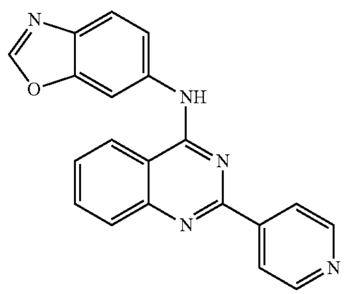 [SMILES: c1ccc2c(Nc3ccc4ncoc4c3)nc(-c3ccncc3)nc2c1] |
| 143 | BC18782 | 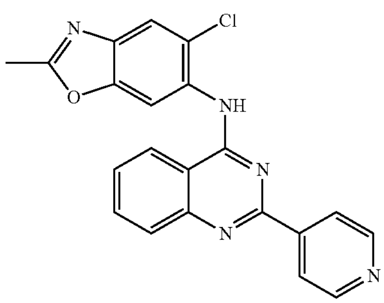 [SMILES: Cc1nc2cc(Cl)c(Nc3nc(-c4ccncc4)nc4ccccc34)cc2o1] |
| 144 | BC18783 | 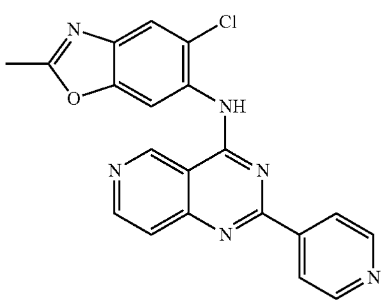 |
| 145 | BC18784 | 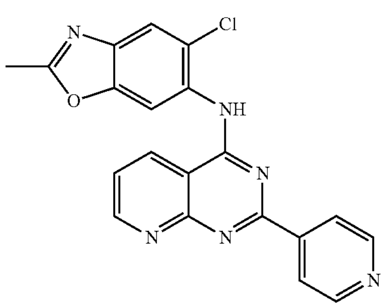 [SMILES: Cc1nc2cc(Cl)c(Nc3nc(-c4ccncc4)nc4ncccc34)cc2o1] |
| 146 | BC18785 | 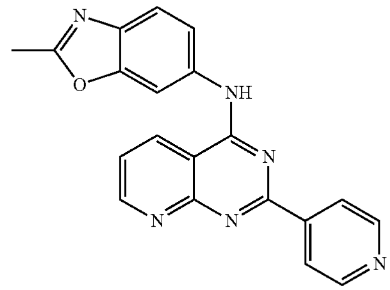 [SMILES: Cc1nc2ccc(Nc3nc(-c4ccncc4)nc4ncccc34)cc2o1] |
| 147 | BC18786 | 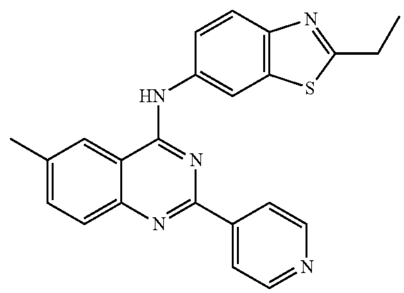 [SMILES: CCc1nc2ccc(Nc3nc(-c4ccncc4)nc4ccc(C)cc34)cc2s1] |
| 148 | BC18787 | 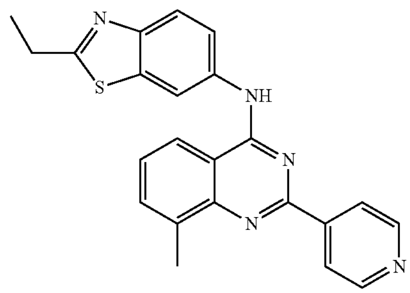 [SMILES: CCc1nc2ccc(Nc3nc(-c4ccncc4)nc4c(C)cccc34)cc2s1] |
| 149 | BC18788 | 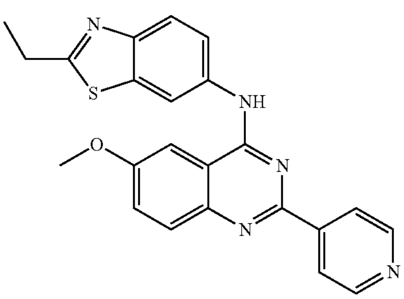 [SMILES: CCc1nc2ccc(Nc3nc(-c4ccncc4)nc4ccc(OC)cc34)cc2s1] |
| 150 | BC18789 | 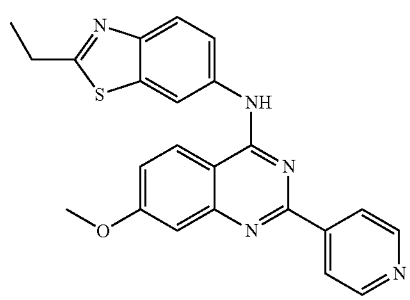 [SMILES: CCc1nc2ccc(Nc3nc(-c4ccncc4)nc4cc(OC)ccc34)cc2s1] |

TABLE 1-continued

| No. | BC code | Structure |
|---|---|---|
| 151 | BC18790 | 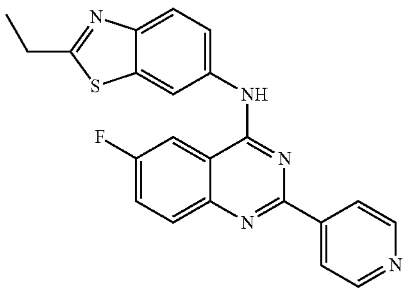 [SMILES: CCc1nc2ccc(Nc3nc(-c4ccncc4)nc4ccc(F)cc34)cc2s1] |
| 152 | BC18791 | 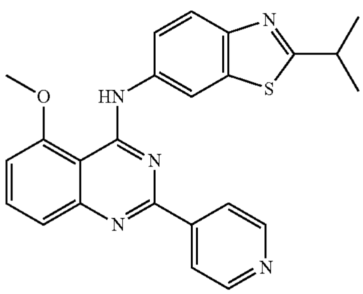 [SMILES: COc1cccc2nc(-c3ccncc3)nc(Nc3ccc4nc(C(C)C)sc4c3)c12] |
| 153 | BC18792 | 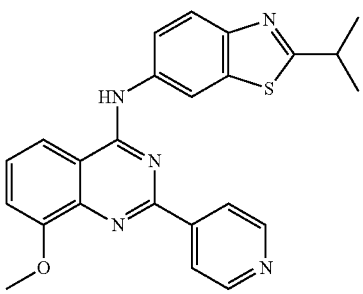 [SMILES: COc1cccc2c(Nc3ccc4nc(C(C)C)sc4c3)nc(-c3ccncc3)nc12] |
| 154 | BC18793 | 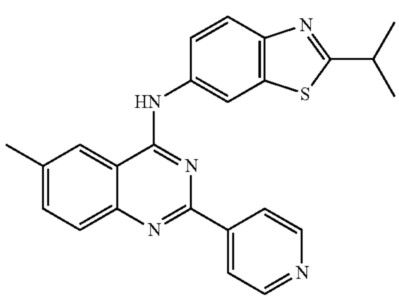 [SMILES: Cc1ccc2nc(-c3ccncc3)nc(Nc3ccc4nc(C(C)C)sc4c3)c2c1] |
| 155 | BC18794 | 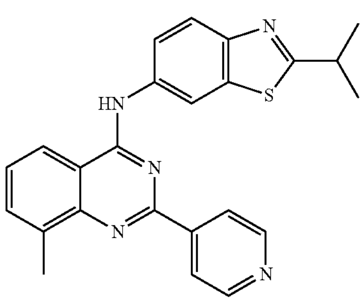 [SMILES: Cc1cccc2c(Nc3ccc4nc(C(C)C)sc4c3)nc(-c3ccncc3)nc12] |
| 156 | BC18816 | |
| 157 | BC18813 | |
| 158 | BC18815 | |

Note:
Cmpd 35 was isolated and tested as TFA salt. Compounds 42, 51, 59, 63, 64, and 65 were each isolated and tested as HCl salt. Compounds 82, 83, 89, 106, 107, 108, 113, 115, 116, 117, 119, 120, and 121 were each isolated and tested as formate salt.

The following compounds shown in Table 1a may prepared using chemical routes that would be readily apparent to one of ordinary skill in the art from readily available starting materials.

TABLE 1a

| No. | BC. Code | Structure |
|---|---|---|
| 352 | BC18795 | 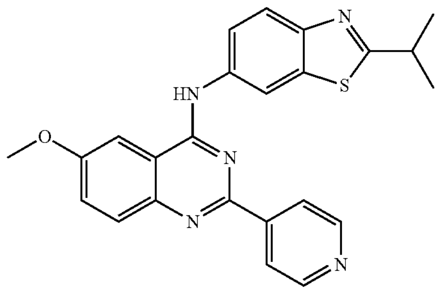 [SMILES: COc1ccc2nc(-c3ccncc3)nc(Nc3ccc4nc(C(C)C)sc4c3)c2c1] |
| 353 | BC18796 | 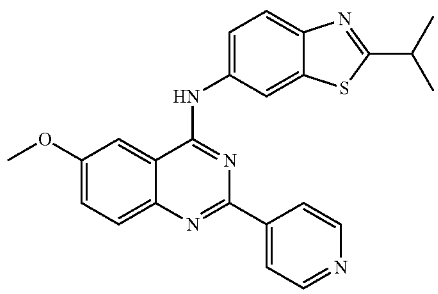 [SMILES: COc1ccc2nc(-c3ccncc3)nc(Nc3ccc4nc(C(C)C)sc4c3)c2c1] |
| 354 | BC18797 | 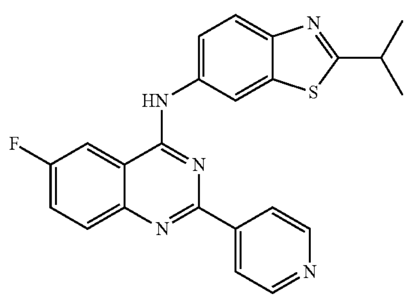 [SMILES: CC(C)c1nc2ccc(Nc3nc(-c4ccncc4)nc4ccc(F)cc34)cc2s1] |
| 355 | BC18798 | 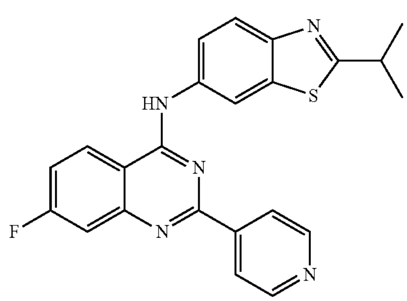 [SMILES: CC(C)c1nc2ccc(Nc3nc(-c4ccncc4)nc4cc(F)ccc34)cc2s1] |
| 356 | BC18799 | 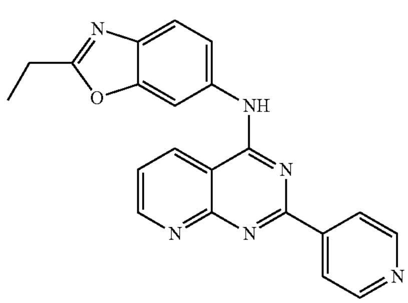 [SMILES: CCc1nc2ccc(Nc3nc(-c4ccncc4)nc4ncccc34)cc2o1] |

TABLE 1a-continued

| No. | BC. Code | Structure |
|---|---|---|
| 357 | BC18800 | 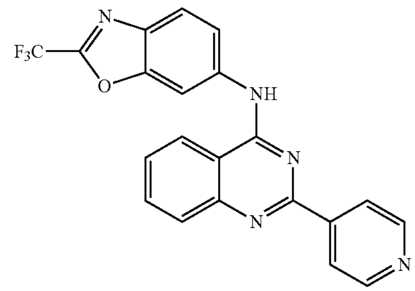 [SMILES: FC(F)(F)c1nc2ccc(Nc3nc(-c4ccncc4)nc4ccccc34)cc2o1] |
| 358 | BC18801 | 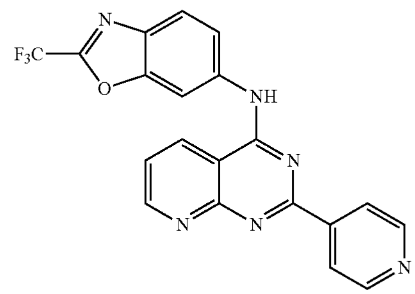 [SMILES: FC(F)(F)c1nc2ccc(Nc3nc(-c4ccncc4)nc4ncccc34)cc2o1] |
| 359 | BC18802 | 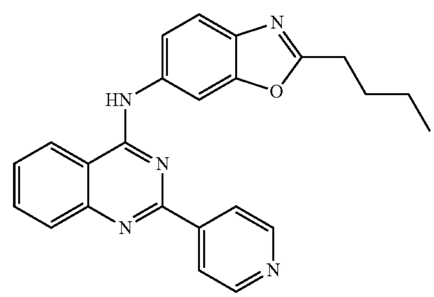 [SMILES: CCCCc1nc2ccc(Nc3nc(-c4ccncc4)nc4ccccc34)cc2o1] |
| 360 | BC18803 | 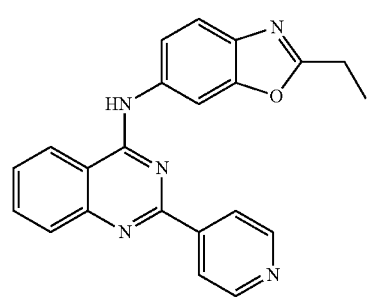 [SMILES: CCc1nc2ccc(Nc3nc(-c4ccncc4)nc4ccccc34)cc2o1] |
| 361 | BC18804 | 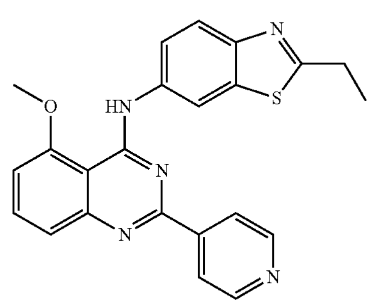 [SMILES: CCc1nc2ccc(Nc3nc(-c4ccncc4)nc4cccc(OC)c34)cc2s1] |

TABLE 1a-continued

| No. | BC. Code | Structure |
|-----|----------|-----------|
| 362 | BC18805 | 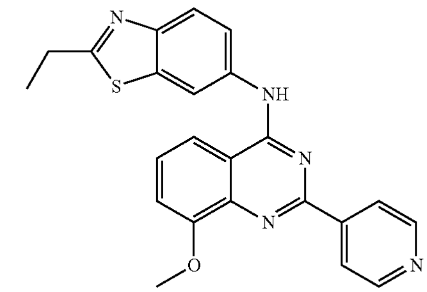 [SMILES: CCc1nc2ccc(Nc3nc(-c4ccncc4)nc4c(OC)cccc34)cc2s1] |
| 363 | BC18806 | 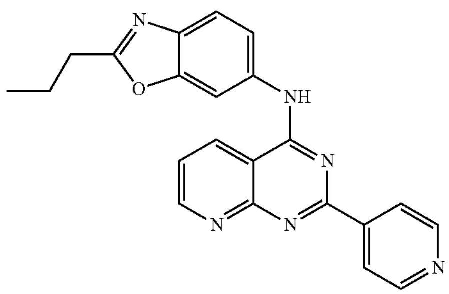 [SMILES: CCCc1nc2ccc(Nc3nc(-c4ccncc4)nc4ncccc34)cc2o1] |
| 364 | BC18807 | 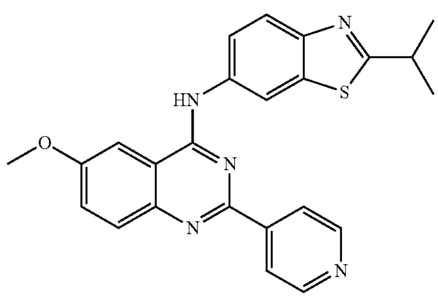 [SMILES: COc1ccc2nc(-c3ccncc3)nc(Nc3ccc4nc(C(C)C)sc4c3)c2c1] |
| 365 | BC18808 | 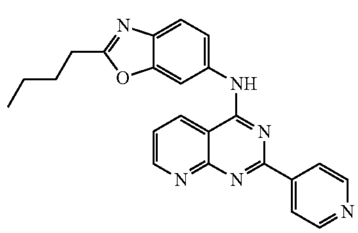 [SMILES: CCCCc1nc2ccc(Nc3nc(-c4ccncc4)nc4ncccc34)cc2o1] |
| 366 | BC18809 | 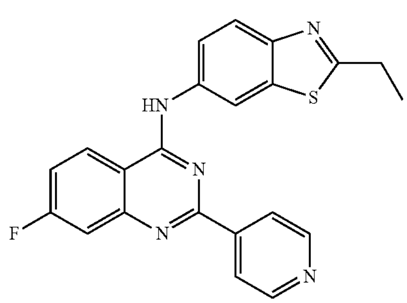 [SMILES: CCc1nc2ccc(Nc3nc(-c4ccncc4)nc4cc(F)ccc34)cc2s1] |
| 367 | BC18810 | |
| 368 | BC18811 | |
| 369 | BC18812 | |
| 370 | BC18814 | |
| 371 | BC18817 | |

TABLE 1a-continued
| BC. No. | Code | Structure |
|---|---|---|
| 372 | BC18818 | 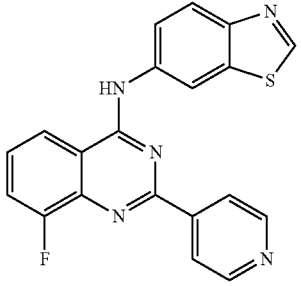 [SMILES: Fc1cccc2c(Nc3ccc4ncsc4c3)nc(-c3ccncc3)nc12] |
| 373 | BC18819 | 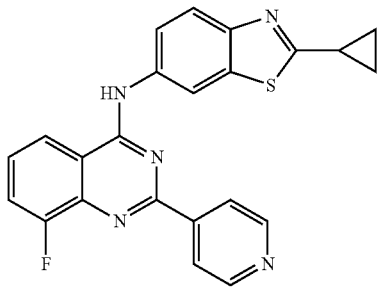 [SMILES: Fc1cccc2c(Nc3ccc4nc(C5CC5)sc4c3)nc(-c3ccncc3)nc12] |
| 374 | BC18820 | 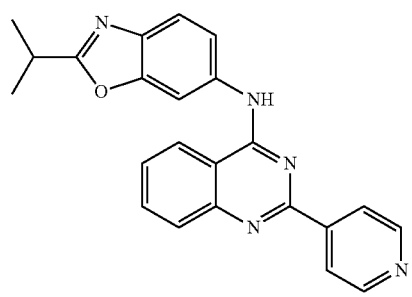 [SMILES: CC(C)c1nc2ccc(Nc3nc(-c4ccncc4)nc4ccccc34)cc2o1] |
| 375 | BC18821 | 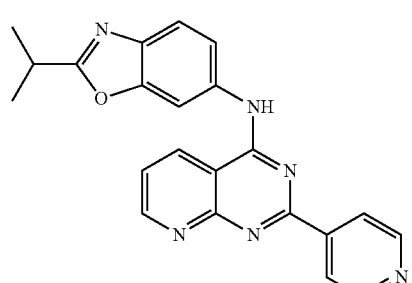 |
| 376 | BC18822 | 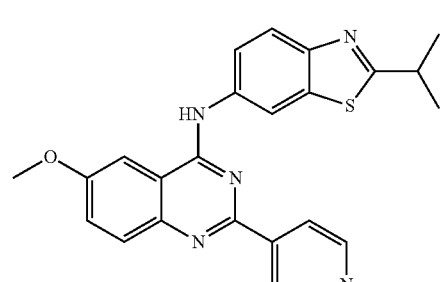 |
| 377 | BC18823 | 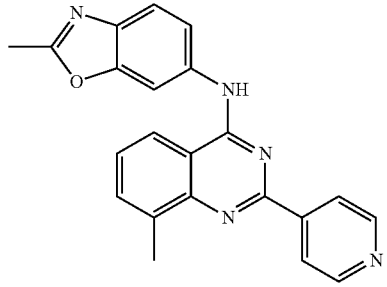 [SMILES: Cc1nc2ccc(Nc3nc(-c4ccncc4)nc4c(C)cccc34)cc2s1] |
| 378 | BC18824 | 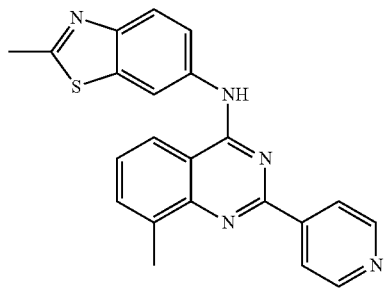 |
| 379 | BC18825 | 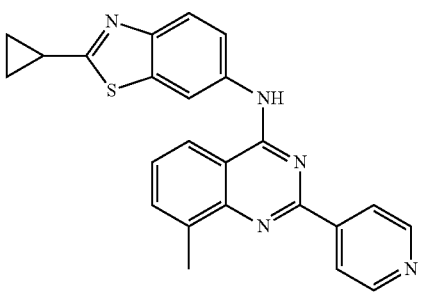 [SMILES: Cc1cccc2c(Nc3ccc4nc(C5CC5)sc4c3)nc(-c3ccncc3)nc12] |
| 380 | BC18826 | 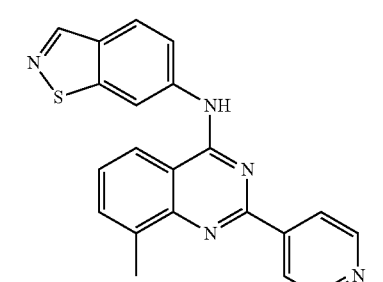 |
| 381 | BC18827 | 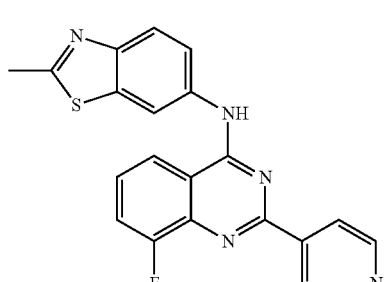 |

TABLE 1a-continued
| No. | BC. Code | Structure |
|---|---|---|
| 382 | BC18828 | 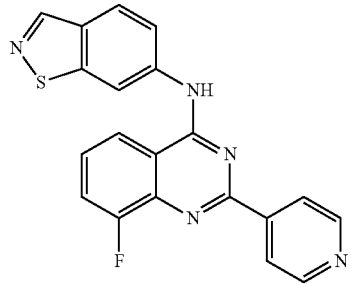 [SMILES: Fc1cccc2c(Nc3ccc4cnsc4c3)nc(-c3ccncc3)nc12] |
| 383 | BC18829 | 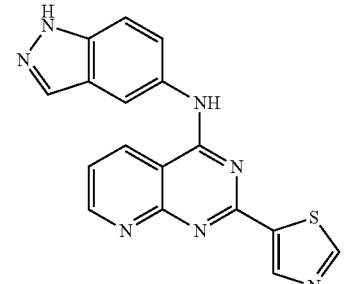 |
| 384 | BC18830 | 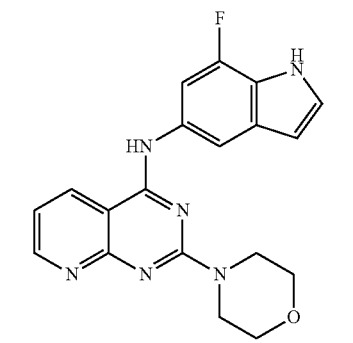 [SMILES: Fc1cc(Nc2nc(N3CCOCC3)nc3ncccc23)cc2cc[nH]c12] |
| 385 | BC18831 | 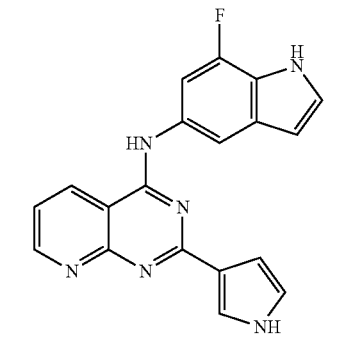 [SMILES: Fc1cc(Nc2nc(-c3cc[nH]c3)nc3ncccc23)cc2cc[nH]c12] |
| 386 | BC18832 | 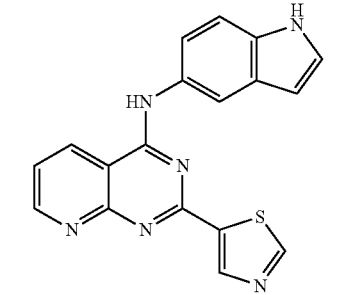 [SMILES: c1cnc2nc(-c3cncs3)nc(Nc3ccc4[nH]ccc4c3)c2c1] |
| 387 | BC18833 | 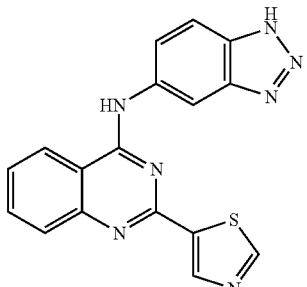 |
| 388 | BC18834 | 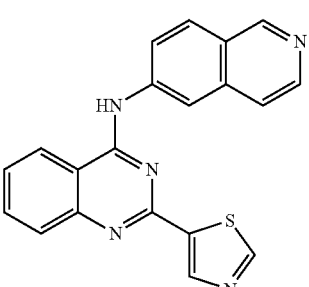 |
| 389 | BC18835 | 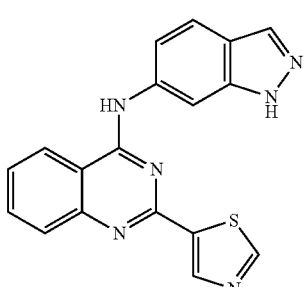 |
| 390 | BC18836 | 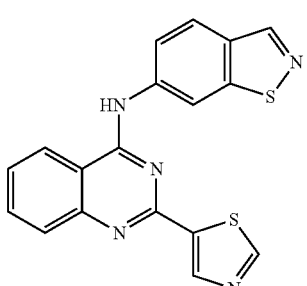 |
| 391 | BC18837 | 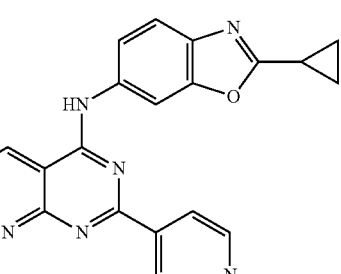 |

TABLE 1a-continued

| No. | BC. Code | Structure |
|-----|----------|-----------|
| 392 | BC18838 | 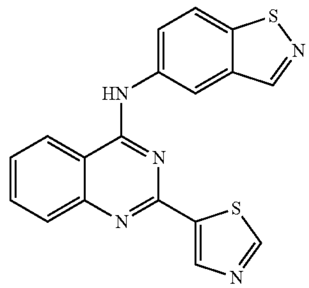 [SMILES: c1ccc2c(Nc3ccc4sncc4c3)nc(-c3cncs3)nc2c1] |
| 393 | BC18839 | 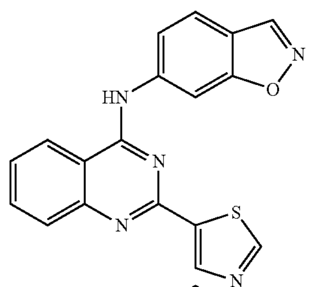 [SMILES: c1ccc2c(Nc3ccc4cnoc4c3)nc(-c3cncs3)nc2c1] |
| 394 | BC18840 | 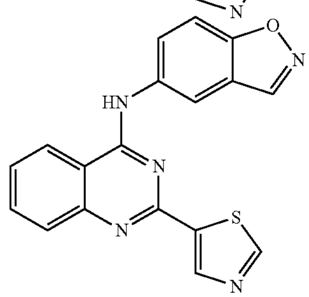 |
| 395 | BC18841 | 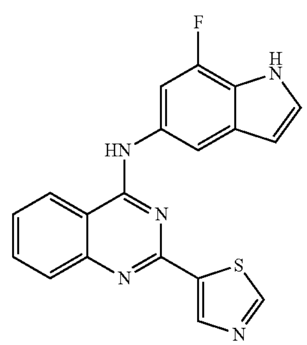 [SMILES: Fc1cc(Nc2nc(-c3cncs3)nc3ccccc23)cc2cc[nH]c12] |
| 396 | BC18845 | 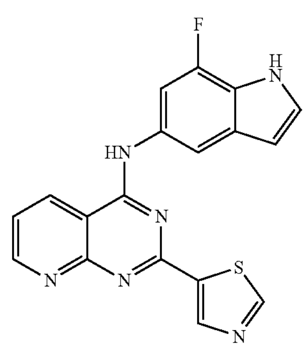 [SMILES: Fc1cc(Nc2nc(-c3cncs3)nc3ncccc23)cc2cc[nH]c12] |

Note:
Compounds 353, 364, and 376 were isolated and tested as HCOOH salts.

The following compounds (free base) provided in Table 2 were obtained from commercial sources (ChemDIV, Inc. and Mol port, Inc.):

TABLE 2

| No. | BC code | Structure |
|-----|---------|-----------|
| 159 | BC1820 | 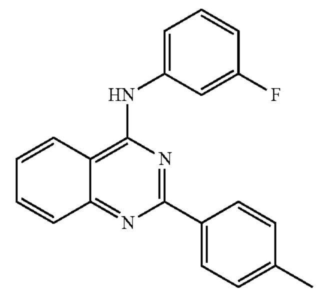 [SMILES: Cc1ccc(-c2nc(Nc3cccc(F)c3)c3ccccc3n2)cc1] |
| 160 | BC18200 | 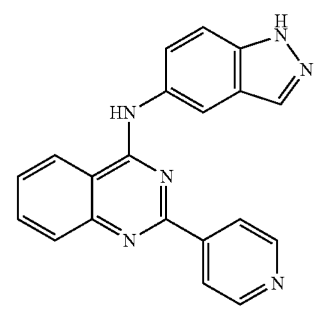 [SMILES: c1ccc2c(Nc3ccc4[nH]ncc4c3)nc(-c3ccncc3)nc2c1] |
| 161 | BC18201 | 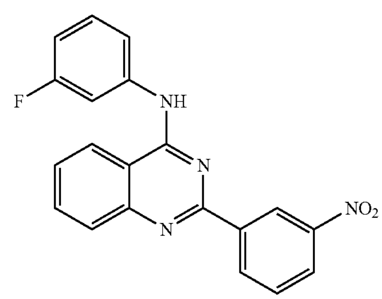 [SMILES: O=[N+]([O-])c1cccc(-c2nc(Nc3cccc(F)c3)c3ccccc3n2)c1] |
| 162 | BC18202 | 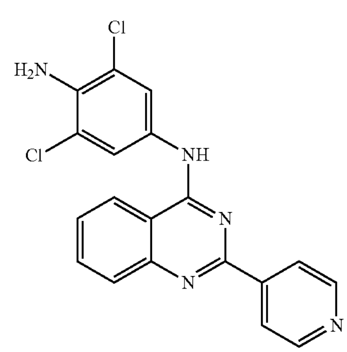 [SMILES: Nc1c(Cl)cc(Nc2nc(-c3ccncc3)nc3ccccc23)cc1Cl] |

TABLE 2-continued

| No. | BC code | Structure |
|-----|---------|-----------|
| 163 | BC18203 | (4-methoxyphenyl at C2; NH-(3-fluoro-4-methylphenyl) at C4 of quinazoline) |
| 164 | BC18204 | 2-(pyridin-4-yl)-N-butylquinazolin-4-amine |
| 165 | BC18205 | N-cyclopropyl-2-(pyridin-4-yl)quinazolin-4-amine |
| 166 | BC18206 | 2-(pyridin-4-yl)-N,N-dipropylquinazolin-4-amine |
| 167 | BC18207 | N-(2-phenylethyl)-2-(pyridin-4-yl)quinazolin-4-amine |
| 168 | BC18208 | N-(2-hydroxyethyl)-2-(pyridin-4-yl)quinazolin-4-amine |
| 169 | BC18209 | N-(cyanomethyl)-2-(pyridin-4-yl)quinazolin-4-amine |
| 170 | BC18210 | N-cyclohexyl-2-(pyridin-4-yl)quinazolin-4-amine |
| 171 | BC18211 | N-[2-(pyridin-2-yl)ethyl]-2-(pyridin-4-yl)quinazolin-4-amine |
| 172 | BC18212 | N-[3-(methylsulfonyl)propyl]-2-(pyridin-4-yl)quinazolin-4-amine |

TABLE 2-continued

| No. | BC code | Structure |
|---|---|---|
| 173 | BC18213 | (structure) |
| 174 | BC18214 | (structure) |
| 175 | BC18215 | (structure) |
| 176 | BC18216 | (structure) |
| 177 | BC18217 | (structure) |Т
| 178 | BC1834 | (structure) |
| 179 | BC18601 | (structure) |
| 180 | BC18602 | (structure) |
| 181 | BC18603 | (structure) |
| 182 | BC18604 | (structure) |

TABLE 2-continued
| No. | BC code | Structure |
|---|---|---|
| 183 | BC18605 | 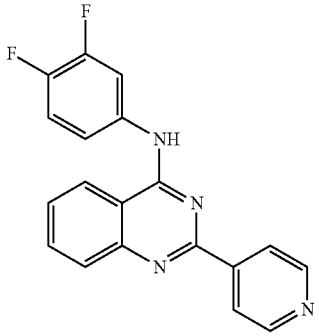 [SMILES: Fc1ccc(Nc2nc(-c3ccncc3)nc3ccccc23)cc1F] |
| 184 | BC18606 | 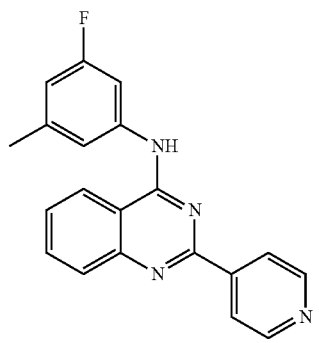 [SMILES: Cc1cc(F)cc(Nc2nc(-c3ccncc3)nc3ccccc23)c1] |
| 185 | BC18609 | 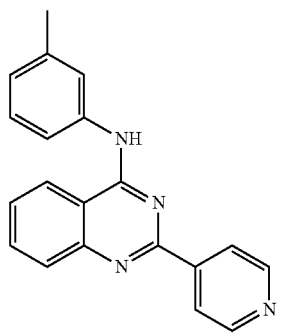 [SMILES: Cc1cccc(Nc2nc(-c3ccncc3)nc3ccccc23)c1] |
| 186 | BC18610 | 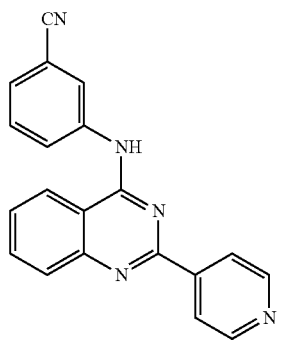 [SMILES: N#Cc1cccc(Nc2nc(-c3ccncc3)nc3ccccc23)c1] |
| 187 | BC18611 | 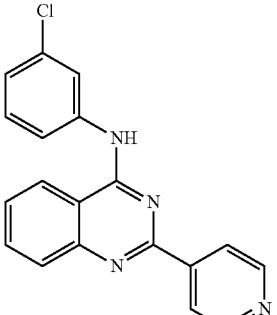 |
| 188 | BC18613 | 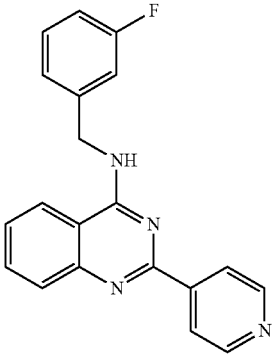 [SMILES: Fc1cccc(CNc2nc(-c3ccncc3)nc3ccccc23)c1] |
| 189 | BC18623 | 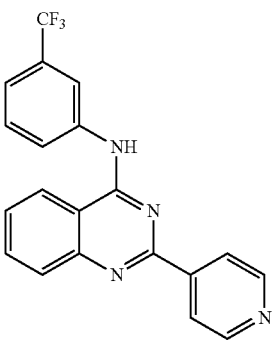 [SMILES: FC(F)(F)c1cccc(Nc2nc(-c3ccncc3)nc3ccccc23)c1] |
| 190 | BC18624 | 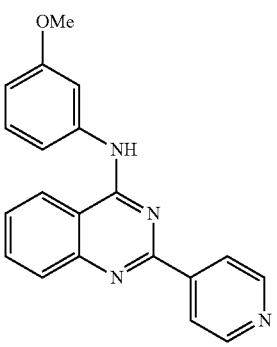 [SMILES: COc1cccc(Nc2nc(-c3ccncc3)nc3ccccc23)c1] |

TABLE 2-continued

| No. | BC code | Structure |
|---|---|---|
| 191 | BC18632 | 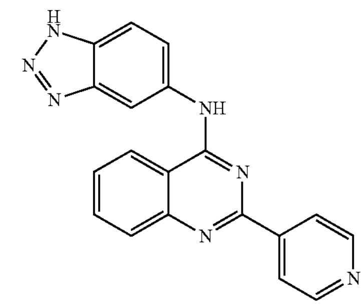 [SMILES: c1ccc2c(Nc3ccc4[nH]nnc4c3)nc(-c3ccncc3)nc2c1] |
| 192 | BC18651 | 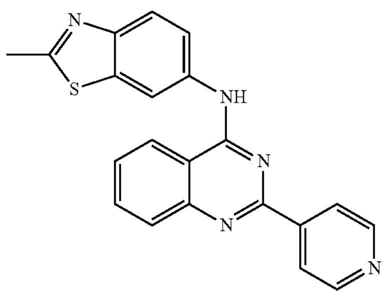 |
| 193 | BC18661 | 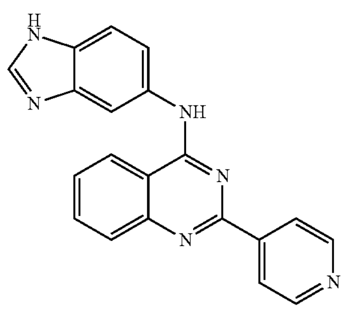 [SMILES: c1ccc2c(Nc3ccc4[nH]cnc4c3)nc(-c3ccncc3)nc2c1] |
| 194 | BC18715 | 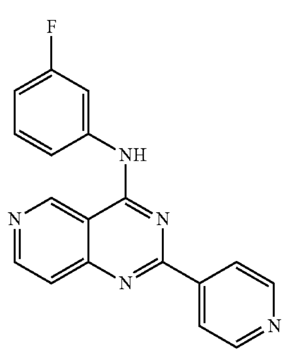 [SMILES: Fc1cccc(Nc2nc(-c3ccncc3)nc3ccncc23)c1] |

The following compounds shown in Table 3 may prepared using chemical routes that would be readily apparent to one of ordinary skill in the art from readily available starting materials.

TABLE 3

| No. | BC code | Structure |
|---|---|---|
| 195 | BC1816 | 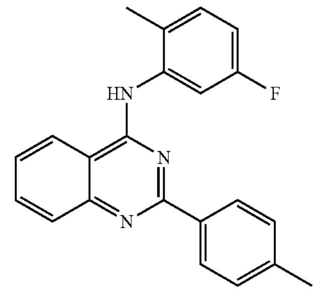 [SMILES: Cc1ccc(-c2nc(Nc3cc(F)ccc3C)c3ccccc3n2)cc1] |
| 196 | BC1835 | 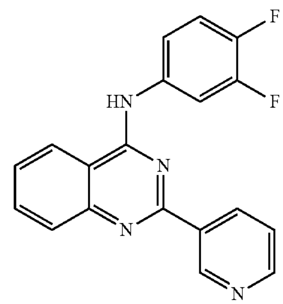 [SMILES: Fc1ccc(Nc2nc(-c3cccnc3)nc3ccccc23)cc1F] |
| 197 | BC1836 | 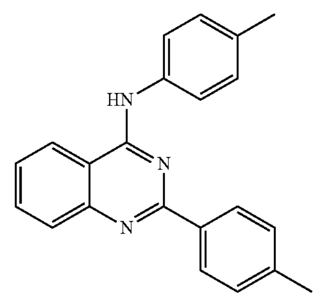 [SMILES: Cc1ccc(Nc2nc(-c3ccc(C)cc3)nc3ccccc23)cc1] |
| 198 | BC1837 | 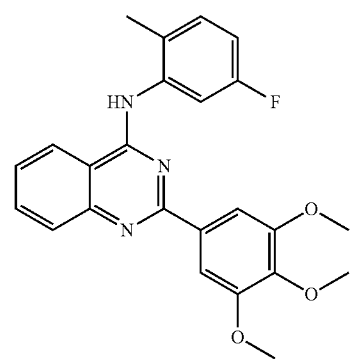 [SMILES: COc1cc(-c2nc(Nc3cc(F)ccc3C)c3ccccc3n2)cc(OC)c1OC] |
| 199 | BC1838 | 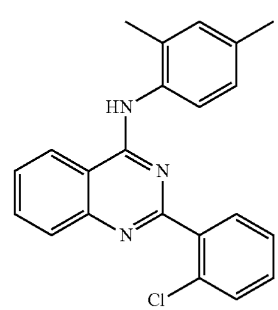 [SMILES: Cc1ccc(Nc2nc(-c3ccccc3Cl)nc3ccccc23)c(C)c1] |

TABLE 3-continued
| No. | BC code | Structure |
|---|---|---|
| 200 | BC1839 | 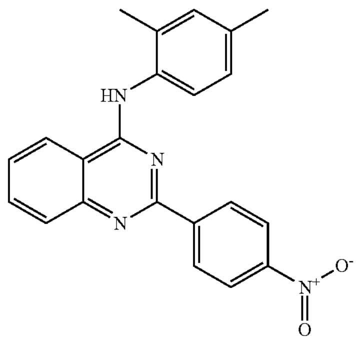 [SMILES: Cc1ccc(Nc2nc(-c3ccc([N+](=O)[O-])cc3)nc3ccccc23)c(C)c1] |
| 201 | BC1840 | 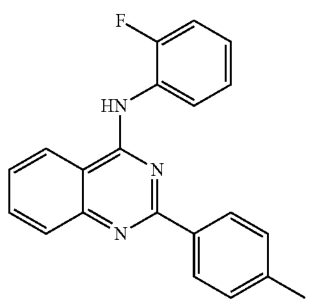 [SMILES: Cc1ccc(-c2nc(Nc3ccccc3F)c3ccccc3n2)cc1] |
| 202 | BC1841 | 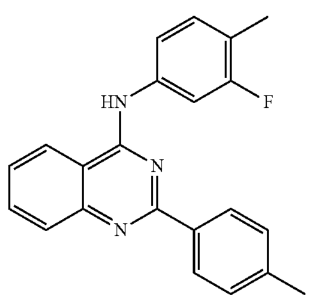 [SMILES: Cc1ccc(-c2nc(Nc3ccc(C)c(F)c3)c3ccccc3n2)cc1] |
| 203 | | 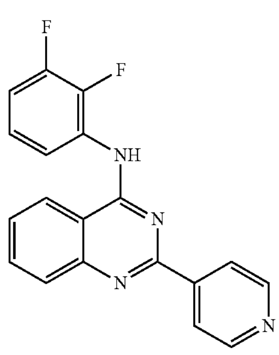 [SMILES: Fc1cccc(Nc2nc(-c3ccncc3)nc3ccccc23)c1F] |
TABLE 3-continued
| No. | BC code | Structure |
|---|---|---|
| 204 | | 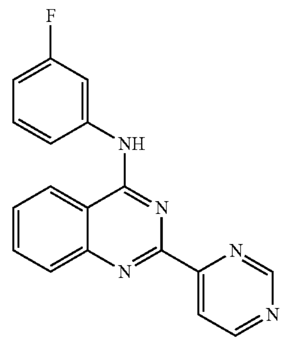 [SMILES: Fc1cccc(Nc2nc(-c3ccncn3)nc3ccccc23)c1] |
| 205 | | 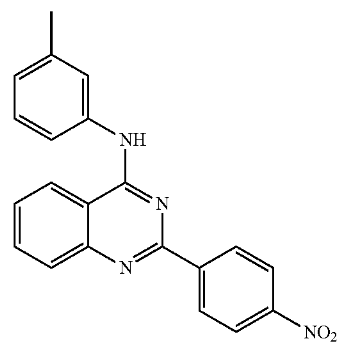 [SMILES: Cc1cccc(Nc2nc(-c3ccc([N+](=O)[O-])cc3)nc3ccccc23)c1] |
| 206 | | 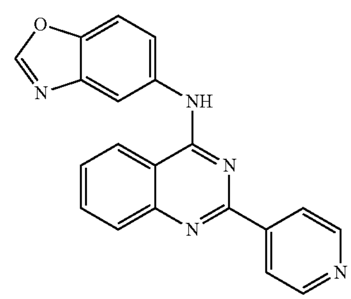 |
| 207 | | 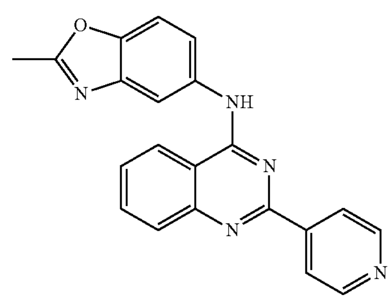 |
| 208 | | 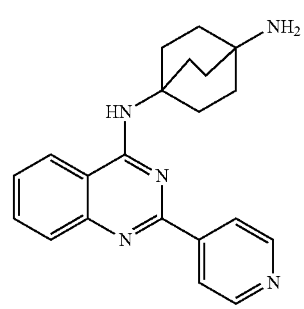 [SMILES: NC12CCC(Nc3nc(-c4ccncc4)nc4ccccc34)(CC1)CC2] |

TABLE 3-continued
| No. | BC code | Structure |
|---|---|---|
| 209 | | 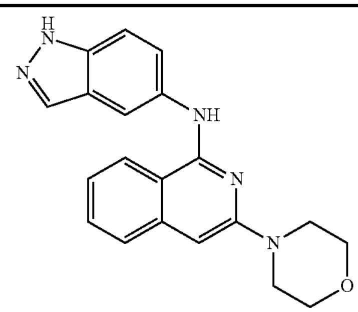 |
| 210 | | 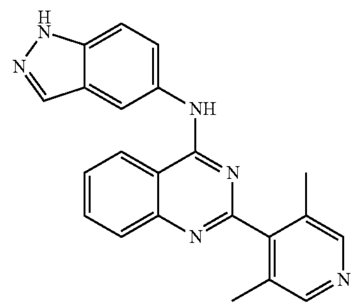 [SMILES: Cc1cncc(C)c1-c1nc(Nc2ccc3[nH]ncc3c2)c2ccccc2n1] |
| 211 | | 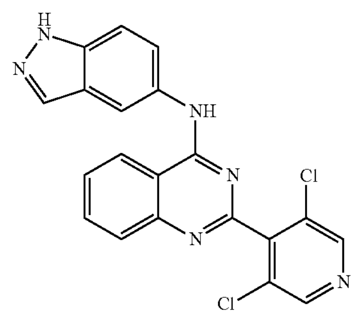 [SMILES: Clc1cncc(Cl)c1-c1nc(Nc2ccc3[nH]ncc3c2)c2ccccc2n1] |
TABLE 3-continued
| No. | BC code | Structure |
|---|---|---|
| 212 | | |
| 213 | | |
Note:
Compounds 197 and 199 were isolated and tested as HCl salts.
The following compounds shown in Table 4 were purchased from ChemDIV, Inc.
TABLE 4
| No. | BC code | Structure |
|---|---|---|
| 214 | BC1770 | 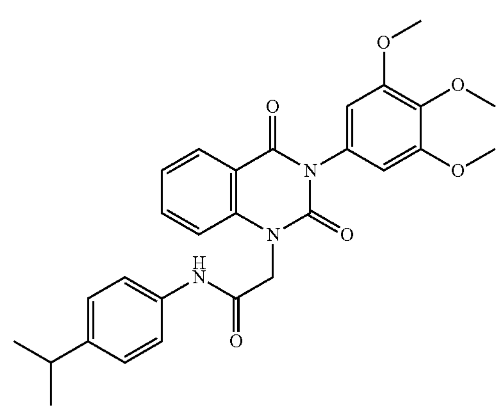 [SMILES: COc1cc(-n2c(=O)c3ccccc3n(CC(=O)Nc3ccc(C(C)C)cc3)c2=O)cc(OC)c1OC] |
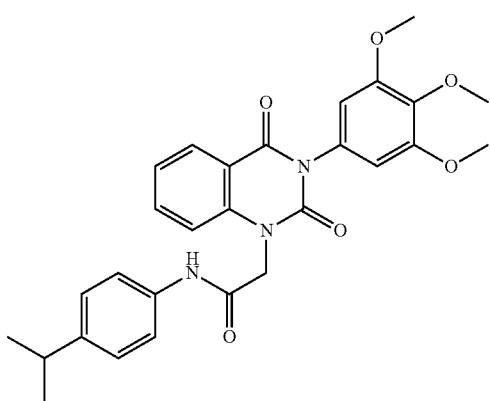

TABLE 4-continued

| No. | BC code | Structure |
|-----|---------|-----------|
| 215 | BC1771 | 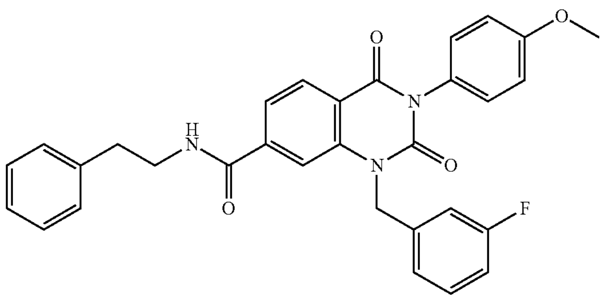 [SMILES: COc1ccc(-n2c(=O)c3ccc(C(=O)NCCc4ccccc4)cc3n(Cc3cccc(F)c3)c2=O)cc1] |
| 216 | BC1772 | 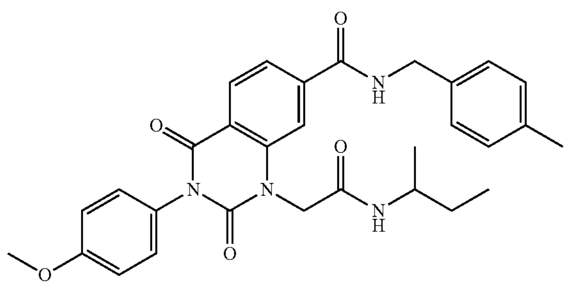 |
| 217 | BC1773 | 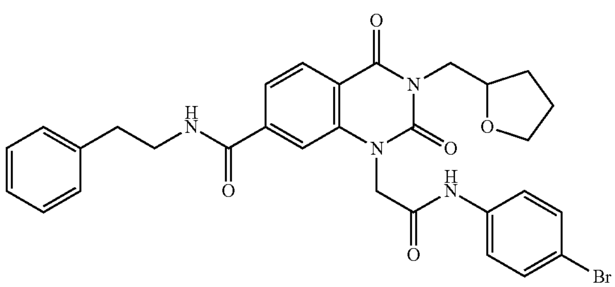 [SMILES: O=C(Cn1c(=O)n(CC2CCCO2)c(=O)c2ccc(C(=O)NCCc3ccccc3)cc21)Nc1ccc(Br)cc1] |
| 218 | BC1774 | 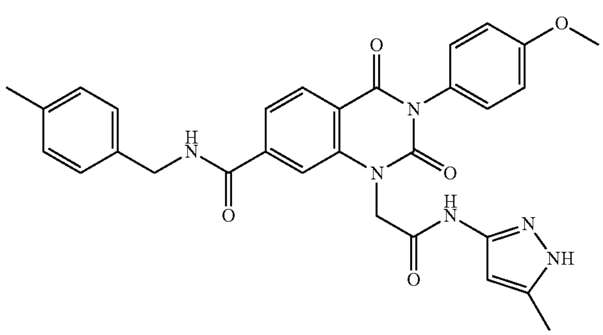 |
| 219 | BC1775 | 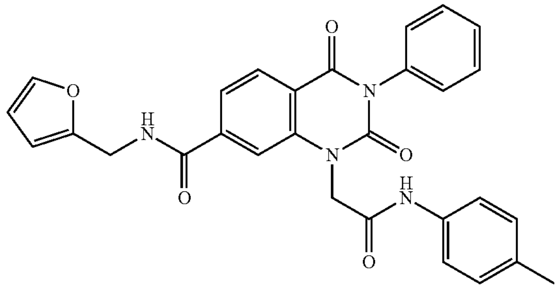 [SMILES: Cc1ccc(NC(=O)Cn2c(=O)n(-c3ccccc3)c(=O)c3ccc(C(=O)NCc4ccco4)cc32)cc1] |

TABLE 4-continued

| No. | BC code | Structure |
|---|---|---|
| 220 | BC1776 | 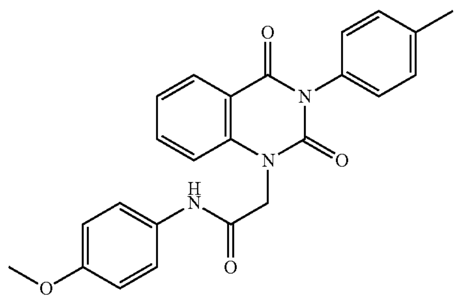 |
| 221 | BC1777 | 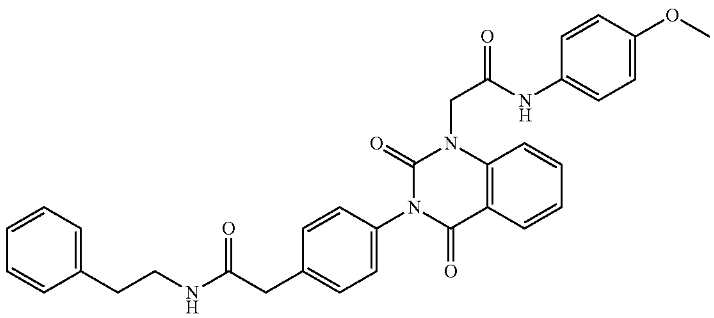 [SMILES: COc1ccc(NC(=O)Cn2c(=O)n(-c3ccc(CC(=O)NCCc4ccccc4)cc3)c(=O)c3ccccc32)cc1] |
| 222 | BC1753 | 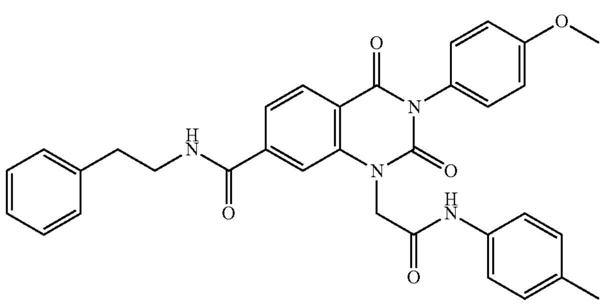 [SMILES: COc1ccc(-n2c(=O)c3ccc(C(=O)NCCc4ccccc4)cc3n(CC(=O)Nc3ccc(C)cc3)c2=O)cc1] |
| 223 | BC1780 | 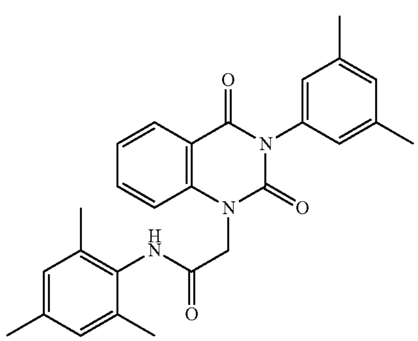 |
| 224 | BC1781 | 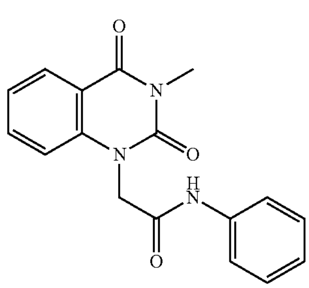 [SMILES: Cn1c(=O)c2ccccc2n(CC(=O)Nc2ccccc2)c1=O] |

TABLE 4-continued

| No. | BC code | Structure |
|---|---|---|
| 225 | BC1782 | 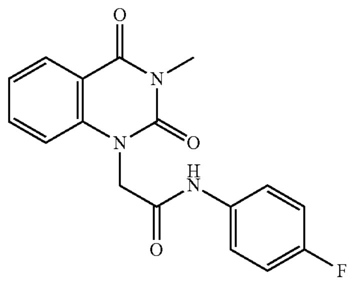 [SMILES: Cn1c(=O)c2ccccc2n(CC(=O)Nc2ccc(F)cc2)c1=O] |
| 226 | BC1783 | 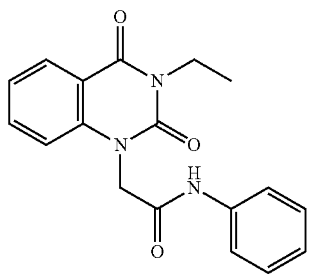 [SMILES: CCn1c(=O)c2ccccc2n(CC(=O)Nc2ccccc2)c1=O] |
| 227 | BC1784 | 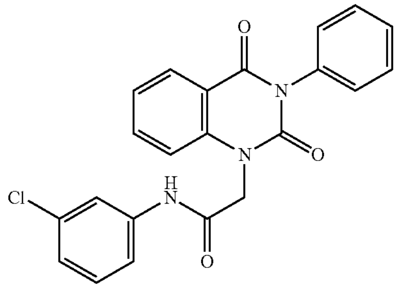 [SMILES: O=C(Cn1c(=O)n(-c2ccccc2)c(=O)c2ccccc21)Nc1cccc(Cl)c1] |
| 228 | BC1785 | 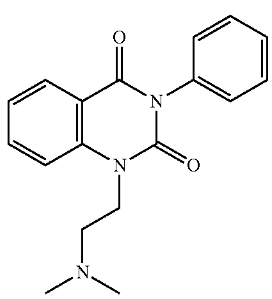 [SMILES: CN(C)CCn1c(=O)n(-c2ccccc2)c(=O)c2ccccc21] |
| 229 | BC1786 | 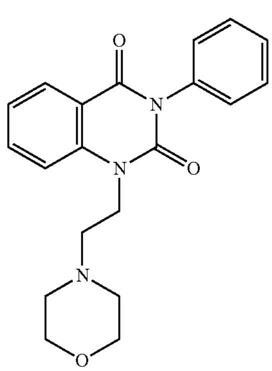 [SMILES: O=c1c2ccccc2n(CCN2CCOCC2)c(=O)n1-c1ccccc1] |

TABLE 4-continued

| No. | BC code | Structure |
|-----|---------|-----------|
| 230 | BC1787  | 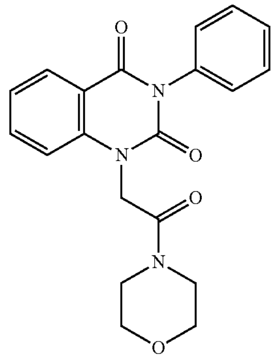 [SMILES: O=C(Cn1c(=O)n(-c2ccccc2)c(=O)c2ccccc21)N1CCOCC1]          |
| 231 | BC1811  | 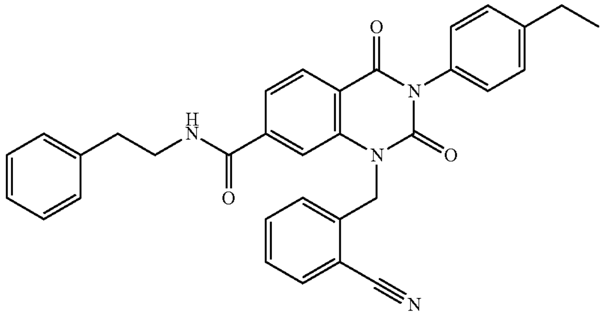 [SMILES: CCc1ccc(-n2c(=O)c3ccc(C(=O)NCCc4ccccc4)cc3n(Cc3ccccc3C#N)c2=O)cc1]          |
| 232 | BC1812  | 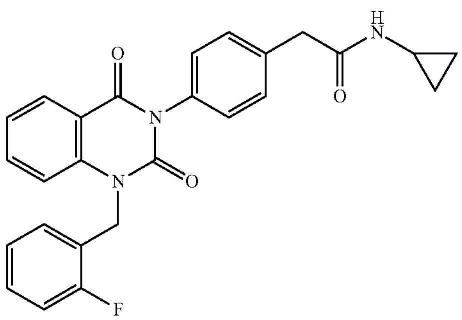 [SMILES: O=C(Cc1ccc(-n2c(=O)c3ccccc3n(Cc3ccccc3F)c2=O)cc1)NC1CC1]          |
| 233 | BC1813  | 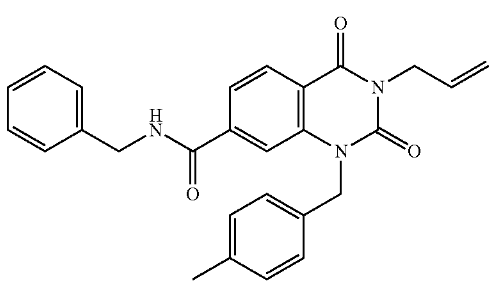 [SMILES: C=CCn1c(=O)c2ccc(C(=O)NCc3ccccc3)cc2n(Cc2ccc(C)cc2)c1=O]          |
| 234 | BC1814  | 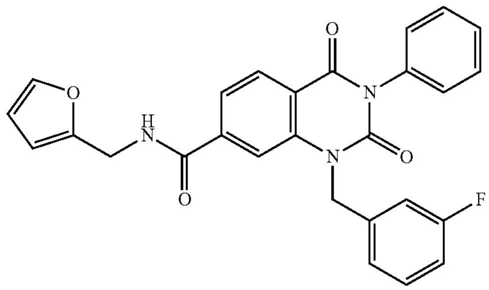 [SMILES: O=C(NCc1ccco1)c1ccc2c(=O)n(-c3ccccc3)c(=O)n(Cc3cccc(F)c3)c2c1]          |

TABLE 4-continued

| No. | BC code | Structure |
|---|---|---|
| 235 | BC1815 | 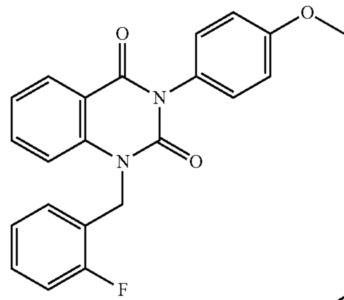 |
| 236 | BC1817 | 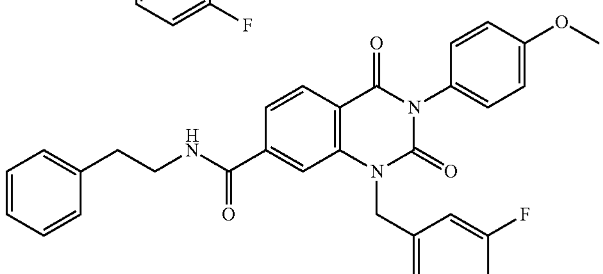 |
| 237 | BC1818 | 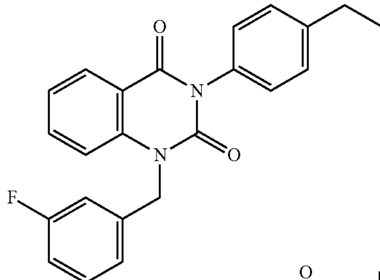 |
| 238 | BC1819 | 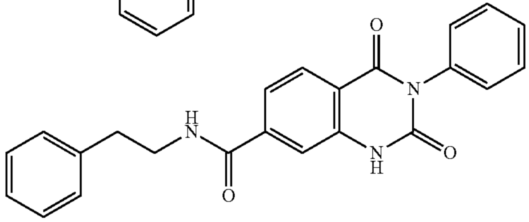 |

The following compounds shown in Table 5 may prepared using chemical routes that would be readily apparent to one of ordinary skill in the art from readily available starting materials.

TABLE 5

| No. | BC code | Structure |
|---|---|---|
| 239 | BC18842 | 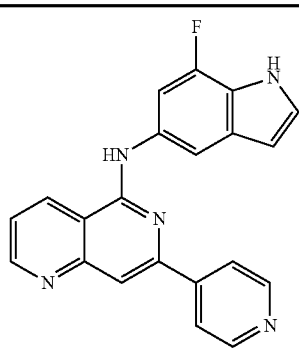 |
| 240 | BC18846 | |

TABLE 5-continued

| No. | BC code | Structure |
|---|---|---|
| 241 | BC18847 | 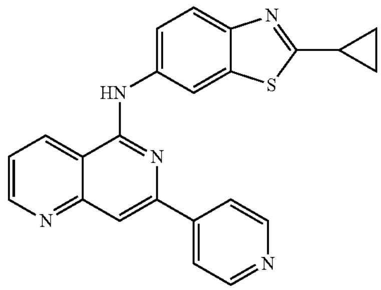 [SMILES: c1cnc2cc(-c3ccncc3)nc(Nc3ccc4nc(C5CC5)sc4c3)c2c1] |
| 242 | BC18848 | 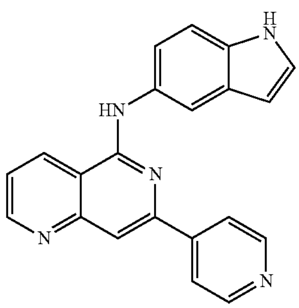 [SMILES: c1cnc2cc(-c3ccncc3)nc(Nc3ccc4[nH]ccc4c3)c2c1] |
| 243 | BC18849 | 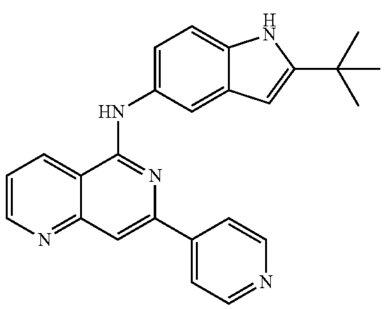 [SMILES: CC(C)(C)c1cc2cc(Nc3nc(-c4ccncc4)cc4ncccc34)ccc2[nH]1] |
| 244 | BC18850 | 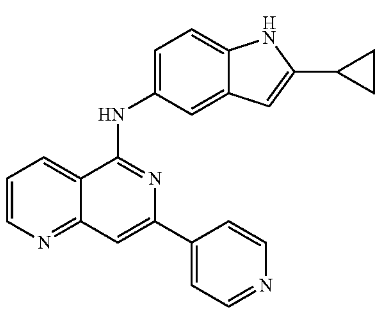 [SMILES: c1cnc2cc(-c3ccncc3)nc(Nc3ccc4[nH]c(C5CC5)cc4c3)c2c1] |
| 245 | BC18851 | 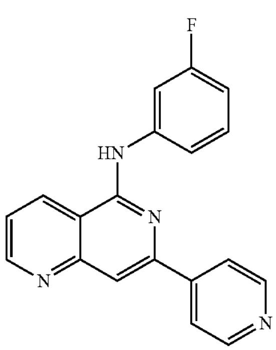 [SMILES: Fc1cccc(Nc2nc(-c3ccncc3)cc3ncccc23)c1] |
| 246 | BC18852 | |
| 247 | BC18853 | |
| 248 | BC18854 | |
| 249 | BC191100 | |

TABLE 5-continued

| No. | BC code | Structure |
|---|---|---|
| 250 | BC191101 | 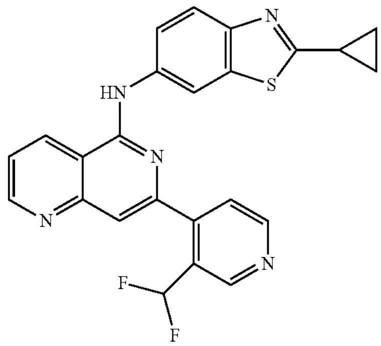 [SMILES: FC(F)c1cnccc1-c1cc2ncccc2c(Nc2ccc3nc(C4CC4)sc3c2)n1] |
| 251 | BC191102 | 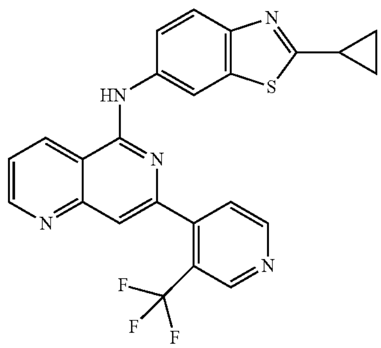 [SMILES: FC(F)(F)c1cnccc1-c1cc2ncccc2c(Nc2ccc3nc(C4CC4)sc3c2)n1] |
| 252 | BC191103 | 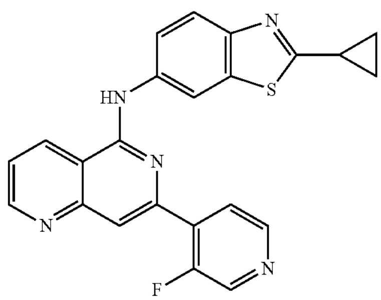 [SMILES: Fc1cnccc1-c1cc2ncccc2c(Nc2ccc3nc(C4CC4)sc3c2)n1] |
| 253 | BC191104 | 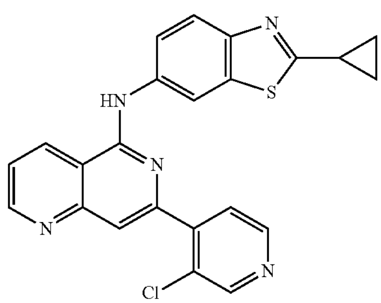 [SMILES: Clc1cnccc1-c1cc2ncccc2c(Nc2ccc3nc(C4CC4)sc3c2)n1] |
| 254 | BC191105 | 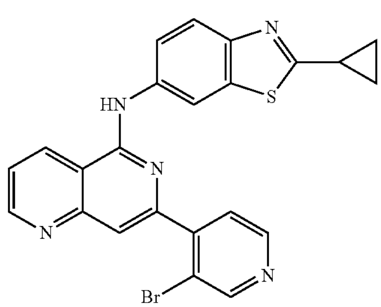 [SMILES: Brc1cnccc1-c1cc2ncccc2c(Nc2ccc3nc(C4CC4)sc3c2)n1] |
| 255 | BC191106 | |
| 256 | BC191107 | |
| 257 | BC191108 | |
| 258 | BC191109 | |
| 259 | BC191110 | |

TABLE 5-continued

| No. | BC code | Structure |
|---|---|---|
| 260 | BC191111 | 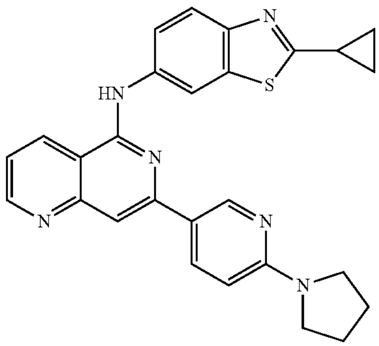 [SMILES: c1cnc2cc(-c3ccc(N4CCCC4)nc3)nc(Nc3ccc4nc(C5CC5)sc4c3)c2c1] |
| 261 | BC191112 | 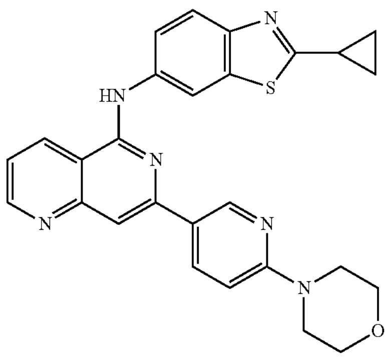 [SMILES: c1cnc2cc(-c3ccc(N4CCOCC4)nc3)nc(Nc3ccc4nc(C5CC5)sc4c3)c2c1] |
| 262 | BC191113 | 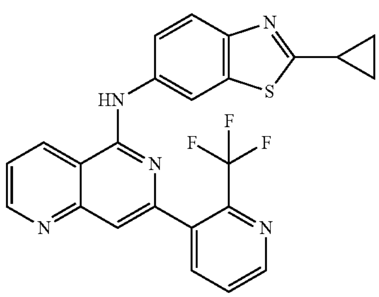 [SMILES: FC(F)(F)c1ncccc1-c1cc2ncccc2c(Nc2ccc3nc(C4CC4)sc3c2)n1] |
| 263 | BC191114 | 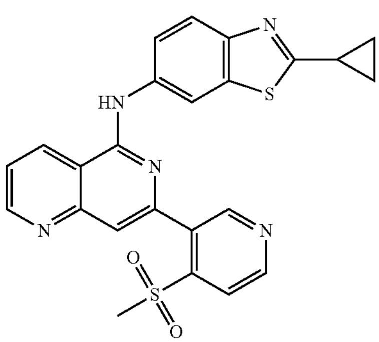 [SMILES: CS(=O)(=O)c1ccncc1-c1cc2ncccc2c(Nc2ccc3nc(C4CC4)sc3c2)n1] |
| 264 | BC191115 | |
| 265 | BC191116 | |
| 266 | BC191117 | |
| 267 | BC191118 | |

TABLE 5-continued

| No. | BC code | Structure |
|---|---|---|
| 268 | BC191119 | 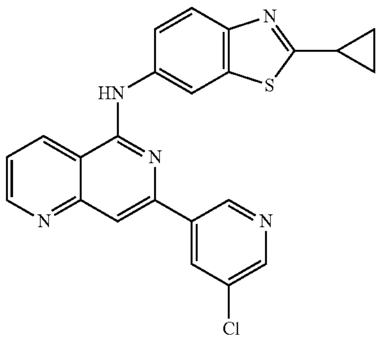 [SMILES: Clc1cncc(-c2cc3ncccc3c(Nc3ccc4nc(C5CC5)sc4c3)n2)c1] |
| 269 | BC191120 | 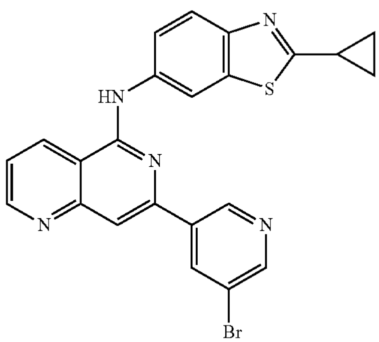 [SMILES: Brc1cncc(-c2cc3ncccc3c(Nc3ccc4nc(C5CC5)sc4c3)n2)c1] |
| 270 | BC191121 | 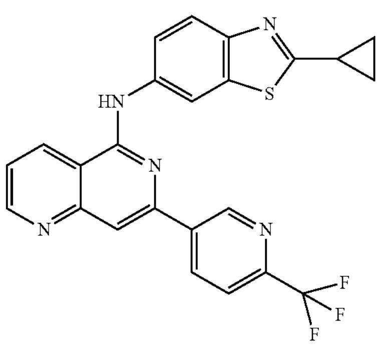 |
| 271 | BC191122 | 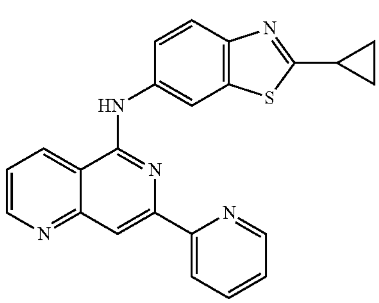 [SMILES: c1ccc(-c2cc3ncccc3c(Nc3ccc4nc(C5CC5)sc4c3)n2)nc1] |
| 272 | BC191123 | |
| 273 | BC191124 | |
| 274 | BC191125 | |
| 275 | BC191126 | |

TABLE 5-continued
| No. | BC code | Structure |
|---|---|---|
| 276 | BC191127 | 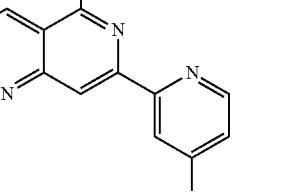 |
| 277 | BC191128 | 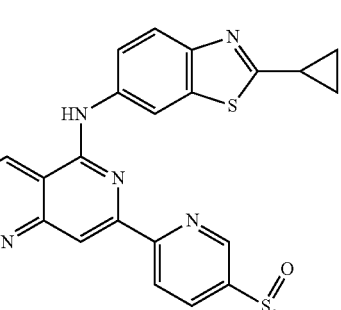 |
| 278 | BC191129 | 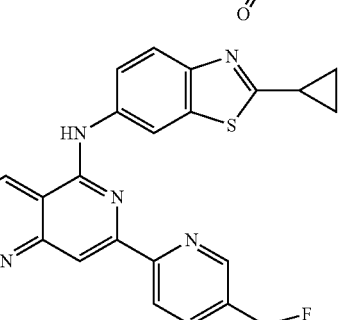 |
| 279 | BC191130 | 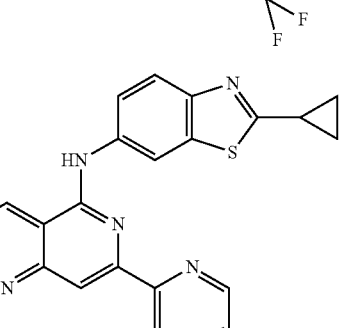 |
| 280 | BC191131 | 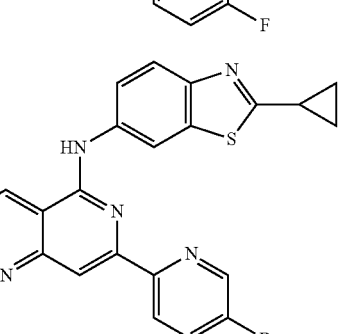 |
TABLE 5-continued
| No. | BC code | Structure |
|---|---|---|
| 281 | BC191132 | 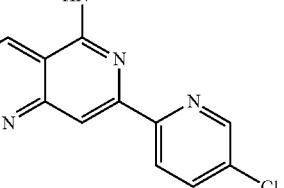 |
| 282 | BC191133 | 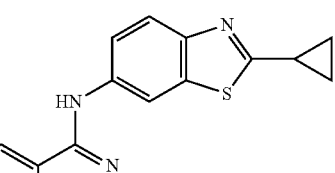 |
| 283 | BC191134 | 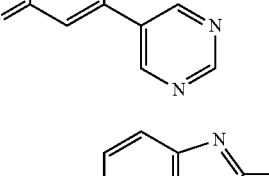 |
| 284 | BC191135 | 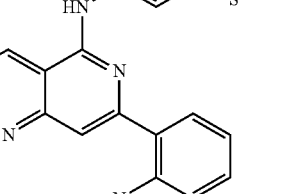 |
| 285 | BC191136 | 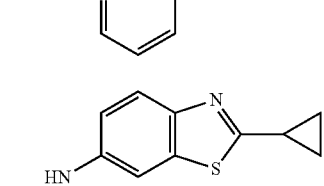 |

TABLE 5-continued
| No. | BC code | Structure |
|---|---|---|
| 286 | BC191137 | 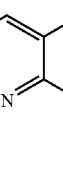 |
| 287 | BC191138 | 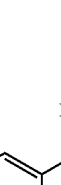 |
| 288 | BC191139 | 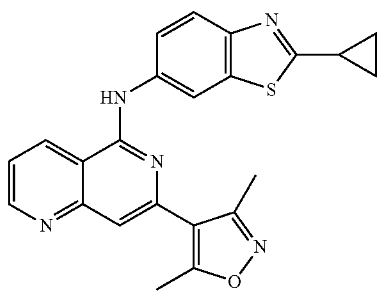 [SMILES: Cc1noc(C)c1-c1cc2ncccc2c(Nc2ccc3nc(C4CC4)sc3c2)n1] |
| 289 | BC191140 | 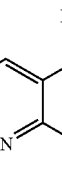 |
| 290 | BC191141 | 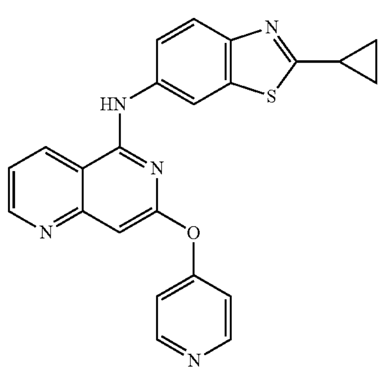 [SMILES: c1cnc2cc(Oc3ccncc3)nc(Nc3ccc4nc(C5CC5)sc4c3)c2c1] |
| 291 | BC191142 | 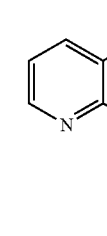 |
| 292 | BC191143 | 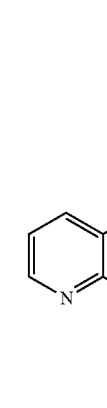 |
| 293 | BC191144 | 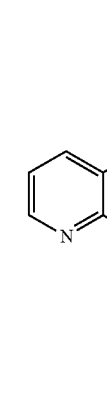 |
| 294 | BC191145 | 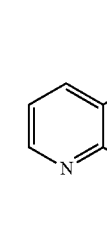 |

TABLE 5-continued
| No. | BC code | Structure |
|---|---|---|
| 295 | BC191146 | 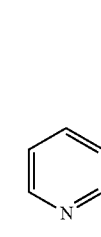 |
| 296 | BC191147 | 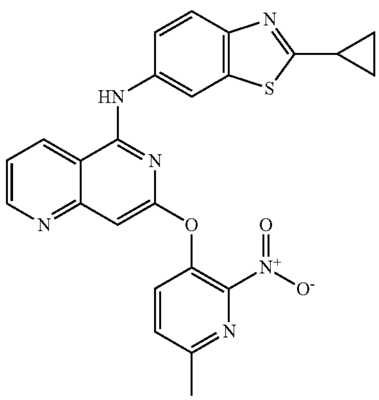 [SMILES: Cc1ccc(Oc2cc3ncccc3c(Nc3ccc4nc(C5CC5)sc4c3)n2)c([N+](=O)[O-])n1] |
| 297 | BC191148 | 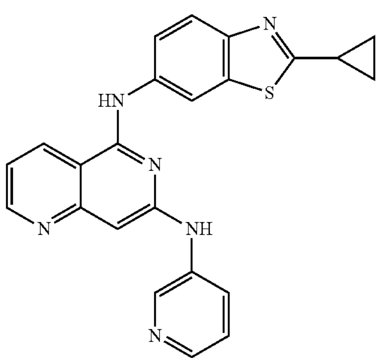 [SMILES: c1cncc(Nc2cc3ncccc3c(Nc3ccc4nc(C5CC5)sc4c3)n2)c1] |
| 298 | BC191149 | 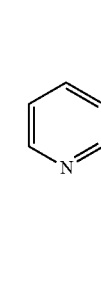 |
| 299 | BC191150 | 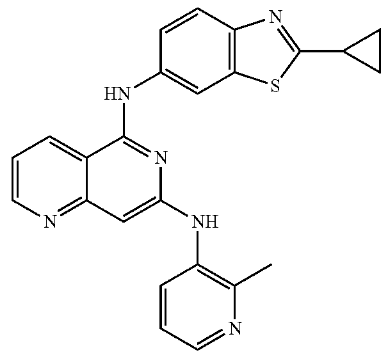 [SMILES: Cc1ncccc1Nc1cc2ncccc2c(Nc2ccc3nc(C4CC4)sc3c2)n1] |
| 300 | BC191151 | 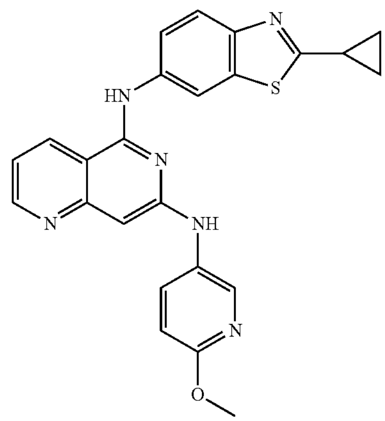 [SMILES: COc1ccc(Nc2cc3ncccc3c(Nc3ccc4nc(C5CC5)sc4c3)n2)cn1] |
| 301 | BC191152 | 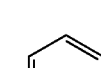 |
| 302 | BC191153 | 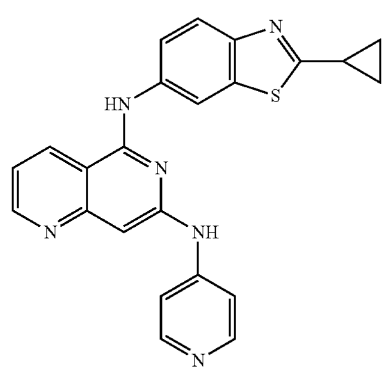 [SMILES: c1cnc2cc(Nc3ccncc3)nc(Nc3ccc4nc(C5CC5)sc4c3)c2c1] |

TABLE 5-continued

| No. | BC code | Structure |
|---|---|---|
| 303 | BC191154 | 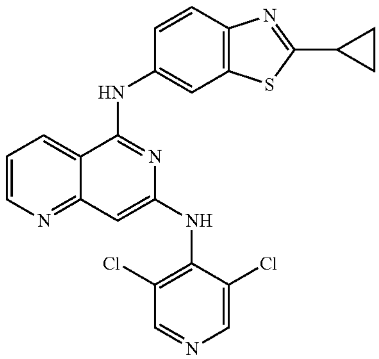 [SMILES: Clc1cncc(Cl)c1Nc1cc2ncccc2c(Nc2ccc3nc(C4CC4)sc3c2)n1] |
| 304 | BC191155 | 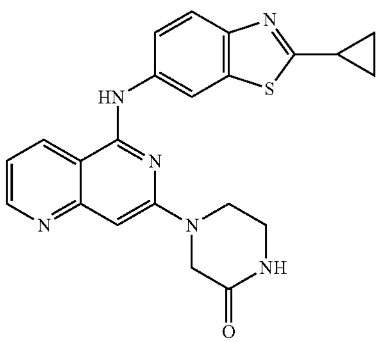 [SMILES: O=C1CN(c2cc3ncccc3c(Nc3ccc4nc(C5CC5)sc4c3)n2)CCN1] |
| 305 | BC191156 | 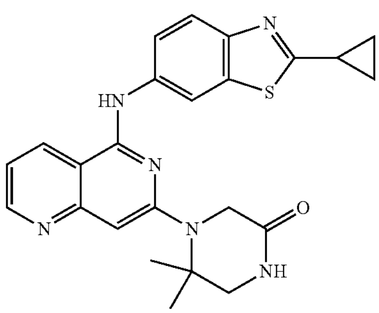 [SMILES: CC1(C)CNC(=O)CN1c1cc2ncccc2c(Nc2ccc3nc(C4CC4)sc3c2)n1] |
| 306 | BC191157 | 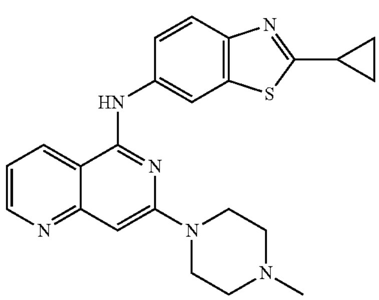 [SMILES: CN1CCN(c2cc3ncccc3c(Nc3ccc4nc(C5CC5)sc4c3)n2)CC1] |
| 307 | BC191158 | |
| 308 | BC191159 | |
| 309 | BC191160 | |
| 310 | BC191161 | |

TABLE 5-continued

| No. | BC code | Structure |
|---|---|---|
| 311 | BC191162 | 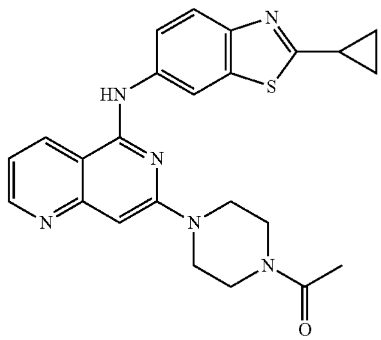 [SMILES: CC(=O)N1CCN(c2cc3ncccc3c(Nc3ccc4nc(C5CC5)sc4c3)n2)CC1] |
| 312 | BC191163 | 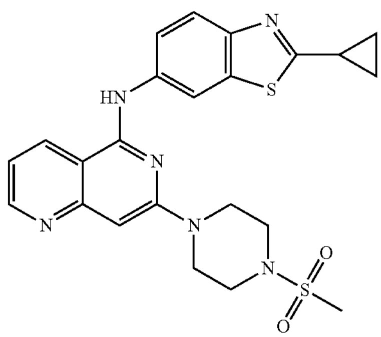 [SMILES: CS(=O)(=O)N1CCN(c2cc3ncccc3c(Nc3ccc4nc(C5CC5)sc4c3)n2)CC1] |
| 313 | BC191164 | 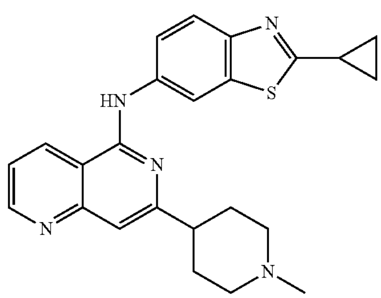 [SMILES: CN1CCC(c2cc3ncccc3c(Nc3ccc4nc(C5CC5)sc4c3)n2)CC1] |
| 314 | BC191165 | 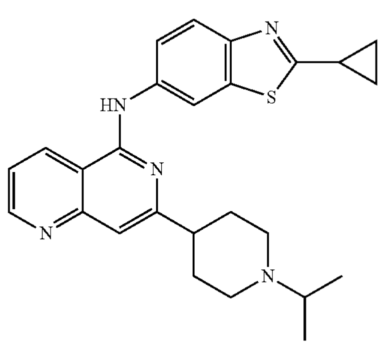 [SMILES: CC(C)N1CCC(c2cc3ncccc3c(Nc3ccc4nc(C5CC5)sc4c3)n2)CC1] |
| 315 | BC191166 | |
| 316 | BC191167 | |
| 317 | BC191168 | |
| 318 | BC191169 | |

TABLE 5-continued

| No. | BC code | Structure |
|---|---|---|
| 319 | BC191170 | |
| 320 | BC191171 | |
| 321 | BC191172 | |
| 322 | BC191173 | |
| 323 | BC191174 | 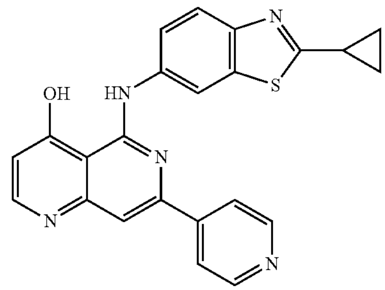 [SMILES: Oc1ccnc2cc(-c3ccncc3)nc(Nc3ccc4nc(C5CC5)sc4c3)c12] |
| 324 | BC191175 | 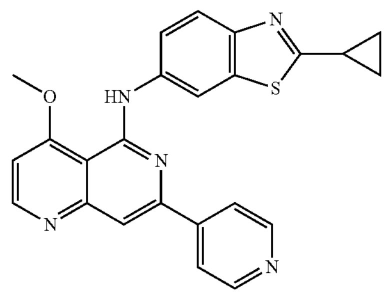 [SMILES: COc1ccnc2cc(-c3ccncc3)nc(Nc3ccc4nc(C5CC5)sc4c3)c12] |
| 325 | BC191176 | 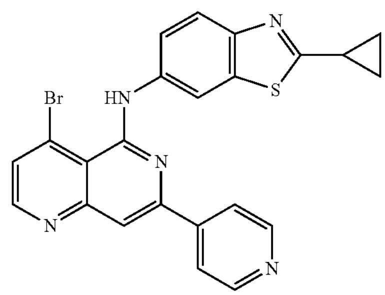 [SMILES: Brc1ccnc2cc(-c3ccncc3)nc(Nc3ccc4nc(C5CC5)sc4c3)c12] |
| 326 | BC191177 | 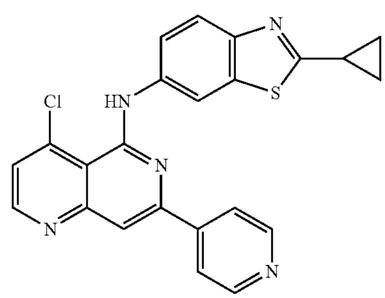 [SMILES: Clc1ccnc2cc(-c3ccncc3)nc(Nc3ccc4nc(C5CC5)sc4c3)c12] |
| 327 | BC191178 | 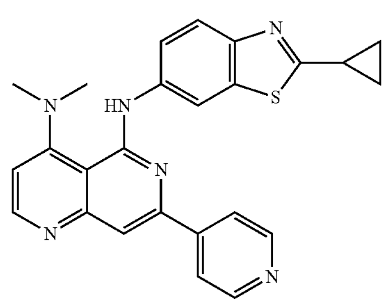 [SMILES: CN(C)c1ccnc2cc(-c3ccncc3)nc(Nc3ccc4nc(C5CC5)sc4c3)c12] |

TABLE 5-continued

| No. | BC code | Structure |
|---|---|---|
| 328 | BC191179 | 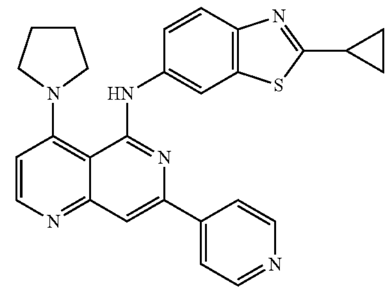 [SMILES: c1cc(-c2cc3nccc(N4CCCC4)c3c(Nc3ccc4nc(C5CC5)sc4c3)n2)ccn1] |
| 329 | BC191180 | 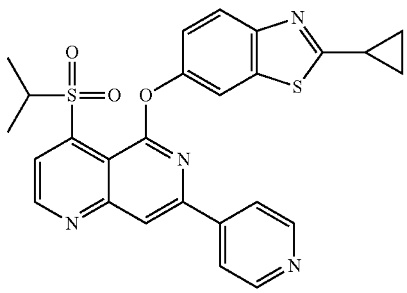 [SMILES: CC(C)S(=O)(=O)c1ccnc2cc(-c3ccncc3)nc(Oc3ccc4nc(C5CC5)sc4c3)c12] |
| 330 | BC191181 | 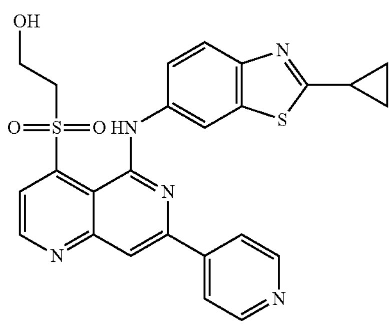 [SMILES: O=S(=O)(CCO)c1ccnc2cc(-c3ccncc3)nc(Nc3ccc4nc(C5CC5)sc4c3)c12] |
| 331 | BC191182 | 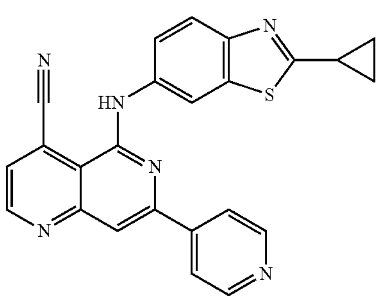 [SMILES: N#Cc1ccnc2cc(-c3ccncc3)nc(Nc3ccc4nc(C5CC5)sc4c3)c12] |
| 332 | BC191183 | |“
| 333 | BC191184 | 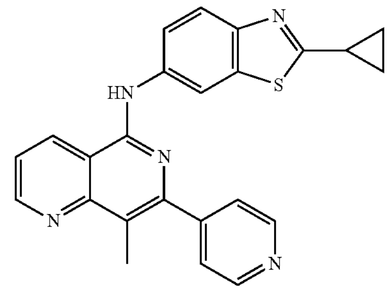 [SMILES: Cc1c(-c2ccncc2)nc(Nc2ccc3nc(C4CC4)sc3c2)c2cccnc12] |
| 334 | BC191185 | 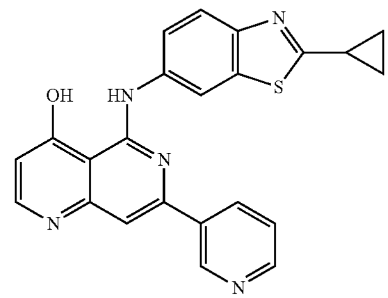 [SMILES: Oc1ccnc2cc(-c3cccnc3)nc(Nc3ccc4nc(C5CC5)sc4c3)c12] |
| 335 | BC191186 | 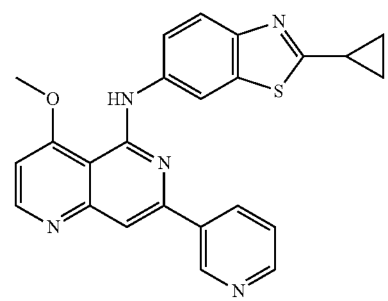 [SMILES: COc1ccnc2cc(-c3cccnc3)nc(Nc3ccc4nc(C5CC5)sc4c3)c12] |
| 336 | BC191187 | 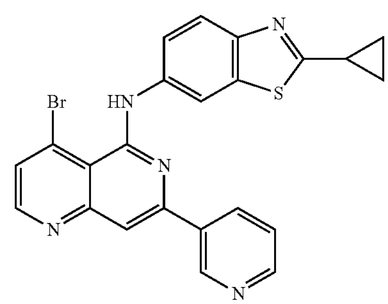 |
| 337 | BC191188 | 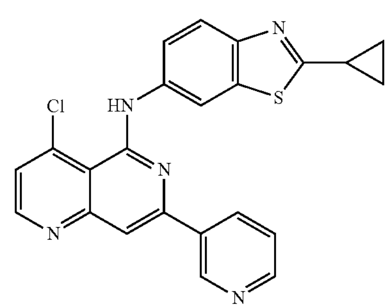 |

TABLE 5-continued

| No. | BC code | Structure |
|---|---|---|
| 338 | BC191189 | 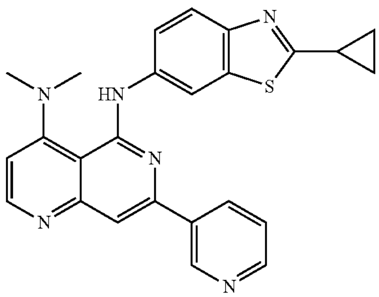 [SMILES: CN(C)c1ccnc2cc(-c3cccnc3)nc(Nc3ccc4nc(C5CC5)sc4c3)c12] |
| 339 | BC191190 | 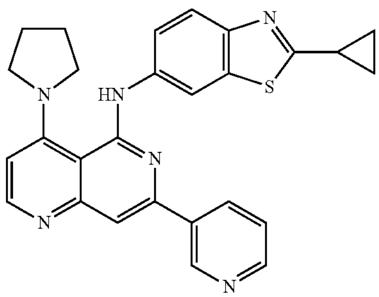 [SMILES: c1cncc(-c2cc3nccc(N4CCCC4)c3c(Nc3ccc4nc(C5CC5)sc4c3)n2)c1] |
| 340 | BC191191 | 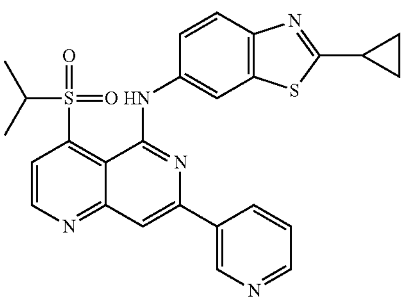 [SMILES: CC(C)S(=O)(=O)c1ccnc2cc(-c3cccnc3)nc(Nc3ccc4nc(C5CC5)sc4c3)c12] |
| 341 | BC191192 | 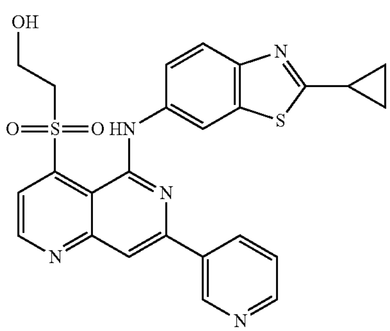 [SMILES: O=S(=O)(CCO)c1ccnc2cc(-c3cccnc3)nc(Nc3ccc4nc(C5CC5)sc4c3)c12] |
| 342 | BC191193 | 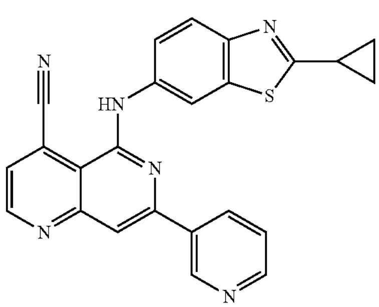 [SMILES: N#Cc1ccnc2cc(-c3cccnc3)nc(Nc3ccc4nc(C5CC5)sc4c3)c12] |
| 343 | BC191194 | |
| 344 | BC191195 | |
| 345 | BC191196 | |
| 346 | BC191197 | |
| 347 | BC191198 | |

TABLE 5-continued

| No. | BC code | Structure |
|---|---|---|
| 348 | BC191199 | 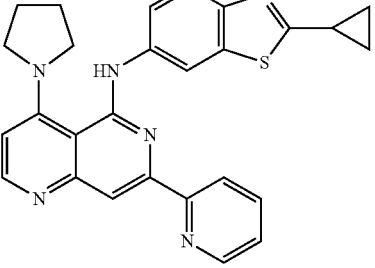 |
| 349 | BC191200 | 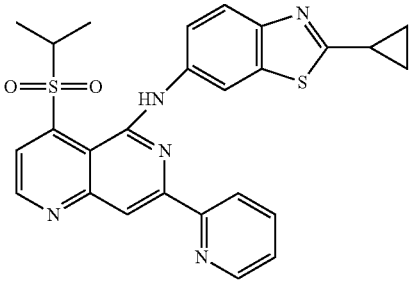 [SMILES: CC(C)S(=O)(=O)c1ccnc2cc(-c3ccccn3)nc(Nc3ccc4nc(C5CC5)sc4c3)c12] |
| 350 | BC191201 | 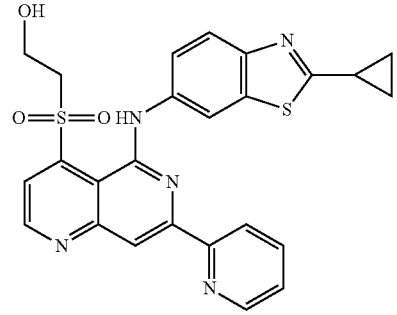 |
| 351 | BC191202 | 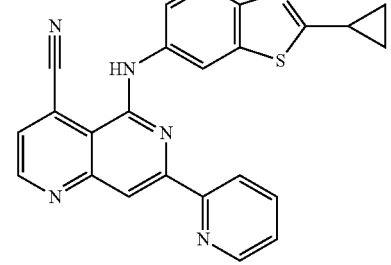 |

Note:
Compounds 239, 240, 242, and 243 were isolated and tested as HCOOH salts compounds 246, 247, and 248 were isolated and tested as HCl salts.

The following compounds shown in Table 3a may prepared using chemical routes that would be readily apparent to one of ordinary skill in the art from readily available starting materials.

TABLE 5a

| No. | BC Code | Structure |
|---|---|---|
| 400 | BC18858 | 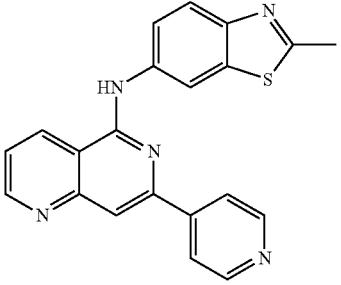 [SMILES: Cc1nc2ccc(Nc3nc(-c4ccncc4)cc4ncccc34)cc2s1] |
| 401 | BC18859 | 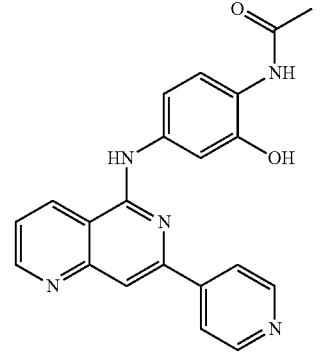 [SMILES: CC(=O)Nc1ccc(Nc2nc(-c3ccncc3)cc3ncccc23)cc1O] |
| 402 | BC18860 | 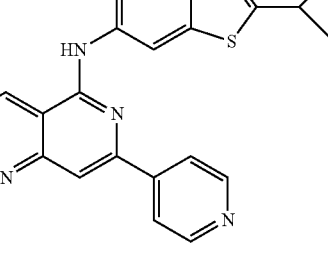 |
|  | BC191500 | 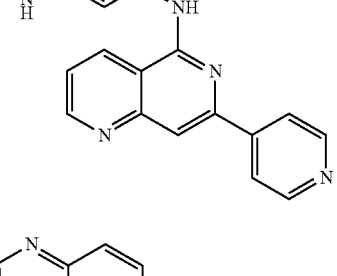 |
|  | BC191501 | 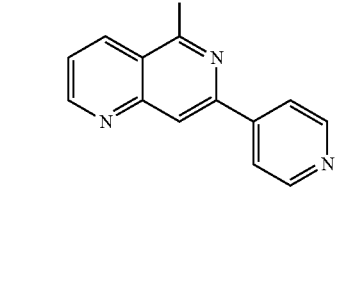 |

TABLE 5a-continued

| No. | BC Code | Structure |
|---|---|---|
| | BC191502 | |
| | BC191503 | |
| | BC191504 | |
| | BC191505 | |
| | BC191507 | |
| | BC191508 | |
| | BC191509 | |
| | BC191510 | |
| | BC191511 | |

TABLE 5a-continued

| No. | BC Code |
|---|---|
| | BC191512 |
| | BC191513 |
| | BC191514 |
| | BC191515 |
| | BC191516 |
| | BC191517 |
| | BC191518 |
| | BC191519 |
| | BC191520 |

TABLE 5a-continued

| No. | BC Code | Structure |
|---|---|---|
| | BC191521 | |
| | BC191522 | |
| | BC191524 | |
| | BC191525 | |
| | BC191526 | |
| | BC191527 | |
| | BC191528 | |
| | BC191529 | |

TABLE 5a-continued
| No. | BC Code | Structure |
|---|---|---|
| | BC191530 | 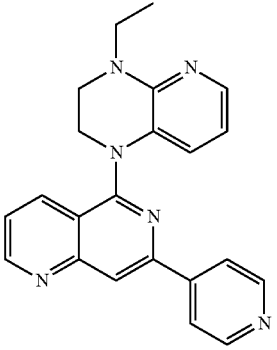 [SMILES: CCN1CCN(c2nc(-c3ccncc3)cc3ncccc23)c2cccnc21] |
| | BC191531 | 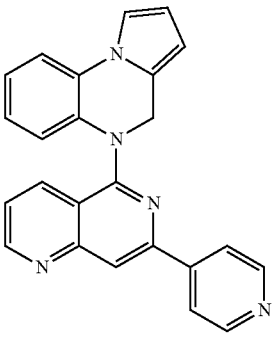 [SMILES: c1ccc2c(c1)N(c1nc(-c3ccncc3)cc3ncccc13)Cc1cccn1-2] |
| | BC191532 | 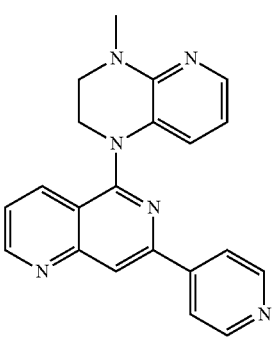 [SMILES: CN1CCN(c2nc(-c3ccncc3)cc3ncccc23)c2cccnc21] |
| | BC191533 | 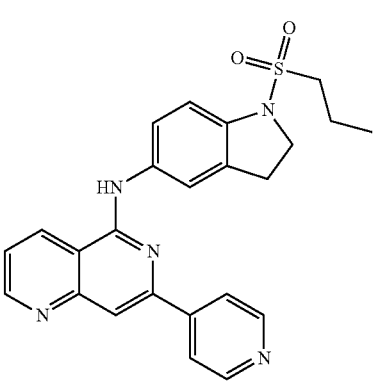 [SMILES: CCCS(=O)(=O)N1CCc2cc(Nc3nc(-c4ccncc4)cc4ncccc34)ccc21] |
| | BC191534 | 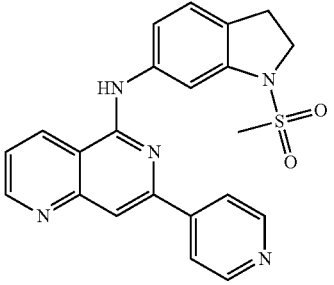 [SMILES: CS(=O)(=O)N1CCc2ccc(Nc3nc(-c4ccncc4)cc4ncccc34)cc21] |
| | BC191535 | 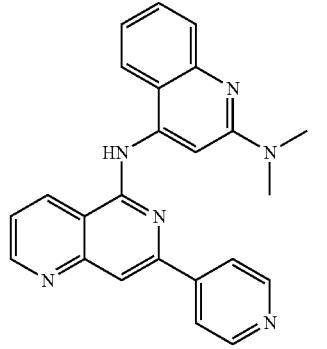 [SMILES: CN(C)c1cc(Nc2nc(-c3ccncc3)cc3ncccc23)c2ccccc2n1] |
| | BC191536 | 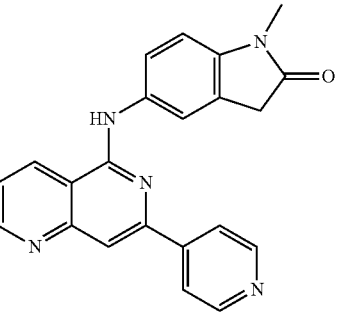 |
| | BC191537 | 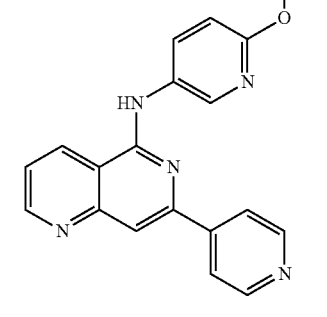 |
| | BC191538 | 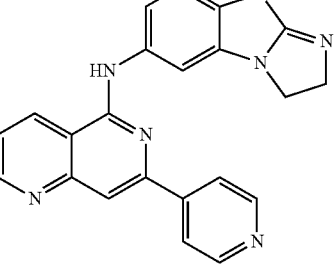 |

TABLE 5a-continued

| No. | BC Code | Structure |
|---|---|---|
| | BC191539 | |
| | BC191540 | |
| | BC191541 | |
| | BC191542 | |
| | BC191543 | |
| | BC191544 | |

The following compounds shown in Table 6 may prepared using chemical routes that would be readily apparent to one of ordinary skill in the art from readily available starting materials.

TABLE 6

| No. | BC code | Structure |
|---|---|---|
| 397 | BC18855 | 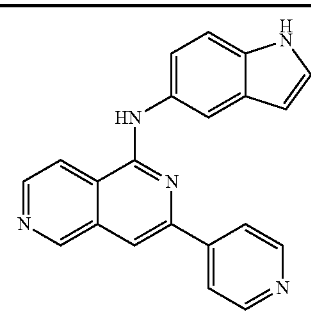 |
| 398 | BC18856 | 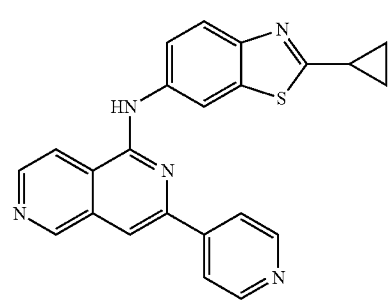 [SMILES: c1cc(-c2cc3cnccc3c(Nc3ccc4nc(C5CC5)sc4c3)n2)ccn1] |

TABLE 6-continued

| No. | BC code | Structure |
|---|---|---|
| 399 | BC18857 | 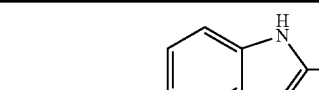 |

Note:
Compounds 397, 398, and 399 were isolated and tested as HCl salts.

Example 2—Assay Results

Assay Protocol

Approximately 2300 primary and immortalized human bronchial epithelial cells (BEAS-2B) stably expressing TFEB-EGFP in 25 μL of HITEs media with 10% FBS were dispensed into 384 well plate (Black with glass bottom) and incubated for 8 hours. Compound serial dilution (DMEM low glucose media with 2% FBS, 25 μL volume) were prepared using a robotic liquid hander. Compound solution were then added to the cell plate and incubated for 18 hours. Cells were then fixed with 4% PFA followed by DAPI staining. TFEB localization was imaged on the GFP channel along with the DAPI signal using a Cytation 5 high content imager. Images were processed through Biotek Gen5 software. Specifically, the DAPI signal was used as the primary mask to quantify the nuclear TFEB-GFP signal. Cytosolic TFEB-GFP signal was quantified through expanding the primary mask. The TFEB nuclear/cytosol ratios were calculated from nuclear TFEB-GFP signal/cytosol TFEB-GFP signal, which determined the compound efficacies.

Compounds efficacies (μM) were determined by the minimal compound concentration needed to increase TFEB nuclear/cytosol ratio by 25%. Activity: "+" equals >25 μM; "++" equals between ≤25 μM and >1 μM; and "+++" equals ≤1 μM.

Toxicity was determined by determining the compound concentration needed to induce greater than 50 percent of cell loss. For toxicity, cell loss of greater than 50 percent at a concentration that equals or is greater than 25 μM was represented as cell loss of greater than 50 percent at a concentration less than 25 μM and greater than 1 μM was represented as and cell loss of greater than 50 percent at a concentration that equals or is less than 1 μM was represented as "+++." The assay results for compounds 1-202, 214-248, 332, 333, and 352-402 are shown in Table A.

TABLE A

Compound efficacy and toxicity results.

| No. | BC code | efficacy | toxicity |
|---|---|---|---|
| 1 | BC18607 | +++ | + |
| 2 | BC18608 | +++ | + |
| 3 | BC18612 | +++ | + |
| 4 | BC18614 | +++ | +++ |
| 5 | BC18615 | + | + |
| 6 | BC18616 | + | + |
| 7 | BC18617 | + | + |
| 8 | BC18618 | + | + |
| 9 | BC18619 | + | + |
| 10 | BC18625 | + | + |
| 11 | BC18626 | +++ | + |
| 12 | BC18627 | +++ | + |
| 13 | BC18628 | + | + |
| 14 | BC18629 | + | + |
| 15 | BC18630 | +++ | + |
| 16 | BC18630 HCl salt | +++ | + |
| 17 | BC18631 | + | + |
| 18 | BC18633 | + | + |
| 19 | BC18634 | + | + |
| 20 | BC18635 | ++ | + |
| 21 | BC18636 | + | + |
| 22 | BC18637 | + | + |
| 23 | BC18639 | +++ | + |
| 24 | BC18640 | +++ | + |
| 25 | BC18641 | +++ | ++ |
| 26 | BC18642 | +++ | +++ |
| 27 | BC18643 | +++ | + |
| 28 | BC18644 | + | + |
| 29 | BC18645 | ++ | + |
| 30 | BC18646 | +++ | +++ |
| 31 | BC18647 | +++ | +++ |
| 32 | BC18648 | +++ | +++ |
| 33 | BC18649 | + | + |
| 34 | BC18652 | +++ | + |
| 35 | BC18653 | +++ | ++ |
| 36 | BC18654 | + | + |
| 37 | BC18655 | ++ | + |
| 38 | BC18656 | + | + |
| 39 | BC18657 | + | + |
| 40 | BC18658 | ++ | + |
| 41 | BC18659 | ++ | ++ |
| 42 | BC18660 | +++ | + |
| 43 | BC18663 | ++ | + |
| 44 | BC18664 | +++ | + |
| 45 | BC18665 | + | + |
| 46 | BC18666 | + | + |
| 47 | BC18667 | +++ | +++ |
| 48 | BC18668 | + | + |
| 49 | BC18669 | + | + |
| 50 | BC18670 | + | + |
| 51 | BC18671 | + | + |
| 52 | BC18672 | + | + |
| 53 | BC18673 | + | + |
| 54 | BC18674 | + | + |
| 55 | BC18675 | + | + |
| 56 | BC18676 | ++ | + |
| 57 | BC18677 | +++ | + |
| 58 | BC18678 | ++ | + |
| 59 | BC18679 | ++ | + |
| 60 | BC18680 | + | + |
| 61 | BC18681 | +++ | ++ |
| 62 | BC18682 | +++ | +++ |
| 63 | BC18683 | + | + |
| 64 | BC18684 | ++ | ++ |
| 65 | BC18685 | + | + |
| 66 | BC18686 | + | + |
| 67 | BC18687 | + | + |
| 68 | BC18688 | + | + |
| 69 | BC18689 | + | + |
| 70 | BC18690 | +++ | + |
| 71 | BC18693 | +++ | + |
| 72 | BC18695 | +++ | +++ |
| 73 | BC18697 | +++ | +++ |
| 74 | BC18698 | +++ | ++ |
| 75 | BC18702 | + | + |
| 76 | BC18703 | + | + |
| 77 | BC18704 | +++ | + |
| 78 | BC18705 | ++ | + |
| 79 | BC18706 | + | + |
| 80 | BC18707 | ++ | + |
| 81 | BC18708 | +++ | ++ |

TABLE A-continued

Compound efficacy and toxicity results.

| No. | BC code | efficacy | toxicity |
|---|---|---|---|
| 82 | BC18709 | +++ | + |
| 83 | BC18711 | ++ | + |
| 84 | BC18713 | +++ | + |
| 85 | BC18714 | +++ | + |
| 86 | BC18717 | +++ | +++ |
| 87 | BC18718 | + | + |
| 88 | BC18720 | + | + |
| 89 | BC18722 | ++ | ++ |
| 90 | BC18724 | +++ | + |
| 91 | BC18725 | +++ | + |
| 92 | BC18726 | ++ | + |
| 93 | BC18727 | + | + |
| 94 | BC18728 | +++ | + |
| 95 | BC18729 | + | + |
| 96 | BC18730 | + | + |
| 97 | BC18731 | +++ | + |
| 98 | BC18732 | +++ | + |
| 99 | BC18733 | +++ | + |
| 100 | BC18734 | + | + |
| 101 | BC18735 | + | + |
| 102 | BC18736 | +++ | + |
| 103 | BC18737 | +++ | + |
| 104 | BC18738 | +++ | + |
| 105 | BC18739 | + | + |
| 106 | BC18740 | + | + |
| 107 | BC18742 | + | + |
| 108 | BC18743 | +++ | + |
| 109 | BC18744 | +++ | + |
| 110 | BC18745 | +++ | + |
| 111 | BC18746 | + | + |
| 112 | BC18747 | +++ | + |
| 113 | BC18748 | +++ | ++ |
| 114 | BC18749 | +++ | ++ |
| 115 | BC18750 | + | + |
| 116 | BC18752 | +++ | + |
| 117 | BC18754 | +++ | + |
| 118 | BC18755 | ++ | + |
| 119 | BC18756 | + | + |
| 120 | BC18757 | + | + |
| 121 | BC18758 | + | + |
| 122 | BC18759 | + | + |
| 123 | BC18760 | ++ | + |
| 124 | BC18761 | +++ | + |
| 125 | BC18762 | ++ | + |
| 126 | BC18763 | ++ | + |
| 127 | BC18764 | ++ | + |
| 128 | BC18765 | +++ | + |
| 129 | BC18766 | +++ | + |
| 130 | BC18767 | +++ | + |
| 131 | BC18768 | +++ | + |
| 132 | BC18769 | +++ | + |
| 133 | BC18770 | +++ | + |
| 134 | BC18771 | +++ | + |
| 135 | BC18772 | ++ | + |
| 136 | BC18773 | +++ | + |
| 137 | BC18774 | +++ | + |
| 138 | BC18775 | +++ | + |
| 139 | BC18776 | + | + |
| 140 | BC18778 | + | + |
| 141 | BC18779 | +++ | ++ |
| 142 | BC18780 | +++ | + |
| 143 | BC18782 | +++ | + |
| 144 | BC18783 | + | + |
| 145 | BC18784 | +++ | + |
| 146 | BC18785 | +++ | + |
| 147 | BC18786 | ++ | + |
| 148 | BC18787 | +++ | + |
| 149 | BC18788 | ++ | ++ |
| 150 | BC18789 | +++ | ++ |
| 151 | BC18790 | +++ | + |
| 152 | BC18791 | ++ | + |
| 153 | BC18792 | ++ | + |
| 154 | BC18793 | +++ | + |
| 155 | BC18794 | +++ | + |
| 156 | BC18795 | +++ | + |
| 157 | BC18796 | +++ | ++ |
| 158 | BC18797 | +++ | + |
| 159 | BC1820 | + | + |
| 160 | BC18200 | +++ | ++ |
| 161 | BC18201 | + | + |
| 162 | BC18202 | + | + |
| 163 | BC18203 | + | + |
| 164 | BC18204 | + | + |
| 165 | BC18205 | + | + |
| 166 | BC18206 | + | + |
| 167 | BC18207 | ++ | + |
| 168 | BC18208 | + | + |
| 169 | BC18209 | + | + |
| 170 | BC18210 | + | + |
| 171 | BC18211 | + | + |
| 172 | BC18212 | + | + |
| 173 | BC18213 | + | + |
| 174 | BC18214 | + | + |
| 175 | BC18215 | + | + |
| 176 | BC18216 | ++ | + |
| 177 | BC18217 | + | + |
| 178 | BC1834 | +++ | + |
| 179 | BC18601 | ++ | + |
| 180 | BC18602 | + | + |
| 181 | BC18603 | +++ | + |
| 182 | BC18604 | + | + |
| 183 | BC18605 | ++ | + |
| 184 | BC18606 | ++ | + |
| 185 | BC18609 | +++ | + |
| 186 | BC18610 | +++ | + |
| 187 | BC18611 | +++ | + |
| 188 | BC18613 | + | + |
| 189 | BC18623 | ++ | + |
| 190 | BC18624 | ++ | + |
| 191 | BC18632 | +++ | + |
| 192 | BC18651 | +++ | + |
| 193 | BC18661 | ++ | ++ |
| 194 | BC18715 | +++ | + |
| 195 | BC1816 | + | + |
| 196 | BC1835 | + | + |
| 197 | BC1836 | + | + |
| 198 | BC1837 | + | + |
| 199 | BC1838 | + | + |
| 200 | BC1839 | ++ | + |
| 201 | BC1840 | + | + |
| 202 | BC1841 | + | + |
| 214 | BC1770 | + | + |
| 215 | BC1771 | ++ | ++ |
| 216 | BC1772 | + | + |
| 217 | BC1773 | + | + |
| 218 | BC1774 | + | + |
| 219 | BC1775 | + | + |
| 220 | BC1776 | + | + |
| 221 | BC1777 | + | + |
| 222 | BC1753 | ++ | ++ |
| 223 | BC1780 | + | + |
| 224 | BC1781 | + | + |
| 225 | BC1782 | + | + |
| 226 | BC1783 | + | + |
| 227 | BC1784 | + | + |
| 228 | BC1785 | + | + |
| 229 | BC1786 | + | + |
| 230 | BC1787 | + | + |
| 231 | BC1811 | ++ | + |
| 232 | BC1812 | + | + |
| 233 | BC1813 | + | + |
| 234 | BC1814 | ++ | + |
| 235 | BC1815 | ++ | + |
| 236 | BC1817 | ++ | + |
| 237 | BC1818 | ++ | + |
| 238 | BC1819 | + | + |
| 239 | BC18842 | ++ | + |
| 240 | BC18846 | +++ | + |
| 241 | BC18847 | +++ | + |
| 242 | BC18848 | +++ | + |
| 243 | BC18849 | +++ | + |
| 244 | BC18850 | +++ | + |

TABLE A-continued

Compound efficacy and toxicity results.

| No. | BC code | efficacy | toxicity |
|---|---|---|---|
| 245 | BC18851 | +++ | + |
| 246 | BC18852 | +++ | + |
| 247 | BC18853 | ++ | + |
| 248 | BC18854 | ++ | + |
| 332 | BC191183/ BC18861 | +++ | + |
| 333 | BC191184/ BC18862 | +++ | + |
| 352 | BC18795 | ++ | + |
| 353 | BC18796 | ++ | + |
| 354 | BC18797 | + | + |
| 355 | BC18798 | ++ | + |
| 356 | BC18799 | +++ | + |
| 357 | BC18800 | + | + |
| 358 | BC18801 | ++ | + |
| 359 | BC18802 | + | + |
| 360 | BC18803 | + | + |
| 361 | BC18804 | ++ | + |
| 362 | BC18805 | + | + |
| 363 | BC18806 | +++ | + |
| 364 | BC18807 | + | + |
| 365 | BC18808 | +++ | + |
| 366 | BC18809 | + | + |
| 367 | BC18810 | ++ | + |
| 368 | BC18811 | ++ | + |
| 369 | BC18812 | + | + |
| 370 | BC18814 | +++ | + |
| 371 | BC18817 | +++ | + |
| 372 | BC18818 | +++ | + |
| 373 | BC18819 | ++ | + |
| 374 | BC18820 | ++ | + |
| 375 | BC18821 | +++ | + |
| 376 | BC18822 | +++ | + |
| 377 | BC18823 | ++ | + |
| 378 | BC18824 | +++ | + |
| 379 | BC18825 | +++ | + |
| 380 | BC18826 | ++ | + |
| 381 | BC18827 | +++ | + |
| 382 | BC18828 | + | + |
| 383 | BC18829 | ++ | + |
| 384 | BC18830 | +++ | + |
| 385 | BC18831 | ++ | + |
| 386 | BC18832 | +++ | + |
| 387 | BC18833 | + | + |
| 388 | BC18834 | + | + |
| 389 | BC18835 | + | + |
| 390 | BC18836 | + | + |
| 391 | BC18837 | +++ | + |
| 392 | BC18838 | + | + |
| 393 | BC18839 | ++ | + |
| 394 | BC18840 | + | + |
| 395 | BC18841 | +++ | + |
| 396 | BC18845 | +++ | + |
| 397 | BC18855 | ++ | + |
| 398 | BC18856 | +++ | + |
| 399 | BC18857 | +++ | + |
| 400 | BC18858 | +++ | + |
| 401 | BC18859 | +++ | + |
| 402 | BC18860 | +++ | + |

Example 3—Using BC1753 to Increase TFEB Polypeptide Levels

Figure 2B:
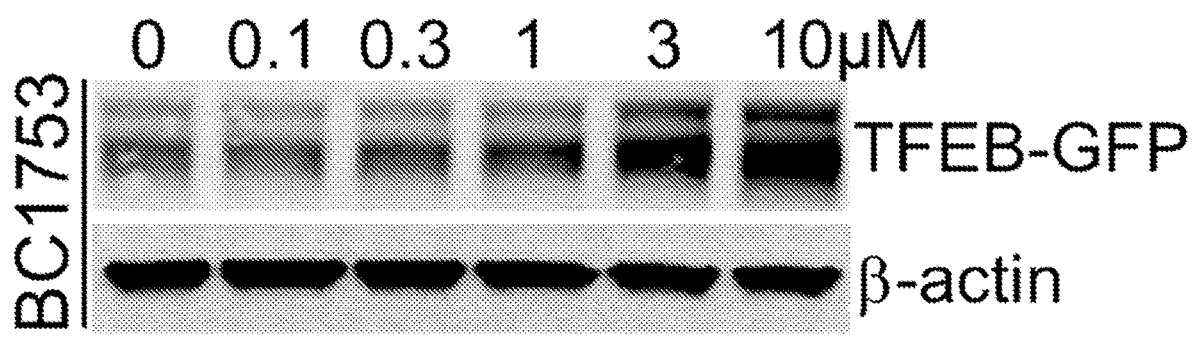
Figure 2C:
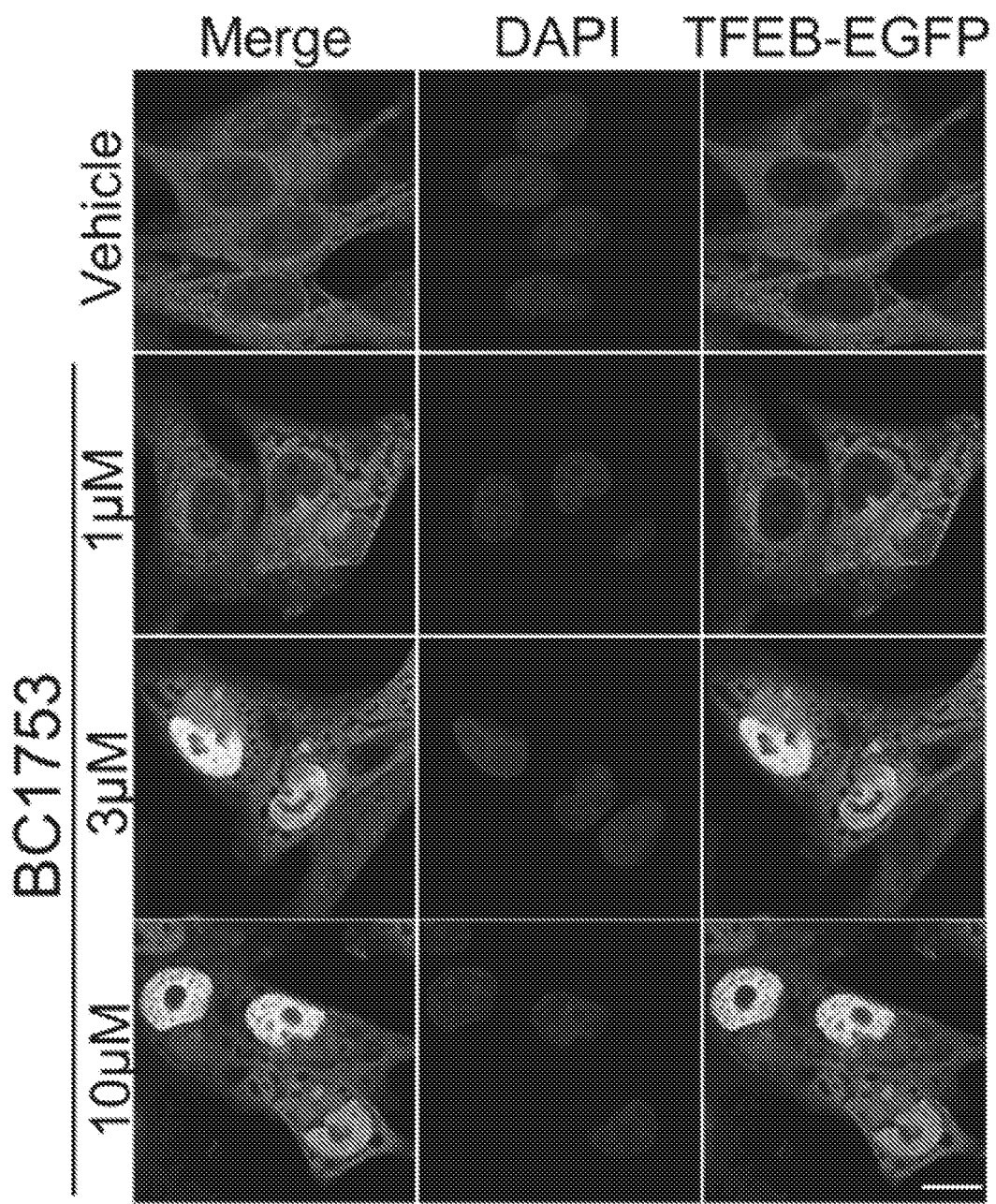

BC1753 (FIG. 2A) was tested for its ability to increase TFEB polypeptide levels. Briefly, murine lung epithelial cells (MLE12) stably expressing TFEB-EGFP were treated with BC1753 in a dose dependent manner for 18 hours. Cells were then collected and assayed by immunoblotting for TFEB-GFP protein levels (FIG. 2B). Murine lung epithelial cells (MLE12) stably expressing TFEB-EGFP were treated with BC1733 in a dose dependent manner for 18 hours. Cells were then fixed with 4% PFA followed by DAPI staining. TFEB localization was imaged on the GFP channel along with the DAPI signal using a Nikon A1 confocal microscope (FIG. 2C). BC1753 drastically increased total TFEB polypeptide levels within cells (FIG. 2B) and increased nuclear TFEB polypeptide accumulation (FIG. 2C).

Figure 3:
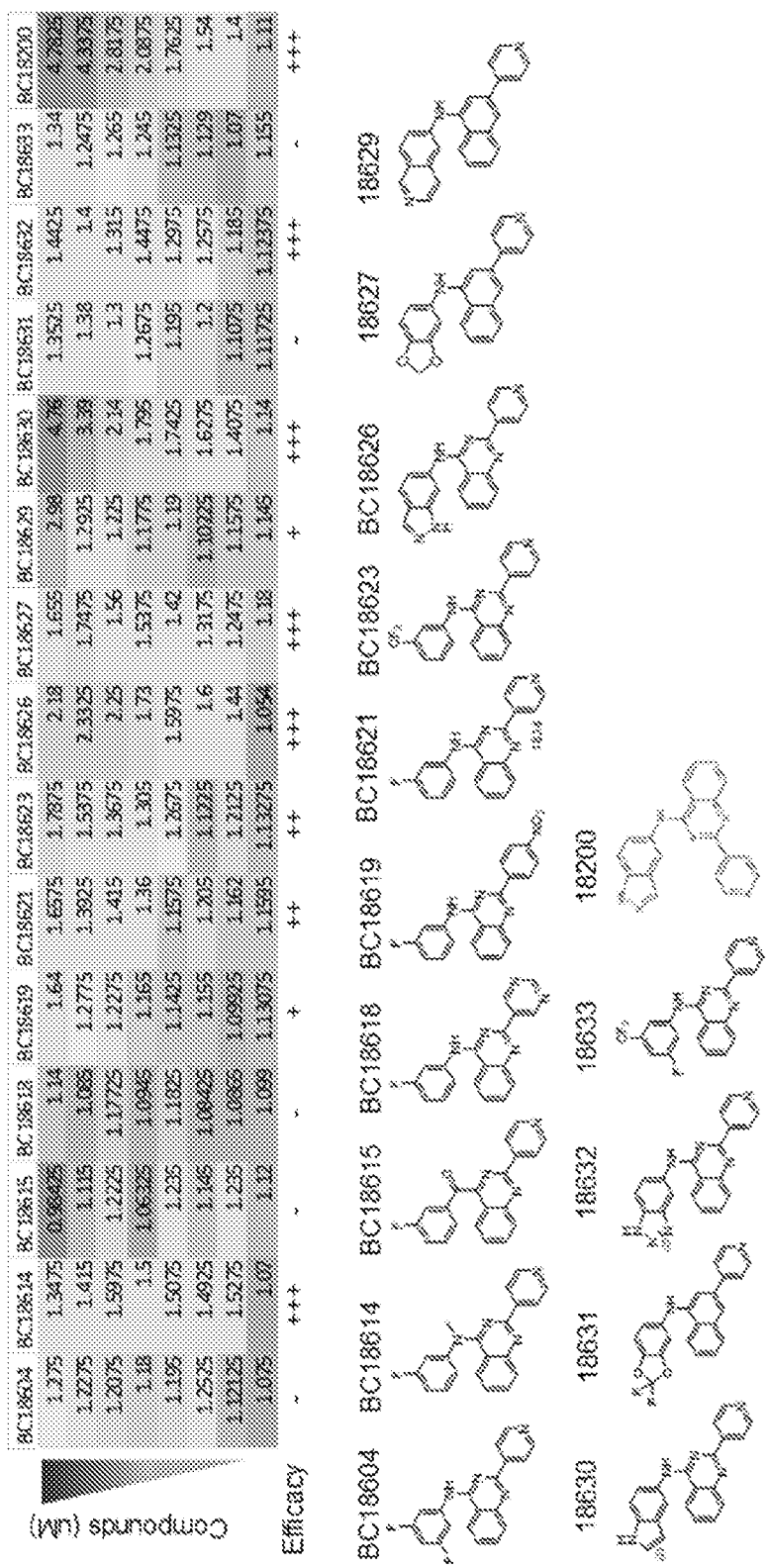
FIG. 3. High content screen assay (384 well) measuring TFEB nuclear accumulation. Approximately 2500 primary and immortalized human bronchial epithelial cells (BEAS-2B) stably expressing TFEB-EGFP in 25 μL of HITEs media with 10% FBS were dispensed into 384 well plate (Black with glass bottom) and incubated for 8 hours. Compound serial dilution (DMEM low glucose media with 2% FBS, 25 μL volume) were prepared using a robotic liquid hander. Compound solutions were then added to the cell plate and incubated for 18 hours. Cells were then fixed with 4% PFA followed by DAPI staining. TFEB localization was imaged on the GFP channel along with the DAPI signal using a Cytation 5 high content imager. Images were processed through Biotek Gen5 software; specifically, the DAPI signal was used as the primary mask to quantify the nuclear TFEB-GFP signal. The cytosolic TFEB-GFP signal was quantified through expanding the primary mask. The TFEB nuclear/cytosol ratios were calculated from nuclear TFEB-GFP signal/cytosol TFEB-GFP signal, which determined the compound efficacy. The table shows the efficacy of the compound (with increased compound concentrations) in increasing TFEB nuclear/cytosol ratio. Compound activities (μM) were determined by the minimal compound concentration needed to increase TFEB nuclear/cytosol ratio by 25%. Activity: "−" equals >25 μM; "+" equals between 25 μM and >10 μM; "++" equals between ≤10 μM and >1 μM; and "+++" equals 1 μM. N=4.

Example 4—Compounds for Increasing TFEB Polypeptide Levels within the Nucleus of Cells A high-content imaging screen was conducted using Beas2B cells that stably express GFP-TFEB. This approach demonstrated robust and accurate measurement of TFEB nuclear/cytosol ratio upon various compound treatments (FIG. 3).

Figure 4A:
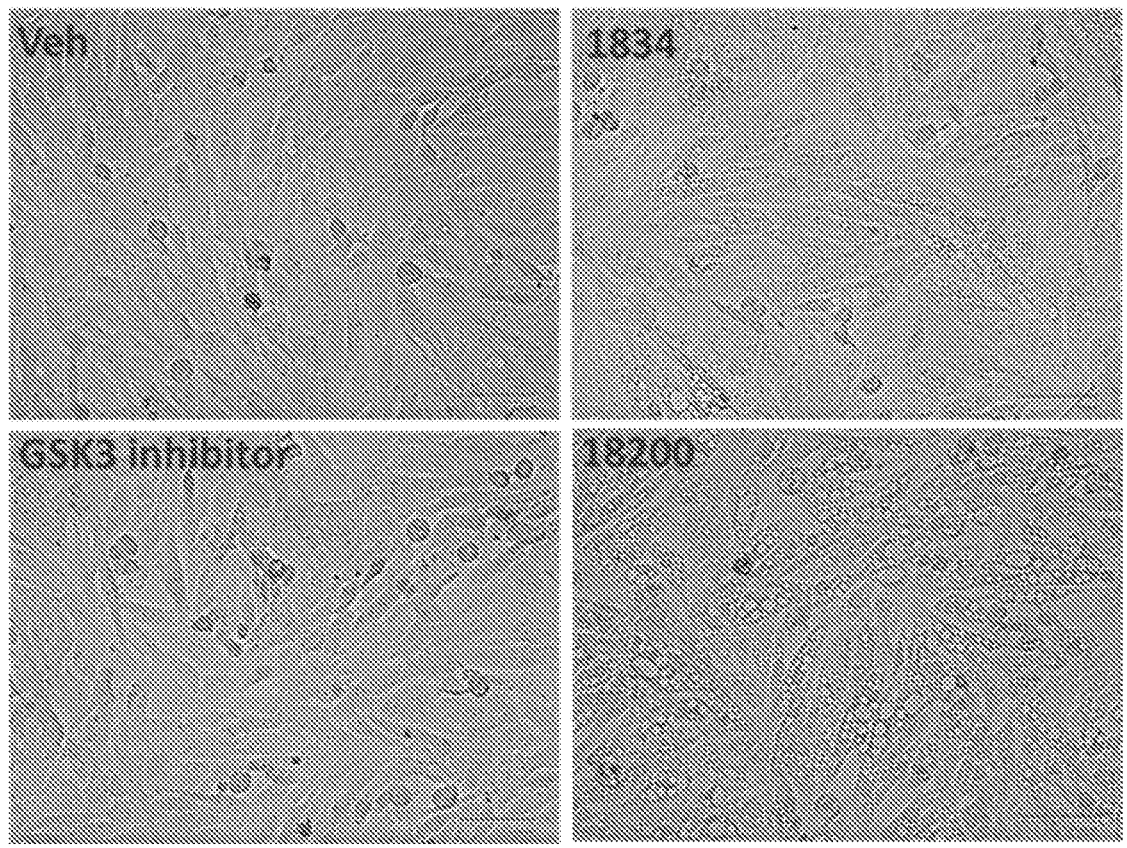
FIGS. 4A-B. Compound 178 (BC1834) and Compound 160 (BC18200) increased lysosome quantity. A. Beas2B cells were treated with Cmpd. 178, Cmpd. 160, or the GSK3b inhibitor TWS119 (1 μM for 18 hours). Cells were then imaged through light microscope. B. Beas2B cells were treated with Cmpd. 178 for 18 hours at the indicated concentrations. Cells were then stained with lysotracker Red (100 nM) for 30 minutes. Cells then were washed and imaged through confocal microscopy.
Figure 4B:
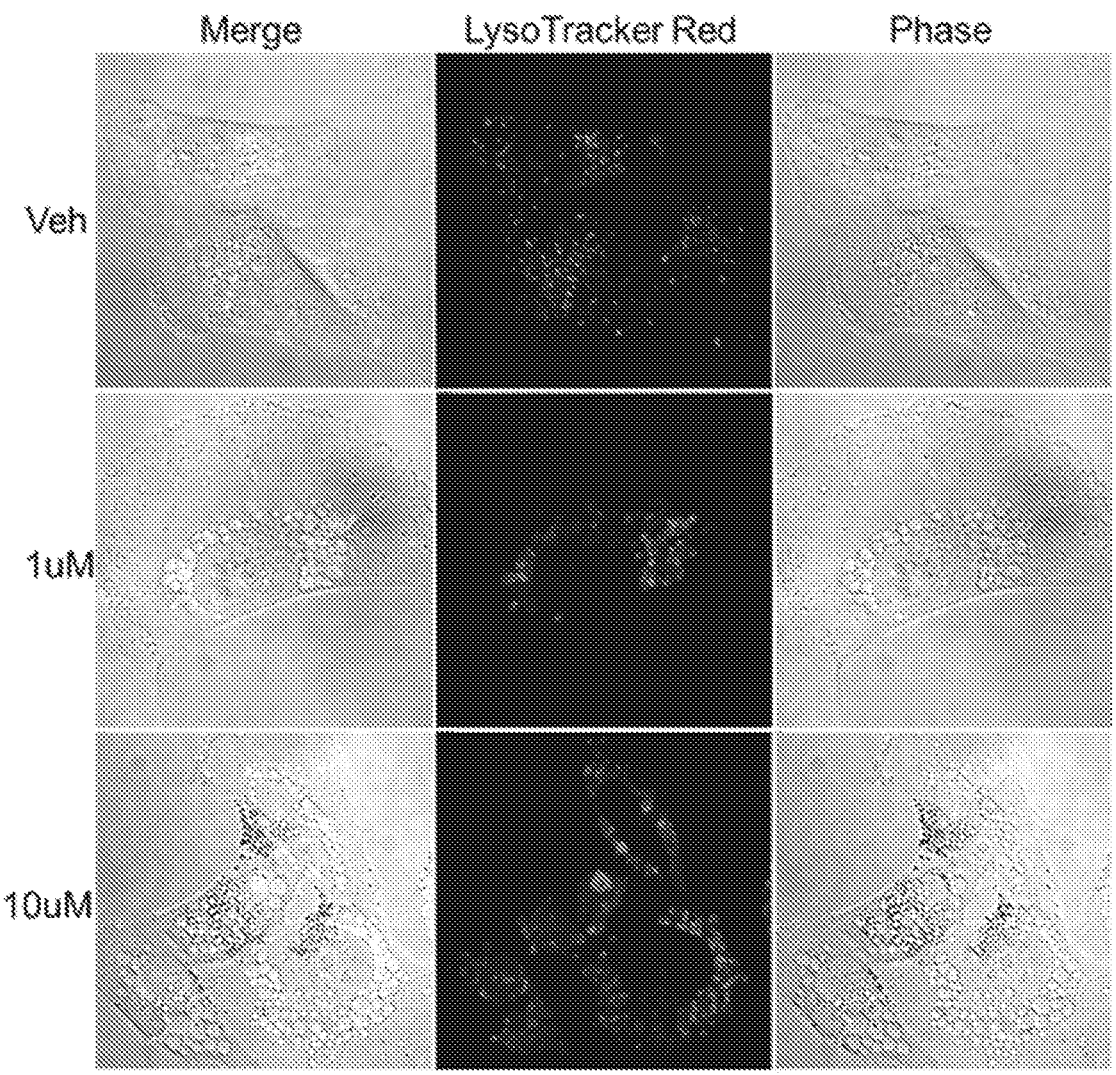
Figure 5A:
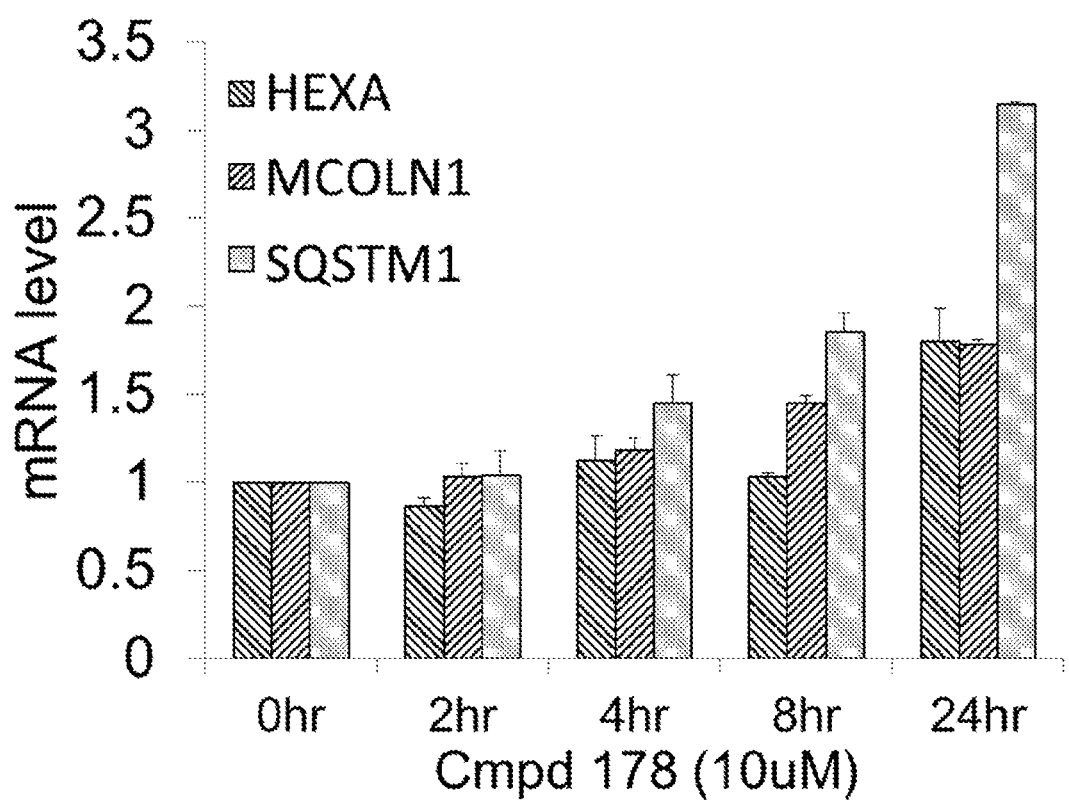
FIGS. 5A-B. Compound 133 and Compound 115 increased lysosomal protein expression and secretion. A. Beas2B cells were treated with Cmpd. 133 at 10 μM for 24 hours. Cells then were collected and assayed for lysosomal protein gene expression. B. Beas2B cells were treated with Cmpd. 115 at the indicated concentration for 18 hours. Secreted b-hexosaminidase activity (a lysosomal enzyme) then was measured and normalized with cellular b-hexosaminidase activity.
Figure 5B:
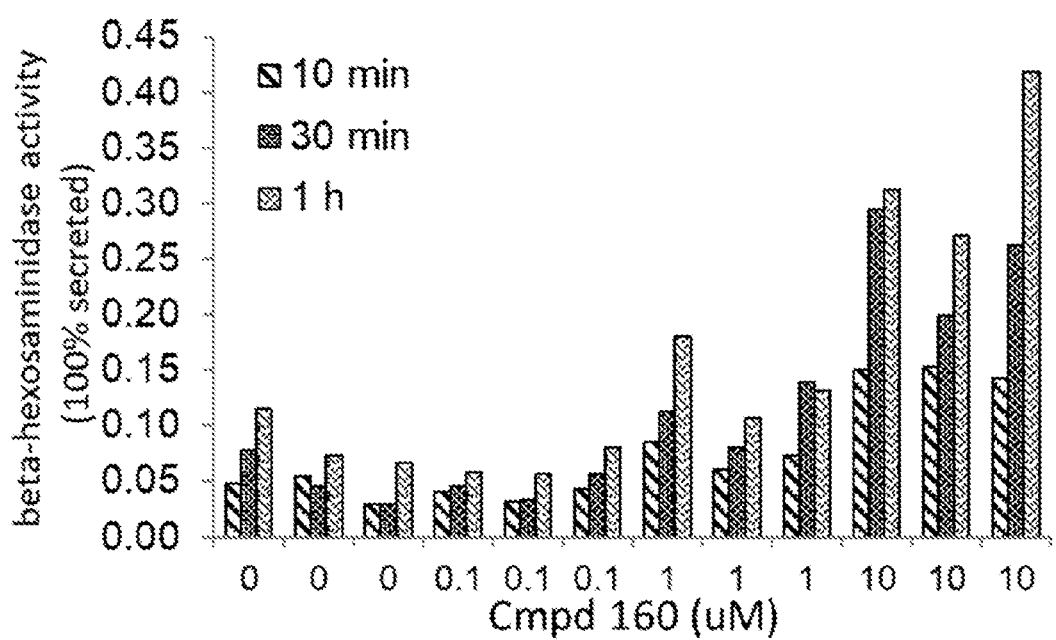

Example 5—Increasing Lysosome Quantity, Lysosomal Protein Expression, and Secretion of Lysosomal Enzymes Compounds 178 (BC1834) and/or 160 (BC18200) at the indicated concentrations were found to increase lysosome quantity (FIGS. 4A-B), to increase lysosomal protein expression (FIG. 5A), and to increase secretion of the lysosomal enzyme beta hexosaminidase (FIG. 5B).

Figure 6A:
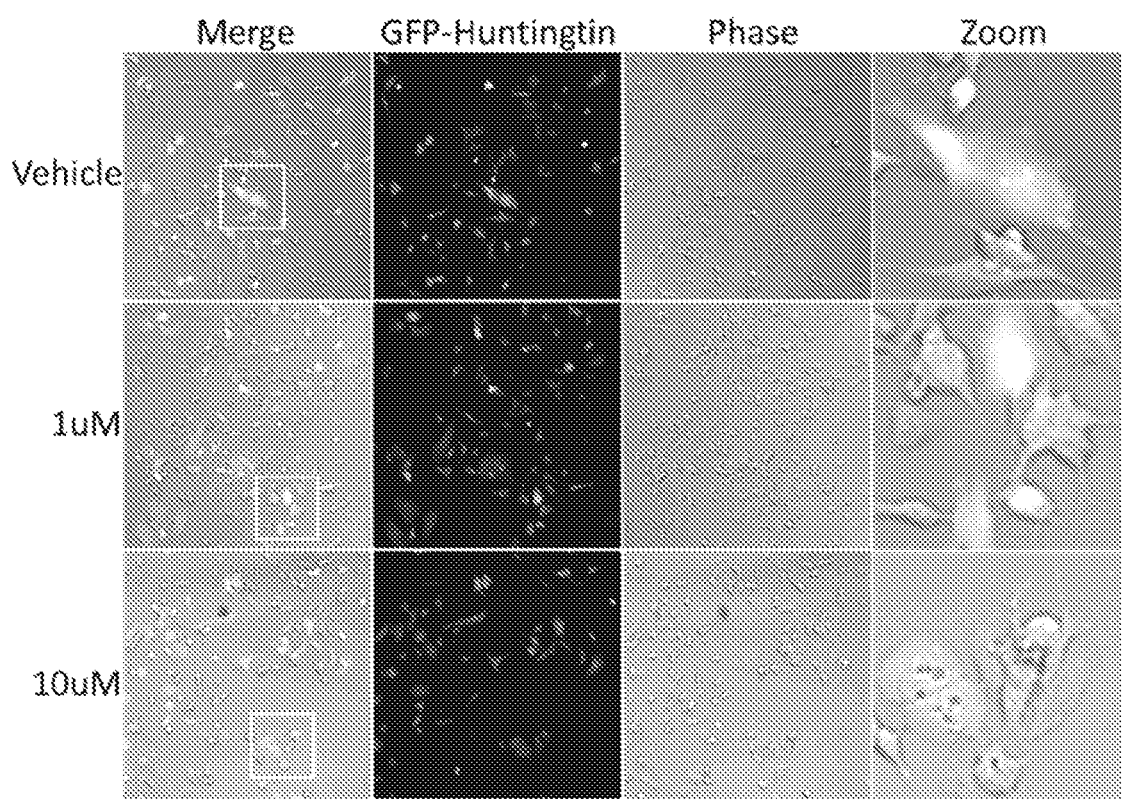
FIGS. 6A-B. Compound 178 reduced Huntingtin gene expression. A-B. SH5Y cells stably transfected with GFP-72Q (Huntingtin) were treated with the indicated amounts of Cmpd. 178 for 24 hours. Cells then were imaged with a confocal microscope or collected and assayed for protein expression using a GFP-Huntingtin immunoblot.
Figure 6B:
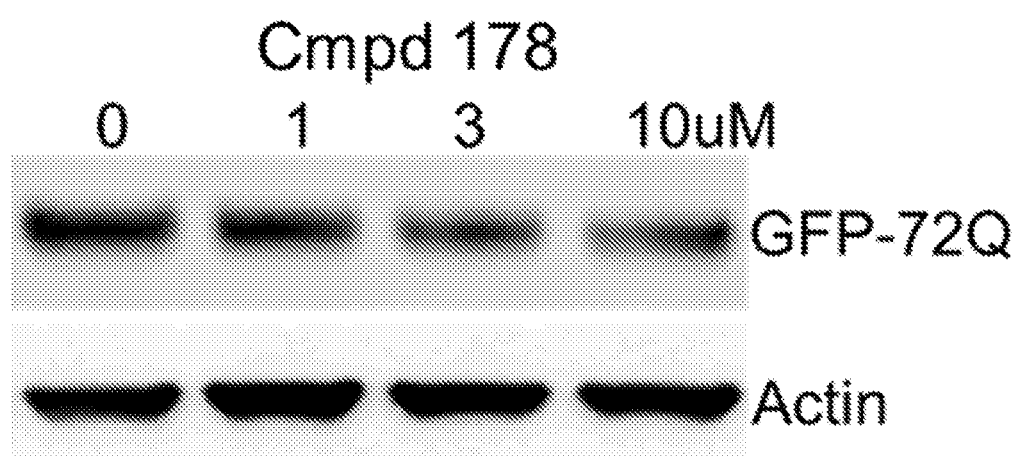

Example 6—Using Compounds Provided Herein to Reduce the Level of Huntingtin Polypeptides Compound 178 (BC1834) was tested for the ability to reduce Huntingtin polypeptide levels within cells. Briefly, Compound 178 was administered to SH5Y cells stably expressing GFP-Huntingtin (72Q). As shown in FIGS. 6A-B, Compound 178 dose dependently reduced GFP-Huntingtin polypeptide levels. These results demonstrate that the compounds provided herein can be used to treat neurological conditions such as Huntington's disease.

Example 7—In Vivo Effects

Figure 7:
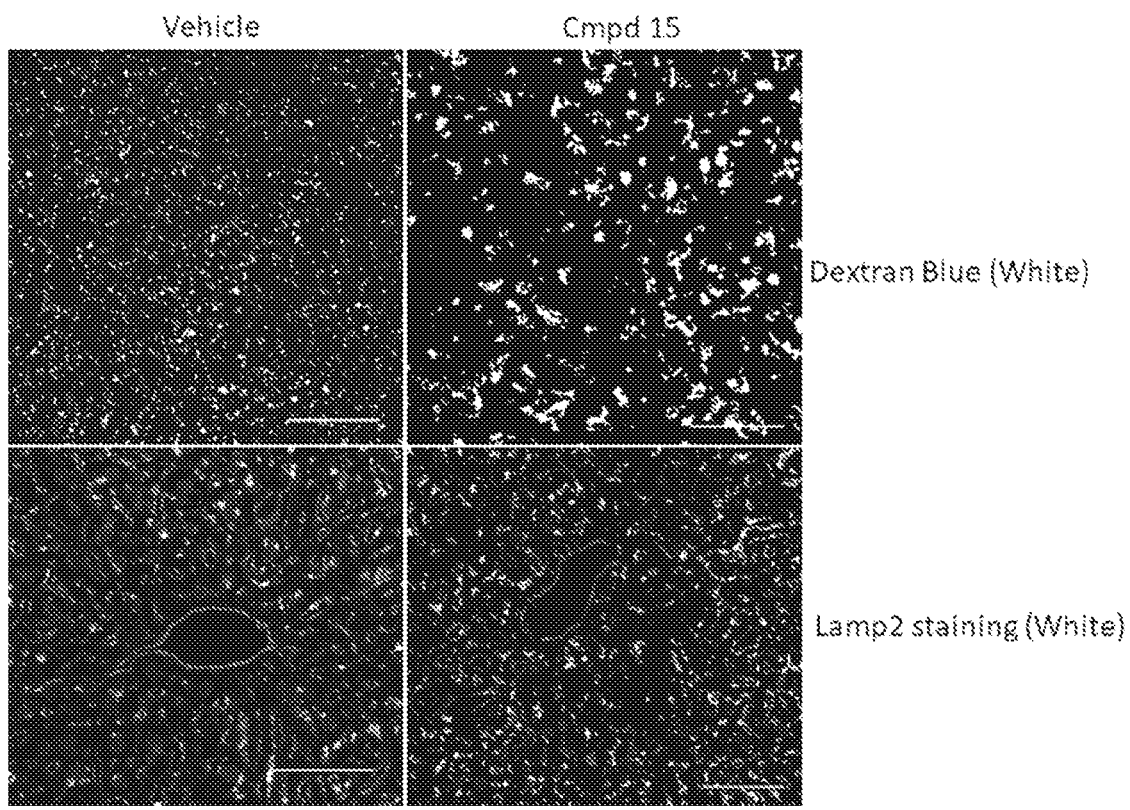
FIG. 7. Compound 15 increases liver lysosomal activity. Female C57BL6 mice were intraperitoneally (i.p.) injected with Cmpd. 15 (50 mg/kg/d) for 4 days. Mice were then intravenously (i.v.) injected with dextran blue. 24 hours later, mice were sacrificed, and livers were removed and imaged through confocal microscopy. White fluorescent signal indicates dextran blue within lysosome and provides a measure of lysosomal number and activity within the hepatic tissue (Upper panels). In another experiment, histological slides from the liver obtained from the above experiment were immunostained with Lamp2 antibody (Lower panels) and revealed enhanced signals with Cmpd 15 treatment. Scale bar: 50 microns.

Female C57BL6 mice were i.p. injected with Compound 15 (30 mg/kg/day) for 4 days. Mice were then i.v. injected with dextran blue. 24 hours later, mice were sacrificed, and liver samples were removed and imaged through confocal microscopy. As shown in FIG. 7, Compound 13 treatment drastically increased lysosomal dextran blue signal and lamp2 staining (pseudo-colored white). These results demonstrate that the compounds provided herein can increase in vivo lysosomal number and activity.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (IIh):

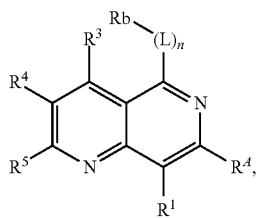

(IIh)

or a pharmaceutically acceptable salt thereof, wherein:

each L is independently selected from O, S, S(=O)$_2$, $C_{1-3}$ alkylene, C(=O), and N($R^N$), wherein said $C_{1-3}$ alkylene is optionally substituted with 1, 2, or 3 substituents independently selected from halo, CN, NO$_2$, OH, $C_{1-3}$ alkoxy, amino, $C_{1-3}$ alkylamino, and di($C_{1-3}$ alkyl)amino;

each $R^N$ is independently selected from H and $C_{1-6}$ alkyl, wherein said $C_{1-6}$ alkyl is optionally substituted with 1, 2, or 3 substituents independently selected from halo, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

n is an integer selected from 1, 2, and 3;

each of $R^1$, $R^3$, $R^4$, and $R^5$, is independently selected from H, halo, CN, NO$_2$, $C_{1-6}$ alkyl, $C_{1-6}$ haloalkyl, $C_{2-6}$ alkenyl, $C_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$ NR$^{c1}$S(O)$_2$R$^{b1}$, S(O)$_2$R$^{b1}$, and S(O)$_2$NR$^{c1}$R$^{d1}$; wherein said $C_{1-6}$ alkyl, $C_{2-6}$ alkenyl, and $C_{2-6}$ alkynyl are each optionally substituted with 1, 2, or 3 substituents independently selected from CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

$R^A$ and $R^B$ are defined as follows:

a. $R^A$ is selected from the group consisting of

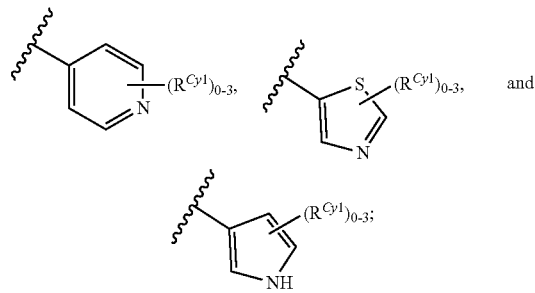

and $R^B$ is selected from $C_{1-6}$ alkyl, $C_{1-6}$ haloalkyl, $C_{2-6}$ alkenyl, $C_{2-6}$ alkynyl, and Cy$^1$, wherein said $C_{1-6}$ alkyl, $C_{2-6}$ alkenyl, and $C_{2-6}$ alkynyl are each optionally substituted with 1, 2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$;

or, when $R^B$ is attached to L which is N($R^N$), $R^B$ and $R^N$ together with the N atom to which they are attached form 4-14 membered heterocycloalkyl, which is optionally substituted with 1, 2, or 3 substituents independently selected from Cy$^1$, halo, CN, NO$_2$, $C_{1-6}$ alkyl, $C_{1-6}$ haloalkyl, $C_{2-6}$ alkenyl, $C_{2-6}$ alkynyl, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; wherein said $C_{1-6}$ alkyl, $C_{2-6}$ alkenyl, and $C_{2-6}$ alkynyl are each optionally substituted with 1, 2, or 3 substituents independently selected from Cy$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, S(O)$_2$R$^{b1}$, and S(O)$_2$NR$^{c1}$R$^{d1}$; or b. $R^A$ is selected from Cy$^{A1}$, O-Cy$^{A1}$, and N($R^N$)-Cy$^{A1}$; $R^B$ is selected from the group consisting of

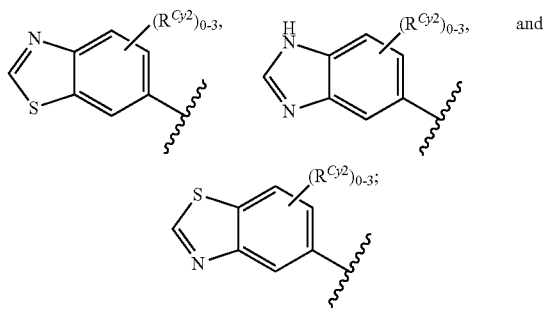

Cy$^{A1}$ is selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from R$^{Cy1}$;

each Cy$^1$ is independently selected from $C_{6-10}$ aryl, 5-10 membered heteroaryl, and 4-14 membered heterocycloalkyl, each of which is optionally substituted with 1, 2, 3, 4, or 5 substituents independently selected from R$^{Cy2}$;

R$^{Cy1}$ and R$^{Cy2}$ are each independently selected from oxo, halo, CN, NO$_2$, Cy$^2$, $C_{1-6}$ alkyl, $C_{1-6}$ haloalkyl, $C_{2-6}$ alkenyl, $C_{2-6}$ alkynyl, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, wherein $R^A$ is selected from $Cy^{A1}$, O-$Cy^{A1}$, and N($R^N$)-$Cy^{A1}$; and $R^B$ is selected from the group consisting of

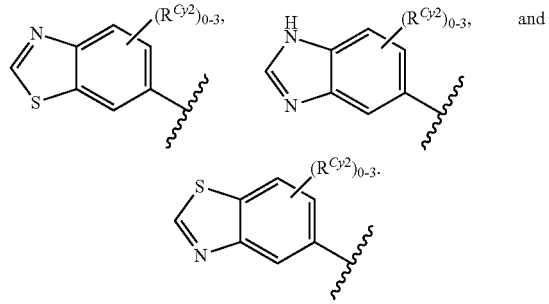

3. The compound of claim 1 wherein $R^A$ is selected from the group consisting of

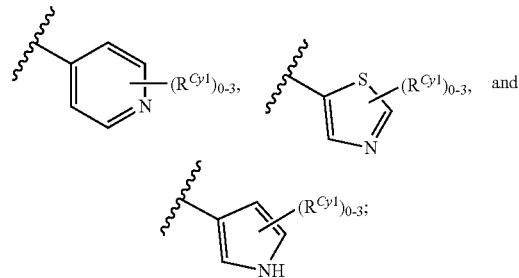

and $R^B$ is selected from $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

or, when $R^B$ is attached to L which is $N(R^N)$, $R^B$ and $R^N$ together with the N atom to which they are attached form 4-14 membered heterocycloalkyl, which is optionally substituted with 1, 2, or 3 substituents independently selected from $Cy^1$, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

4. The compound of claim 1, or a pharmaceutically acceptable salt thereof, wherein:

L is NH;

$R^A$ is selected from the group consisting of

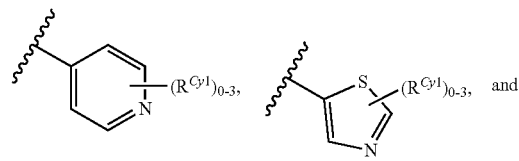

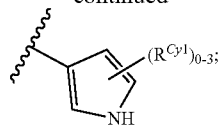
and
R[B] is selected from the group consisting of
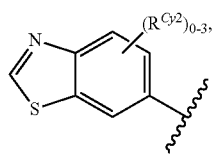 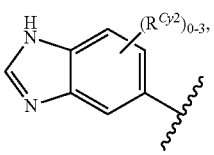 and
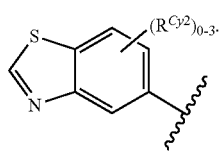
5. The compound of claim 1, wherein the compound has the Formula
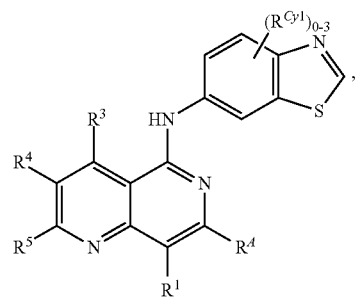
or a pharmaceutically acceptable salt thereof.
6. The compound of claim 1 selected from the group consisting of
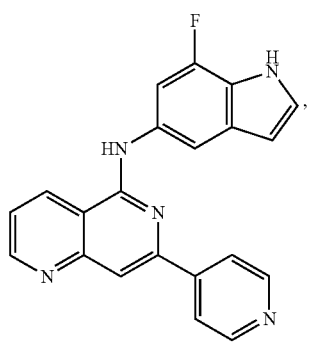
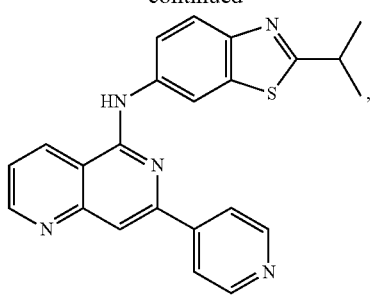
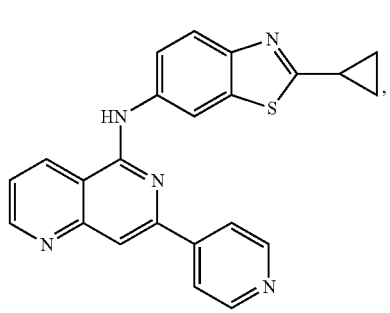
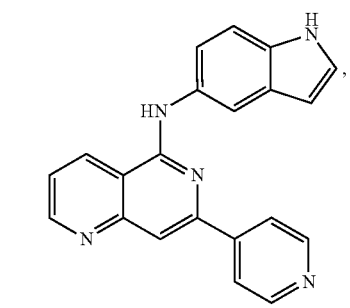
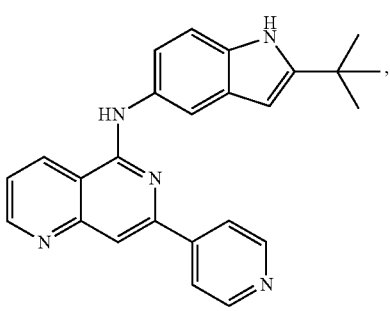
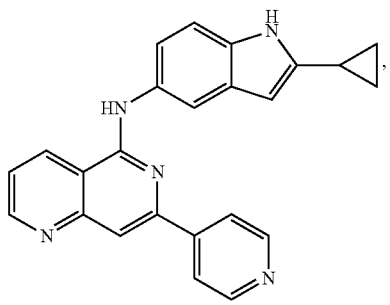

-continued
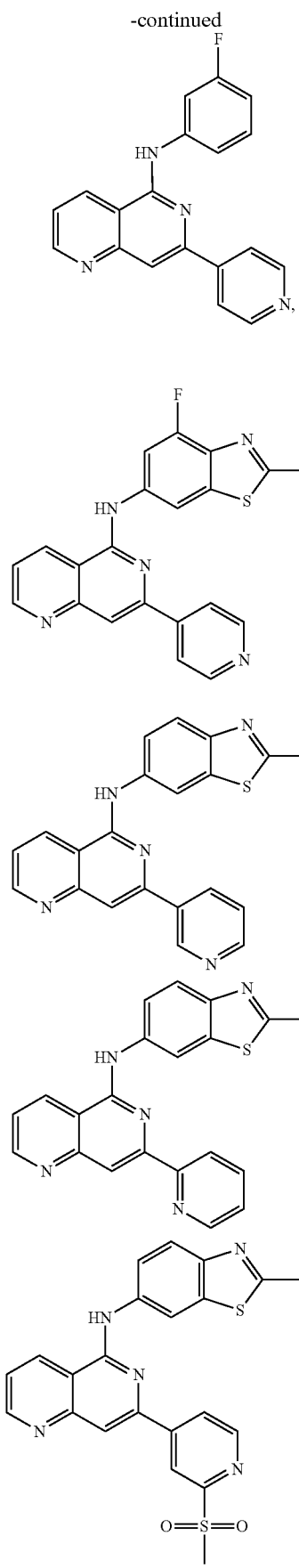
-continued
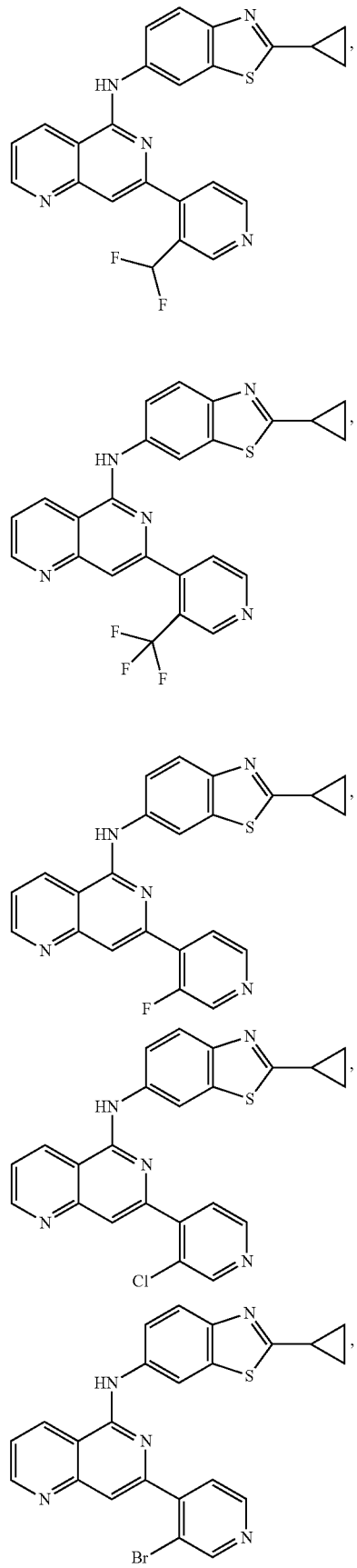

-continued
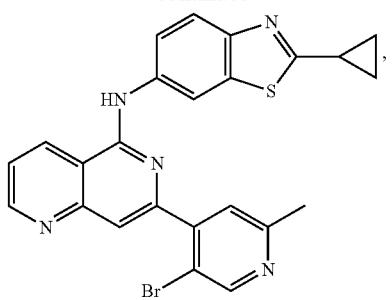
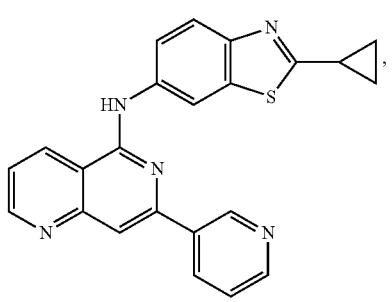
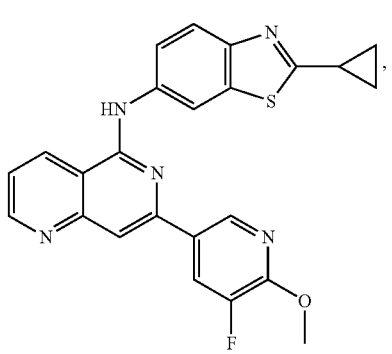
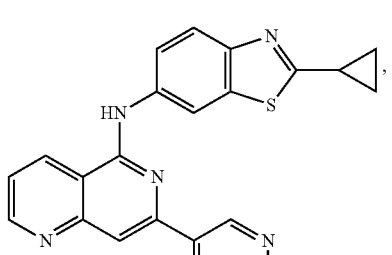
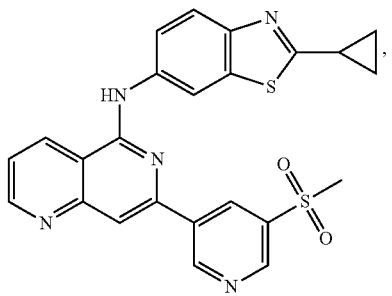
-continued
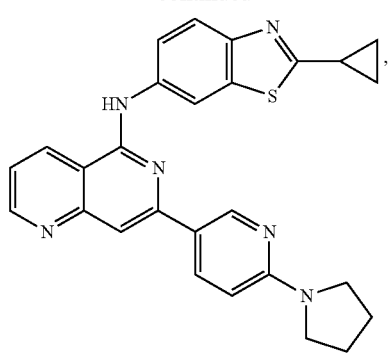
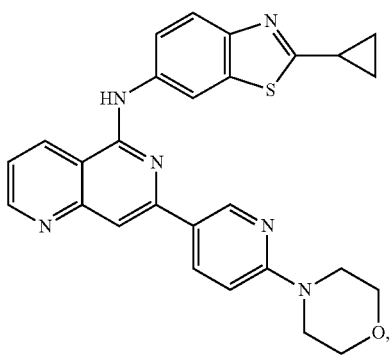
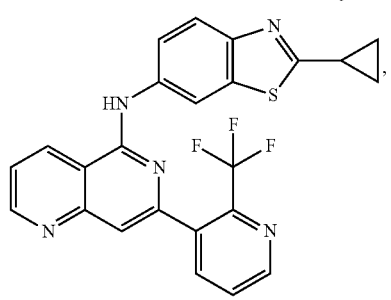
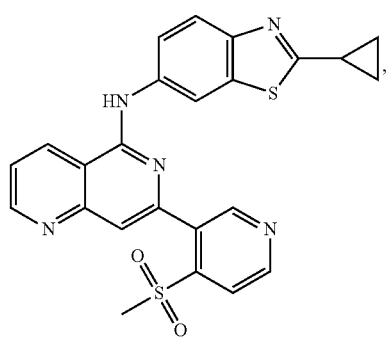
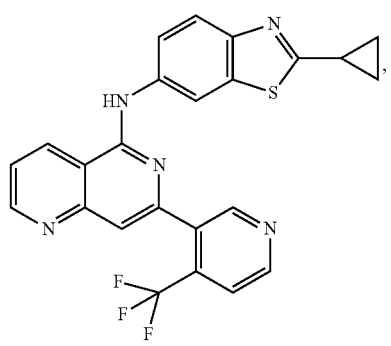

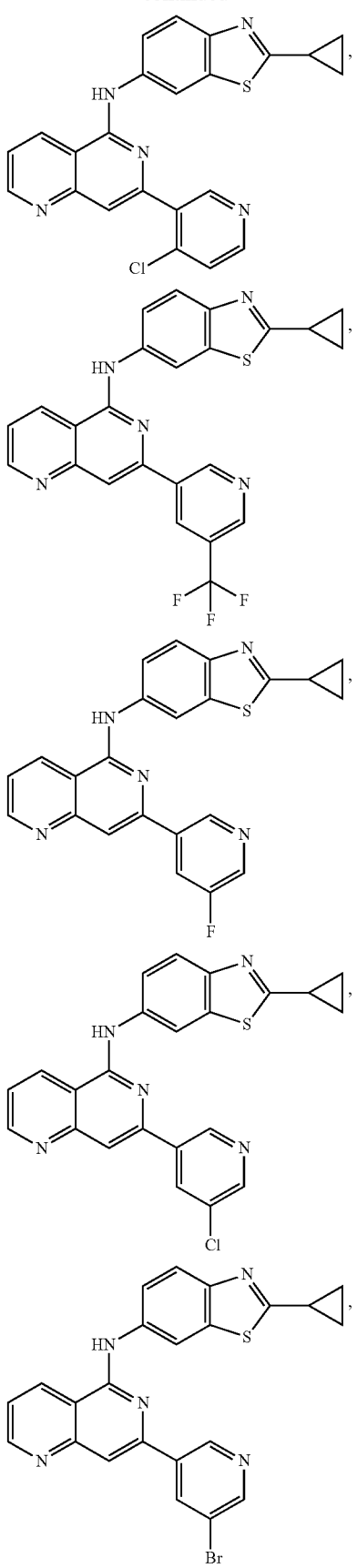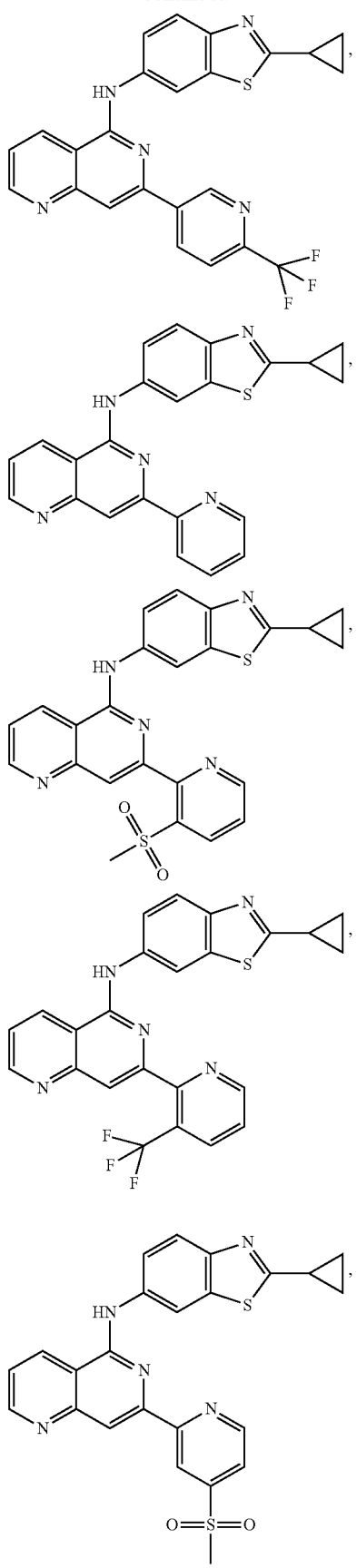

267
-continued
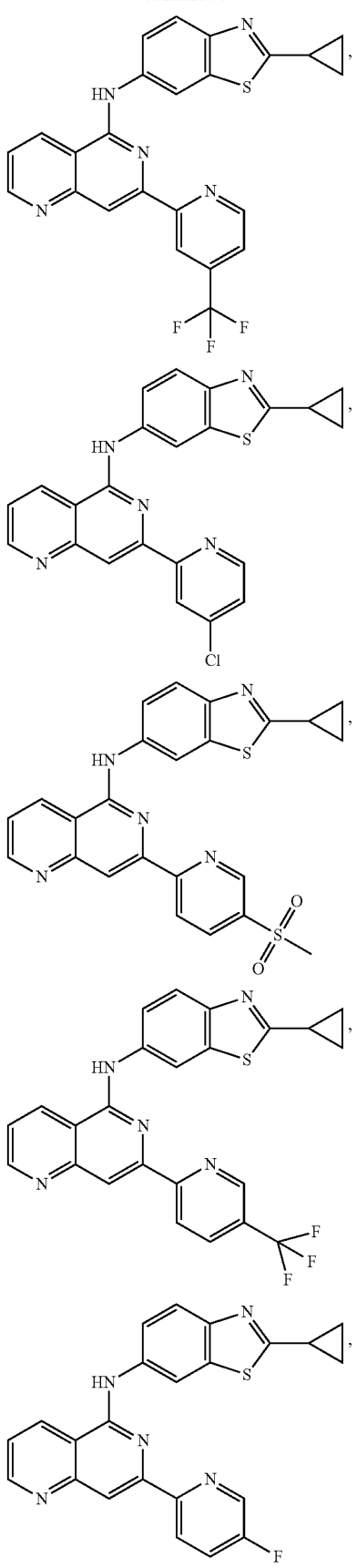
268
-continued
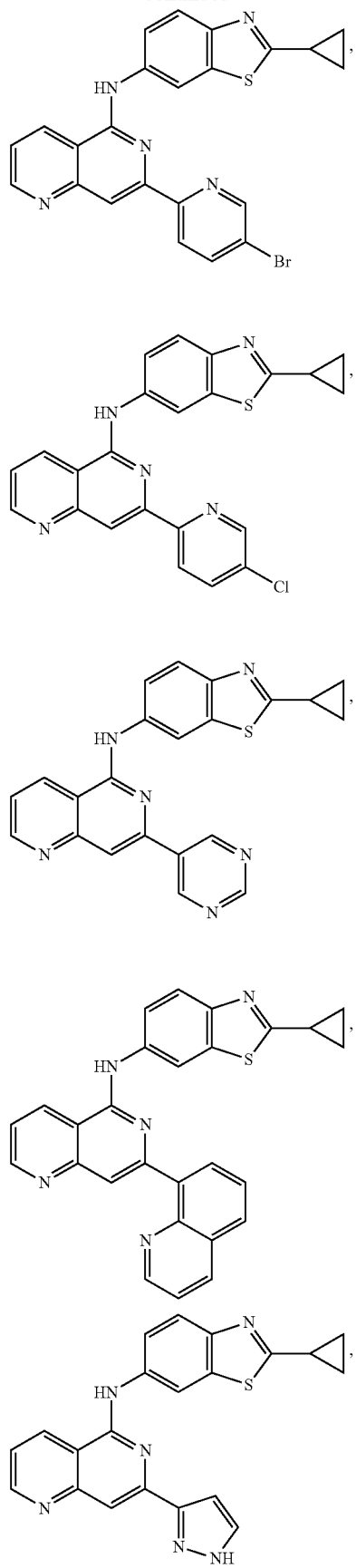

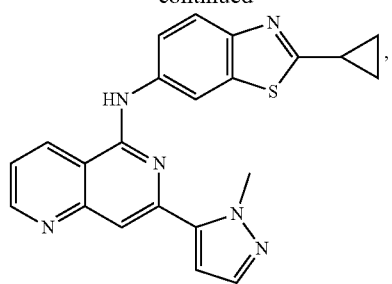
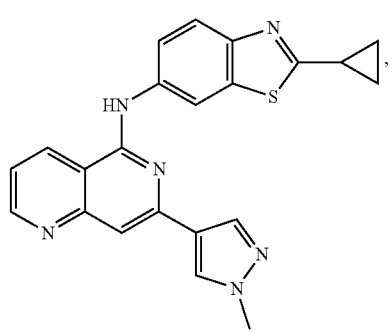
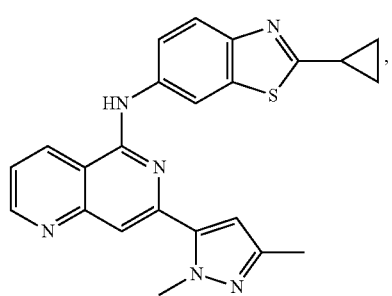
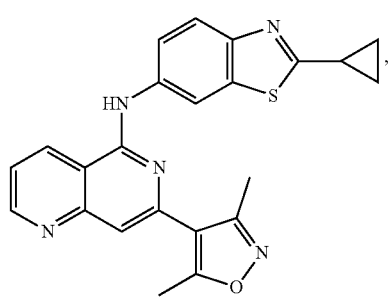
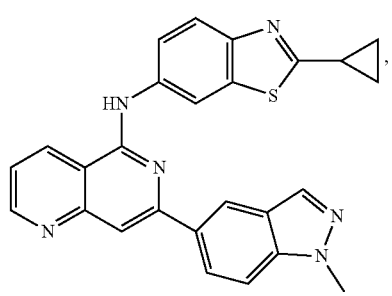
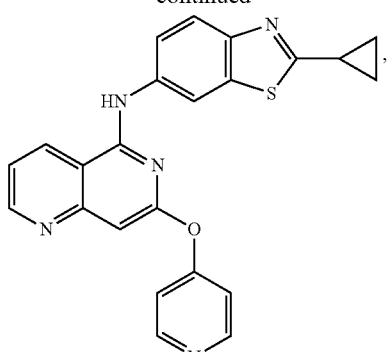
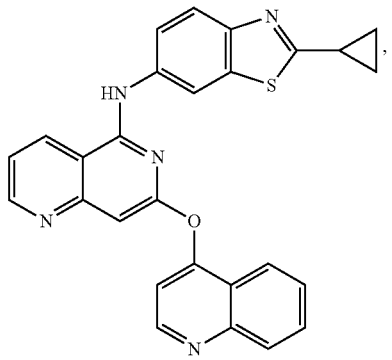
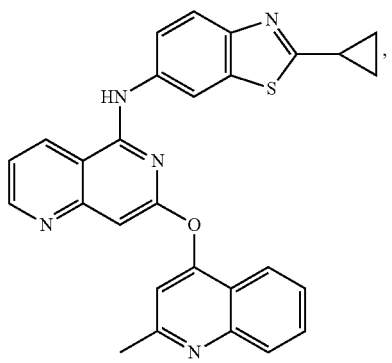
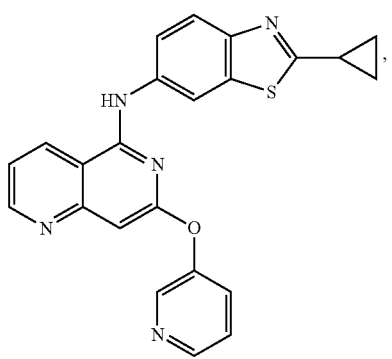

-continued
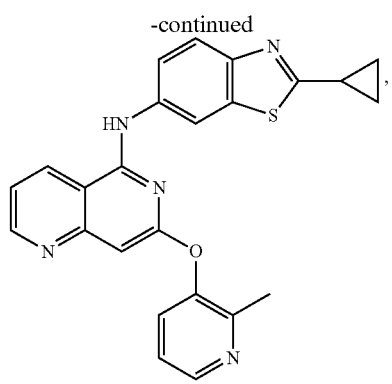
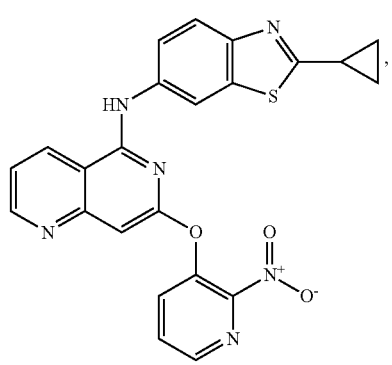
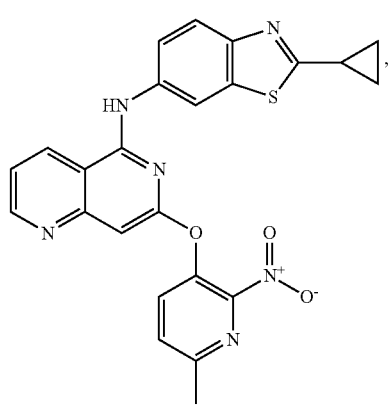
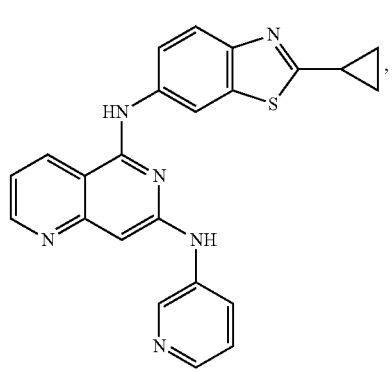
-continued
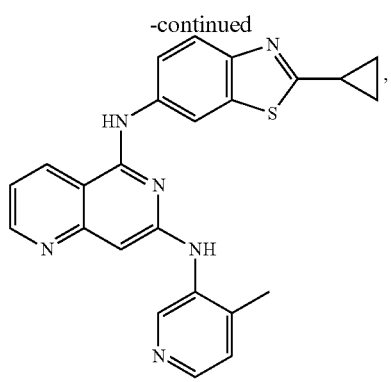
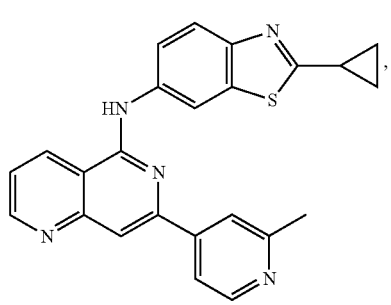
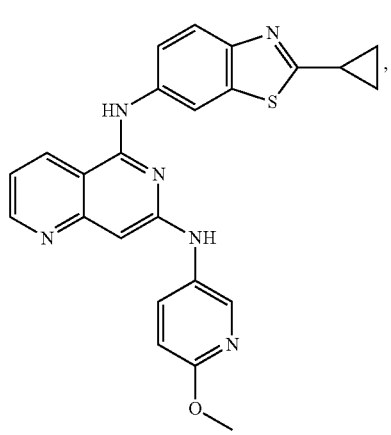
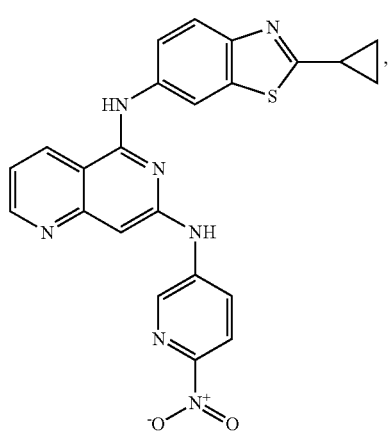

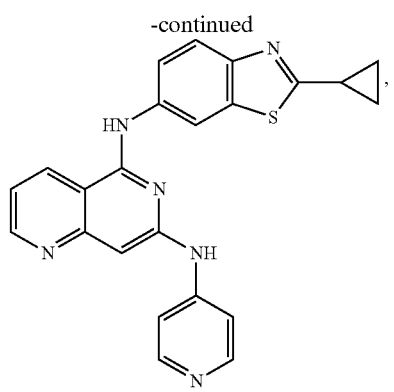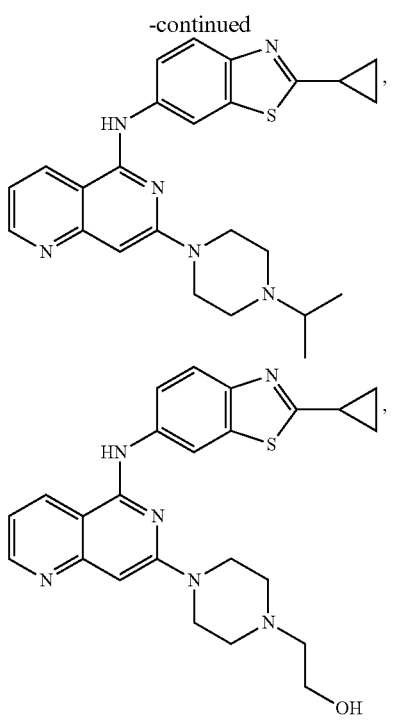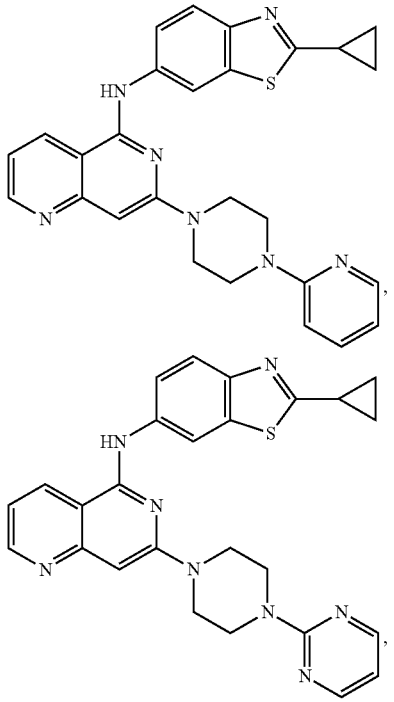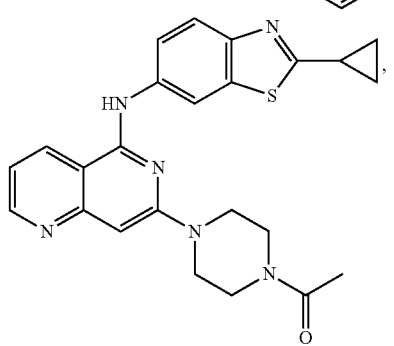

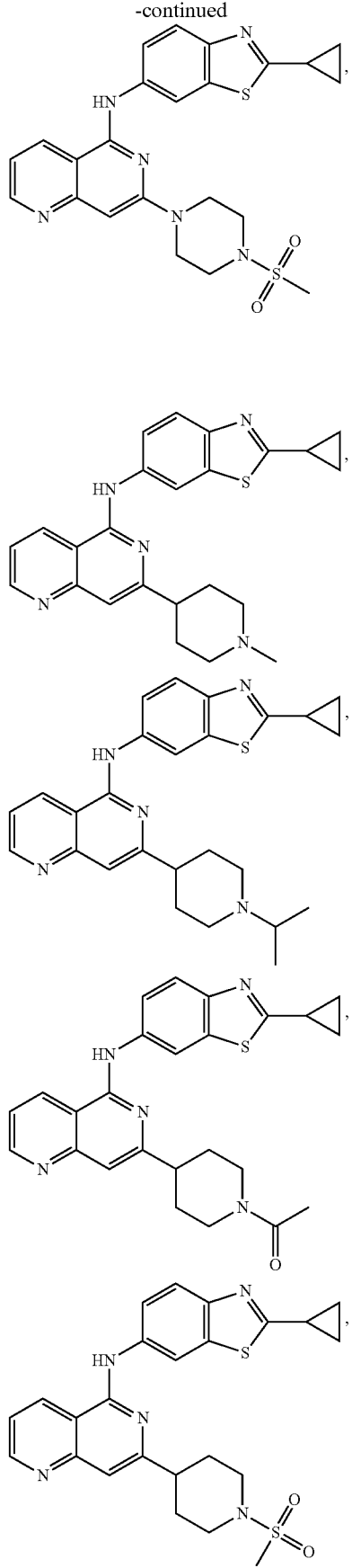
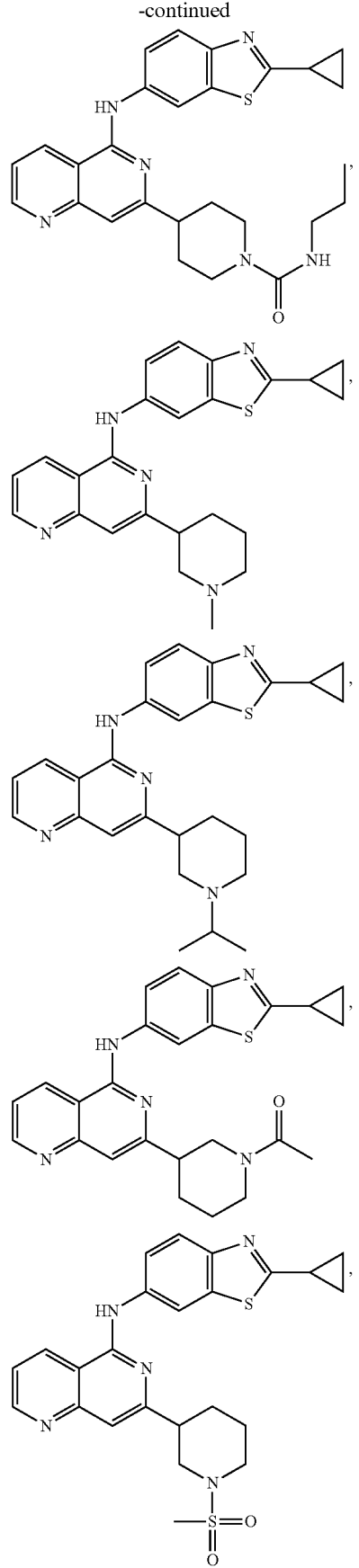

277                                    278

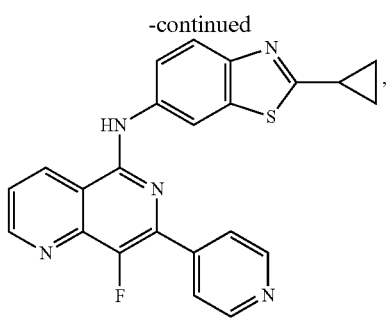
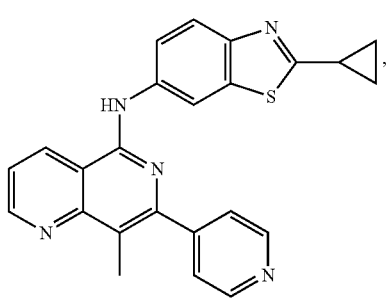
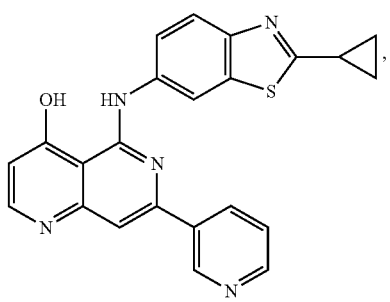
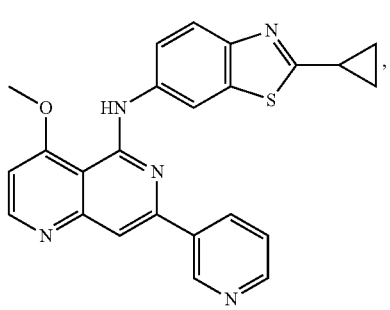
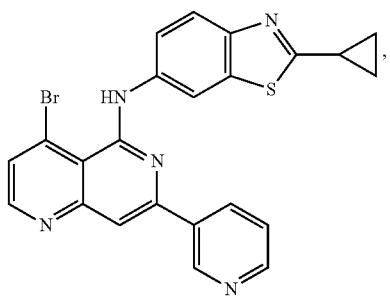
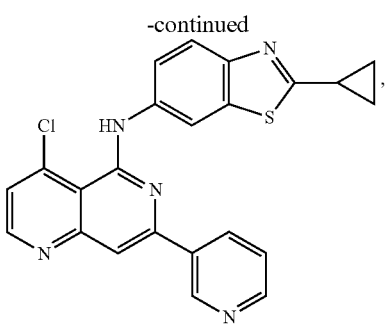
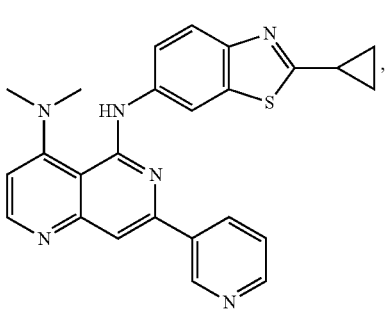
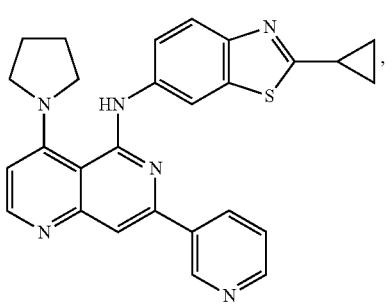
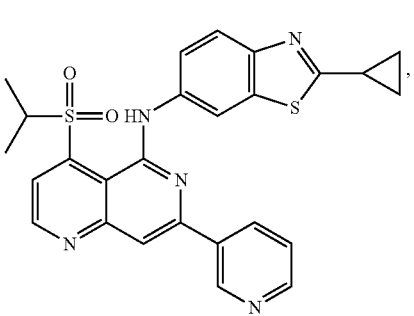
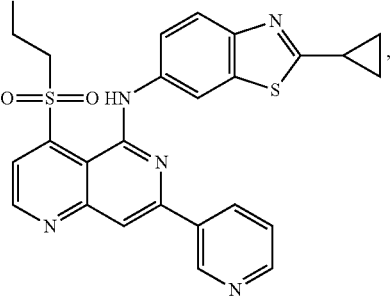

-continued
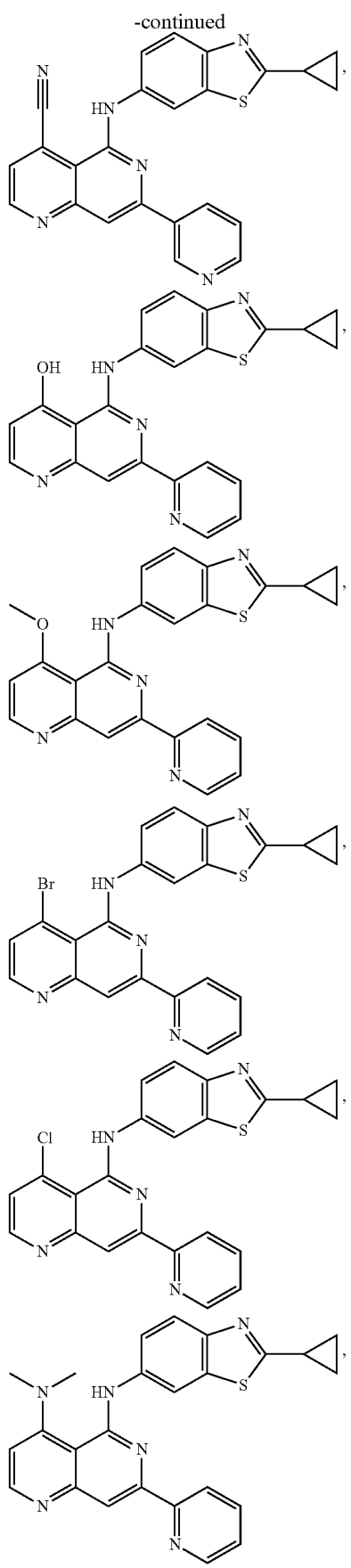
-continued
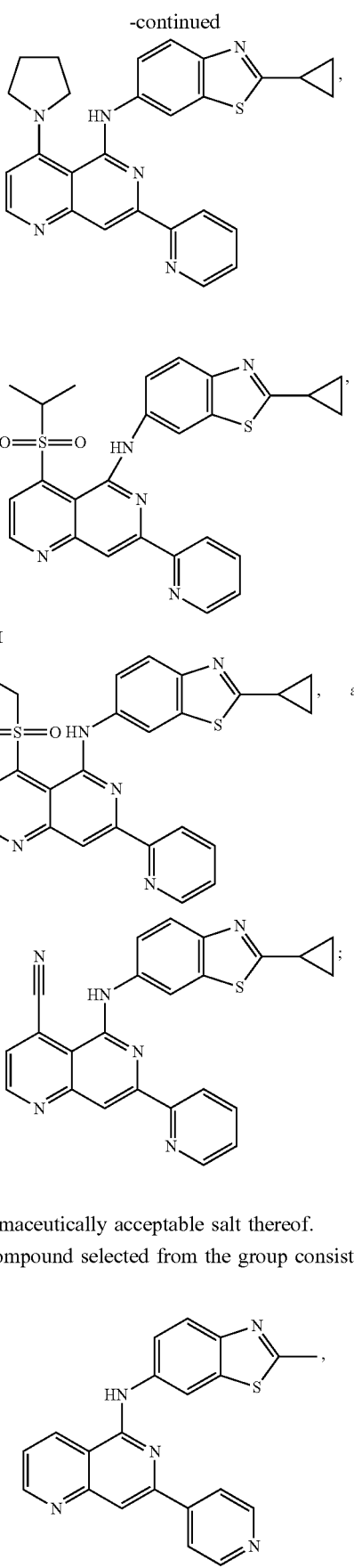
or a pharmaceutically acceptable salt thereof.
7. A compound selected from the group consisting of

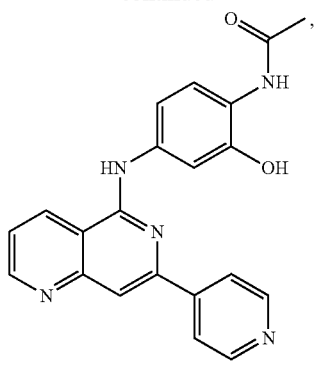
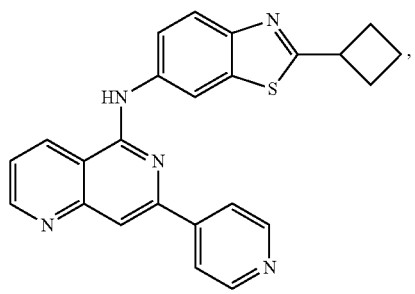
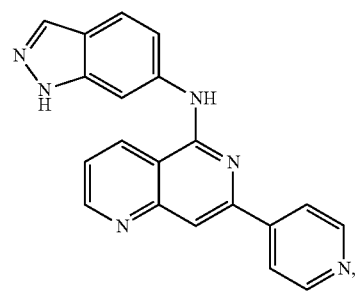
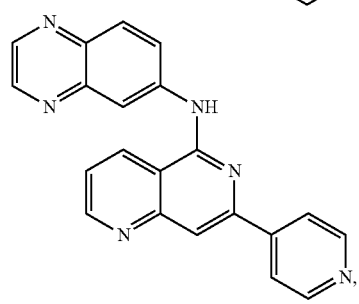
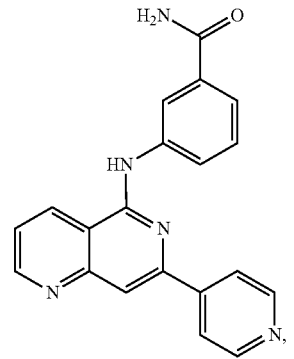
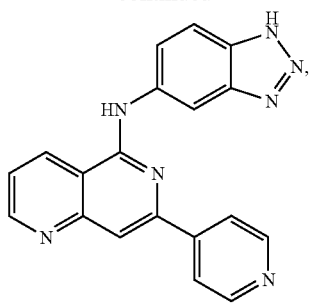
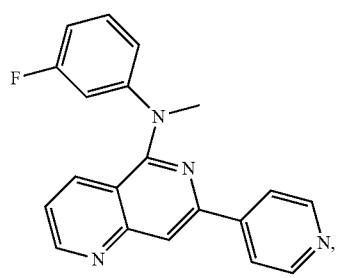
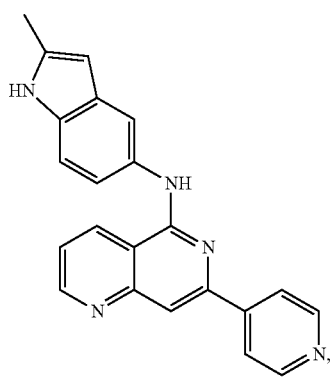
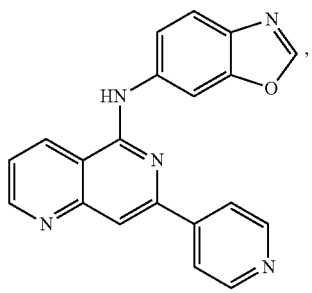
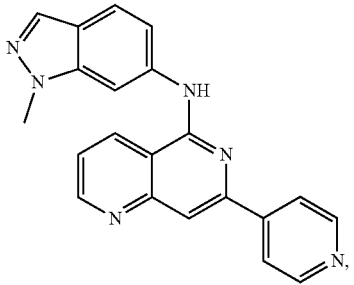

-continued
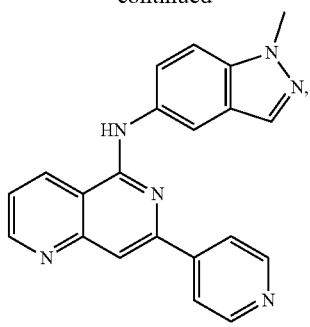
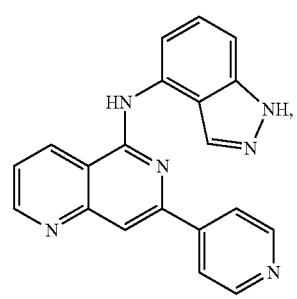
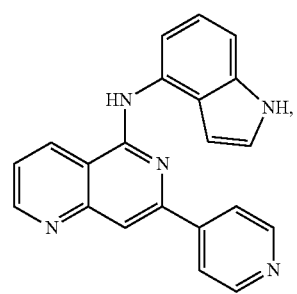
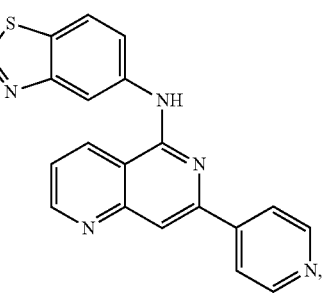
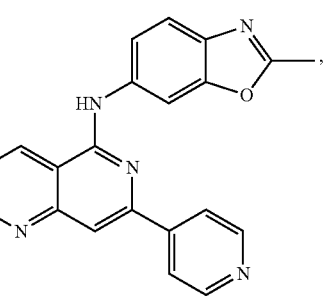
-continued
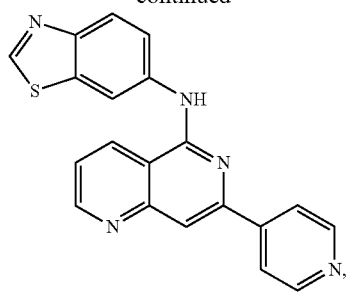
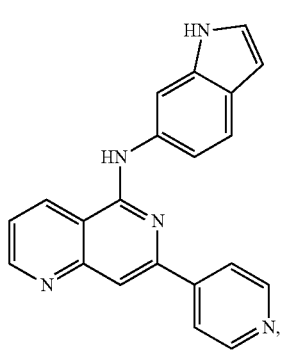
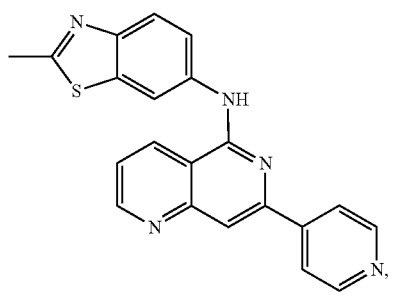
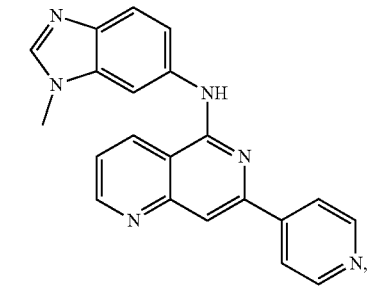
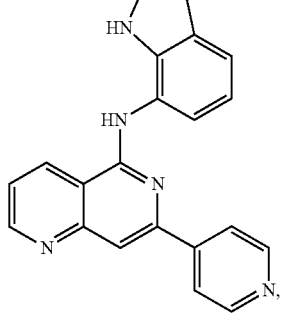

287
-continued
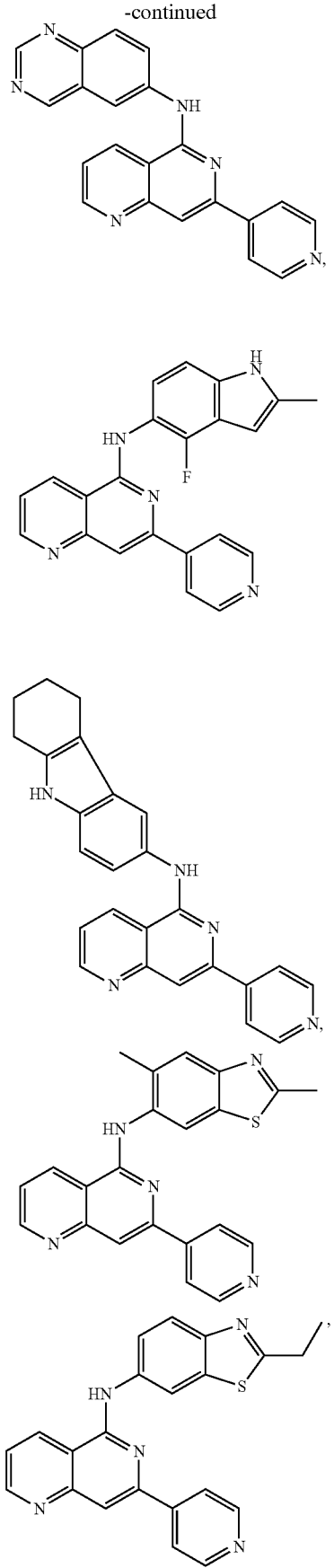
288
-continued
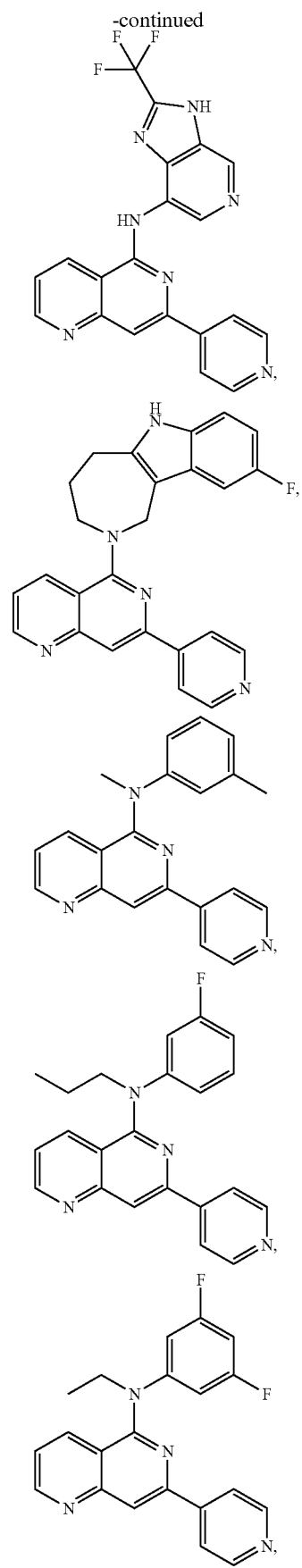

289
-continued
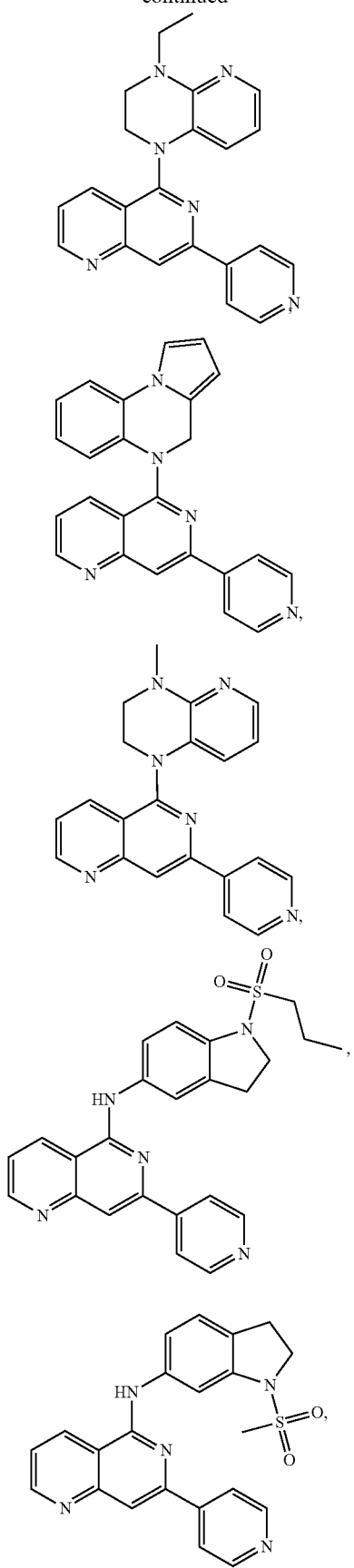
290
-continued
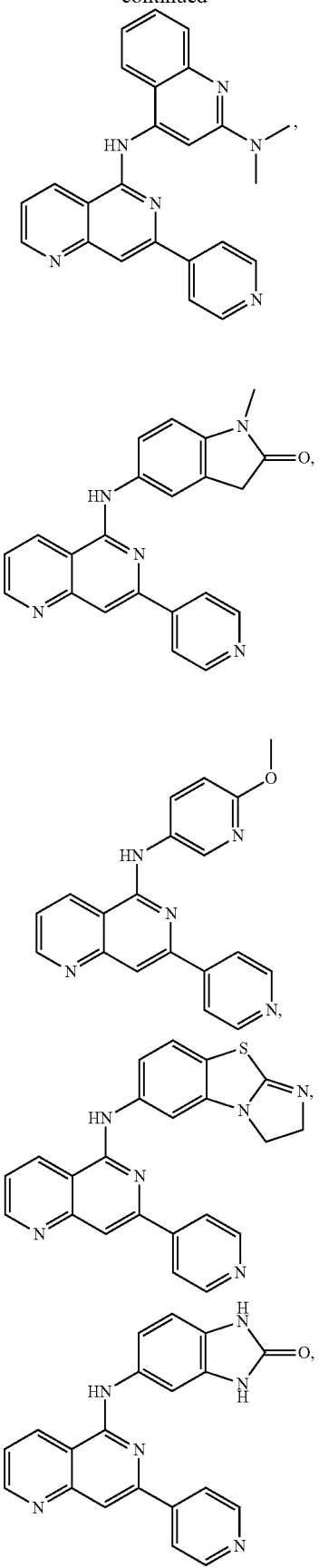

-continued

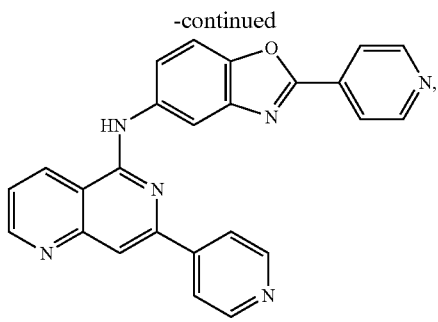

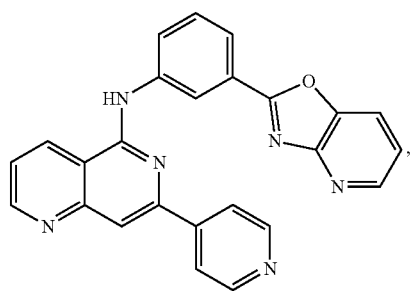

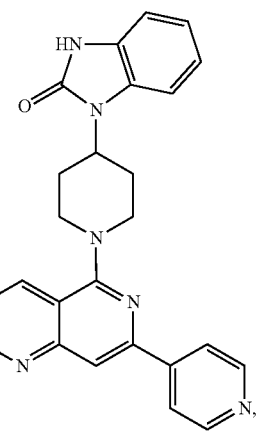

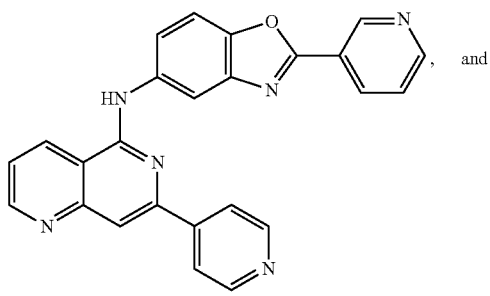, and

-continued

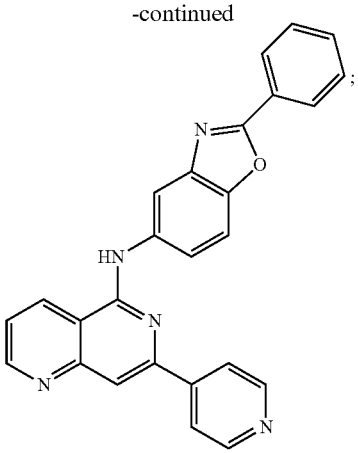

or a pharmaceutically acceptable salt thereof.

8. A pharmaceutical composition comprising an effective amount of a compound of claim 1, or a pharmaceutically acceptable salt thereof; and a pharmaceutically acceptable carrier.

9. A method for increasing TFEB polypeptide levels within a nucleus of a cell within a mammal, wherein said method comprises administering, to said mammal, a compound of claim 1, or a pharmaceutically acceptable salt thereof.

10. A method of treating a mammal having a disease, disorder, or condition responsive to an increase in TFEB polypeptide levels within a nucleus of a cell, wherein said method comprises administering, to said mammal, a compound of according to claim 1, or a pharmaceutically acceptable salt thereof.

11. The method of claim 10, wherein said mammal is a human.

12. The method of claim 10, wherein said method comprises treating a mammal having a lysosomal storage disease (LSD).

13. The method of claim 12, wherein said LSD is selected from the group consisting of Krabbe disease, Sanfilippo syndrome, multiple sulfatase deficiency, alpha-mannosidosis, Fabry disease, Hunter syndrome, Scheie syndrome, Sanfilippo syndrome, Maroteaux-Lamy syndrome, hyaluronidase deficiency, sialidosis, mucolipidin 1 deficiency, neuronal ceroid lipofuscinoses (Batten Disease), mucopolysaccharidoses Type I, II, III, IV, VI, VII, and IX, Hurler-Scheie syndrome, Morquio syndrome, glycoproteinosis, multiple sulfatase deficiency, glycogen storage disease, metachromatic Leukodystrophy, Sly syndrome, I-cell disease, Danon disease, Niemann-Pick disease type A, B, C1 and C2, Sandhoff disease, lysosomal acid lipase deficiency, GM2 gangliosidoses, Tay-Sachs disease, Gaucher disease, Salla disease, Pompe disease, Danon disease, cholesteryl ester storage disease, aspartylglucosaminuria, cystinosis, mucolipidosis type I-IV, Schindler disease type I and II, Wolman disease, fucosidosis, pycnodysostosis and free sialic acid storage disease.

14. The method of claim 10, wherein said method comprises treating a mammal having an acute or chronic inflammation disorder.

15. The method of claim 14, wherein said acute or chronic inflammation disorder is selected from the group consisting of asthma, chronic obstructive lung disease, pulmonary fibrosis, hypersensitivity pneumonitis, radiation pneumonitis, pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, Crohn's disease, ulcerative colitis, colitis, sepsis, vasculitis, bursitis, connective tissue disease, systemic lupus erythematosis (SLE), polymyalgia rheumatica, scleroderma, Wegener's granulomatosis, temporal arteritis, vasculitis, cryoglobulinemia, multiple sclerosis, viral or influenza-induced inflammation, chronic bacterial colonization or persistent intracellular pathogen, and impaired responsiveness to antigenic challenge or vaccines administration.

16. The method of claim 10, wherein said method comprises treating a mammal having an age-related disorder.

17. The method of claim 16, wherein said age-related disorder is selected from the group consisting of neurodegenerative diseases, metabolic diseases, metabolic syndrome, NASH, fatty liver, diabetes, sarcopenia, fraility, age-related wet and dry macular degeneration, inherited or acquired retinal degenerative diseases, age-related hearing loss, early or late cognitive decline, early or late cognitive impairment, osteoporosis, age-related organ dysfunction, and age-related immune dysfunctions.

18. The method of claim 10, wherein said method comprises treating a mammal having Alzheimer's disease, ALS, Huntington's disease, Parkinson's disease, primary age-related tauopathy, progressive supranuclear palsy, frontotemporal dementia, chronic traumatic encephalopathy, or traumatic brain injury.

19. The method of claim 10, wherein said method comprises treating a mammal having an inherited or acquired disease of muscle.

20. The method of claim 19, wherein the inherited or acquired disease of muscle is selected from the group consisting of myofibrillar myopathy, sporadic inclusion body myositis, inclusion body myopathy with frontotemporal dementia (IBMFTD), and cardiomyopathy.

\* \* \* \* \*

UNITED STATES PATENT AND TRADEMARK OFFICE
CERTIFICATE OF CORRECTION

| | | |
|---|---|---|
| PATENT NO. | : 12,286,442 B2 | Page 1 of 1 |
| APPLICATION NO. | : 17/420597 | |
| DATED | : April 29, 2025 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this
Sixteenth Day of December, 2025

John A. Squires
*Director of the United States Patent and Trademark Office*